(12) United States Patent
Hu et al.

(10) Patent No.: US 8,809,008 B2
(45) Date of Patent: *Aug. 19, 2014

(54) BIOMARKERS FOR IMPAIRED GLUCOSE TOLERANCE AND METHODS USING THE SAME

(71) Applicants: Yun Fu Hu, Chapel Hill, NC (US); Costel Chirila, Durham, NC (US); Danny Alexander, Cary, NC (US); Michael Milburn, Cary, NC (US); Matthew W. Mitchell, Durham, NC (US); Walter Gall, Chapel Hill, NC (US); Kay A. Lawton, Raleigh, NC (US)

(72) Inventors: Yun Fu Hu, Chapel Hill, NC (US); Costel Chirila, Durham, NC (US); Danny Alexander, Cary, NC (US); Michael Milburn, Cary, NC (US); Matthew W. Mitchell, Durham, NC (US); Walter Gall, Chapel Hill, NC (US); Kay A. Lawton, Raleigh, NC (US)

(73) Assignee: Metabolon, Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/966,475

(22) Filed: Aug. 14, 2013

(65) Prior Publication Data
US 2013/0338031 A1    Dec. 19, 2013

Related U.S. Application Data

(62) Division of application No. 13/457,620, filed on Apr. 27, 2012, now Pat. No. 8,546,098, which is a division of application No. 12/218,980, filed on Jul. 17, 2008, now Pat. No. 8,187,830.

(60) Provisional application No. 60/950,286, filed on Jul. 17, 2007, provisional application No. 61/037,628, filed on Mar. 18, 2008.

(51) Int. Cl.
C12Q 1/54    (2006.01)

(52) U.S. Cl.
USPC ......................................................... 435/14

(58) Field of Classification Search
USPC ......................................................... 435/14
See application file for complete search history.

(56) References Cited

U.S. PATENT DOCUMENTS

| | | | |
|---|---|---|---|
| 5,367,052 A | 11/1994 | Cooper et al. | |
| 6,153,419 A | 11/2000 | Aisaka et al. | |
| 6,653,094 B2 | 11/2003 | Anderson et al. | |
| 7,005,255 B2 | 2/2006 | Kaddurah-Daouk et al. | |
| 7,329,489 B2 | 2/2008 | Kaddurah-Daouk et al. | |
| 7,648,825 B2 | 1/2010 | Ellis et al. | |
| 8,187,830 B2 * | 5/2012 | Hu et al. | 435/14 |
| 8,546,098 B2 * | 10/2013 | Hu et al. | 435/14 |
| 2004/0101874 A1 | 5/2004 | Ghosh et al. | |
| 2005/0014132 A1 | 1/2005 | Kaddurah-Daouk et al. | |
| 2005/0014257 A1 | 1/2005 | Crooke et al. | |
| 2006/0134676 A1 | 6/2006 | Kaddurah-Daouk et al. | |
| 2006/0134677 A1 | 6/2006 | Kaddurah-Daouk et al. | |
| 2006/0134678 A1 | 6/2006 | Kaddurah-Daouk et al. | |
| 2007/0003946 A1 | 1/2007 | Ma et al. | |
| 2007/0026389 A1 | 2/2007 | Kaddurah-Daouk et al. | |
| 2007/0026458 A1 | 2/2007 | Polidori et al. | |
| 2007/0072203 A1 | 3/2007 | Kaddurah-Daouk et al. | |
| 2009/0155826 A1 | 6/2009 | Hu et al. | |
| 2010/0236321 A1 | 9/2010 | Bethan et al. | |
| 2012/0122981 A1 * | 5/2012 | Hu et al. | 514/560 |
| 2013/0295692 A1 * | 11/2013 | Wiemer et al. | 436/501 |

FOREIGN PATENT DOCUMENTS

WO    WO 2006066263    6/2006

OTHER PUBLICATIONS

Bonora et al., "Prevalence of Insulin Resistance in Metabolic Disorders," Diabetes, vol. 47, (Oct. 1998), pp. 1643-1649.
Bugianesi et al., "Insulin Resistance in Non-Diabetic Patients with Non-Alcoholic Fatty Liver Disease: Sites and Mechanisms," Diabetologia, vol. 48, (2005), pp. 634-642.
Geissler et al., "Analysis of Urine Organic Acids using Linear Retention Indices for the Determination of Metabolic Disorders," (Mar. 2, 2007), [online] [retrieved on Feb. 15, 2011]. Retrieved from http://license.icopyright.net/user/viewFreeUse.act?fuid=MTE3NTI2NDk%3D.
International Preliminary Report on Patentability, issued in commonly assigned PCT/US2010/029399, dated Oct. 13, 2011.
International Preliminary Report on Patentability, issued in PCT/US2008/008756, dated Aug. 31, 2010.
International Search Report, issued in commonly assigned PCT/US2010/029399, dated May 27, 2010.
International Search Report, issued in PCT/US2008/008756, dated Dec. 22, 2008.
Kassel et al., "Urinary Metabolites of L-Threonine in Type 1 Diabetes Determined by Combined Gas Chromatography/Chemical Ionization Mass Spectrometry," Biomedical and Environmental Mass Spectrometry, vol. 13, (1986), pp. 535-540.
Lawton et al., "Analysis of the Adult Human Plasma Metabolome," Pharmacogenomics, vol. 9, No. 4, (Apr. 2008), pp. 383-397.
Pitkänen, "Mannose, Mannitol, Fructose, and 1,5-anhydroglucitol Concentrations Measured by Gas Chromatography/Mass Sepectrometry in Blood Plasma of Diabetic Patients," Clinica Chimica Acta, vol. 251, (1996), pp. 91-103.

(Continued)

Primary Examiner — Ralph Gitomer
(74) Attorney, Agent, or Firm — Brinks Gilson & Lione

(57) ABSTRACT

Biomarkers relating to insulin resistance, pre-diabetes, type-2 diabetes, metabolic syndrome, atherosclerosis, and cardiomyopathy are provided, as well as methods for using such biomarkers as biomarkers for insulin resistance, pre-diabetes, type-2 diabetes, metabolic syndrome, atherosclerosis, and cardiomyopathy. In addition, methods for modulating the respective disorders or conditions of a subject are also provided. Also provided are suites of small molecule entities as biomarkers for insulin resistance, pre-diabetes, type-2 diabetes, metabolic syndrome, atherosclerosis, and cardiomyopathy.

20 Claims, 30 Drawing Sheets

(56) References Cited

OTHER PUBLICATIONS

Ryals et al., "Metabolon, Inc.," Pharmacogenomics, vol. 8, No. 7, (Jul. 2007), pp. 863-866.
Sakul et al., "Familiality of Physical and Metabolic Characteristics that Predict the Development of Non-Insulin-Dependent Diabetes Mellitus in Pima Indians," Am. J. Hum. Genet., vol. 60, (1997), pp. 651-656.
Salek et al., "A Metabolomic Comparison of Urinary Changes in Type-2 Diabetes in Mouse, Rat and Human," Physiol Genomics, vol. 29, (2007), pp. 99-108.
Salek et al., "A Metabolomic Comparison of Urinary Changes in Type-2 Diabetes in Mouse, Rat and Human," Physiol Genomics, vol. 29, (2007), pp. 99-108—Supplementary Information, S1-513.
Search Report, issued in commonly assigned Singapore Application No. 200908426-0, dated Mar. 1, 2011.
Shima et al., "Urinary Endogenous Concentrations of GHB and its Isomers in Healthy Humans and Diabetics," Forensic Science International, vol. 149, (2005), pp. 171-179.
Sidossis et al., "Glucose Plus Insulin Regulate Fat Oxidation by Controlling the Rate of Fatty Acid Entry into the Mitochondria," J. Clin. Invest., vol. 98, No. 10, (Nov. 1996), pp. 2244-2250.
Siebenand, "Ein Tropfen Blut bringt Sicherheit," Pharm. Ztg., vol. 151, (2006), pp. 34-38.
Wang et al., "Plasma Fatty Acid Composition and Incidence of Diabetes in Middle Aged Adults: The Atherosclerosis Risk in Communities (ARIC) Study," American J of Clinical Nutrition, vol. 78, No. 1, (Jul. 2003), pp. 91-98.
Yamanouchi et al., "Serum 1,5-anhydroglucitol (1,5 AG): New Clinical Marker for Glycemic Control," Diabetes Research and Clinical Practice, 24 Suppl, (1994), pp. S261-S268.
Yu et al., "Quantitative Analysis of Polar Lipids in the Nanoliter Level of Rat Serum by Liquid Chromatography/Mass Spectrometry/Mass Spectrometry," Exp Biol Med, vol. 234, (Feb. 2009), pp. 157-163.

* cited by examiner

Early Stage (Initiation)
Plasma AGE_2mo: LDb males vs C57BL/6 MALES

Mid Stage

Later Stage

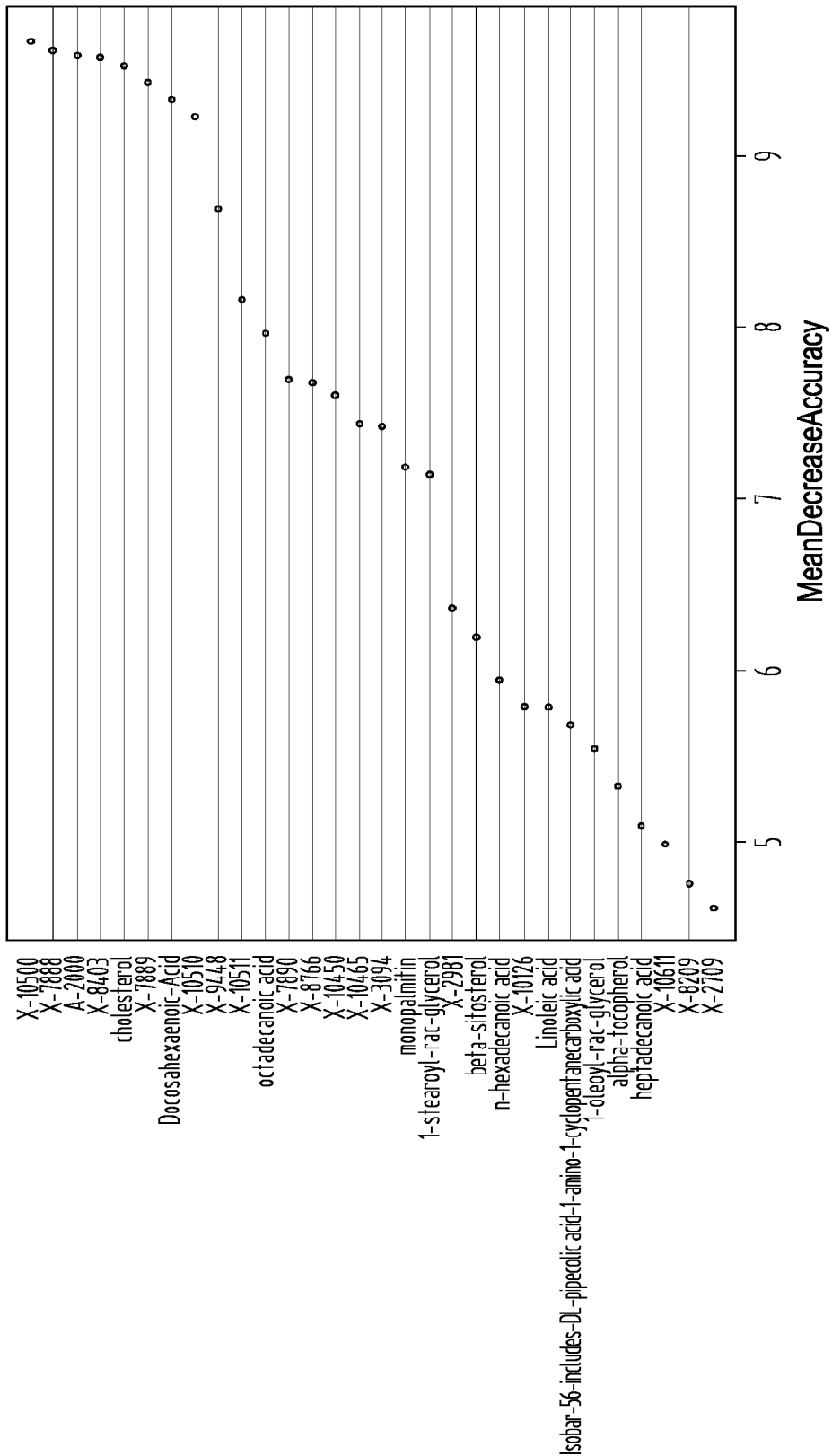

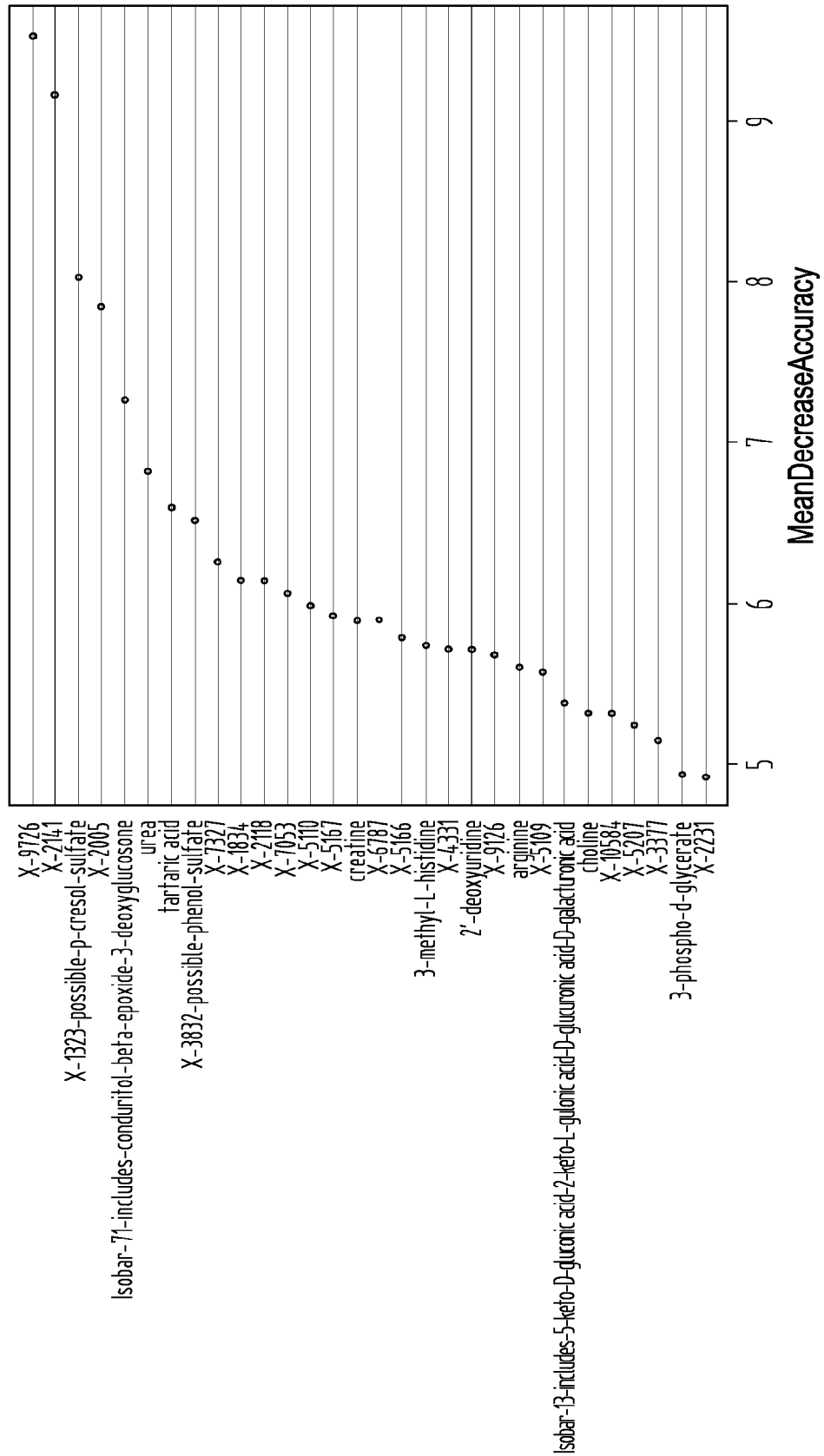

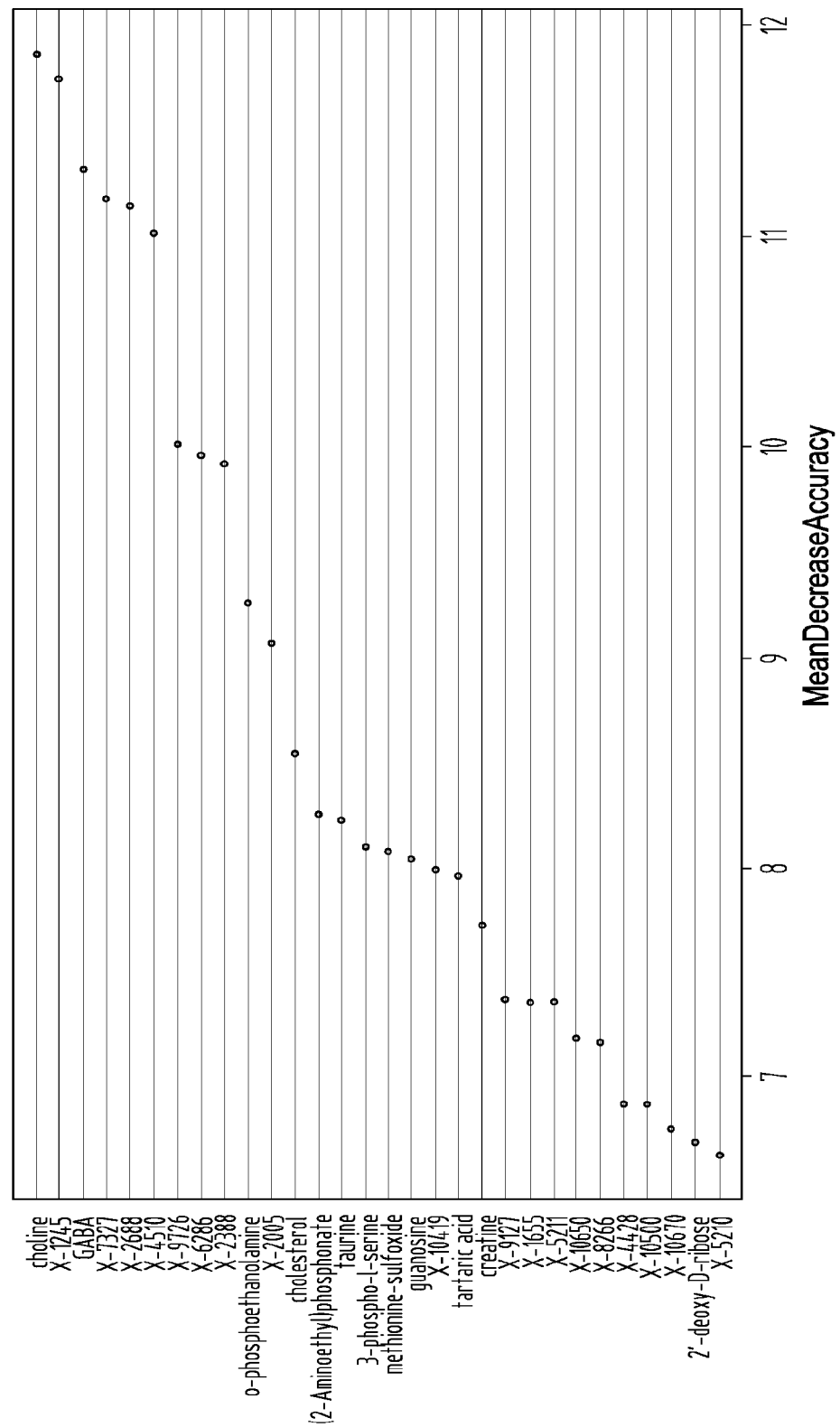

Later Stage
Aorta AGE_8mo: LDb males vs C57BL/6 MALES

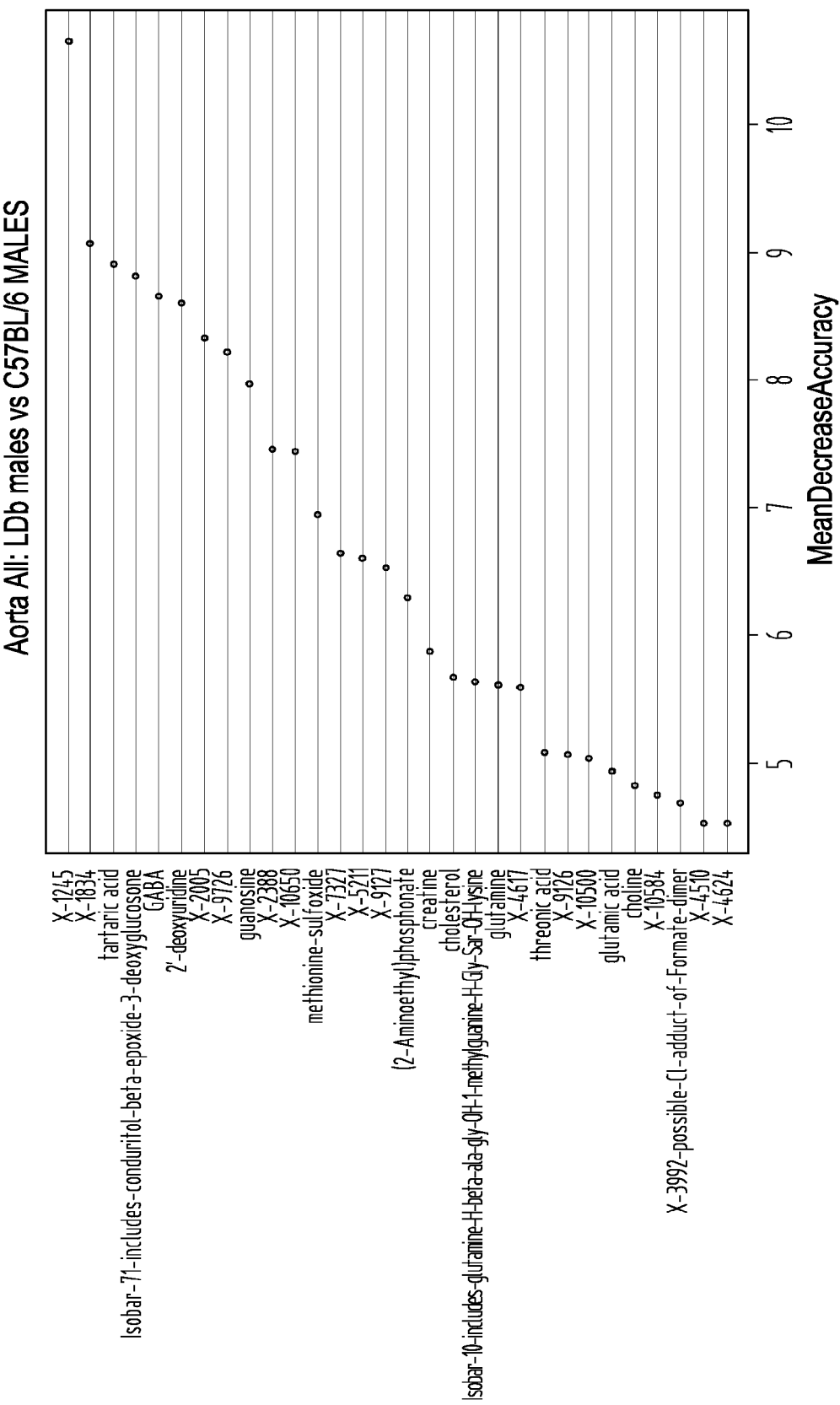
FIG. 11D ALL

Early Stage (Initiation)

Mid Stage

Late Stage

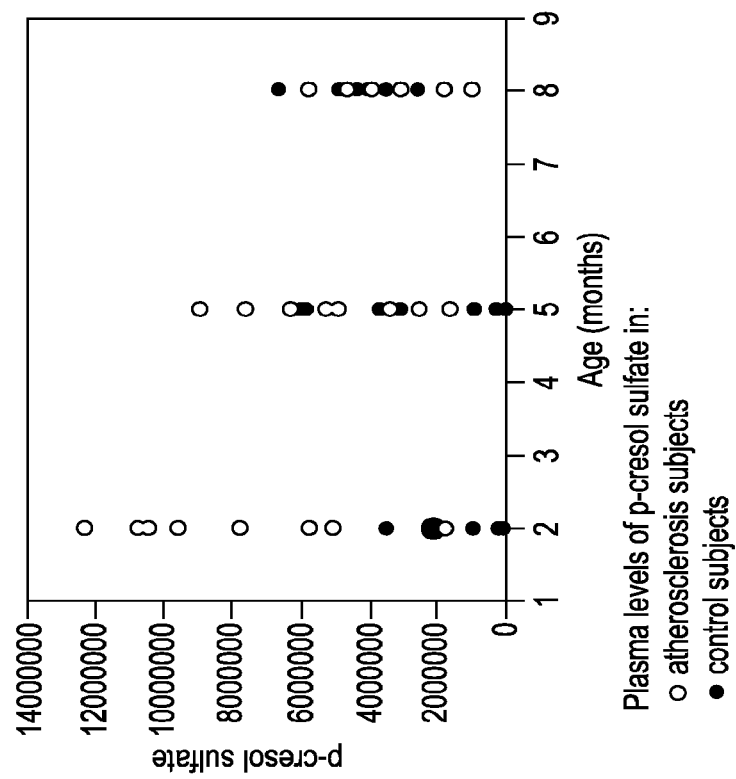
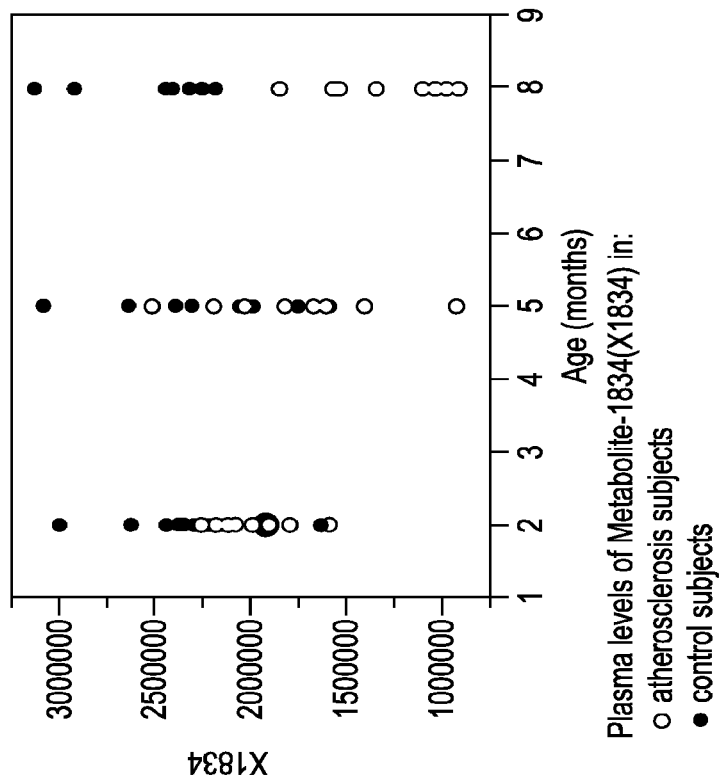

BIOMARKERS FOR IMPAIRED GLUCOSE TOLERANCE AND METHODS USING THE SAME

CROSS-REFERENCE TO RELATED APPLICATIONS

This application is a divisional of U.S. patent application Ser. No. 13/457,620, filed Apr. 27, 2012, now U.S. Pat. No. 8,546,098, which is a divisional of U.S. patent application Ser. No. 12/218,980, filed Jul. 17, 2008, now U.S. Pat. No. 8,187,830, which claims the benefit of U.S. Provisional Application No. 60/950,286, filed Jul. 17, 2007, and U.S. Provisional Application No. 61/037,628, filed Mar. 18, 2008, the entireties of which are hereby incorporated by reference herein.

FIELD

The invention generally relates to biomarkers, methods for identifying biomarkers correlated to insulin resistance, cardiovascular disease, and metabolic-syndrome-related disorders and methods based on the same biomarkers.

BACKGROUND

Diabetes is classified as either type 1 (early onset) or type 2 (adult onset), with type 2 comprising 90-95% of the cases of diabetes. Diabetes is the final stage in a disease process that begins to affect individuals long before the diagnosis of diabetes is made. Type 2 diabetes develops over 10 to 20 years and results from an impaired ability to utilize glucose (glucose utilization) due to impaired sensitivity to insulin (insulin resistance).

In pre-diabetes, insulin becomes less effective at helping tissues metabolize glucose. Pre-diabetics may be detectable as early as 20 years before diabetic symptoms become evident. Studies have shown that although patients show very few symptoms, long-term physiological damage is already occurring at this stage. Up to 60% of these individuals will progress to type 2 diabetes within 10 years.

The American Diabetes Association (ADA) has recommended routine screening to detect patients with pre-diabetes. Current screening methods for pre-diabetes include the fasting plasma glucose (FPG) test, the oral glucose tolerance test (OGTT), the fasting insulin test and the hyperinsulinemic euglycemic clamp (HI clamp). The first two tests are used clinically whereas the latter two tests are used extensively in research but rarely in the clinic. In addition, mathematical means (e.g., HOMA, QUICKI) that consider the fasting glucose and insulin levels together have been proposed. However, normal plasma insulin concentrations vary considerably between individuals as well as within an individual throughout the day. Further, these methods suffer from variability and methodological differences between laboratories and do not correlate rigorously with glucose clamp studies.

Worldwide, an estimated 194 million adults have type 2 diabetes and this number is expected to increase to 333 million by 2025, largely due to the epidemic of obesity in westernized societies. In the United States, it is estimated that over 54 million adults are pre-diabetic, depending on the level of insulin resistance. There are approximately 1.5 million new cases of type 2 diabetes a year in the United States. The annual US healthcare cost for diabetes is estimated at $174 billion. This figure has risen more than 32% since 2002. In industrialized countries such as the U.S., about 25% of medical expenditures treat glycemic control, 50% is associated with general medical care associated with diabetes, and the remaining 25% of the costs go to treat long-term complications, primarily cardiovascular disease. Considering the distribution of the healthcare costs and the fact that insulin resistance is a direct causal factor in cardiovascular disease and diabetes progression, it is no surprise that cardiovascular disease accounts for 70-80% of the mortality observed for diabetic patients. Detecting and preventing type 2 diabetes has become a major health care priority.

Diabetes may also lead to the development of other diseases or conditions, or is a risk factor in the development of conditions such as Metabolic Syndrome and cardiovascular diseases. Metabolic Syndrome is the clustering of a set of risk factors in an individual. According to the American Heart Association these risk factors include: abdominal obesity, decreased ability to properly process glucose (insulin resistance or glucose intolerance), dyslipidemia (high triglycerides, high LDL, low HDL cholesterol), hypertension, prothrombotic state (high fibrinogen or plasminogen activator inhibitor-1 in the blood) and proinflammatory state (elevated C-reactive protein in the blood). Metabolic Syndrome is also known as syndrome X, insulin resistance syndrome, obesity syndrome, dysmetabolic syndrome and Reaven's syndrome. Patients diagnosed with Metabolic Syndrome are at an increased risk of developing diabetes, cardiac and vascular disease. It is estimated that, in the United States, 20% of the adults (>50 million people) have metabolic syndrome. While it can affect anyone at any age, the incidence increases with increasing age and in individuals who are inactive, and significantly overweight, especially with excess abdominal fat.

Type 2 diabetes is the most common form of diabetes in the United States. According to the American Diabetes Foundation over 90% of the US diabetics suffer from Type 2 diabetes. Individuals with Type 2 diabetes have a combination of increased insulin resistance and decreased insulin secretion that combine to cause hyperglycemia. Most persons with Type 2 diabetes have Metabolic Syndrome.

The diagnosis for Metabolic Syndrome is based upon the clustering of three or more of the risk factors in an individual. There are no well-accepted criteria for diagnosing the metabolic syndrome. The criteria proposed by the National Cholesterol Education Program (NCEP) Adult Treatment Panel III (ATP III), with minor modifications, are currently recommended and widely used.

The American Heart Association and the National Heart, Lung, and Blood Institute recommend that the metabolic syndrome be identified as the presence of three or more of these components: increased waist circumference (Men—equal to or greater than 40 inches (102 cm), Women—equal to or greater than 35 inches (88 cm); elevated triglycerides (equal to or greater than 150 mg/dL); reduced HDL ("good") cholesterol (Men—less than 40 mg/dL, Women—less than 50 mg/dL); elevated blood pressure (equal to or greater than 130/85 mm Hg); elevated fasting glucose (equal to or greater than 100 mg/dL).

Type 2 diabetes develops slowly and often people first learn they have type 2 diabetes through blood tests done for another condition or as part of a routine exam. In some cases, type 2 diabetes may not be detected before damage to eyes, kidneys or other organs has occurred. A need exists for an objective, biochemical evaluation (e.g. lab test) that can be administered by a primary care provider to identify individuals that are at risk of developing Metabolic Syndrome or Type 2 diabetes.

Newer, more innovative molecular diagnostics that reflect the mechanisms of the patho-physiological progression to pre-diabetes and diabetes are needed because the prevalence of pre-diabetes and diabetes is increasing in global epidemic proportions. Mirroring the obesity epidemic, pre-diabetes and diabetes are largely preventable but are frequently undiagnosed or diagnosed too late due to the asymptomatic nature of the progression to clinical disease.

Therefore there is an unmet need for diagnostic biomarkers and tests that can identify pre-diabetics at risk of developing type 2 diabetes and to determine the risk of disease progression in subjects with insulin resistance. Insulin resistance biomarkers and diagnostic tests can better identify and determine the risk of diabetes development in a pre-diabetic subject, can monitor disease development and progression and/or regression, can allow new therapeutic treatments to be developed and can be used to test therapeutic agents for efficacy on reversing pre-diabetes and/or preventing diabetes. Further, a need exists for diagnostic biomarkers to more effectively assess the efficacy and safety of pre-diabetic and diabetic therapeutic candidates.

SUMMARY OF THE INVENTION

In one embodiment, the present disclosure provides a method of diagnosing insulin resistance in a subject, the method comprising analyzing a biological sample from a subject to determine the level(s) of one or more biomarkers for insulin resistance in the sample, where the one or more biomarkers are selected from one or more biomarkers listed in Tables 4, 5, 6, 7, 8, 9A, 9B, 27, 28, 29 and combinations thereof; and comparing the level(s) of the one or more biomarkers in the sample to insulin resistance-positive and/or insulin resistance-negative reference levels of the one or more biomarkers in order to diagnose whether the subject is insulin resistant.

In another embodiment, the present disclosure provides a method of predicting the glucose disposal rate in a subject, the method comprising, analyzing a biological sample from a subject to determine the level(s) of one or more biomarkers for insulin resistance in the sample, where the one or more biomarkers are selected from one or more biomarkers listed in Tables 4, 5, 6, 7, 8, 9A, 9B, and combinations thereof; and comparing the level(s) of the one or more biomarkers in the sample to glucose disposal reference levels of the one or more biomarkers in order to predict the glucosal disposal rate in the subject.

The disclosure also provides a method of classifying a subject according to glucose tolerance from normal glucose tolerance (NGT), impaired fasting glucose tolerance (IFG), or impaired glucose tolerance (IGT), to type-2 diabetes, the method comprising, analyzing a biological sample from a subject to determine the level(s) of one or more biomarkers for glucose tolerance in the sample, where the one or more biomarkers are selected from one or more biomarkers listed in Tables 4, 5, 6, 7, 8, 9A, 9B, and combinations thereof; and comparing the level(s) of the one or more biomarkers in the sample to glucose tolerance reference levels of the one or more biomarkers in order to classify the subject as having NGT, IFG, IGT, or diabetic.

Further provided is a method of determining susceptibility of a subject to developing type-2 diabetes, the method comprising, analyzing a biological sample from a subject to determine the level(s) of one or more biomarkers for pre-diabetes in the sample, where the one or more biomarkers are selected from one or more biomarkers listed in Tables 4, 5, 6, 7, 8, 9A, 9B, and combinations thereof; and comparing the level(s) of the one or more biomarkers in the sample to diabetes-positive and/or diabetes-negative reference levels of the one or more biomarkers in order to diagnose whether the subject is susceptible to developing type-2 diabetes.

The present disclosure also provides a method of determining an insulin resistance score in a subject, the method comprising, analyzing a biological sample from a subject to determine the level(s) of one or more biomarkers in the sample, where the one or more biomarkers are selected from one or more biomarkers listed in Tables 4, 5, 6, 7, 8, 9A, 9B, and combinations thereof; and comparing the level(s) of the one or more biomarkers in the sample to insulin resistance reference levels of the one or more biomarkers in order to determine an insulin resistance score for the subject.

In another embodiment, the present disclosure provides a method of monitoring the progression or regression of pre-diabetes in a subject, the method comprising, analyzing a biological sample from a subject to determine the level(s) of one or more biomarkers for pre-diabetes in the sample, where the one or more biomarkers are selected from one or more biomarkers listed in Tables 4, 5, 6, 7, 8, 9A, 9B, and combinations thereof; and comparing the level(s) of the one or more biomarkers in the sample to pre-diabetes progression and/or pre-diabetes-regression reference levels of the one or more biomarkers in order to monitor the progression or regression of pre-diabetes in a subject.

In yet another embodiment, the present disclosure provides a method of monitoring the efficacy of insulin resistance treatment, the method comprising: analyzing a first biological sample from a subject to determine the level(s) of one or more biomarkers for pre-diabetes, the first sample obtained from the subject at a first time point wherein the one or more biomarkers are selected from one or more biomarkers listed in Tables 4, 5, 6, 7, and 8, and combinations thereof; treating the subject for insulin resistance; analyzing a second biological sample from the subject to determine the level(s) of the one or more biomarkers, the second sample obtained from the subject at a second time point after treatment; comparing the level(s) of one or more biomarkers in the first sample to the level(s) of the one or more biomarkers in the second sample to assess the efficacy of the treatment for treating insulin resistance.

The present disclosure further provides a method of diagnosing whether a subject has metabolic syndrome, the method comprising, analyzing a biological sample from a subject to determine the level(s) of one or more biomarkers for metabolic syndrome in the sample, where the one or more biomarkers are selected from one or more biomarkers listed in Tables 12 and 13, analyzing the biological sample to determine the level(s) of one or more biomarkers for glucose disposal, obesity, and/or cardiovascular disease, wherein the one or more biomarkers for glucose disposal, obesity, and/or cardiovascular disease are selected from one or more biomarkers identified in Tables 4, 5, 6, 7, 8, 9A, 9B, 14, 15, 16, 17, 21, 22, 23, 25, 26, 27, 28, and combinations thereof; and comparing the level(s) of the one or more biomarkers in the sample to the respective disorder-positive and/or disorder-negative reference levels of the one or more biomarkers in order to diagnose whether the subject has the metabolic syndrome.

In another embodiment, the present disclosure provides a method of diagnosing a cardiovascular disease in a subject, the method comprising, analyzing a biological sample from a subject to determine the level(s) of one or more biomarkers for a cardiovascular disease in the sample, where the one or more biomarkers are selected from one or more biomarkers listed in Tables 14, 15, 16, 17, 21, 22, 23, 25, and combinations thereof; and comparing the level(s) of the one or more biomarkers in the sample to disease-positive and/or disease-negative reference levels of the one or more biomarkers in order to diagnose whether the subject has cardiomyopathy or atherosclerosis.

The disclosure further provides a method for determining whether a subject is predisposed to becoming obese, the method comprising: analyzing a biological sample from a subject to determine the level(s) of one or more biomarkers for obesity in the sample, where the one or more biomarkers are selected from one or more biomarkers listed in Table 26; and comparing the level(s) of the one or more biomarkers in the sample to obesity-positive and/or obesity-negative and/or lean-positive and/or lean-negative reference levels of the one or more biomarkers in order to determine whether the subject is susceptible to obesity.

In yet a further embodiment, the disclosure provides a method for determining whether a therapeutic agent is capable of inducing weight gain in a subject, the method comprising: analyzing a biological sample from a subject receiving a therapeutic agent to determine the level(s) of one or more biomarkers for obesity in the sample, where the one or more biomarkers are selected from one or more biomarkers listed in Table 26; and comparing the level(s) of the one or more biomarkers in the sample to obesity-positive and/or obesity-negative and/or lean-positive and/or lean-negative reference levels of the one or more biomarkers in order to determine whether the subject is susceptible to gaining weight.

The present disclosure also provides a method for predicting a subject's response to a course of treatment for pre-diabetes or diabetes, the method comprising: analyzing a biological sample from a subject to determine the level(s) of one or more biomarkers for pre-diabetes, where the one or more biomarkers are selected from one or more biomarkers listed in Table 27; comparing the level(s) of one or more biomarkers in the sample to treatment-positive and/or treatment-negative reference levels of the one or more biomarkers to predict whether the subject is likely to respond to a course of treatment.

The disclosure also provides a method for monitoring a subject's response to a treatment for pre-diabetes or diabetes, the method comprising: analyzing a first biological sample from a subject to determine the level(s) of one or more biomarkers for pre-diabetes, the first sample obtained from the subject at a first time point where the one or more biomarkers are selected from one or more biomarkers listed in Table 28; administering the composition to the subject; analyzing a second biological sample from the subject to determine the level(s) of the one or more biomarkers, the second sample obtained from the subject at a second time point after administration of the composition; comparing the level(s) of one or more biomarkers in the first sample to the level(s) of the one or more biomarkers in the second sample to assess the efficacy of the composition for treating pre-diabetes or diabetes.

BRIEF DESCRIPTION OF THE DRAWINGS

FIG. 17 provides an example of plasma levels of Metabolite-X1834 in atherosclerosis subjects and control subjects at different ages.

FIG. 18 provides an example of plasma levels of p-cresol-sulfate in atherosclerosis subjects and control subjects at different ages.

DETAILED DESCRIPTION OF THE INVENTION

The present invention relates to biomarkers of pre-diabetes (e.g. impaired glucose tolerance, impaired fasting glucose tolerance, insulin resistance) and type-2 diabetes; methods for diagnosis of pre-diabetes and type 2 diabetes; methods of determining predisposition to pre-diabetes and type 2 diabetes; methods of monitoring progression/regression of pre-diabetes and type 2 diabetes; methods of assessing efficacy of compositions for treating pre-diabetes and type 2 diabetes; methods of screening compositions for activity in modulating biomarkers of pre-diabetes and type 2 diabetes; methods of treating pre-diabetes and type 2 diabetes; as well as other methods based on biomarkers of pre-diabetes and type 2 diabetes.

Current blood tests for insulin resistance perform poorly for early detection of insulin resistance or involve significant medical procedures.

Using metabolomic analysis, panels of metabolites that can be used in a simple blood test to predict insulin resistance as measured by the "gold standard" of hyperinsulinemic euglycemic clamps in at least two independent cohorts of subjects were discovered.

Figure 5:
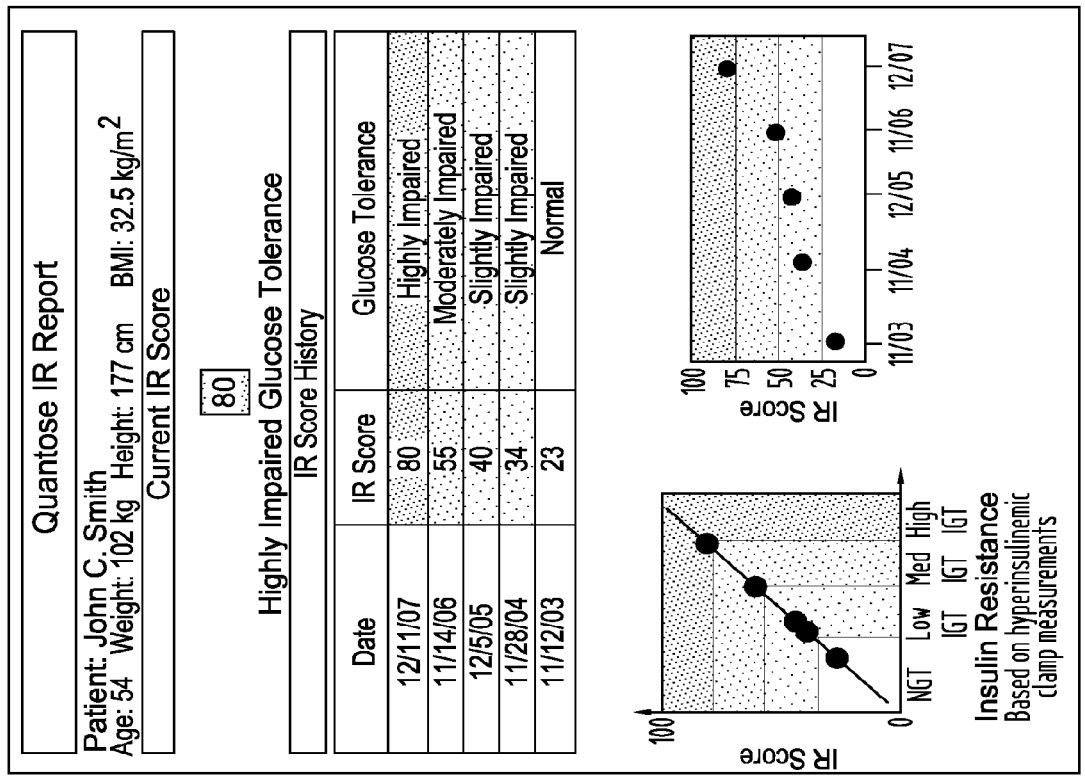
FIG. 5 provides a schematic example of a report describing prophetic results of an algorithm using insulin resistance biomarkers to determine a subject's level of insulin resistance that is reported as an "IR Score" and containing additional clinical information (e.g. BMI, demographic information).
Figure 6:
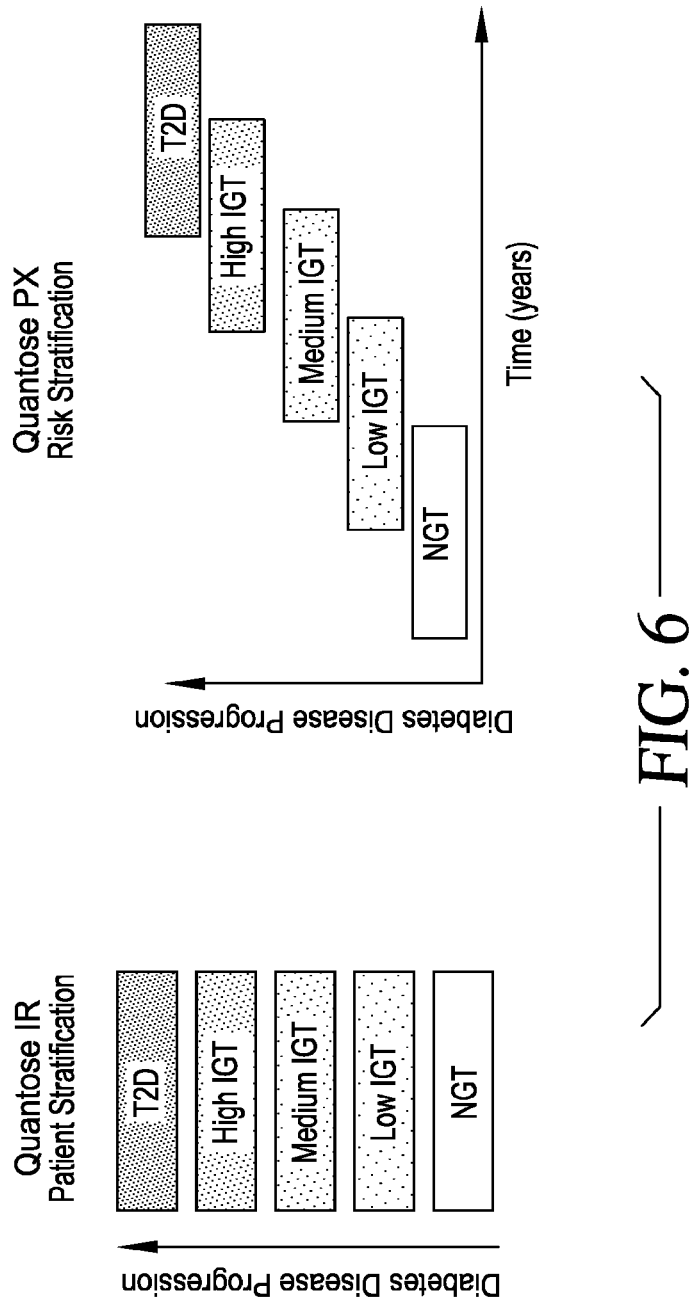
FIG. 6 provides a schematic illustration comparing the use of biomarkers for patient stratification according to the level of insulin resistance and the use of biomarkers for patient risk stratification for the progression of insulin resistance.
Figure 7:
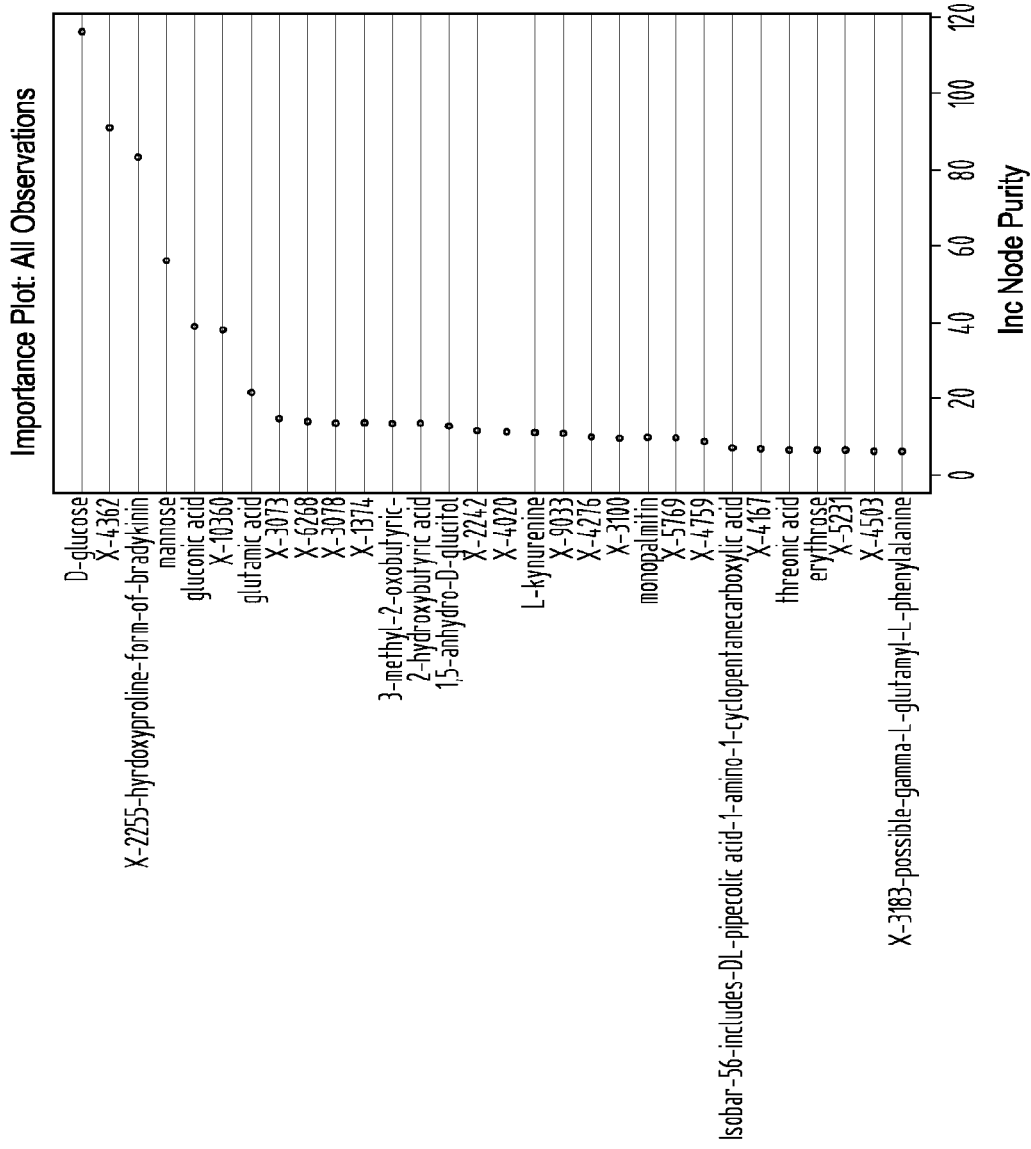
FIG. 7 provides a Random Forest Analysis Importance plot of one embodiment of metabolites that are useful biomarkers for predicting glucose disposal.

Independent studies were carried out to identify a set of biomarkers that when used with a polynomic algorithm will enable the early detection of changes in insulin resistance in a subject. The instant invention provides the subject with a score indicating the level of insulin resistance ("IR Score") of the subject. The score can be based upon clinically significant changed reference level for a biomarker and/or combination of biomarkers. The reference level can be derived from an algorithm or computed from indices for impaired glucose tolerance and can be presented in a report as shown in FIG. 5. The IR Score places the subject in the range of insulin resistance from normal to high. Disease progression or remission can be monitored by periodic determination and monitoring of the IR Score. Response to therapeutic intervention can be determined by monitoring the IR Score. The IR Score can also be used to evaluate drug efficacy.

The present invention also relates to biomarkers of metabolic syndrome and cardiovascular diseases, such as atherosclerosis and cardiomyopathy; methods for diagnosis of such diseases and syndromes; methods of determining predisposition to such diseases and syndromes; methods of monitoring progression/regression of such diseases and syndromes; methods of assessing efficacy of compositions for treating such diseases and syndromes; methods of screening compositions for activity in modulating biomarkers of such diseases and syndromes; methods of treating such diseases and syndromes; as well as other methods based on biomarkers of such diseases and syndromes.

Prior to describing this invention in further detail, however, the following terms will first be defined.

Definitions:

"Biomarker" means a compound, preferably a metabolite, that is differentially present (i.e., increased or decreased) in a biological sample from a subject or a group of subjects having a first phenotype (e.g., having a disease) as compared to a biological sample from a subject or group of subjects having a second phenotype (e.g., not having the disease). A biomarker may be differentially present at any level, but is generally present at a level that is increased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100%, by at least 110%, by at least 120%, by at least 130%, by at least 140%, by at least 150%, or more; or is generally present at a level that is decreased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, or by 100% (i.e., absent). A biomarker is preferably differentially present at a level that is statistically significant (e.g., a p-value less than 0.05 and/or a q-value of less than 0.10 as determined using either Welch's T-test or Wilcoxon's rank-sum Test). Alternatively, the biomarkers demonstrate a correlation with pre-diabetes, or particular levels of pre-diabetes. The range of possible correlations is between negative (−) 1 and positive (+) 1. A result of negative (−) 1 means a perfect negative correlation and a positive (+) 1 means a perfect positive correlation, and 0 means no correlation at all. A "substantial positive correlation" refers to a biomarker having a correlation from +0.25 to +1.0 with a disorder or with a clinical measurement (e.g., Rd), while a "substantial negative correlation" refers to a correlation from −0.25 to −1.0 with a given disorder or clinical measurement. A "significant positive correlation" refers to a biomarker having a correlation of from +0.5 to +1.0 with a given disorder or clinical measurement (e.g., Rd), while a "significant negative correlation" refers to a correlation to a disorder of from −0.5 to −1.0 with a given disorder or clinical measurement.

The "level" of one or more biomarkers means the absolute or relative amount or concentration of the biomarker in the sample.

"Sample" or "biological sample" or "specimen" means biological material isolated from a subject. The biological sample may contain any biological material suitable for detecting the desired biomarkers, and may comprise cellular and/or non-cellular material from the subject. The sample can be isolated from any suitable biological tissue or fluid such as, for example, adipose tissue, aortic tissue, liver tissue, blood, blood plasma, serum, or urine.

"Subject" means any animal, but is preferably a mammal, such as, for example, a human, monkey, non-human primate, rat, mouse, cow, dog, cat, pig, horse, or rabbit.

A "reference level" of a biomarker means a level of the biomarker that is indicative of a particular disease state, phenotype, or lack thereof, as well as combinations of disease states, phenotypes, or lack thereof. A "positive" reference level of a biomarker means a level that is indicative of a particular disease state or phenotype. A "negative" reference level of a biomarker means a level that is indicative of a lack of a particular disease state or phenotype. For example, a "pre-diabetes-positive reference level" of a biomarker means a level of a biomarker that is indicative of a positive diagnosis of pre-diabetes in a subject, and a "pre-diabetes-negative reference level" of a biomarker means a level of a biomarker that is indicative of a negative diagnosis of pre-diabetes in a subject. As another example, a "pre-diabetes-progression-positive reference level" of a biomarker means a level of a biomarker that is indicative of progression of the pre-diabetes in a subject, and a "pre-diabetes-regression-positive reference level" of a biomarker means a level of a biomarker that is indicative of regression of the pre-diabetes. A "reference level" of a biomarker may be an absolute or relative amount or concentration of the biomarker, a presence or absence of the biomarker, a range of amount or concentration of the biomarker, a minimum and/or maximum amount or concentration of the biomarker, a mean amount or concentration of the biomarker, and/or a median amount or concentration of the biomarker; and, in addition, "reference levels" of combinations of biomarkers may also be ratios of absolute or relative amounts or concentrations of two or more biomarkers with respect to each other. Appropriate positive and negative reference levels of biomarkers for a particular disease state, phenotype, or lack thereof may be determined by measuring levels of desired biomarkers in one or more appropriate subjects, and such reference levels may be tailored to specific populations of subjects (e.g., a reference level may be age-matched so that comparisons may be made between biomarker levels in samples from subjects of a certain age and reference levels for a particular disease state, phenotype, or lack thereof in a certain age group). Such reference levels may also be tailored to specific techniques that are used to measure levels of biomarkers in biological samples (e.g., LC-MS, GC-MS, etc.), where the levels of biomarkers may differ based on the specific technique that is used.

"Non-biomarker compound" means a compound that is not differentially present in a biological sample from a subject or a group of subjects having a first phenotype (e.g., having a first disease) as compared to a biological sample from a subject or group of subjects having a second phenotype (e.g., not having the first disease). Such non-biomarker compounds may, however, be biomarkers in a biological sample from a subject or a group of subjects having a third phenotype (e.g., having a second disease) as compared to the first phenotype (e.g., having the first disease) or the second phenotype (e.g., not having the first disease).

"Metabolite", or "small molecule", means organic and inorganic molecules which are present in a cell. The term does not include large macromolecules, such as large proteins (e.g., proteins with molecular weights over 2,000, 3,000, 4,000, 5,000, 6,000, 7,000, 8,000, 9,000, or 10,000), large nucleic acids (e.g., nucleic acids with molecular weights of over 2,000, 3,000, 4,000, 5,000, 6,000, 7,000, 8,000, 9,000, or 10,000), or large polysaccharides (e.g., polysaccharides with a molecular weights of over 2,000, 3,000, 4,000, 5,000, 6,000, 7,000, 8,000, 9,000, or 10,000). The small molecules of the cell are generally found free in solution in the cytoplasm or in other organelles, such as the mitochondria, where they form a pool of intermediates which can be metabolized further or used to generate large molecules, called macromolecules. The term "small molecules" includes signaling molecules and intermediates in the chemical reactions that transform energy derived from food into usable forms. Examples of small molecules include sugars, fatty acids, amino acids, nucleotides, intermediates formed during cellular processes, and other small molecules found within the cell.

"Metabolic profile", or "small molecule profile", means a complete or partial inventory of small molecules within a targeted cell, tissue, organ, organism, or fraction thereof (e.g., cellular compartment). The inventory may include the quantity and/or type of small molecules present. The "small molecule profile" may be determined using a single technique or multiple different techniques.

"Metabolome" means all of the small molecules present in a given organism.

"Metabolic disorder" refers to disorders or diseases that result in perturbation of the normal physiological state of homeostasis due to an alteration in metabolism (anabolism and/or catabolism). An alteration in metabolism can result from an inability to break down (catabolize) a substance that should be broken down (e.g. phenylalanine) and as a result the substance and/or an intermediate substance builds up to toxic levels, or from an inability to produce (anabolize) some essential substance (e.g. insulin).

Figure 24:
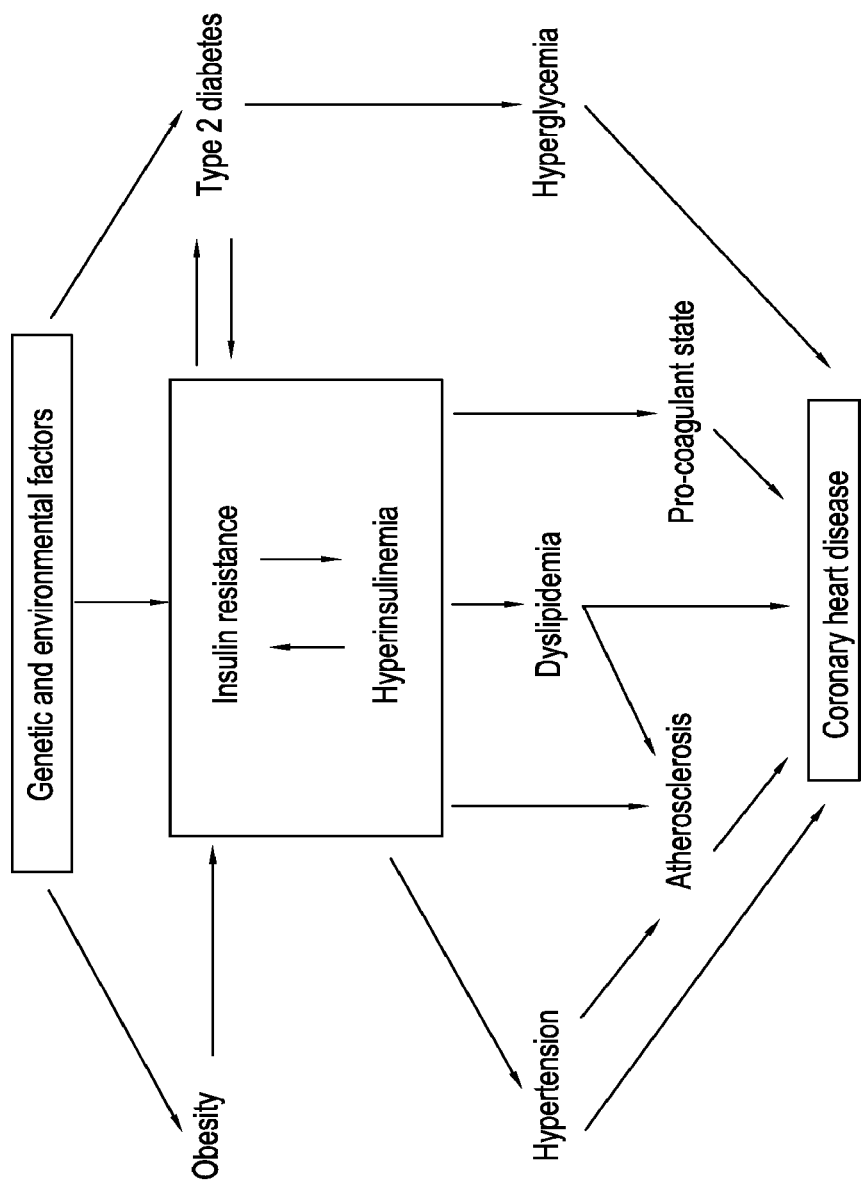
FIG. 24 provides and illustration of the inter-relationships of the various risk factors for metabolic syndrome.

"Metabolic syndrome" refers to the concept of a clustering of metabolic risk factors that come together in a single individual and lead to a high risk of developing diabetes and/or cardiovascular diseases. The main features of metabolic syndrome include insulin resistance, hypertension (high blood pressure), cholesterol abnormalities, dyslipidemia, triglyceride abnormalities, an increased risk for clotting and excess body weight, especially in the abdomen, or obesity. Metabolic syndrome is also known as syndrome X, insulin resistance syndrome, obesity syndrome, dysmetabolic syndrome and Reaven's syndrome. The inter-relationships of the various risk factors for metabolic syndrome are illustrated in FIG. 24. The presence of three or more of the risk factors in a single individual is indicative of metabolic syndrome. The American Heart Association suggests that metabolic syndrome be diagnosed by the presence of three or more of the following components: (1) an elevated waste circumference (men, equal to or greater than 40 inches (102 cm); women, equal to or greater than 35 inches (88 cm)); (2) elevated triglycerides (equal to or greater than 150 mg/dL); (3) reduced High Density Lipids or HDL (men, less than 40 mg/dL; women, less than 50 mg/dL); (4) elevated blood pressure (equal to or greater than 130/85 mm Hg); and (5) elevated fasting glucose (equal to or greater than 100 mg/dL).

"Metabolic syndrome-related metabolic disorder" as used herein refers to metabolic syndrome as well as obesity, insulin resistance, type-2 diabetes, atherosclerosis, and cardiomyopathy.

"Diabetes" refers to a group of metabolic diseases characterized by high blood sugar (glucose) levels which result from defects in insulin secretion or action, or both.

"Type 2 diabetes" refers to one of the two major types of diabetes, the type in which the beta cells of the pancreas produce insulin, at least in the early stages of the disease, but the body is unable to use it effectively because the cells of the body are resistant to the action of insulin. In later stages of the disease the beta cells may stop producing insulin. Type 2 diabetes is also known as insulin-resistant diabetes, non-insulin dependent diabetes and adult-onset diabetes.

"Pre-diabetes" refers to one or more early diabetic conditions including impaired glucose utilization, abnormal or impaired fasting glucose levels, impaired glucose tolerance, impaired insulin sensitivity and insulin resistance.

"Insulin resistance" refers to the condition when cells become resistant to the effects of insulin—a hormone that regulates the uptake of glucose into cells—or when the amount of insulin produced is insufficient to maintain a normal glucose level. Cells are diminished in the ability to respond to the action of insulin in promoting the transport of the sugar glucose from blood into muscles and other tissues (i.e. sensitivity to insulin decreases). Eventually, the pancreas produces far more insulin than normal and the cells continue to be resistant. As long as enough insulin is produced to overcome this resistance, blood glucose levels remain normal. Once the pancreas is no longer able to keep up, blood glucose starts to rise, resulting in diabetes. Insulin resistance ranges from normal (insulin sensitive) to insulin resistant (IR).

"Insulin sensitivity" refers to the ability of cells to respond to the effects of insulin to regulate the uptake and utilization of glucose. Insulin sensitivity ranges from normal to Insulin Resistant (IR).

The "IR Score" is a measure of insulin resistance based upon the insulin resistance biomarkers and algorithms of the instant invention that will allow the physician to place the patient on the spectrum of glucose tolerance, from normal to high.

"Glucose utilization" refers to the absorption of glucose from the blood by muscle and fat cells and utilization of the sugar for cellular metabolism. The uptake of glucose into cells is stimulated by insulin.

"Rd" refers to glucose disposal rate, a metric for glucose utilization. The rate at which glucose disappears from the blood (disposal rate) is an indication of the ability of the body to respond to insulin (i.e. insulin sensitivity). There are several methods to determine Rd and the hyperinsulinemic euglycemic clamp is regarded as the "gold standard" method. In this technique, while a fixed amount of insulin is infused, the blood glucose is "clamped" at a predetermined level by the titration of a variable rate of glucose infusion. The underlying principle is that upon reaching steady state, by definition, glucose disposal is equivalent to glucose appearance. During hyperinsulinemia, glucose disposal (Rd) is primarily accounted for by glucose uptake into skeletal muscle, and glucose appearance is equal to the sum of the exogenous glucose infusion rate plus the rate of hepatic glucose output (HGO). The rate of glucose infusion during the last 30 minutes of the test determines insulin sensitivity. If high levels (Rd=7.5 mg/min or higher) are required, the patient is insulin-sensitive. Very low levels (Rd=4.0 mg/min or lower) indicate that the body is resistant to insulin action. Levels between 4.0 and 7.5 mg/min (Rd values between 4.0 mg/min and 7.5 mg/min) are not definitive and suggest "impaired glucose tolerance," an early sign of insulin resistance.

"Impaired fasting glucose (IFG)" and "impaired glucose tolerance (IGT)" are the two clinical definitions of "pre-diabetes". IFG is defined as a fasting blood glucose concentration of 100-125 mg/dL. IGT is defined as a postprandial (after eating) blood glucose concentration of 140-199 mg/dL. It is known that IFG and IGT do not always detect the same pre-diabetic populations. Between the two populations there is approximately a 60% overlap observed. Fasting plasma glucose levels are a more efficient means of inferring a patient's pancreatic function, or insulin secretion, whereas postprandial glucose levels are more frequently associated with inferring levels of insulin sensitivity or resistance. IGT is known to identify a greater percentage of the pre-diabetic population compared to IFG. The IFG condition is associated with lower insulin secretion, whereas the IGT condition is known to be strongly associated with insulin resistance. Numerous studies have been carried out that demonstrate that IGT individuals with normal FPG values are at increased risk for cardiovascular disease. Patients with normal FPG values may have abnormal postprandial glucose values and are often unaware of their risk for pre-diabetes, diabetes, and cardiovascular disease.

"Fasting plasma glucose (FPG) test" is a simple test measuring blood glucose levels after an 8 hour fast. According to the ADA, blood glucose concentration of 100-125 mg/dL is considered IFG and defines pre-diabetes whereas ≥126 mg/dL defines diabetes. As stated by the ADA, FPG is the preferred test to diagnose diabetes and pre-diabetes due to its ease of use, patient acceptability, lower cost, and relative reproducibility. The weakness in the FPG test is that patients are quite advanced toward Type 2 Diabetes before fasting glucose levels change.

"Oral glucose tolerance test (OGTT)", a dynamic measurement of glucose, is a postprandial measurement of a patient's blood glucose levels after oral ingestion of a 75 g glucose drink. Traditional measurements include a fasting blood sample at the beginning of the test, a one hour time point blood sample, and a 2 hour time point blood sample. A patient's blood glucose concentration at the 2 hour time point defines the level of glucose tolerance: Normal glucose tolerance (NGT)≤140 mg/dL blood glucose; Impaired glucose tolerance (IGT)=140-199 mg/dL blood glucose; Diabetes ≥200 mg/dL blood glucose. As stated by the ADA, even though the OGTT is known to be more sensitive and specific at diagnosing pre-diabetes and diabetes, it is not recommended for routine clinical use because of its poor reproducibility and difficulty to perform in practice.

"Fasting insulin test" measures the circulating mature form of insulin in plasma. The current definition of hyperinsulinemia is difficult due to lack of standardization of insulin immunoassays, cross-reactivity to proinsulin forms, and no consensus on analytical requirements for the assays. Within-assay CVs range from 3.7%-39% and among-assay CVs range from 12%-66%. Therefore, fasting insulin is not commonly measured in the clinical setting and is limited to the research setting.

The "hyperinsulinemic euglycemic clamp (HI clamp)" is considered worldwide as the "gold standard" for measuring insulin resistance in patients. It is performed in a research setting, requires insertion of two catheters into the patient and the patient must remain immobilized for up to six hours. The HI clamp involves creating steady-state hyperinsulinemia by insulin infusion, along with parallel glucose infusion in order to quantify the required amount of glucose to maintain euglycemia (normal concentration of glucose in the blood; also called normoglycemia). The result is a measure of the insulin-dependent glucose disposal rate (Rd), measuring the peripheral uptake of glucose by the muscle (primarily) and adipose tissues. This rate of glucose uptake is notated by M, whole body glucose metabolism by insulin action under steady state conditions. Therefore, a high M indicates high insulin sensitivity and a lower M value indicates reduced insulin sensitivity, i.e. insulin resistance. The HI clamp requires three trained professionals to carry out the procedure, including simultaneous infusions of insulin and glucose over 2-4 hours and frequent blood sampling every 5 minutes for analysis of insulin and glucose levels. Due to the high cost, complexity, and time required for the HI clamp, this procedure is strictly limited to the clinical research setting.

"Obesity" refers to a chronic condition defined by an excess amount body fat. The normal amount of body fat (expressed as percentage of body weight) is between 25-30% in women and 18-23% in men. Women with over 30% body fat and men with over 25% body fat are considered obese.

"Body Mass Index, (or BMI)" refers to a calculation that uses the height and weight of an individual to estimate the amount of the individual's body fat. Too much body fat (e.g. obesity) can lead to illnesses and other health problems. BMI is the measurement of choice for many physicians and researchers studying obesity. BMI is calculated using a mathematical formula that takes into account both height and weight of the individual. BMI equals a person's weight in kilograms divided by height in meters squared. (BMI=kg/m$^2$). Subjects having a BMI less than 19 are considered to be underweight, while those with a BMI of between 19 and 25 are considered to be of normal weight, while a BMI of between 25 to 29 are generally considered overweight, while individuals with a BMI of 30 or more are typically considered obese. Morbid obesity refers to a subject having a BMI of 40 or greater.

"Cardiovascular disease" refers to any disease of the heart or blood vessels. Cardiovascular or heart disease includes but is not limited to, for example, angina, arrhythmia, coronary artery disease (CAD), coronary heart disease, cardiomyopathy (including dilated cardiomyopathy, restrictive cardiomyopathy, arrhythmogenic right ventricular cardiomyopathy, and diabetic cardiomyopathy) heart attack (myocardial infarction), heart failure, hypertrophic cardiomyopathy, mitral regurgitation, mitral valve prolapse, pulmonary stenosis, etc. Blood vessel disease includes but is not limited to, for example, peripheral vascular disease, artery disease, carotid artery disease, deep vein thrombosis, venous diseases, atherosclerosis, etc.

I. Biomarkers

The biomarkers described herein were discovered using metabolomic profiling techniques. Such metabolomic profiling techniques are described in more detail in the Examples set forth below as well as in U.S. Pat. Nos. 7,005,255 and 7,329,489 and U.S. patent application Ser. Nos. 11/357,732 (Publication No. 2007/0026389), 11/301,077 (Publication No. 2006/0134676), 11/301,078 (Publication No. 2006/0134677), 11/301,079 (Publication No. 2006/0134678), and 11/405,033 (Publication No. US 2007/0072203), the entire contents of which are hereby incorporated herein by reference.

Generally, metabolic profiles may be determined for biological samples from human subjects diagnosed with a condition such as pre-diabetes as well as from one or more other groups of human subjects (e.g., healthy control subjects with normal glucose tolerance, subjects with impaired glucose tolerance, subjects with insulin resistance). The metabolic profile for a pre-diabetes disorder may then be compared to the metabolic profile for biological samples from the one or more other groups of subjects. The comparisons may be conducted using models or algorithms, such as those described herein. Those molecules differentially present, including those molecules differentially present at a level that is statistically significant, in the metabolic profile of samples from subjects with a pre-diabetes disorder as compared to another group (e.g., healthy control subjects not pre-diabetic) may be identified as biomarkers to distinguish those groups.

Biomarkers for use in the methods disclosed herein may be obtained from any source of biomarkers related to pre-diabetes and/or type-2 diabetes. Biomarkers for use in methods disclosed herein relating to pre-diabetes include those listed in Tables 4, 5, 6, 7, 8, 9A, 9B, 27, 28, 29, and combinations and subsets thereof. In one embodiment, the biomarkers include those listed in Tables 4, 5, 6, 7, 8, 9A, 9B, 27, 28, and combinations thereof. Additional biomarkers include those disclosed in U.S. Application No. 60/950,286, the entirety of which is hereby incorporated by reference in its entirety. In one aspect, the biomarkers correlate to insulin resistance.

Biomarkers for use in methods disclosed herein relating to metabolic syndrome-related metabolic disorders include those listed in Tables 4, 5, 6, 7, 8, 9A, 9B, 12, 13, 14, 15, 16, 17, 21, 22, 23, 25, 26, 27, 28, 29, and combinations thereof. For example, biomarkers for use in distinguishing, or aiding in distinguishing, between subjects having metabolic syndrome and subjects not having metabolic syndrome include those biomarkers identified in Tables 4, 5, 6, 7, 8, 9A, 9B, 12, 13, 14, 15, 16, 17, 21, 22, 23, 25, 26, 27, 28, 29, and combinations thereof. In one aspect, biomarkers for use in methods relating to metabolic syndrome include one or more of those listed in Tables 12 and 13. In another aspect biomarkers for use in methods relating to metabolic syndrome using plasma samples obtained from a subject include one or more of those listed in Table 12. In a preferred aspect, the biomarkers for use in methods disclosed herein related to metabolic syndrome using plasma samples obtained from a subject include one or more of the biomarkers N-acetylglycine, metabolite-6346, metabolite-8792, gamma-glu-leu, metabolite-4806, metabolite-3165, metabolite-7762, metabolite-3030, metabolite-5978, metabolite-3218, metabolite-2000, metabolite-5848, metabolite-3370, malic acid, metabolite-3843, metabolite-4275, metabolite-3094, metabolite-4167, metabolite-3073, aldosterone, metabolite-1320, metabolite-2185, phenylalanine, metabolite-2139, glutamic acid, alpha-tocopherol, metabolite-5767, metabolite-5346, metabolite-9855, and 1-octadecanol, and combinations thereof. In yet another aspect, biomarkers for use in methods relating to metabolic syndrome using serum samples obtained from a subject include one or more of those listed in Table 13. In a preferred aspect, the biomarkers for use in metabolic syndrome methods disclosed herein using serum samples obtained from a subject include one or more of the biomarkers metabolite-8792, metabolite-5767, metabolite-2139, metabolite-8402, metabolite-3073, phenylalanine, metabolite-4929, metabolite-3370, nonanate, N-acetylglycine, metabolite-5848, metabolite-3077, monopalmitin, dioctyl-phthalate, octadecanoic acid, cholesterol, metabolite-2608, metabolite-6272, metabolite-3012, D-glucose, metabolite-2986, metabolite-4275, metabolite-6268, tyrosine, metabolite-10683, metabolite-2000, alpha-tocopherol, metabolite-2469, xanthine, and metabolite-2039, and combinations thereof.

In another aspect, biomarkers for use in methods disclosed herein relating to metabolic syndrome may include the use of one or more biomarkers listed in Tables 12 and/or 13 in combination with one or more biomarkers in one or more of Tables 4, 5, 6, 7, 8, 9A, 9B, 14, 15, 16, 17, 21, 22, 23, 25, 26, 27, 28, or combinations thereof. For example, biomarkers for use in methods relating to metabolic syndrome may include one or more biomarkers listed in Tables 12 and/or 13 in combination with one or more biomarkers associated with insulin resistance, such as those listed in Tables 4, 5, 6, 7, 8, 9A, 9B, 27, 28, or combinations thereof.

Biomarkers for use in methods disclosed herein relating to pre-diabetic or diabetic conditions, such as impaired insulin sensitivity, insulin resistance, or type-2 diabetes include one or more of those listed in Tables 4, 5, 6, 7, 8, 9A, 9B, 27, 28, and combinations thereof. Such biomarkers allow subjects to be classified as insulin resistant, insulin impaired, or insulin sensitive. In one aspect, biomarkers for use in distinguishing or aiding in distinguishing, between subjects having impaired insulin sensitivity from subjects not having impaired insulin sensitivity include one or more of those listed in Table 4, 5, 6, 7, 8, 9A, and/or 9B. In another aspect, biomarkers for use in diagnosing insulin resistance include one or more of those listed in Tables 4, 5, 6, 7, 8, 9A, and/or 9B. In another example, biomarkers for use in distinguishing subjects having insulin resistance from subject not having insulin resistance include one or more of those listed in Tables 4, 5, 6, 7, 8, 9A, and/or 9B. In another example, biomarkers for use in categorizing, or aiding in categorizing, a subject as having impaired fasting glucose levels or impaired glucose tolerance include one or more of those listed in Tables 4, 5, 6, 7, 8, 9A, and/or 9B.

Figure 10A:
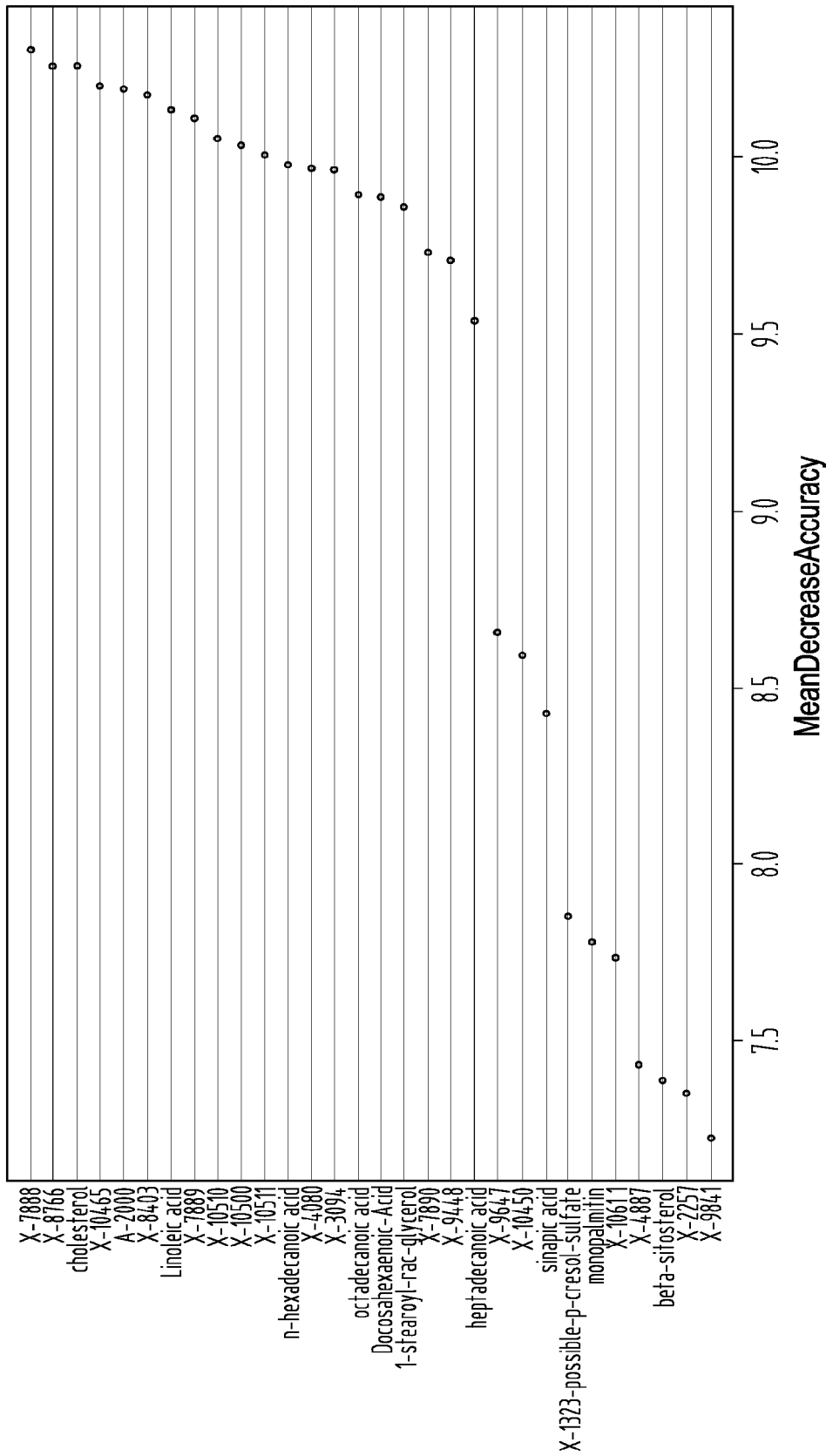
FIG. 10 provides a Random Forest Analysis Importance Plots of embodiments of metabolites from plasma that are useful biomarkers for predicting atherosclerosis at early (initiation) (FIG. 10A), mid (FIG. 10B), later (FIG. 10C), or all (FIG. 10D) stages of the disease.
Figure 10B:
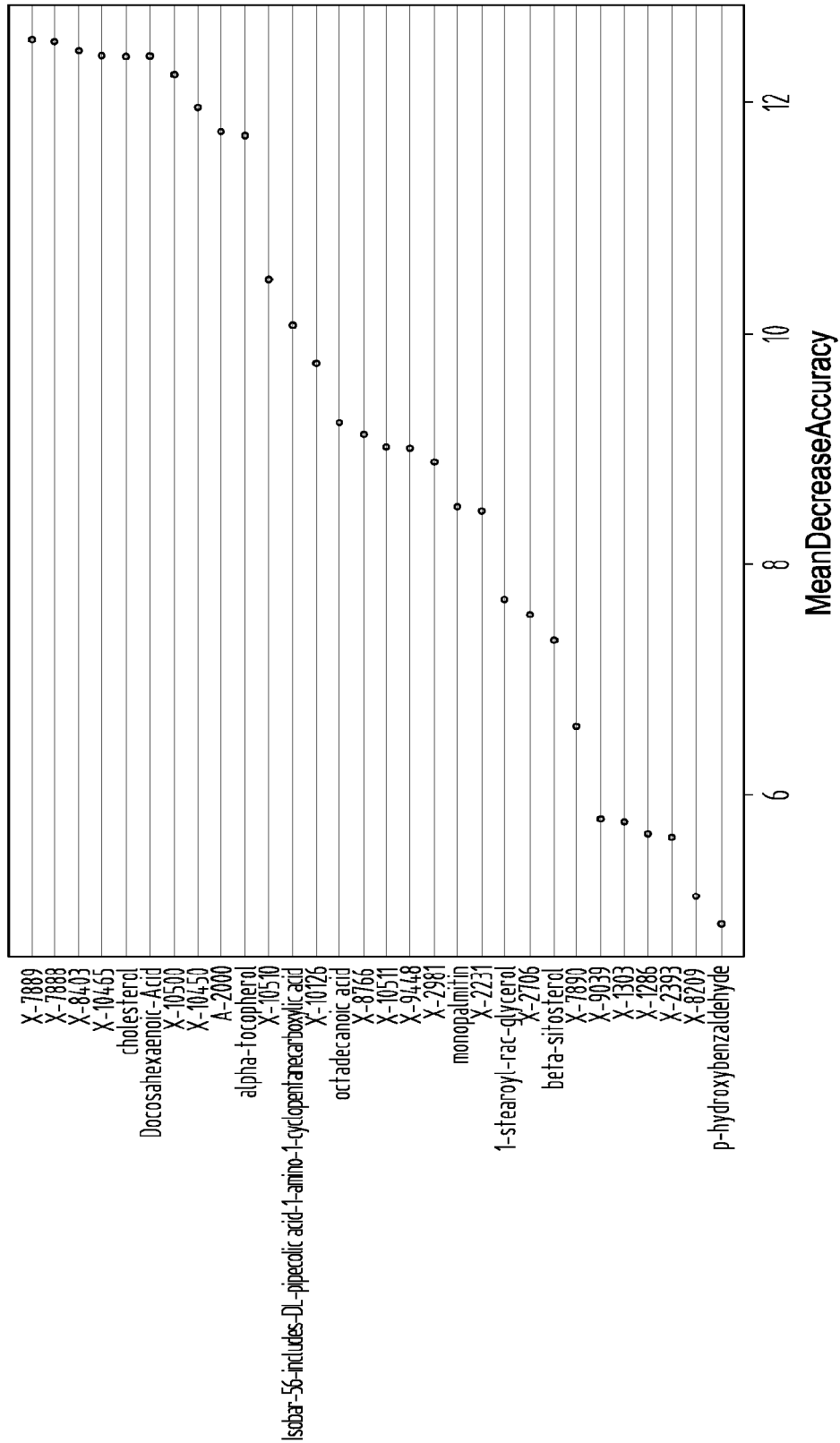
Figure 10C:
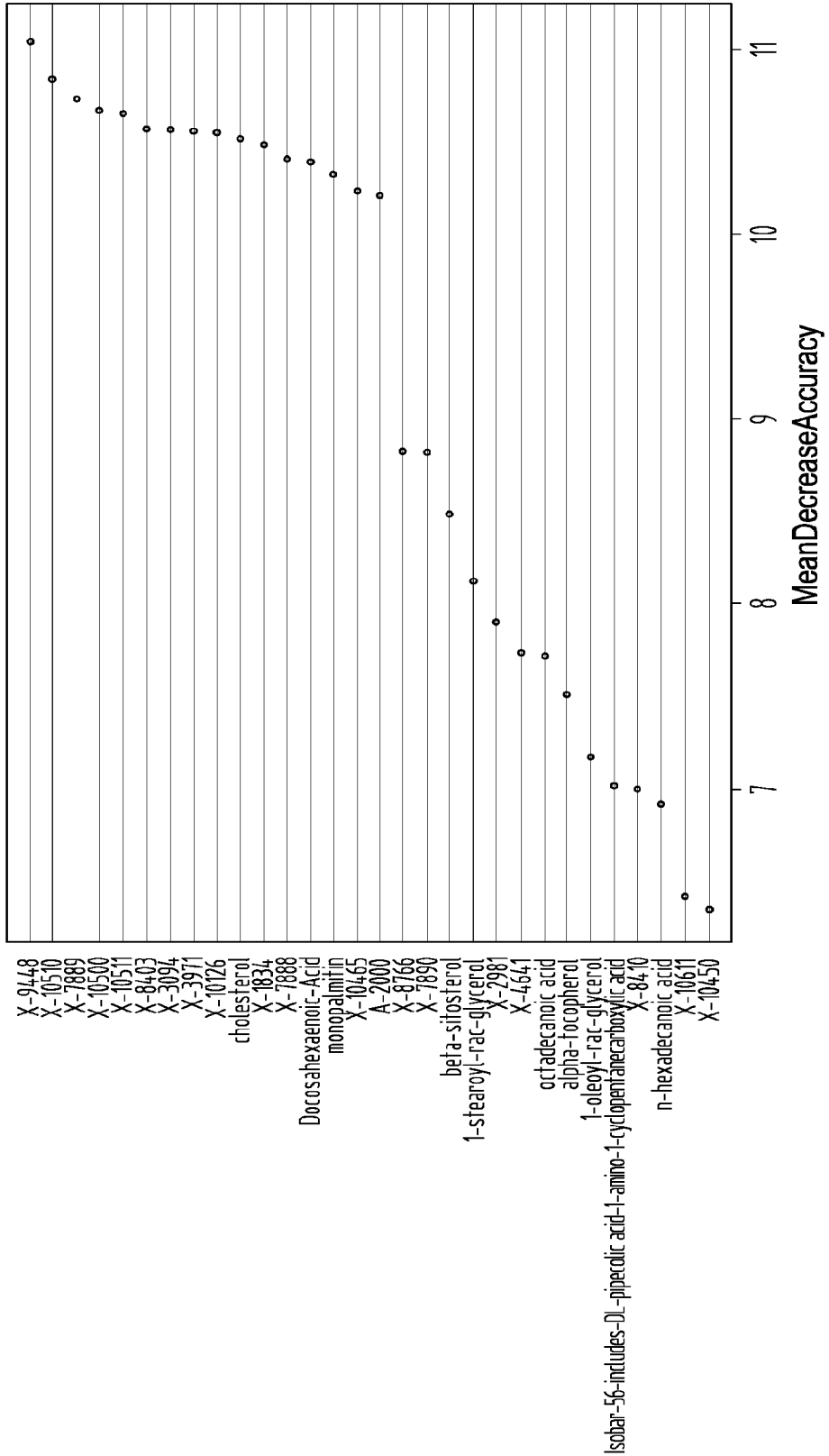
Figure 11C:
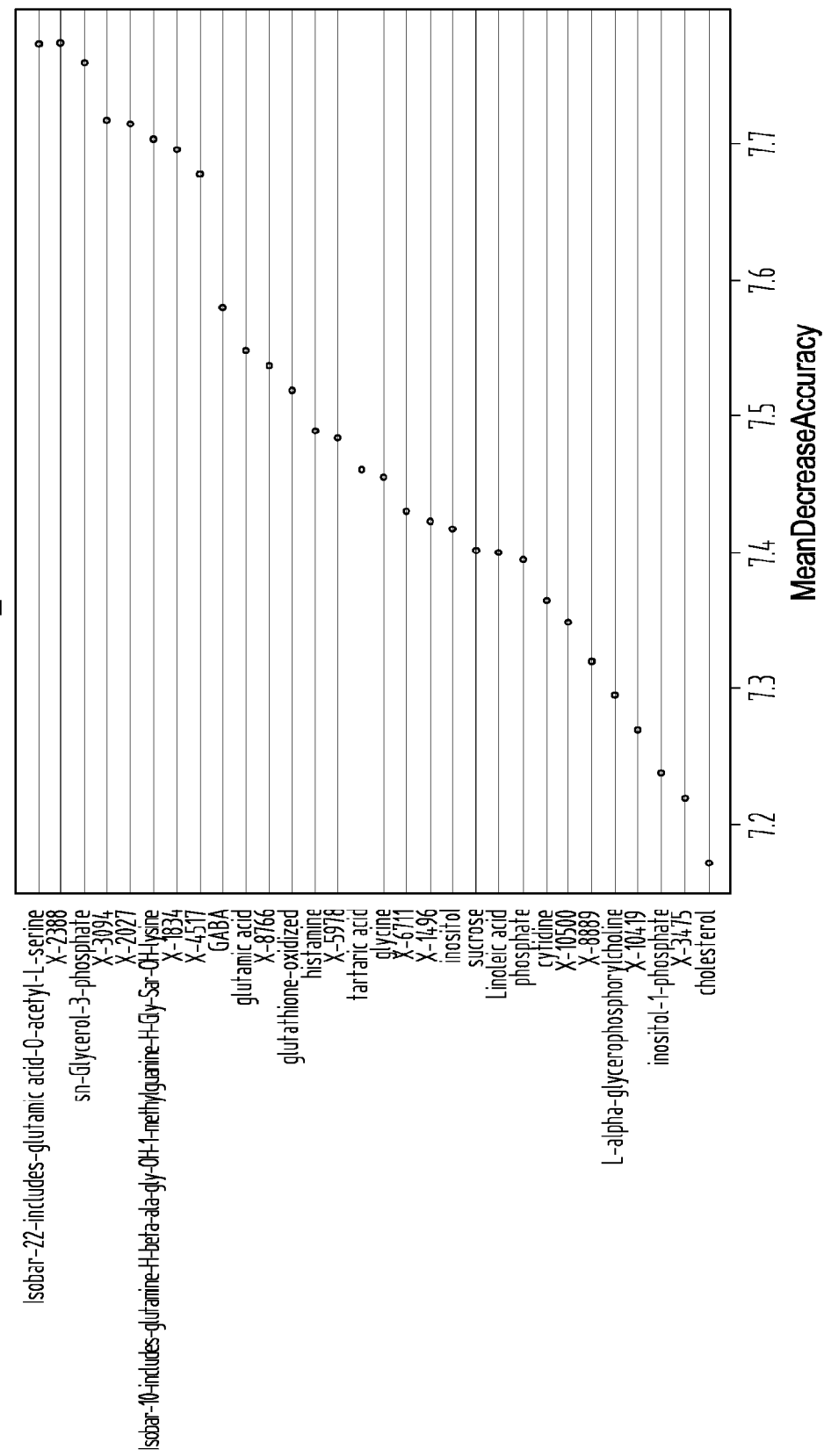
FIG. 11 provides a Random Forest Analysis Importance Plots of embodiments of metabolites from aorta tissue that are useful biomarkers for predicting atherosclerosis at early (initiation) (FIG. 11A), mid (FIG. 11B), later (FIG. 11C), or all (FIG. 11D) stages of the disease.
Figure 12A:
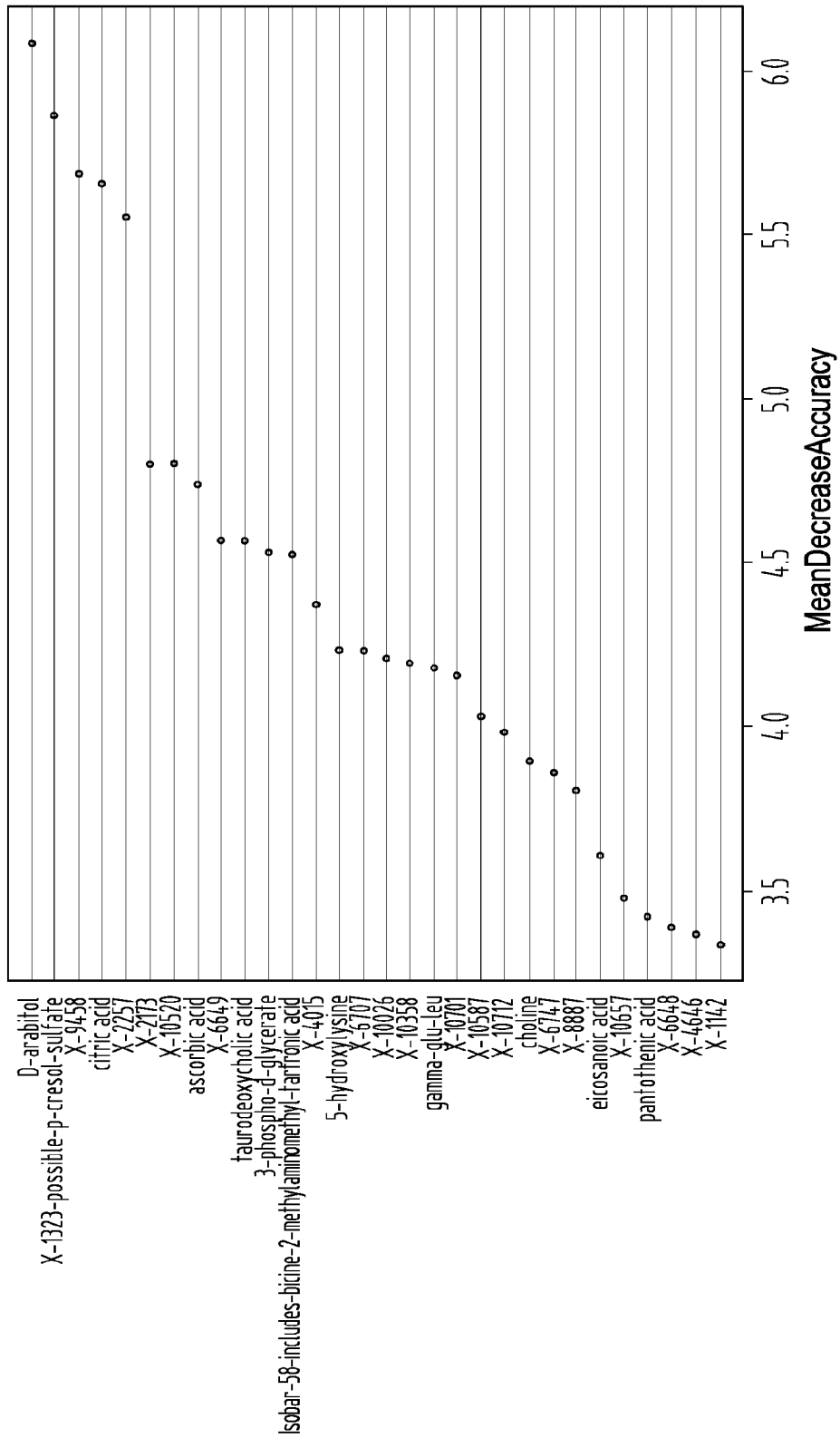
FIG. 12 provides a Random Forest Analysis Importance Plots of embodiments of metabolites from liver tissue that are useful biomarkers for predicting atherosclerosis at early (initiation) (FIG. 12A), mid (FIG. 12B), later (FIG. 12C), or all (FIG. 12D) stages of the disease.
Figure 12B:
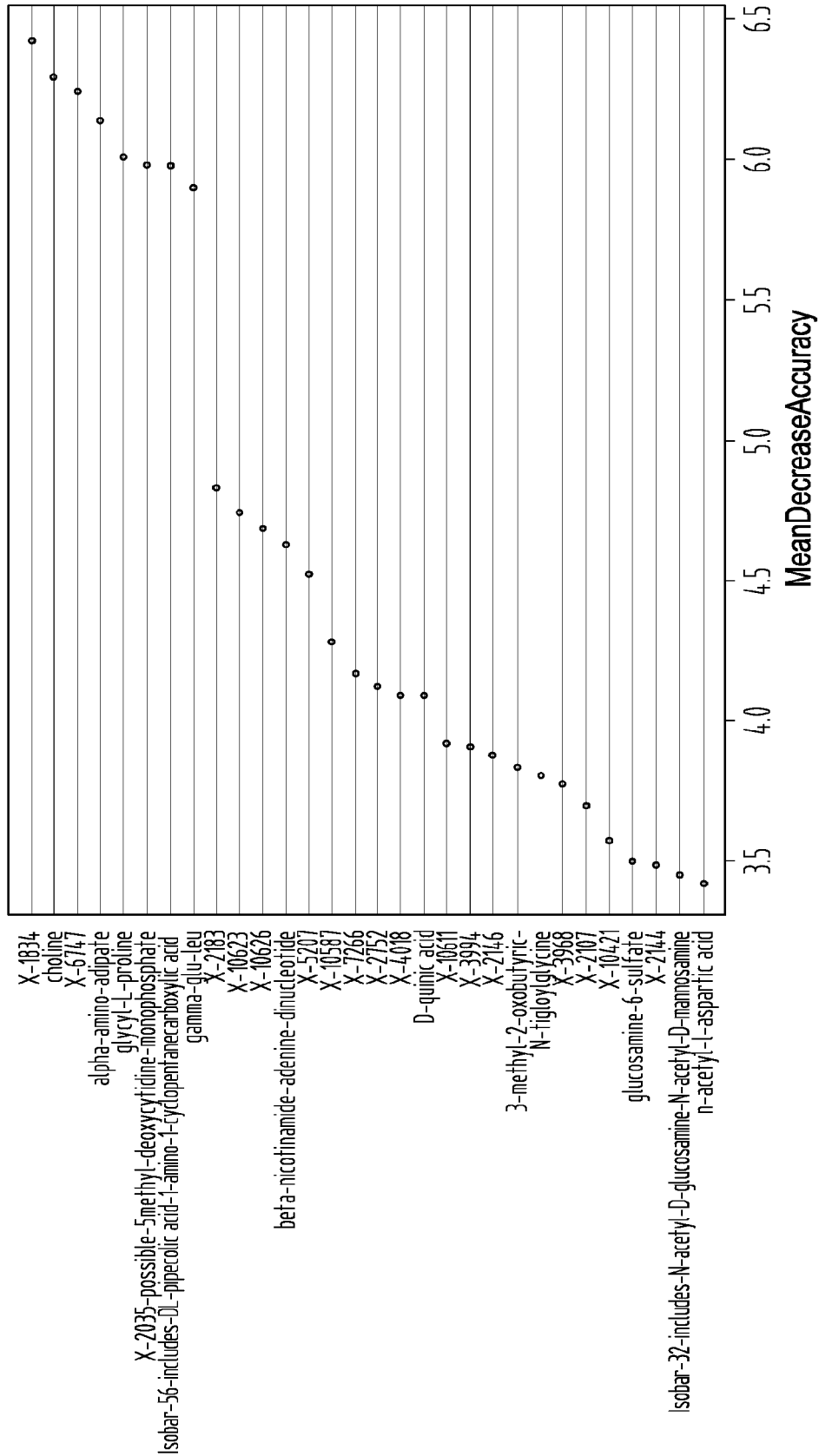
Figure 12C:
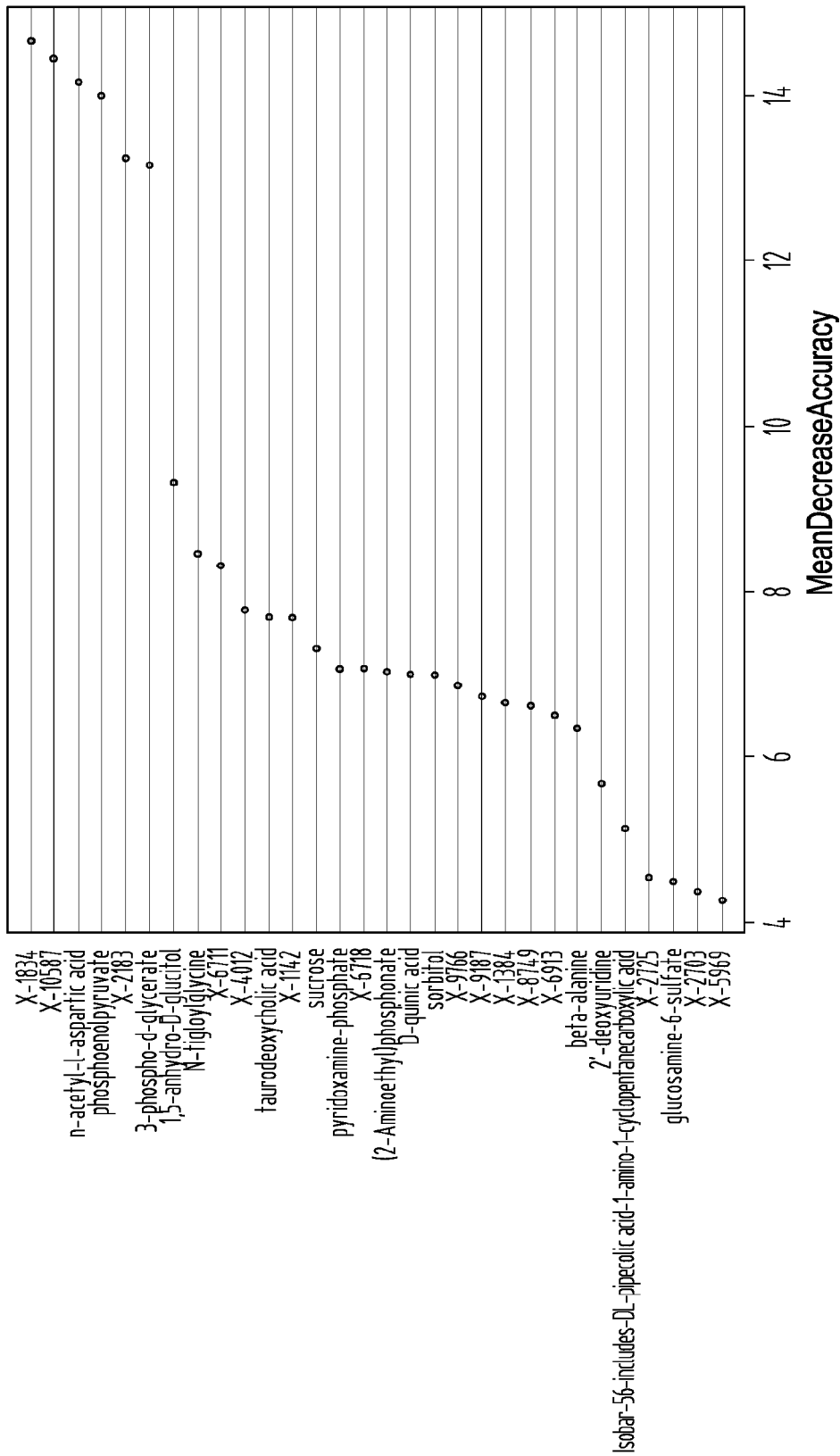
Figure 12D:
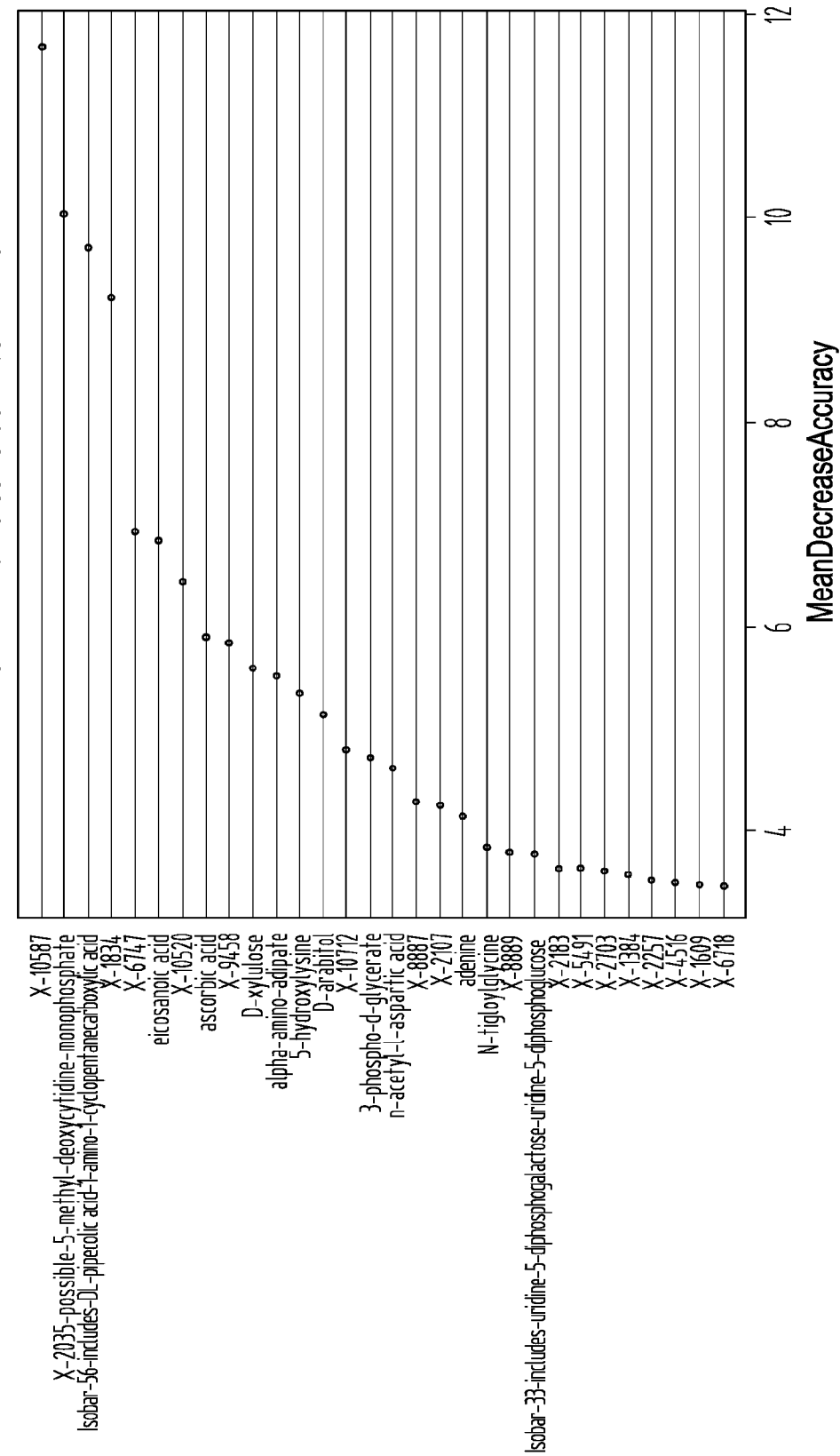
Figure 14:
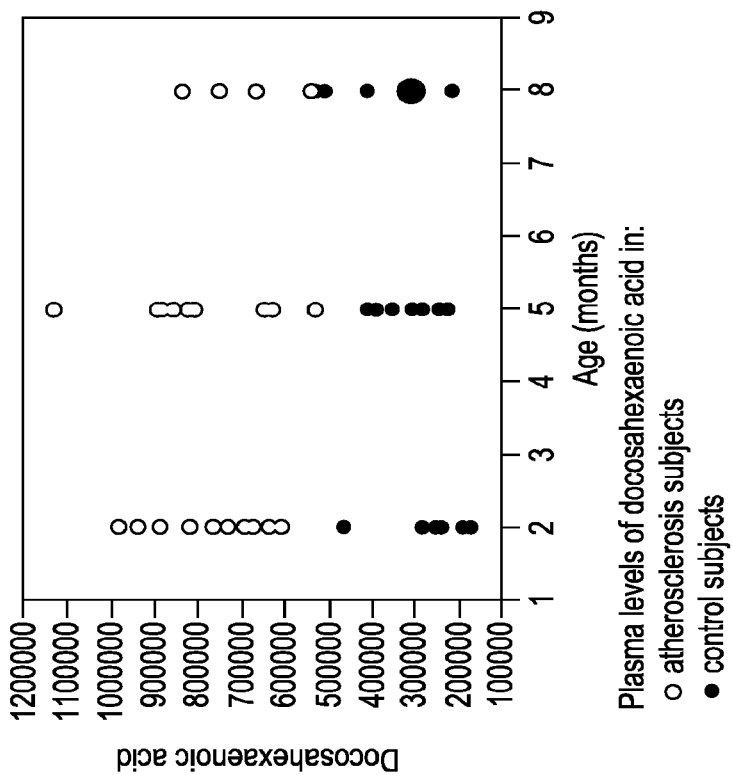
FIG. 14 provides an example of plasma levels of docosahexaenoic acid in atherosclerosis subjects and control subjects at different ages.
Figure 13:
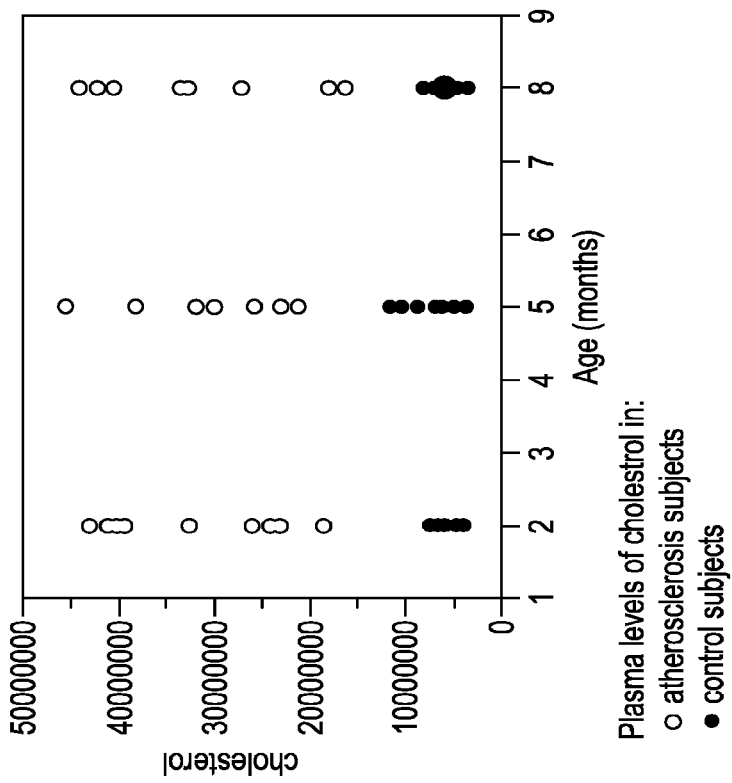
FIG. 13 provides an example of plasma levels of cholesterol in atherosclerosis subjects and control subjects at different ages.
Figure 16:
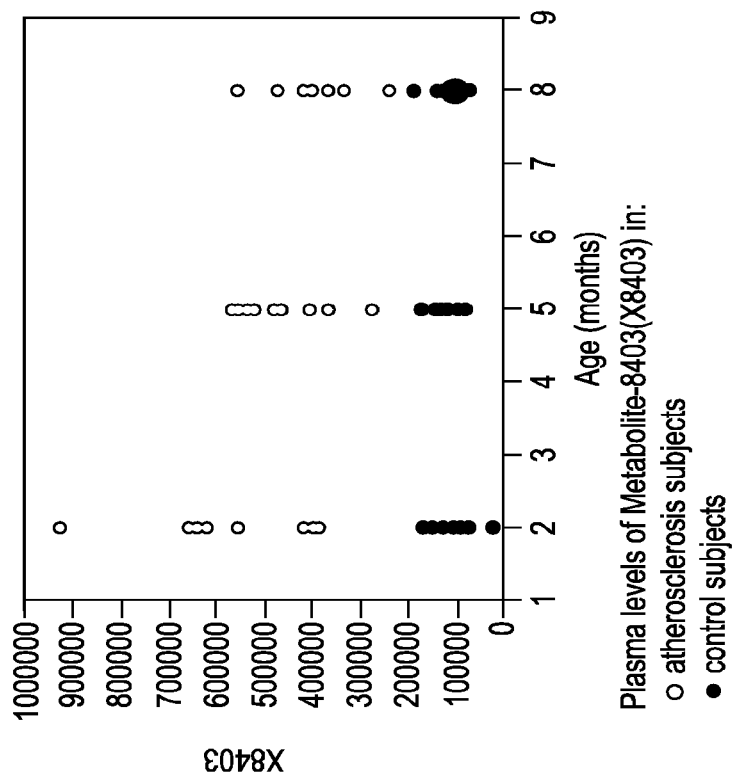
FIG. 16 provides an example of plasma levels of Metabolite-X8403 in atherosclerosis subjects and control subjects at different ages.
Figure 15:
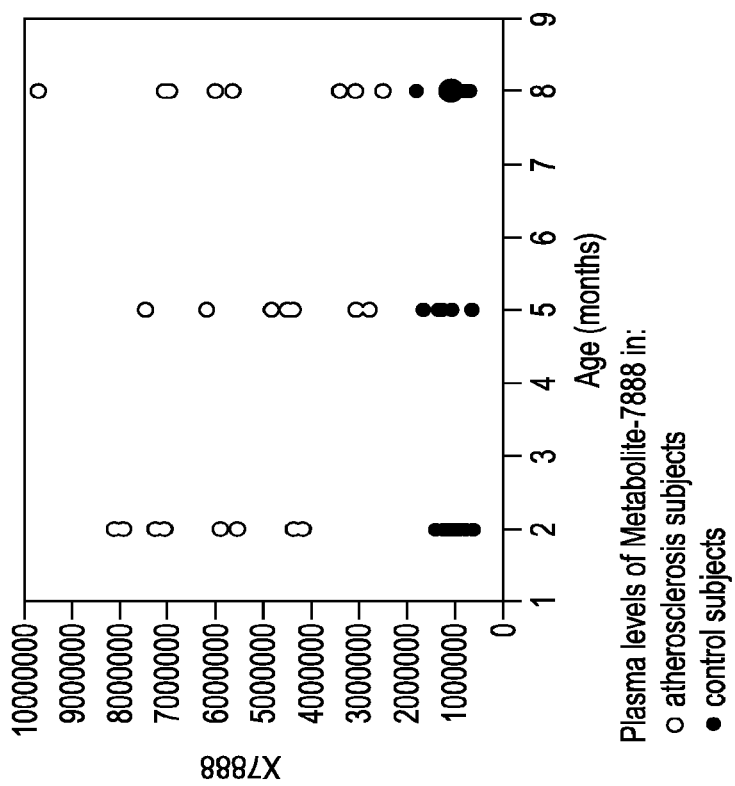
FIG. 15 provides an example of plasma levels of Metabolite-7888 in atherosclerosis subjects and control subjects at different ages.

Biomarkers for use in methods disclosed herein relating to atherosclerosis include one or more of those listed in Tables 14, 15, 16, and/or 17 and combinations thereof. For example, biomarkers for use in distinguishing, or aiding in distinguishing, atherosclerotic subjects from non-atherosclerotic subjects include one or more of those biomarkers listed in Tables 14, 15, 16, 17, 3-methylhistidine, p-cresol sulfate, mannose, glucose, and/or gluconate, and combinations thereof. In one aspect biomarkers for use in methods relating to atherosclerosis using plasma samples from a subject include one or more of 3-methylhistidine, p-cresol sulfate, mannose, glucose, gluconate, and those listed in Tables 14 and 17. In another aspect biomarkers for use in methods relating to atherosclerosis using aortic samples from a subject include one or more of those listed in Table 15. In yet another aspect, biomarkers for use in methods relating to atherosclerosis using liver samples from a subject include one or more of those listed in Table 16. In one aspect, preferred biomarkers for use in methods involving subjects in an early stage of atherosclerosis include the biomarkers identified in FIGS. 10A, 11A, and 12A. Preferred biomarkers for use in methods involving subjects in a mid-stage of atherosclerosis include the biomarkers identified in FIGS. 10B, 11B, and 12B. Preferred biomarkers for use in methods involving subjects in a later stage of atherosclerosis include the biomarkers identified in FIGS. 10C, 11C, and 12C. Preferred biomarkers for use in methods involving subjects in any stage of atherosclerosis include the biomarkers identified in FIGS. 10D, 11D, and 12D.

Biomarkers for use in methods disclosed herein relating to cardiomyopathy include one or more of those biomarkers listed in Tables 21, 22, 23, and/or 25. Such markers may be used, for example, to distinguish, or aiding in distinguishing, between subjects having cardiomyopathy from subjects not having cardiomyopathy. In one aspect, biomarkers for use in methods relating to cardiomyopathy using cardiac tissue samples from a subject include one or more of those listed in Table 21. In another aspect, biomarkers for use in methods relating to cardiomyopathy using plasma samples from a subject include one or more of those listed in Table 22 and/or 23.

Biomarkers for use in methods disclosed herein relating to obesity include one or more of those biomarkers listed in Table 26. Such markers may be used, for example, to distinguish obese subjects from lean subjects. Such markers may also be used in combination with biomarkers for pre-diabetes, metabolic syndrome, atherosclerosis, or cardiomyopathy. In another aspect, the markers may be used, for example, to determine susceptibility to obesity or weight gain. In another aspect, the markers may be used, for example, to determine if a therapeutic agent is likely to induce weight gain in a subject.

Any number of biomarkers may be used in the methods disclosed herein. That is, the disclosed methods may include the determination of the level(s) of one biomarker, two or more biomarkers, three or more biomarkers, four or more biomarkers, five or more biomarkers, six or more biomarkers, seven or more biomarkers, eight or more biomarkers, nine or more biomarkers, ten or more biomarkers, fifteen or more biomarkers, etc., including a combination of all of the biomarkers in each or all of Tables 4, 5, 6, 7, 8, 9A, 9B, 14, 15, 16, 17, 21, 22, 23, 25, 26, 27, 28, 29, or any fraction thereof. In another aspect, the number of biomarkers for use in the disclosed methods include the levels of about thirty or less biomarkers, twenty-five or less, twenty or less, fifteen or less, ten or less, nine or less, eight or less, seven or less, six or less, five or less biomarkers. In another aspect, the number of biomarkers for use in the disclosed methods include the levels of one, two, three, four, five, six, seven, eight, nine, ten, eleven, twelve, thirteen, fourteen, fifteen, twenty, twenty-five, or thirty biomarkers.

Although the identities of some of the biomarkers compounds are not known at this time, such identities are not necessary for the identification of the biomarkers in biological samples from subjects, as the "unnamed" compounds have been sufficiently characterized by analytical techniques to allow such identification. The analytical characterization of all such "unnamed" compounds is listed in the Examples. Such "unnamed" biomarkers are designated herein using the nomenclature "Metabolite" followed by a specific metabolite number.

In addition, the methods disclosed herein using the biomarkers listed in the tables may be used in combination with clinical diagnostic measures of the respective conditions. Combinations with clinical diagnostics may facilitate the disclosed methods, or confirm results of the disclosed methods (for example, facilitating or confirming diagnosis, monitoring progression or regression, and/or determining predisposition to pre-diabetes).

Finally, where the potential identity of a compound is proposed for an "unnamed" metabolite and such identity has not been confirmed, the nomenclature of "possible" (along with the potential compound identity) follows the "Metabolite" number. Such proposed identity should not be considered as limiting the analytical characterization of the otherwise "unnamed" compounds.

II. Diagnostic Methods

The biomarkers described herein may be used to diagnose, or to aid in diagnosing, whether a subject has a disease or condition, such as insulin resistance, pre-diabetes, type-2 diabetes, metabolic syndrome, atherosclerosis, or cardiomyopathy. For example, biomarkers for use in diagnosing, or aiding in diagnosing, whether a subject has a insulin resistance include one or more of those identified in Tables 4, 5, 6, 7, 8, 9A, 9B, 27, 28, 29, and combinations thereof. In one embodiment, the biomarkers include one or more of those identified in Tables 4, 5, 6, 7, 8, 9A, 9B, 27, 28, and combinations thereof. In another embodiment, combinations of biomarkers include those, such as 2-hydroxybutyrate in combination with one or more biomarkers indentified in Tables 4, 5, 6, 7, 8, 9A, 9B, 27, 28, and/or 29.

Methods for diagnosing, or aiding in diagnosing, whether a subject has a disease or condition, such as pre-diabetes, metabolic syndrome, atherosclerosis, or cardiomyopathy, may performed using one or more of the biomarkers identified in the respective tables provided herein. A method of diagnosing (or aiding in diagnosing) whether a subject has a disease or condition, such as pre-diabetes, metabolic syndrome, atherosclerosis, or cardiomyopathy, comprises (1) analyzing a biological sample from a subject to determine the level(s) of one or more biomarkers of the disease or condition in the sample and (2) comparing the level(s) of one or more biomarkers in the sample to disease- or condition-positive and/or disease- or condition-negative reference levels of the one or more biomarkers to diagnose (or aid in the diagnosis of) whether the subject has the disease or condition. For example, a method of diagnosing (or aiding in diagnosing) whether a subject is pre-diabetic comprises (1) analyzing a biological sample from a subject to determine the level(s) of one or more biomarkers of pre-diabetes in the sample and (2) comparing the level(s) of the one or more biomarkers in the sample to pre-diabetes-positive and/or pre-diabetes-negative reference levels of the one or more biomarkers in order to diagnose (or aid in the diagnosis of) whether the subject has pre-diabetes. The one or more biomarkers that are used are selected from Tables 4, 5, 6, 7, 8, 9A, 9B, and combinations thereof. When such a method is used in aiding in the diagnosis of a disease or condition, such as insulin resistance, pre-diabetes, metabolic syndrome, atherosclerosis, or cardiomyopathy, the results of the method may be used along with other methods (or the results thereof) useful in the clinical determination of whether a subject has a given disease or condition. Methods useful in the clinical determination of whether a subject has a disease or condition such as pre-diabetes, metabolic syndrome, atherosclerosis, or cardiomyopathy are known in the art. For example, methods useful in the clinical determination of whether a subject has pre-diabetes include, for example, glucose disposal rates (Rd), body weight measurements, waist circumference measurements, BMI determinations, Peptide YY measurements, Hemoglobin A1C measurements, adiponectin measurements, fasting plasma glucose measurements, free fatty acid measurements, fasting plasma insulin measurements, and the like. Methods useful for the clinical determination of atherosclerosis and/or cardiomyopathy in a subject include angiography, stress-testing, blood tests (e.g. to measure homocysteine, fibrinogen, lipoprotein (a), small LDL particles, and c-reactive protein levels), electrocardiography, echocardiography, computed tomography (CT) scans, ankle/brachial index, and intravascular ultrasounds.

In another example, the identification of biomarkers for diseases or conditions such as insulin resistance, pre-diabetes, metabolic syndrome, atherosclerosis, and cardiomyopathy, allows for the diagnosis of (or for aiding in the diagnosis of) such diseases or conditions in subjects presenting one or more symptoms of the disease or condition. For example, a method of diagnosing (or aiding in diagnosing) whether a subject has insulin resistance comprises (1) analyzing a biological sample from a subject to determine the level(s) of one or more biomarkers of insulin resistance in the sample and (2) comparing the level(s) of the one or more biomarkers in the sample to insulin resistance-positive and/or insulin resistance-negative reference levels of the one or more biomarkers in order to diagnose (or aid in the diagnosis of) whether the subject has insulin resistance. The one or more biomarkers that are used are selected from Tables 4, 5, 6, 7, 8, 9A, and/or 9B. The biomarkers for insulin resistance may also be used to classify subjects as being either insulin resistant, insulin sensitive, or having impaired insulin sensitivity. As described in Example 2, below, biomarkers are identified that may be used to classify subjects as being insulin resistant, insulin sensitive, or having impaired insulin sensitivity. The biomarkers in Tables 4, 5, 6, 7, 8, 9A, and/or 9B, may also be used to classify subjects as having impaired fasting glucose levels or impaired glucose tolerance or normal glucose tolerance. Thus, the biomarkers may indicate compounds that increase and decrease as the glucose disposal rate increases. By determining appropriate reference levels of the biomarkers for each group (insulin resistant, insulin impaired, insulin sensitive), subjects can be diagnosed appropriately. The results of this method may be combined with the results of clinical measurements to aid in the diagnosis of insulin resistance or for categorizing the subject as having NGT, IFG, or IGT.

Increased insulin resistance correlates with the glucose disposal rate (Rd) as measured by the HI clamp. As exemplified below, metabolomic analysis was carried out to identify biomarkers that correlate with the glucose disposal rate (Rd). These biomarkers can be used in a mathematical model to determine the glucose disposal rate of the subject. The insulin sensitivity of the individual can be determined using this model. Using metabolomic analysis, panels of metabolites that can be used in a simple blood test to predict insulin resistance as measured by the "gold standard" of hyperinsulinemic euglycemic clamps in at least two independent cohorts of subjects were discovered. In another example, biomarkers are identified that correlate with the results of oral glucose tolerance tests (OGTT) for use in categorizing subjects as having normal glucose tolerance (NGT), impaired fasting glucose levels (IFG), or impaired glucose tolerance (IGT).

Independent studies were carried out to identify a set of biomarkers that when used with a polynomic algorithm will enable the early detection of changes in insulin resistance in a subject. In one aspect, the instant invention provides the subject with a score indicating the level of insulin resistance ("IR Score") of the subject. The score is based upon clinically significant changed reference level for a biomarker and/or combination of biomarkers. The reference level can be derived from an algorithm or computed from indices for impaired glucose tolerance and can be presented in a report as shown in FIG. 5. The IR Score places the subject in the range of insulin resistance from normal (i.e. insulin sensitive) to high. Disease progression or remission can be monitored by periodic determination and monitoring of the IR Score. Response to therapeutic intervention can be determined by monitoring the IR Score. The IR Score can also be used to evaluate drug efficacy.

Methods for determining a subject's insulin resistance score (IR score) may be performed using one or more of the biomarkers identified in the respective Tables provided herein. For example, a method for determining the IR score of a subject comprises the steps of: (1) analyzing a biological sample from a subject to determine the level(s) of one or more insulin resistance biomarkers in the sample, and (2) comparing the level(s) of the one or more insulin resistance biomarkers in the sample to insulin resistance reference levels of the one or more biomarkers in order to determine the subject's insulin resistance score. The one or more biomarkers that are used may be selected from Tables 4, 5, 6, 7, 8, 9A, 9B, and combinations thereof. The method may employ any number of markers selected from Tables 4, 5, 6, 7, 8, 9A, and/or 9B, including 1, 2, 3, 4, 5, 6, 7, 8, 9, 10, or more markers. Multiple biomarkers may be correlated with a given condition, such as insulin resistance, by any method, including statistical methods such as regression analysis.

Also as exemplified below, metabolomic analysis was carried out to identify biomarkers that correlate with metabolic syndrome, atherosclerosis, cardiomyopathy, and other diseases or conditions. Such biomarkers may be used in the methods of the present invention to analyze biological samples to identify or measure the level of the biomarkers in the sample.

Any suitable method may be used to analyze the biological sample in order to determine the level(s) of the one or more biomarkers in the sample. Suitable methods include chromatography (e.g., HPLC, gas chromatography, liquid chromatography), mass spectrometry (e.g., MS, MS-MS), enzyme-linked immunosorbent assay (ELISA), antibody linkage, other immunochemical techniques, and combinations thereof. Further, the level(s) of the one or more biomarkers may be measured indirectly, for example, by using an assay that measures the level of a compound (or compounds) that correlates with the level of the biomarker(s) that are desired to be measured.

After the level(s) of the one or more biomarker(s) is determined, the level(s) may be compared to disease or condition reference level(s) of the one or more biomarker(s) to determine a rating for each of the one or more biomarker(s) in the sample. The rating(s) may be aggregated using any algorithm to create a score, for example, an insulin resistance (IR) score, for the subject. The algorithm may take into account any factors relating to the disease or condition, such as insulin resistance, including the number of biomarkers, the correlation of the biomarkers to the disease or condition, etc.

In one example, the subject's insulin resistance score may be correlated to any index indicative of a level insulin resistance, from normal glucose tolerance to insulin resistant. For example, a subject having an insulin resistance score of less than 25 may indicate that the subject has normal glucose tolerance; a score of between 26 and 50 may indicate that the subject has low impaired glucose tolerance; a score of between 51 and 75 may indicate that the subject has medium impaired glucose tolerance; a score of between 76 and 100 may indicate that the subject has high impaired glucose tolerance; and a score above 100 may indicate that the subject has type-2 diabetes.

III. Monitoring Disease or Condition Progression/Regression

The identification of biomarkers herein allows for monitoring progression/regression of the respective diseases or conditions (e.g. pre-diabetes, metabolic syndrome, atherosclerosis, cardiomyopathy, insulin resistance, etc.) in a subject. A method of monitoring the progression/regression of disease or condition, such as pre-diabetes, type-2 diabetes, metabolic syndrome, atherosclerosis, and cardiomyopathy, in a subject comprises (1) analyzing a first biological sample from a subject to determine the level(s) of one or more biomarkers for the respective disease or condition selected from Tables 4, 5, 6, 7, 8, 9A, 9B, 14, 15, 16, 17, 21, 22, 23, 25, 26, 27, 28, and combinations thereof in the first sample obtained from the subject at a first time point, (2) analyzing a second biological sample from a subject to determine the level(s) of the one or more biomarkers, the second sample obtained from the subject at a second time point, and (3) comparing the level(s) of one or more biomarkers in the first sample to the level(s) of the one or more biomarkers in the second sample in order to monitor the progression/regression of the disease or condition in the subject. The results of the method are indicative of the course of the disease or condition (i.e., progression or regression, if any change) in the subject.

In one embodiment, the results of the method may be based on Insulin Resistance (IR) Score which is indicative of the insulin resistance in the subject and which can be monitored over time. By comparing the IR Score from a first time point sample to the IR Score from at least a second time point sample the progression or regression of IR can be determined. Such a method of monitoring the progression/regression of pre-diabetes and/or type-2 diabetes in a subject comprises (1) analyzing a first biological sample from a subject to determine an IR score for the first sample obtained from the subject at a first time point, (2) analyzing a second biological sample from a subject to determine a second IR score, the second sample obtained from the subject at a second time point, and (3) comparing the IR score in the first sample to the IR score in the second sample in order to monitor the progression/regression of pre-diabetes and/or type-2 diabetes in the subject.

Using the biomarkers and algorithm of the instant invention for progression monitoring may guide, or assist a physician's decision to implement preventative measures such as dietary restrictions, exercise, or early-stage drug treatment.

IV. Determining Predisposition to a Disease or Condition

The biomarkers identified herein may also be used in the determination of whether a subject not exhibiting any symptoms of a disease or condition, such as pre-diabetes, type-2 diabetes, metabolic syndrome, atherosclerosis, or cardiomyopathy. The biomarkers may be used, for example, to determine whether a subject is predisposed to developing, for example, insulin resistance. Such methods of determining whether a subject having no symptoms of a particular disease or condition such as pre-diabetes, type-2 diabetes, metabolic syndrome, atherosclerosis, or cardiomyopathy, is predisposed to developing a particular disease or condition comprise (1) analyzing a biological sample from a subject to determine the level(s) of one or more biomarkers listed in the respective tables (e.g. Tables 4, 5, 6, 7, 8, 9A, 9B, 14, 15, 16, 17, 21, 22, 23, 25, 26, and combinations thereof) in the sample and (2) comparing the level(s) of the one or more biomarkers in the sample to disease- or condition-positive and/or disease- or condition-negative reference levels of the one or more biomarkers in order to determine whether the subject is predisposed to developing the respective disease or condition. For example, the identification of biomarkers for insulin resistance allows for the determination of whether a subject having no symptoms of insulin resistance is predisposed to developing insulin resistance. A method of determining whether a subject having no symptoms of insulin resistance is predisposed to developing insulin resistance comprises (1) analyzing a biological sample from a subject to determine the level(s) of one or more biomarkers listed in Tables 4, 5, 6, 7, 8, 9A, and 9B, and combinations thereof in the sample and (2) comparing the level(s) of the one or more biomarkers in the sample to insulin resistance-positive and/or insulin resistance-negative reference levels of the one or more biomarkers in order to determine whether the subject is predisposed to developing insulin resistance. The results of the method may be used along with other methods (or the results thereof) useful in the clinical determination of whether a subject is predisposed to developing the disease or condition.

After the level(s) of the one or more biomarkers in the sample are determined, the level(s) are compared to disease- or condition-positive and/or disease- or condition-negative reference levels in order to predict whether the subject is predisposed to developing a disease or condition such as pre-diabetes, type-2 diabetes, metabolic syndrome, atherosclerosis, or cardiomyopathy. Levels of the one or more biomarkers in a sample corresponding to the disease- or condition-positive reference levels (e.g., levels that are the same as the reference levels, substantially the same as the reference levels, above and/or below the minimum and/or maximum of the reference levels, and/or within the range of the reference levels) are indicative of the subject being predisposed to developing the disease or condition. Levels of the one or more biomarkers in a sample corresponding to disease- or condition-negative reference levels (e.g., levels that are the same as the reference levels, substantially the same as the reference levels, above and/or below the minimum and/or maximum of the reference levels, and/or within the range of the reference levels) are indicative of the subject not being predisposed to developing the disease or condition. In addition, levels of the one or more biomarkers that are differentially present (especially at a level that is statistically significant) in the sample as compared to disease- or condition-negative reference levels may be indicative of the subject being predisposed to developing the disease or condition. Levels of the one or more biomarkers that are differentially present (especially at a level that is statistically significant) in the sample as compared to disease-condition-positive reference levels are indicative of the subject not being predisposed to developing the disease or condition.

By way of example, after the level(s) of the one or more biomarkers in the sample are determined, the level(s) are compared to insulin resistance-positive and/or insulin resistance-negative reference levels in order to predict whether the subject is predisposed to developing insulin resistance. Levels of the one or more biomarkers in a sample corresponding to the insulin resistance-positive reference levels (e.g., levels that are the same as the reference levels, substantially the same as the reference levels, above and/or below the minimum and/or maximum of the reference levels, and/or within the range of the reference levels) are indicative of the subject being predisposed to developing insulin resistance. Levels of the one or more biomarkers in a sample corresponding to the insulin resistance-negative reference levels (e.g., levels that are the same as the reference levels, substantially the same as the reference levels, above and/or below the minimum and/or maximum of the reference levels, and/or within the range of the reference levels) are indicative of the subject not being predisposed to developing insulin resistance. In addition, levels of the one or more biomarkers that are differentially present (especially at a level that is statistically significant) in the sample as compared to insulin resistance-negative reference levels are indicative of the subject being predisposed to developing insulin resistance. Levels of the one or more biomarkers that are differentially present (especially at a level that is statistically significant) in the sample as compared to insulin resistance-positive reference levels are indicative of the subject not being predisposed to developing insulin resistance. Although insulin resistance is discussed in this example, predisposition to the other diseases or conditions may also be determined in accordance with this method by using one or more of the respective biomarkers as set forth above.

Furthermore, it may also be possible to determine reference levels specific to assessing whether or not a subject that does not have a disease or condition such as insulin resistance, pre-diabetes, type-2 diabetes, metabolic syndrome, atherosclerosis, or cardiomyopathy, is predisposed to developing a disease or condition. For example, it may be possible to determine reference levels of the biomarkers for assessing different degrees of risk (e.g., low, medium, high) in a subject for developing a disease or condition. Such reference levels could be used for comparison to the levels of the one or more biomarkers in a biological sample from a subject.

V. Monitoring Therapeutic Efficacy:

The biomarkers provided also allow for the assessment of the efficacy of a composition for treating a disease or condition such as insulin resistance, pre-diabetes, type-2 diabetes, metabolic syndrome, atherosclerosis, or cardiomyopathy. For example, the identification of biomarkers for insulin resistance also allows for assessment of the efficacy of a composition for treating insulin resistance as well as the assessment of the relative efficacy of two or more compositions for treating insulin resistance. Such assessments may be used, for example, in efficacy studies as well as in lead selection of compositions for treating the disease or condition.

Thus, also provided are methods of assessing the efficacy of a composition for treating a disease or condition such as insulin resistance, pre-diabetes, type-2 diabetes, metabolic syndrome, atherosclerosis, or cardiomyopathy comprising (1) analyzing, from a subject (or group of subjects) having a disease or condition such as pre-diabetes, type-2 diabetes, metabolic syndrome, atherosclerosis, or cardiomyopathy and currently or previously being treated with a composition, a biological sample (or group of samples) to determine the level(s) of one or more biomarkers for the disorder selected from Tables 4, 5, 6, 7, 8, 9A, 9B, 14, 15, 16, 17, 21, 22, 23, 25, 26, 27, 28, and combinations thereof, and (2) comparing the level(s) of the one or more biomarkers in the sample to (a) level(s) of the one or more biomarkers in a previously-taken biological sample from the subject, wherein the previously-taken biological sample was obtained from the subject before being treated with the composition, (b) disease- or condition-positive reference levels of the one or more biomarkers, (c) disease- or condition-negative reference levels of the one or more biomarkers, (d) disease- or condition-progression-positive reference levels of the one or more biomarkers, and/or (e) disease- or condition-regression-positive reference levels of the one or more biomarkers. The results of the comparison are indicative of the efficacy of the composition for treating the respective disease or condition.

The change (if any) in the level(s) of the one or more biomarkers over time may be indicative of progression or regression of the disease or condition in the subject. To characterize the course of a given disease or condition in the subject, the level(s) of the one or more biomarkers in the first sample, the level(s) of the one or more biomarkers in the second sample, and/or the results of the comparison of the levels of the biomarkers in the first and second samples may be compared to the respective disease- or condition-positive and/or disease- or condition-negative reference levels of the one or more biomarkers. If the comparisons indicate that the level(s) of the one or more biomarkers are increasing or decreasing over time (e.g., in the second sample as compared to the first sample) to become more similar to the disease- or condition-positive reference levels (or less similar to the disease- or condition-negative reference levels), then the results are indicative of the disease's or condition's progression. If the comparisons indicate that the level(s) of the one or more biomarkers are increasing or decreasing over time to become more similar to the disease- or condition-negative reference levels (or less similar to the disease- or condition-positive reference levels), then the results are indicative of the disease's or condition's regression.

For example, in order to characterize the course of insulin resistance in the subject, the level(s) of the one or more biomarkers in the first sample, the level(s) of the one or more biomarkers in the second sample, and/or the results of the comparison of the levels of the biomarkers in the first and second samples may be compared to insulin resistance-positive and/or insulin resistance-negative reference levels of the one or more biomarkers. If the comparisons indicate that the level(s) of the one or more biomarkers are increasing or decreasing over time (e.g., in the second sample as compared to the first sample) to become more similar to the insulin resistance-positive reference levels (or less similar to the insulin resistance-negative reference levels), then the results are indicative of insulin resistance progression. If the comparisons indicate that the level(s) of the one or more biomarkers are increasing or decreasing over time to become more similar to the insulin resistance-negative reference levels (or less similar to the insulin resistance-positive reference levels), then the results are indicative of insulin resistance regression.

The second sample may be obtained from the subject any period of time after the first sample is obtained. In one aspect, the second sample is obtained 1, 2, 3, 4, 5, 6, or more days after the first sample or after the initiation of the administration of a composition. In another aspect, the second sample is obtained 1, 2, 3, 4, 5, 6, 7, 8, 9, 10, or more weeks after the first sample or after the initiation of the administration of a composition. In another aspect, the second sample may be obtained 1, 2, 3, 4, 5, 6, 7, 8, 9, 10, 11, 12, or more months after the first sample or after the initiation of the administration of a composition.

The course of a disease or condition such as insulin resistance, pre-diabetes, type-2 diabetes, metabolic syndrome, atherosclerosis, or cardiomyopathy in a subject may also be characterized by comparing the level(s) of the one or more biomarkers in the first sample, the level(s) of the one or more biomarkers in the second sample, and/or the results of the comparison of the levels of the biomarkers in the first and second samples to disease- or condition-progression-positive and/or disease- or condition-regression-positive reference levels. If the comparisons indicate that the level(s) of the one or more biomarkers are increasing or decreasing over time (e.g., in the second sample as compared to the first sample) to become more similar to the disease- or condition-progression-positive reference levels (or less similar to the disease- or condition-regression-positive reference levels), then the results are indicative of the disease or condition progression. If the comparisons indicate that the level(s) of the one or more biomarkers are increasing or decreasing over time to become more similar to the disease- or condition-regression-positive reference levels (or less similar to the disease- or condition-progression-positive reference levels), then the results are indicative of disease or condition regression.

As with the other methods described herein, the comparisons made in the methods of monitoring progression/regression of a disease or condition such as insulin resistance, pre-diabetes, type-2 diabetes, metabolic syndrome, atherosclerosis, or cardiomyopathy in a subject may be carried out using various techniques, including simple comparisons, one or more statistical analyses, and combinations thereof.

The results of the method may be used along with other methods (or the results thereof) useful in the clinical monitoring of progression/regression of the disease or condition in a subject.

As described above in connection with methods of diagnosing (or aiding in the diagnosis of) a disease or condition such as insulin resistance, pre-diabetes, type-2 diabetes, metabolic syndrome, atherosclerosis, or cardiomyopathy, any suitable method may be used to analyze the biological samples in order to determine the level(s) of the one or more biomarkers in the samples. In addition, the level(s) one or more biomarkers, including a combination of all of the biomarkers in Tables 4, 5, 6, 7, 8, 9A, 9B, 14, 15, 16, 17, 21, 22, 23, 25, 26, 27, and/or 28, or any fraction thereof, may be determined and used in methods of monitoring progression/regression of the respective disease or condition in a subject.

Such methods could be conducted to monitor the course of disease or condition development in subjects, for example the course of pre-diabetes to type-2 diabetes in a subject having pre-diabetes, or could be used in subjects not having a disease or condition (e.g., subjects suspected of being predisposed to developing the disease or condition) in order to monitor levels of predisposition to the disease or condition.

Clinical studies from around the world have been carried out to test whether anti-diabetic therapies, such as metformin or acarbose, can prevent diabetes progression in pre-diabetic patients. These studies have shown that such therapies can prevent diabetes onset. From the U.S. Diabetes Prevention Program (DPP), metformin reduced the rate of progression to diabetes by 38% and lifestyle and exercise intervention reduced the rate of progression to diabetes by 56%. Because of such successes, the ADA has revised its 2008 Standards of Medical Care in Diabetes to include the following statements in the section on Prevention/Delay of Type 2 Diabetes: "In addition to lifestyle counseling, metformin may be considered in those who are at very high risk (combined IFG and IGT plus other risk factors) and who are obese and under 60 years of age."

Pharmaceutical companies have carried out studies to assess whether certain classes of drugs, such as the PPARγ class of insulin sensitizers, can prevent diabetes progression. Similar to the DPP trial, some of these studies have shown great promise and success for preventing diabetes, whereas others have exposed a certain amount of risk associated with certain anti-diabetic pharmacologic treatments when given to the general pre-diabetic population as defined by current IR diagnostics. Pharmaceutical companies are in need of diagnostics that can identify and stratify high risk pre-diabetics so they can assess the efficacy of their pre-diabetic therapeutic candidates more effectively and safely.

Considering the infrequency of the oral glucose tolerance test (OGTT) procedures in the clinical setting, a new diagnostic test that directly measures insulin resistance in a fasted sample would enable a physician to identify and stratify patients who are moving toward the etiology of pre-diabetes and cardiovascular disease much earlier.

VI. Identification of Responders and Non-Responders to Therapeutic:

The biomarkers provided also allow for the identification of subjects in whom the composition for treating a disease or condition such as pre-diabetes, type-2 diabetes, metabolic syndrome, atherosclerosis, or cardiomyopathy is efficacious (i.e. patient responds to therapeutic). For example, the identification of biomarkers for insulin resistance also allows for assessment of the subject response to a composition for treating insulin resistance as well as the assessment of the relative patient response to two or more compositions for treating insulin resistance. Such assessments may be used, for example, in selection of compositions for treating the disease or condition for certain subjects.

Thus, also provided are methods of predicting the response of a patient to a composition for treating a disease or condition such as pre-diabetes, type-2 diabetes, metabolic syndrome, atherosclerosis, or cardiomyopathy comprising (1) analyzing, from a subject (or group of subjects) having a disease or condition such as pre-diabetes, type-2 diabetes, metabolic syndrome, atherosclerosis, or cardiomyopathy and currently or previously being treated with a composition, a biological sample (or group of samples) to determine the level(s) of one or more biomarkers for the disorder selected from Tables 4, 5, 6, 7, 8, 9A, 9B, 14, 15, 16, 17, 21, 22, 23, 25, 26, 27, and 28, and combinations thereof, and (2) comparing the level(s) of the one or more biomarkers in the sample to (a) level(s) of the one or more biomarkers in a previously-taken biological sample from the subject, wherein the previously-taken biological sample was obtained from the subject before being treated with the composition, (b) disease- or condition-positive reference levels of the one or more biomarkers, (c) disease- or condition-negative reference levels of the one or more biomarkers, (d) disease- or condition-progression-positive reference levels of the one or more biomarkers, and/or (e) disease- or condition-regression-positive reference levels of the one or more biomarkers. The results of the comparison are indicative of the response of the patient to the composition for treating the respective disease or condition.

The change (if any) in the level(s) of the one or more biomarkers over time may be indicative of response of the subject to the therapeutic. To characterize the course of a given therapeutic in the subject, the level(s) of the one or more biomarkers in the first sample, the level(s) of the one or more biomarkers in the second sample, and/or the results of the comparison of the levels of the biomarkers in the first and second samples may be compared to the respective disease- or condition-positive and/or disease- or condition-negative reference levels of the one or more biomarkers. If the comparisons indicate that the level(s) of the one or more biomarkers are increasing or decreasing over time (e.g., in the second sample as compared to the first sample) to become more similar to the disease- or condition-positive reference levels (or less similar to the disease- or condition-negative reference levels), then the results are indicative of the patient not responding to the therapeutic. If the comparisons indicate that the level(s) of the one or more biomarkers are increasing or decreasing over time to become more similar to the disease- or condition-negative reference levels (or less similar to the disease- or condition-positive reference levels), then the results are indicative of the patient responding to the therapeutic.

For example, in order to characterize the patient response to a therapeutic for insulin resistance, the level(s) of the one or more biomarkers in the first sample, the level(s) of the one or more biomarkers in the second sample, and/or the results of the comparison of the levels of the biomarkers in the first and second samples may be compared to insulin resistance-positive and/or insulin resistance-negative reference levels of the one or more biomarkers. If the comparisons indicate that the level(s) of the one or more biomarkers are increasing or decreasing over time (e.g., in the second sample as compared to the first sample) to become more similar to the insulin resistance-positive reference levels (or less similar to the insulin resistance-negative reference levels), then the results are indicative of non-response to the therapeutic. If the comparisons indicate that the level(s) of the one or more biomarkers are increasing or decreasing over time to become more similar to the insulin resistance-negative reference levels (or less similar to the insulin resistance-positive reference levels), then the results are indicative of response to the therapeutic.

The second sample may be obtained from the subject any period of time after the first sample is obtained. In one aspect, the second sample is obtained 1, 2, 3, 4, 5, 6, or more days after the first sample. In another aspect, the second sample is obtained 1, 2, 3, 4, 5, 6, 7, 8, 9, 10, or more weeks after the first sample or after the initiation of treatment with the composition. In another aspect, the second sample may be obtained 1, 2, 3, 4, 5, 6, 7, 8, 9, 10, 11, 12, or more months after the first sample or after the initiation of treatment with the composition.

As with the other methods described herein, the comparisons made in the methods of determining a patient response to a therapeutic for a disease or condition such as insulin resistance, pre-diabetes, type-2 diabetes, metabolic syndrome, atherosclerosis, or cardiomyopathy in a subject may be carried out using various techniques, including simple comparisons, one or more statistical analyses, and combinations thereof.

The results of the method may be used along with other methods (or the results thereof) useful in determining a patient response to a therapeutic for the disease or condition in a subject.

As described above in connection with methods of diagnosing (or aiding in the diagnosis of) a disease or condition such as pre-diabetes, type-2 diabetes, metabolic syndrome, atherosclerosis, or cardiomyopathy, any suitable method may be used to analyze the biological samples in order to determine the level(s) of the one or more biomarkers in the samples. In addition, the level(s) one or more biomarkers, including a combination of all of the biomarkers in Tables 4, 5, 6, 7, 8, 9A, 9B, 14, 15, 16, 17, 21, 22, 23, 25, 26, 27, and/or 28, or any fraction thereof, may be determined and used in methods of monitoring progression/regression of the respective disease or condition in a subject.

Such methods could be conducted to monitor the patient response to a therapeutic for a disease or condition development in subjects, for example the course of pre-diabetes to type-2 diabetes in a subject having pre-diabetes, or could be used in subjects not having a disease or condition (e.g., subjects suspected of being predisposed to developing the disease or condition) in order to monitor levels of predisposition to the disease or condition.

Pharmaceutical companies have carried out studies to assess whether certain classes of drugs, such as the PPARγ class of insulin sensitizers, can prevent diabetes progression. Some of these studies have shown great promise and success for preventing diabetes, whereas others have exposed a certain amount of risk associated with certain anti-diabetic pharmacologic treatments when given to the general pre-diabetic population as defined by current IR diagnostics. Pharmaceutical companies are in need of diagnostics that can identify responders and non-responders in order to stratify high risk pre-diabetics to assess the efficacy of their pre-diabetic therapeutic candidates more effectively and safely. A new diagnostic test that discriminates non-responding from responding patients to a therapeutic would enable pharmaceutical companies to identify and stratify patients that are likely to respond to the therapeutic agent and target specific therapeutics for certain cohorts that are likely to respond to the therapeutic.

VII. Methods of Screening a Composition for Activity in Modulating Biomarkers

The biomarkers provided herein also allow for the screening of compositions for activity in modulating biomarkers associated with a disease or condition, such as pre-diabetes, type-2 diabetes, metabolic syndrome, atherosclerosis, and cardiomyopathy, which may be useful in treating the disease or condition. Such methods comprise assaying test compounds for activity in modulating the levels of one or more biomarkers selected from the respective biomarkers listed in the respective tables. Such screening assays may be conducted in vitro and/or in vivo, and may be in any form known in the art useful for assaying modulation of such biomarkers in the presence of a test composition such as, for example, cell culture assays, organ culture assays, and in vivo assays (e.g., assays involving animal models). For example, the identification of biomarkers for insulin resistance also allows for the screening of compositions for activity in modulating biomarkers associated with insulin resistance, which may be useful in treating insulin resistance. Methods of screening compositions useful for treatment of insulin resistance comprise assaying test compositions for activity in modulating the levels of one or more biomarkers in Tables 4, 5, 6, 7, 8, 9A, 9B, 27, and/or 28. Although insulin resistance is discussed in this example, the other diseases and conditions such as pre-diabetes, type-2 diabetes, metabolic syndrome, atherosclerosis, and cardiomyopathy may also be diagnosed or aided to be diagnosed in accordance with this method by using one or more of the respective biomarkers as set forth above.

The methods for screening a composition for activity in modulating one or more biomarkers of a disease or condition such as insulin resistance, pre-diabetes, type-2 diabetes, metabolic syndrome, atherosclerosis, and cardiomyopathy comprise (1) contacting one or more cells with a composition, (2) analyzing at least a portion of the one or more cells or a biological sample associated with the cells to determine the level(s) of one or more biomarkers of a disease or condition selected from the biomarkers provided in Tables 4, 5, 6, 7, 8, 9A, 9B, 14, 15, 16, 17, 21, 22, 23, 25, and/or 26; and (3) comparing the level(s) of the one or more biomarkers with predetermined standard levels for the one or more biomarkers to determine whether the composition modulated the level(s) of the one or more biomarkers. In one embodiment, a method for screening a composition for activity in modulating one or more biomarkers of insulin resistance comprises (1) contacting one or more cells with a composition, (2) analyzing at least a portion of the one or more cells or a biological sample associated with the cells to determine the level(s) of one or more biomarkers of insulin resistance selected from Tables 4, 5, 6, 7, 8, 9A, and/or 9B; and (3) comparing the level(s) of the one or more biomarkers with predetermined standard levels for the one or more biomarkers to determine whether the composition modulated the level(s) of the one or more biomarkers. As discussed above, the cells may be contacted with the composition in vitro and/or in vivo. The predetermined standard levels for the one or more biomarkers may be the levels of the one or more biomarkers in the one or more cells in the absence of the composition. The predetermined standard levels for the one or more biomarkers may also be the level(s) of the one or more biomarkers in control cells not contacted with the composition.

In addition, the methods may further comprise analyzing at least a portion of the one or more cells or a biological sample associated with the cells to determine the level(s) of one or more non-biomarker compounds of a disease or condition, such as pre-diabetes, type-2 diabetes, metabolic syndrome, atherosclerosis, and cardiomyopathy. The levels of the non-biomarker compounds may then be compared to predetermined standard levels of the one or more non-biomarker compounds.

Any suitable method may be used to analyze at least a portion of the one or more cells or a biological sample associated with the cells in order to determine the level(s) of the one or more biomarkers (or levels of non-biomarker compounds). Suitable methods include chromatography (e.g., HPLC, gas chromatography, liquid chromatography), mass spectrometry (e.g., MS, MS-MS), ELISA, antibody linkage, other immunochemical techniques, biochemical or enzymatic reactions or assays, and combinations thereof. Further, the level(s) of the one or more biomarkers (or levels of non-biomarker compounds) may be measured indirectly, for example, by using an assay that measures the level of a compound (or compounds) that correlates with the level of the biomarker(s) (or non-biomarker compounds) that are desired to be measured.

VIII. Method of Identifying Potential Drug Targets

The disclosure also provides methods of identifying potential drug targets for diseases or conditions such as insulin resistance, pre-diabetes, type-2 diabetes, metabolic syndrome, atherosclerosis, and cardiomyopathy, using the biomarkers listed in Tables 4, 5, 6, 7, 8, 9A, 9B, 14, 15, 16, 17, 21, 22, 23, 25, 26, 27, and/or 28. A method for identifying a potential drug target for a disease or condition such as pre-diabetes, type-2 diabetes, metabolic syndrome, atherosclerosis and cardiomyopathy comprises (1) identifying one or more biochemical pathways associated with one or more biomarkers for a metabolic syndrome-related metabolic disorder selected from the respective tables (Tables 4, 5, 6, 7, 8, 9A, 9B, 14, 15, 16, 17, 21, 22, 23, 25, 26, 27, and/or 28); and (2) identifying a protein (e.g., an enzyme) affecting at least one of the one or more identified biochemical pathways, the protein being a potential drug target for the disease or condition. For example, the identification of biomarkers for insulin resistance also allows for the identification of potential drug targets for insulin resistance. A method for identifying a potential drug target for insulin resistance comprises (1) identifying one or more biochemical pathways associated with one or more biomarkers for insulin resistance selected from Tables 4, 5, 6, 7, 8, 9A, 9B, 27, and/or 28, and (2) identifying a protein (e.g., an enzyme) affecting at least one of the one or more identified biochemical pathways, the protein being a potential drug target for insulin resistance. Although insulin resistance is discussed in this example, the other diseases or conditions such as type-2 diabetes, metabolic syndrome, atherosclerosis and cardiomyopathy, may also be diagnosed or aided to be diagnosed in accordance with this method by using one or more of the respective biomarkers as set forth above.

Another method for identifying a potential drug target for a disease or condition such as pre-diabetes, type-2 diabetes, metabolic syndrome, atherosclerosis, and cardiomyopathy comprises (1) identifying one or more biochemical pathways associated with one or more biomarkers for a metabolic syndrome-related metabolic disorder selected from the respective table(s) (Tables 4, 5, 6, 7, 8, 9A, 9B, 14, 15, 16, 17, 21, 22, 23, 25, 26, 27, and/or 28) and one or more non-biomarker compounds of the disease or condition and (2) identifying a protein affecting at least one of the one or more identified biochemical pathways, the protein being a potential drug target for the disease or condition. For example, a method for identifying a potential drug target for insulin resistance comprises (1) identifying one or more biochemical pathways associated with one or more biomarkers for insulin resistance selected from Tables 4, 5, 6, 7, 8, 9A, 9B, 27, and/or 28, and one or more non-biomarker compounds of insulin resistance and (2) identifying a protein affecting at least one of the one or more identified biochemical pathways, the protein being a potential drug target for insulin resistance.

One or more biochemical pathways (e.g., biosynthetic and/or metabolic (catabolic) pathway) are identified that are associated with one or more biomarkers (or non-biomarker compounds). After the biochemical pathways are identified, one or more proteins affecting at least one of the pathways are identified. Preferably, those proteins affecting more than one of the pathways are identified.

A build-up of one metabolite (e.g., a pathway intermediate) may indicate the presence of a 'block' downstream of the metabolite and the block may result in a low/absent level of a downstream metabolite (e.g. product of a biosynthetic pathway). In a similar manner, the absence of a metabolite could indicate the presence of a 'block' in the pathway upstream of the metabolite resulting from inactive or non-functional enzyme(s) or from unavailability of biochemical intermediates that are required substrates to produce the product. Alternatively, an increase in the level of a metabolite could indicate a genetic mutation that produces an aberrant protein which results in the over-production and/or accumulation of a metabolite which then leads to an alteration of other related biochemical pathways and result in dysregulation of the normal flux through the pathway; further, the build-up of the biochemical intermediate metabolite may be toxic or may compromise the production of a necessary intermediate for a related pathway. It is possible that the relationship between pathways is currently unknown and this data could reveal such a relationship.

The proteins identified as potential drug targets may then be used to identify compositions that may be potential candidates for treating a particular disease or condition, such as insulin resistance, including compositions for gene therapy.

IX. Methods of Treatment

In another aspect, methods for treating a disease or condition such as pre-diabetes, type-2 diabetes, metabolic syndrome, atherosclerosis, and cardiomyopathy are provided. The methods generally involve treating a subject having a disease or condition such as pre-diabetes, type-2 diabetes, metabolic syndrome, atherosclerosis, and cardiomyopathy with an effective amount of one or more biomarker(s) that are lowered in a subject having the disease or condition as compared to a healthy subject not having the disease or condition.

The biomarkers that may be administered may comprise one or more of the biomarkers in Tables 4, 5, 6, 7, 8, 9A, 9B, 14, 15, 16, 17, 21, 22, 23, 25, 26, 27, 28, and/or 29 that are decreased in a disease or condition state as compared to subjects not having that disease or condition. Such biomarkers could be isolated based on the identity of the biomarker compound (i.e. compound name). The biomarkers that are currently unnamed metabolites could be isolated based on the analytical characterizations for the biomarkers listed in the Examples below (e.g. Table 29). In some embodiments, the biomarkers that are administered are one or more biomarkers listed in Tables 4, 5, 6, 7, 8, 9A, 9B, 14, 15, 16, 17, 21, 22, 23, 25, 26, 27, 28, and/or 29 that are decreased in a metabolic syndrome-related metabolic disorder and that have a p-value less than 0.05 or a q-value less than 0.10, or both a p-value less than 0.05 and a q-value less than 0.10, as determined by using a Welch's T-test or a Wilcoxon's rank sum Test. In other embodiments, the biomarkers that are administered are one or biomarkers listed in Tables 4, 5, 6, 7, 8, 9A, 9B, 14, 15, 16, 17, 21, 22, 23, 25, 26, 27, 28, and/or 29 that are decreased in a disease or condition and that have either a positive or negative correlation with a disease or condition. In one embodiment, the biomarkers have a positive or negative correlation either ≥+0.5 or ≤−0.5, respectively, with a disease or condition. In other embodiments, the biomarkers that are administered are one or more biomarkers listed in Tables 4, 5, 6, 7, 8, 9A, 9B, 14, 15, 16, 17, 21, 22, 23, 25, 26, 27, 28, and/or 29 that are decreased in a disease or condition by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, or by 100% (i.e., absent). In one example, the identification of biomarkers for insulin resistance also allows for the treatment of insulin resistance. For example, in order to treat a subject having insulin resistance, an effective amount of one or more insulin resistance biomarkers that are lowered in subjects having insulin resistance as compared to a healthy subject not having insulin resistance may be administered to the subject. The biomarkers that may be administered may comprise one or more of the biomarkers in Tables 4, 5, 6, 7, 8, 9A, 9B, 27, 28, and/or 29 that are decreased in a subject having insulin resistance. Although insulin resistance is discussed in this example, the other diseases or conditions, such as type-2 diabetes, metabolic syndrome, atherosclerosis, and cardiomyopathy, may also be treated in accordance with this method by using one or more of the respective biomarkers as set forth above.

X. Methods of Using the Biomarkers for Other Diseases or Conditions

In another aspect, at least some of the biomarkers disclosed herein for a particular disease or condition may also be biomarkers for other diseases or conditions. For example, it is believed that at least some of the insulin resistance biomarkers may be used in the methods described herein for other diseases or conditions (e.g., metabolic syndrome). That is, the methods described herein with respect to insulin resistance may also be used for diagnosing (or aiding in the diagnosis of) a disease or condition such as type-2 diabetes, metabolic syndrome, atherosclerosis, or cardiomyopathy, methods of monitoring progression/regression of such a disease or condition, methods of assessing efficacy of compositions for treating such a disease or condition, methods of screening a composition for activity in modulating biomarkers associated with such a disease or condition, methods of identifying potential drug targets for such diseases and conditions, and methods of treating such diseases and conditions. Such methods could be conducted as described herein with respect to insulin resistance.

XI. Other Methods

Other methods of using the biomarkers discussed herein are also contemplated. For example, the methods described in U.S. Pat. No. 7,005,255 and U.S. patent application Ser. Nos. 11/357,732, 10/695,265 (Publication No. 2005/0014132), 11/301,077 (Publication No. 2006/0134676), 11/301,078 (Publication No. 2006/0134677), 11/301,079 (Publication No. 2006/0134678), and 11/405,033 may be conducted using a small molecule profile comprising one or more of the biomarkers disclosed herein.

In any of the methods listed herein, the biomarkers that are used may be selected from those biomarkers in Tables 4, 5, 6, 7, 8, 9A, 9B, 14, 15, 16, 17, 21, 22, 23, 25, 26, 27, 28, and/or 29 having p-values of less than 0.05 and/or those biomarkers in Tables 4, 5, 6, 7, 8, 9A, 9B, 14, 15, 16, 17, 21, 22, 23, 25, 26, 27, 28, and/or 29 having q-values less than 0.10, and/or having a positive or negative correlation either ≥+0.5 or ≤−0.5, respectively, with a disorder. The biomarkers that are used in any of the methods described herein may also be selected from those biomarkers in Tables 4, 5, 6, 7, 8, 9A, 9B, 14, 15, 16, 17, 21, 22, 23, 25, 26, 27, 28, and/or 29 that are decreased in a metabolic syndrome-related metabolic disorder (as compared to the control or remission) or that are decreased in remission (as compared to control or a particular disease or condition) by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, or by 100% (i.e., absent); and/or those biomarkers in Tables 4, 5, 6, 7, 8, 9A, 9B, 14, 15, 16, 17, 21, 22, 23, 25, 26, 27, 28, and/or 29 that are increased in a given disease or condition (as compared to the control or remission) or that are increased in remission (as compared to the control or a given disease or condition) by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100%, by at least 110%, by at least 120%, by at least 130%, by at least 140%, by at least 150%, or more.

EXAMPLES

I. General Methods

A. Identification of Metabolic Profiles

Each sample was analyzed to determine the concentration of several hundred metabolites. Analytical techniques such as GC-MS (gas chromatography-mass spectrometry) and LC-MS (liquid chromatography-mass spectrometry) were used to analyze the metabolites. Multiple aliquots were simultaneously, and in parallel, analyzed, and, after appropriate quality control (QC), the information derived from each analysis was recombined. Every sample was characterized according to several thousand characteristics, which ultimately amount to several hundred chemical species. The techniques used were able to identify novel and chemically unnamed compounds.

B. Statistical Analysis:

The data was analyzed using several statistical methods to identify molecules (either known, named metabolites or unnamed metabolites) present at differential levels in a definable population or subpopulation (e.g., biomarkers for metabolic syndrome biological samples compared to control biological samples or compared to patients in remission from insulin resistance) useful for distinguishing between the definable populations (e.g., insulin resistance and control, insulin resistance and remission, remission and control). Other molecules (either known, named metabolites or unnamed metabolites) in the definable population or subpopulation were also identified.

Random forest analyses were used for classification of samples into groups (e.g. disease or healthy, insulin resistant or normal insulin sensitivity, atherosclerosis or normal, metabolic syndrome or obese but not metabolic syndrome). Random forests give an estimate of how well we can classify individuals in a new data set into each group, in contrast to a t-test, which tests whether the unknown means for two populations are different or not. Random forests create a set of classification trees based on continual sampling of the experimental units and compounds. Then each observation is classified based on the majority votes from all the classification trees.

Regression analysis was performed using the Random Forest Regression method and the Univariate Correlation/Linear Regression method to build models that are useful to identify the biomarker compounds that are associated with disease or disease indicators (e.g. atherosclerosis, metabolic syndrome, Rd) and then to identify biomarker compounds useful to classify individuals according to for example, the level of glucose utilization as normal, insulin impaired, or insulin resistant. Biomarker compounds that are useful to predict disease or measures of disease (e.g. atherosclerosis, metabolic syndrome, Rd) and that are positively or negatively correlated with disease or measures of disease (e.g. atherosclerosis, metabolic syndrome, Rd) were identified in these analyses. All of the biomarker compounds identified in these analyses were statistically significant ($p<0.05$, $q<0.1$).

Recursive partitioning relates a 'dependent' variable (Y) to a collection of independent ('predictor') variables (X) in order to uncover—or simply understand—the elusive relationship, $Y=f(X)$. The analysis was performed with the JMP program (SAS) to generate a decision tree. The statistical significance of the "split" of the data can be placed on a more quantitative footing by computing p-values, which discern the quality of a split relative to a random event. The significance level of each "split" of data into the nodes or branches of the tree was computed as p-values, which discern the quality of the split relative to a random event. It was given as LogWorth, which is the negative log 10 of a raw p-value.

Statistical analyses were performed with the program "R" available on the worldwide web at the website cran.r-project.org and in JMP 6.0.2 (SAS® Institute, Cary, N.C.).

Example 2

Biomarkers of Pre-Diabetes

2A: Identification of Biomarkers that Correlate with Glucose Disposal

A combination of biomarkers were discovered that, when used in an algorithm, correlate with the glucose disposal rate (i.e. Rd). Further, the initial panel of biomarkers can be narrowed for the development of targeted assays comprised of 15-30 candidate metabolites. An algorithm to predict insulin resistance was developed.

Several studies were conducted to identify biomarkers that correlate with glucose disposal. In a first study, plasma samples were collected from 113 lean, obese or diabetic subjects that had received treatment with one of three different thiazolidinedione drugs (T=troglitazone, R=rosiglitazone, or P=pioglitazone) (Table 1). Base line samples obtained from the subjects prior to treatment (S=baseline) served as controls. One to three plasma samples were obtained from each subject, with samples collected at baseline (all subjects; A), and after 12 weeks (B) or 4 weeks (C) of drug treatment (Table 2). Glucose disposal rate was measured in every subject by the hyperinsulinemic euglycemic (HI) clamp following each blood draw. A total of 198 plasma samples were collected for analysis.

TABLE 1

Gender and treatments of the study 1 cohort.

| GROUP | GENDER | P | R | S | T | Total |
|---|---|---|---|---|---|---|
| Lean | F | 1 | 0 | 1 | 1 | 3 |
|  | M | 7 | 0 | 12 | 8 | 27 |
| Obese | F | 2 | 0 | 3 | 1 | 6 |
|  | M | 7 | 0 | 14 | 8 | 29 |
| Diabetic | F | 0 | 7 | 3 | 1 | 11 |
|  | M | 8 | 13 | 7 | 9 | 37 |
| Total |  | 25 | 20 | 40 | 28 | 113 |

TABLE 2

Treatment and collection time of the study 1 cohort.

| GROUP | TIME | P | R | S | T | Total |
|---|---|---|---|---|---|---|
| L | A | 8 | 0 | 13 | 9 | 30 |
|  | B | 8 | 0 | 0 | 8 | 16 |
| O | A | 9 | 0 | 17 | 9 | 35 |
|  | B | 9 | 0 | 0 | 9 | 18 |
|  | C | 9 | 0 | 0 | 0 | 9 |
| D | A | 8 | 19 | 10 | 9 | 46 |
|  | B | 8 | 20 | 0 | 10 | 38 |
|  | C | 6 | 0 | 0 | 0 | 6 |
| Total |  | 65 | 39 | 40 | 54 | 198 |

In a second study, plasma samples were collected from 402 subjects that were balanced for age and gender. The subjects underwent HI clamp to determine the glucose disposal rate (Rd) of each individual. Based upon an Oral Glucose Tolerance Test (OGTT) or a Fasting Plasma Glucose Test (FPGT) the glucose tolerance of the subjects was designated as Normal glucose tolerance (NGT), Impaired Fasting Glucose (IFG) or Impaired Glucose Tolerance (IGT). The cohort is described in Table 3.

TABLE 3

Cohort Description, Study 2

| | | | Age | | Rd | |
|---|---|---|---|---|---|---|
| Group | Gender | N | Mean | Std Dev | Mean | Std Dev |
| NGT | female | 155 | 44.64 | 8.02 | 8.5 | 3.09 |
|  | male | 148 | 44.03 | 8.62 | 8.38 | 2.77 |
| IFG | female | 5 | 46.8 | 6.53 | 6.13 | 3.32 |
|  | male | 12 | 45.25 | 9.63 | 4.67 | 2.57 |
| IGT | female | 45 | 45.56 | 7.81 | 4.19 | 1.81 |
|  | male | 37 | 45.73 | 7.8 | 4.73 | 2.27 |

Abbreviations
Rd: Glucose disposal rate
NGT: Normal Glucose Tolerant (OGTT, <140 mg/dL or <7.8 mmol/L)
IFG: Impaired Fasting Glucose (Fasting plasma glucose, 100-125 mg/dL or 5.6-6.9 mmol/L)
IGT: Impaired Glucose Tolerant (OGTT, 140-199 mg/dL or 7.8-11.0 mmol/L)

All samples from both studies were analyzed by GC-MS and LC-MS to identify and quantify the small molecules present in the samples. Over 400 compounds were detected in the samples.

Statistical analyses were performed to determine the compounds that are useful as biomarkers. Linear regression was used to correlate the baseline levels of individual compounds with the glucose disposal rate (Rd) as measured by the euglycemic hyperinsulinemic clamp for each individual. This analysis was followed by Random Forest analysis to identify variables most useful for Rd modeling. Then, LASSO regression analysis was performed on the cross-validated variables from the Random Forest analysis to pick the combination of variables useful to predict Rd.

2B: Biomarkers of Glucose Utilization, Molecules Positively and Negatively Correlated with Glucose Disposal Rate (Rd)

Biomarkers were discovered by (1) analyzing blood samples drawn from different groups of human subjects to determine the levels of metabolites in the samples and then (2) statistically analyzing the results to determine those metabolites that were differentially present in the groups of subjects and the metabolites that correlate with the glucose disposal rate, an indicator of insulin sensitivity.

The plasma samples used for the analysis were from the cohorts described in Tables 1, 2 and 3; the subjects had various rates of glucose disposal (Rd). Based on the Rd value subjects were classified as insulin resistant (Rd≤4), insulin impaired (4<Rd<7.5) or insulin sensitive (Rd>7.5). After the levels of metabolites were determined, the data was analyzed using Univariate Correlation/Linear Regression.

As listed below in Table 4, biomarkers were discovered that were correlated with the glucose disposal rate (Rd), an indicator of insulin sensitivity.

Table 4 includes, for each listed biomarker, the p-value determined in the statistical analysis of the data concerning the biomarkers, and the correlation (Con) with Rd. A positive correlation indicates that the level of the biomarker increases as the glucose disposal rate increases. A negative correlation indicates that the level of the biomarker decreases as the glucose disposal rate increases. The range of possible correlations is between negative (−)1.0 and positive (+)1.0. A result of negative (−)1.0 means a perfect negative correlation, a positive (+)1.0 means a perfect positive correlation, and 0 means no correlation at all. The term "Isobar" as used in the table indicates the compounds that could not be distinguished from each other on the analytical platform used in the analysis (i.e., the compounds in an isobar elute at nearly the same time and have similar (and sometimes exactly the same) quant ions, and thus cannot be distinguished).

The results of this analysis showed the individual compounds that are correlated with Rd in both study 1 and study 2; these biomarkers are listed in Table 4. For each biomarker the study, compound name, database identifier, median importance are given. The Library ID (LIB_ID) indicates the analytical platform that was used to measure the biomarker compound. GC-MS is indicated by Library ID (Lib_ID) 50 whereas LC-MS is indicated by Library ID 61, 200, and 201. The biomarker compounds are ordered in the table by the statistical significance of the correlation (P-value). "RF_Rank" refers to the importance score obtained for the biomarker from Random Forest analysis. "Comp_ID" refers to the internal database identifier for that compound in our internal compound library.

TABLE 4

Biomarker correlation with Rd

| Study | Comp_ID | Compound Name | Lib_ID | RF_Rank | Correlation | R-square | P-value |
|---|---|---|---|---|---|---|---|
| 2 | 21044 | 2-hydroxybutyrate (AHB) | 50 | 1 | −4.47E−01 | 0.200 | 1.21E−14 |
| 1 | 20488 | glucose | 50 | 1 | 3.69E−01 | 0.136 | 1.21E−14 |
| 1 | 587 | gluconate | 50 | 2 | −6.11E−01 | 0.373 | 8.73E−13 |
| 1 | 1336 | palmitate (16:0) | 201 | 5 | −5.95E−01 | 0.355 | 4.37E−12 |
| 1 | 33416 | Metabolite - 12064 | 201 | 9 | −5.94E−01 | 0.353 | 5.09E−12 |
| 1 | 20675 | 1,5-anhydroglucitol (1,5-AG) | 201 | 13 | 5.93E−01 | 0.352 | 5.62E−12 |
| 1 | 12751 | glutamate-2 | 50 | 3 | −5.82E−01 | 0.339 | 1.66E−11 |
| 1 | 1121 | margarate (17:0) | 50 | 4 | −5.52E−01 | 0.304 | 2.88E−10 |
| 1 | 584 | mannose | 50 | 6 | −5.50E−01 | 0.303 | 3.28E−10 |
| 1 | 31535 | Bradykinin, hydroxyproline form | 61 | 6 | 1.22E−08 | 0.295 | 7.09E−10 |
| 1 | 21044 | 2-hydroxybutyrate (AHB) | 50 | 14 | −5.40E−01 | 0.292 | 7.75E−10 |
| 1 | 27719 | galactonic acid | 50 | 1 | −5.40E−01 | 0.291 | 8.28E−10 |
| 1 | 16235 | Isobar.19 (1,5-AG etc) | 61 | 31 | 1.96E−08 | 0.287 | 1.43E−09 |
| 1 | 33388 | Metabolite - 12037 | 201 | 19 | −5.32E−01 | 0.283 | 1.58E−09 |
| 2 | 1359 | oleate (18:1(n − 9)) | 201 | 3 | −3.54E−01 | 0.125 | 2.15E−09 |
| 1 | 1358 | stearate (18:0) | 201 | 15 | −5.22E−01 | 0.273 | 3.57E−09 |
| 1 | 27392 | dipalmitin | 50 | 8 | −5.18E−01 | 0.268 | 4.97E−09 |
| 1 | 32569 | Metabolite - 11252 | 200 | 56 | −5.10E−01 | 0.260 | 9.09E−09 |
| 1 | 33232 | Metabolite - 11887 | 201 | 41 | −5.03E−01 | 0.253 | 1.60E−08 |
| 1 | 21047 | 3-methyl-2-oxobutyrate | 201 | 42 | −5.03E−01 | 0.253 | 1.64E−08 |
| 1 | 10737 | Isobar.1 (mannose, glucose etc) | 61 | 36 | 1.72E−07 | 0.254 | 1.75E−08 |
| 1 | 22570 | Metabolite - 9033 | 50 | 62 | −4.98E−01 | 0.248 | 2.24E−08 |
| 1 | 32566 | Metabolite - 11249 | 200 | 70 | −4.95E−01 | 0.245 | 2.82E−08 |
| 1 | 18369 | gamma-glutamylleucine | 200 | 12 | −4.95E−01 | 0.245 | 2.95E−08 |
| 1 | 25602 | Metabolite - 10432 | 50 | 39 | −4.91E−01 | 0.241 | 3.79E−08 |
| 1 | 27722 | erythrose | 50 | 43 | −4.91E−01 | 0.241 | 3.84E−08 |
| 1 | 32630 | oleate (18:1(n − 9)) | 201 | 54 | −4.86E−01 | 0.236 | 5.47E−08 |
| 1 | 27888 | Metabolite - 10609 | 50 | 10 | −4.85E−01 | 0.235 | 5.87E−08 |
| 1 | 24077 | Metabolite - 9727 | 50 | 22 | −4.85E−01 | 0.235 | 6.15E−08 |
| 1 | 32696 | Metabolite - 11379 | 201 | 37 | −4.84E−01 | 0.234 | 6.50E−08 |
| 1 | 12666 | Threonine | 50 | 9 | 4.82E−07 | 0.235 | 7.02E−08 |
| 1 | 32551 | Metabolite - 11234 | 201 | 34 | −4.83E−01 | 0.233 | 7.11E−08 |

TABLE 4-continued

Biomarker correlation with Rd

| Study | Comp_ID | Compound Name | Lib_ID | RF_Rank | Correlation | R-square | P-value |
|---|---|---|---|---|---|---|---|
| 1 | 30288 | Metabolite - 10750 | 50 | 25 | −4.82E−01 | 0.232 | 7.39E−08 |
| 1 | 33413 | Metabolite - 12061 | 201 | 16 | −4.80E−01 | 0.231 | 8.27E−08 |
| 1 | 60 | leucine | 200 | 58 | −4.80E−01 | 0.230 | 8.52E−08 |
| 1 | 21127 | palmitoylglycerol (monopalmitin) | 50 | 60 | −4.75E−01 | 0.225 | 1.23E−07 |
| 1 | 32393 | glutamylvaline | 200 | 11 | −4.74E−01 | 0.225 | 1.26E−07 |
| 1 | 19462 | Metabolite - 6446 | 50 | 30 | −4.74E−01 | 0.225 | 1.28E−07 |
| 1 | 16120 | Metabolite - 4055 | 50 | 38 | −4.73E−01 | 0.223 | 1.44E−07 |
| 1 | 32515 | valine | 200 | 71 | −4.72E−01 | 0.223 | 1.49E−07 |
| 1 | 5628 | Metabolite- 1086 | 61 | 5 | 1.12E−06 | 0.221 | 1.96E−07 |
| 1 | 32704 | Metabolite - 11387 | 200 | 115 | −4.68E−01 | 0.219 | 1.99E−07 |
| 1 | 32571 | Metabolite - 11254 | 200 | 97 | −4.66E−01 | 0.217 | 2.25E−07 |
| 1 | 32501 | dihomo-alpha-linolenate (20:3(n − 3)) | 201 | 26 | −4.66E−01 | 0.217 | 2.31E−07 |
| 1 | 17627 | Metabolite - 4986 | 50 | 24 | −4.61E−01 | 0.213 | 3.05E−07 |
| 1 | 32402 | gondoate (20:1(n − 9)) | 201 | 101 | −4.48E−01 | 0.201 | 7.10E−07 |
| 1 | 32575 | Metabolite - 11258 | 200 | 241 | −4.47E−01 | 0.200 | 7.75E−07 |
| 1 | 32970 | Metabolite - 11653 | 201 | 51 | −4.45E−01 | 0.198 | 8.81E−07 |
| 1 | 16512 | Metabolite- 4275 | 50 | 54 | 3.95E−06 | 0.2 | 8.91E−07 |
| 1 | 12757 | Metabolite - 3078 | 50 | 52 | 4.44E−01 | 0.197 | 9.64E−07 |
| 1 | 27718 | creatine | 200 | 27 | −4.41E−01 | 0.194 | 1.16E−06 |
| 1 | 30832 | Metabolite - 10814 | 50 | 47 | −4.40E−01 | 0.193 | 1.23E−06 |
| 1 | 30290 | Metabolite - 10752 | 50 | 121 | −4.38E−01 | 0.192 | 1.36E−06 |
| 1 | 32703 | Metabolite - 11386 | 200 | 94 | −4.37E−01 | 0.191 | 1.47E−06 |
| 1 | 577 | fructose | 50 | 93 | −4.36E−01 | 0.190 | 1.53E−06 |
| 1 | 22116 | 4-methyl-2-oxopentanoate | 201 | 74 | −4.35E−01 | 0.189 | 1.65E−06 |
| 1 | 33172 | Metabolite - 11827 | 201 | 61 | 4.35E−01 | 0.189 | 1.67E−06 |
| 1 | 22600 | Metabolite - 9043 | 50 | 90 | −4.31E−01 | 0.186 | 2.05E−06 |
| 1 | 1125 | isoleucine | 200 | 137 | −4.31E−01 | 0.185 | 2.14E−06 |
| 1 | 19490 | Metabolite - 6488 | 50 | 32 | −4.28E−01 | 0.183 | 2.46E−06 |
| 1 | 16518 | Metabolite - 4276 | 50 | 18 | −4.26E−01 | 0.182 | 2.78E−06 |
| 1 | 15122 | glycerol | 50 | 45 | −4.25E−01 | 0.181 | 2.93E−06 |
| 1 | 12782 | Metabolite - 3100 | 50 | 17 | −4.23E−01 | 0.179 | 3.39E−06 |
| 1 | 33242 | Metabolite - 11897 | 201 | 77 | −4.21E−01 | 0.177 | 3.75E−06 |
| 1 | 17330 | Metabolite - 4769 | 50 | 35 | 4.21E−01 | 0.177 | 3.86E−06 |
| 1 | 32672 | Metabolite - 02546_200 | 200 | 67 | 4.14E−01 | 0.171 | 5.69E−06 |
| 1 | 33237 | Metabolite - 11892 | 201 | 124 | −4.12E−01 | 0.170 | 6.48E−06 |
| 1 | 32673 | linoleate (18:2(n − 6)) | 201 | 28 | −4.07E−01 | 0.166 | 8.49E−06 |
| 1 | 32545 | Metabolite - 11228 | 201 | 64 | −4.03E−01 | 0.163 | 1.05E−05 |
| 1 | 32751 | Metabolite - 11434 | 201 | 63 | −4.03E−01 | 0.162 | 1.06E−05 |
| 1 | 22895 | Metabolite - 9299 | 50 | 72 | −3.99E−01 | 0.159 | 1.34E−05 |
| 2 | 33488 | 5-alpha-Cholest-7-en-3-beta-ol | 50 | 11 | −2.61E−01 | 0.068 | 1.40E−05 |
| 1 | 32517 | Metabolite - 11203 | 200 | 82 | 3.98E−01 | 0.158 | 1.42E−05 |
| 1 | 33415 | Metabolite - 12063 | 201 | 44 | −3.97E−01 | 0.158 | 1.46E−05 |
| 1 | 32682 | Metabolite - 11365 | 201 | 29 | −3.94E−01 | 0.155 | 1.72E−05 |
| 2 | 32761 | Metabolite - 11444 | 201 | 12 | −2.58E−01 | 0.067 | 1.77E−05 |
| 2 | 32338 | glycine | 50 | 13 | 2.58E−01 | 0.066 | 1.83E−05 |
| 1 | 32749 | Metabolite - 11432 | 201 | 107 | −3.91E−01 | 0.153 | 2.04E−05 |
| 1 | 1110 | arachidonate (20:4(n − 6)) | 50 | 49 | −3.90E−01 | 0.152 | 2.12E−05 |
| 1 | 33138 | Metabolite - 11793 | 200 | 96 | −3.88E−01 | 0.150 | 2.39E−05 |
| 2 | 33447 | palmitoleate (16:1(n − 7)) | 201 | 15 | −2.53E−01 | 0.064 | 2.59E−05 |
| 1 | 32504 | n-3 DPA (22:5(n − 3)) | 201 | 31 | −3.83E−01 | 0.147 | 3.05E−05 |
| 1 | 18868 | Metabolite - 5847 | 50 | 80 | −3.80E−01 | 0.144 | 3.56E−05 |
| 1 | 27738 | threonate | 50 | 53 | 3.75E−01 | 0.141 | 4.62E−05 |
| 1 | 32552 | Metabolite - 11235 | 201 | 73 | −3.75E−01 | 0.140 | 4.68E−05 |
| 1 | 27279 | Metabolite - 10511 | 50 | 7 | −3.69E−01 | 0.136 | 6.11E−05 |
| 1 | 32547 | Metabolite - 11230 | 201 | 163 | −3.68E−01 | 0.135 | 6.55E−05 |
| 1 | 19377 | Metabolite - 6272 | 50 | 194 | −3.66E−01 | 0.134 | 7.40E−05 |
| 1 | 32416 | alpha-linolenate (18:3(n − 3)) | 201 | 65 | −3.66E−01 | 0.134 | 7.41E−05 |
| 1 | 33080 | Metabolite - 11735 | 200 | 50 | 3.63E−01 | 0.132 | 8.27E−05 |
| 1 | 22320 | Metabolite - 8889 | 50 | 177 | 3.62E−01 | 0.131 | 8.90E−05 |
| 1 | 32945 | Metabolite - 11628 | 201 | 197 | −3.60E−01 | 0.130 | 9.48E−05 |
| 2 | 599 | pyruvate | 50 | 18 | −2.31E−01 | 0.053 | 1.00E−04 |
| 2 | 33453 | alpha-ketoglutarate | 50 | 17 | −2.35E−01 | 0.055 | 1.00E−04 |
| 2 | 1105 | linoleate (18:2(n − 6)) | 201 | 16 | −2.44E−01 | 0.059 | 1.00E−04 |
| 1 | 527 | lactate | 50 | 76 | −3.58E−01 | 0.128 | 1.06E−04 |
| 1 | 15676 | 3-methyl-2-oxovalerate | 201 | 216 | −3.53E−01 | 0.125 | 1.35E−04 |
| 1 | 32836 | peptide - HWESASXX | 200 | 33 | −3.47E−01 | 0.121 | 1.76E−04 |
| 1 | 32637 | Metabolite - 11320 | 201 | 100 | 3.45E−01 | 0.119 | 1.91E−04 |
| 2 | 15749 | hydrocinnamic acid | 201 | 21 | 2.26E−01 | 0.051 | 2.00E−04 |
| 2 | 1648 | serine | 50 | 19 | 2.27E−01 | 0.052 | 2.00E−04 |
| 1 | 15500 | carnitine | 200 | 310 | −3.38E−01 | 0.114 | 2.64E−04 |
| 1 | 16496 | pyruvate | 50 | 119 | −3.35E−01 | 0.113 | 3.00E−04 |
| 1 | 32559 | Metabolite - 11242 | 201 | 87 | −3.35E−01 | 0.112 | 3.11E−04 |

TABLE 4-continued

Biomarker correlation with Rd

| Study | Comp_ID | Compound Name | Lib_ID | RF_Rank | Correlation | R-square | P-value |
|---|---|---|---|---|---|---|---|
| 1 | 32632 | Metabolite - 11315 | 200 | 110 | 3.31E−01 | 0.110 | 3.61E−04 |
| 2 | 33587 | Isobar-cis-9-cis-11-trans-11-eicosenoate | 201 | 23 | −2.16E−01 | 0.046 | 4.00E−04 |
| 2 | 32401 | trigonelline (N-methylnicotinate) | 200 | 22 | 2.16E−01 | 0.047 | 4.00E−04 |
| 1 | 21630 | Metabolite - 8402 | 50 | 36 | −3.27E−01 | 0.107 | 4.40E−04 |
| 1 | 16666 | Metabolite - 4365 | 50 | 272 | −3.25E−01 | 0.105 | 4.79E−04 |
| 1 | 16665 | Metabolite - 4364 | 50 | 105 | 3.24E−01 | 0.105 | 4.98E−04 |
| 1 | 19983 | Metabolite - 6955 | 50 | 122 | −3.24E−01 | 0.105 | 4.99E−04 |
| 2 | 32405 | 3-indolepropionate | 50 | 24 | 2.10E−01 | 0.044 | 5.00E−04 |
| 1 | 31509 | Metabolite - 10931 | 50 | 220 | −3.21E−01 | 0.103 | 5.66E−04 |
| 1 | 27889 | Metabolite - 10610 | 50 | 95 | −3.19E−01 | 0.102 | 6.12E−04 |
| 1 | 16650 | Metabolite - 4360 | 50 | 125 | −3.18E−01 | 0.101 | 6.37E−04 |
| 1 | 32644 | Metabolite - 11327 | 200 | 111 | −3.18E−01 | 0.101 | 6.39E−04 |
| 2 | 32445 | 3-methylxanthine | 201 | 26 | 2.06E−01 | 0.042 | 7.00E−04 |
| 1 | 19370 | Metabolite - 6268 | 50 | 179 | 3.14E−01 | 0.099 | 7.47E−04 |
| 1 | 32702 | Metabolite - 11385 | 200 | 221 | −3.13E−01 | 0.098 | 7.73E−04 |
| 1 | 19576 | Metabolite - 6627 | 50 | 135 | −3.12E−01 | 0.098 | 7.97E−04 |
| 2 | 32757 | Metabolite - 11440 | 201 | 28 | −2.03E−01 | 0.041 | 8.00E−04 |
| 1 | 12663 | serine-2 | 50 | 20 | 3.11E−01 | 0.097 | 8.44E−04 |
| 1 | 19494 | Metabolite - 6506 | 50 | 236 | −3.10E−01 | 0.096 | 8.82E−04 |
| 1 | 32628 | palmitoleate (16:1(n − 7)) | 201 | 83 | −3.10E−01 | 0.096 | 8.90E−04 |
| 1 | 59 | histidine | 201 | 355 | −3.09E−01 | 0.096 | 9.00E−04 |
| 1 | 32516 | Metabolite - 11202 | 200 | 134 | 3.08E−01 | 0.095 | 9.69E−04 |
| 1 | 33087 | peptide - RPPGFSPF | 200 | 127 | −3.04E−01 | 0.093 | 1.11E−03 |
| 2 | 31453 | cysteine | 50 | 29 | −1.95E−01 | 0.038 | 1.30E−03 |
| 1 | 16138 | Metabolite - 4080 | 50 | 371 | −3.00E−01 | 0.090 | 1.30E−03 |
| 2 | 24074 | Metabolite - 9706 | 50 | 30 | 1.94E−01 | 0.038 | 1.40E−03 |
| 1 | 32595 | Metabolite - 08993_200 | 200 | 48 | −2.97E−01 | 0.088 | 1.46E−03 |
| 1 | 16509 | Metabolite - 4273 | 50 | 369 | 2.96E−01 | 0.088 | 1.50E−03 |
| 1 | 32735 | Metabolite - 01911_200 | 200 | 146 | −2.96E−01 | 0.088 | 1.53E−03 |
| 1 | 30281 | glycine-2 | 50 | 154 | 2.95E−01 | 0.087 | 1.58E−03 |
| 1 | 32519 | Metabolite - 11205 | 200 | 120 | 2.95E−01 | 0.087 | 1.59E−03 |
| 2 | 33531 | Metabolite - 12116 | 200 | 31 | 1.91E−01 | 0.036 | 1.60E−03 |
| 1 | 64 | phenylalanine | 200 | 21 | −2.90E−01 | 0.084 | 1.89E−03 |
| 1 | 32548 | Metabolite - 11231 | 201 | 131 | −2.90E−01 | 0.084 | 1.89E−03 |
| 1 | 22154 | bradykinin | 200 | 55 | −2.89E−01 | 0.084 | 2.00E−03 |
| 1 | 32348 | 2-aminobutyrate | 200 | 297 | −2.86E−01 | 0.082 | 2.25E−03 |
| 1 | 31537 | peptide - HWESASXXR | 200 | 99 | −2.84E−01 | 0.081 | 2.41E−03 |
| 1 | 32747 | Metabolite - 01142_201 | 201 | 148 | −2.83E−01 | 0.080 | 2.48E−03 |
| 1 | 32550 | Metabolite - 02272_201 | 201 | 176 | 2.82E−01 | 0.080 | 2.59E−03 |
| 2 | 15753 | hippurate | 200 | 35 | 1.82E−01 | 0.033 | 2.70E−03 |
| 2 | 32198 | acetylcarnitine | 200 | 34 | −1.82E−01 | 0.033 | 2.70E−03 |
| 1 | 21188 | stearoylglycerol (monostearin) | 50 | 196 | −2.78E−01 | 0.077 | 2.97E−03 |
| 1 | 12626 | Metabolite - 3003 | 50 | 198 | 2.77E−01 | 0.077 | 3.10E−03 |
| 1 | 32654 | Metabolite - 11337 | 200 | 84 | −2.73E−01 | 0.075 | 3.53E−03 |
| 1 | 21421 | Metabolite - 8214 | 50 | 98 | −2.73E−01 | 0.075 | 3.58E−03 |
| 2 | 32807 | Metabolite - 11490 | 201 | 38 | −1.74E−01 | 0.030 | 4.10E−03 |
| 1 | 606 | uridine | 201 | 230 | −2.69E−01 | 0.072 | 4.16E−03 |
| 1 | 19487 | Metabolite - 6486 | 50 | 78 | −2.69E−01 | 0.072 | 4.18E−03 |
| 1 | 32412 | butyrylcarnitine | 200 | 389 | −2.69E−01 | 0.072 | 4.20E−03 |
| 2 | 32616 | Metabolite - 11299 | 201 | 41 | 1.72E−01 | 0.030 | 4.60E−03 |
| 1 | 25459 | Metabolite - 10395 | 50 | 285 | −2.62E−01 | 0.068 | 5.35E−03 |
| 1 | 33210 | Metabolite - 11865 | 201 | 171 | 2.61E−01 | 0.068 | 5.47E−03 |
| 1 | 27264 | Metabolite - 10503 | 50 | 181 | 2.59E−01 | 0.067 | 5.85E−03 |
| 1 | 32578 | Metabolite - 11261 | 200 | 223 | −2.58E−01 | 0.067 | 5.93E−03 |
| 1 | 32609 | Metabolite - 01345_201 | 201 | 57 | 2.58E−01 | 0.067 | 5.94E−03 |
| 1 | 25609 | Metabolite - 10439 | 50 | 150 | −2.57E−01 | 0.066 | 6.19E−03 |
| 1 | 12768 | Metabolite - 3088 | 50 | 91 | 2.56E−01 | 0.065 | 6.49E−03 |
| 1 | 18120 | Metabolite - 5348 | 50 | 108 | −2.56E−01 | 0.065 | 6.53E−03 |
| 2 | 3147 | xanthine | 50 | 44 | −1.65E−01 | 0.027 | 6.60E−03 |
| 2 | 15990 | glycerophosphorylcholine (GPC) | 200 | 45 | 1.64E−01 | 0.027 | 6.90E−03 |
| 1 | 2730 | gamma-glutamylglutamine | 200 | 109 | 2.51E−01 | 0.063 | 7.60E−03 |
| 1 | 32701 | urate | 200 | 85 | −2.50E−01 | 0.063 | 7.80E−03 |
| 1 | 33227 | Metabolite - 11882 | 201 | 23 | −2.49E−01 | 0.062 | 8.01E−03 |
| 1 | 19934 | inositol | 50 | 227 | −2.44E−01 | 0.059 | 9.62E−03 |
| 1 | 25402 | Metabolite - 10360 | 50 | 129 | −2.44E−01 | 0.059 | 9.63E−03 |
| 1 | 32520 | Metabolite - 11206 | 200 | 218 | −2.43E−01 | 0.059 | 9.91E−03 |
| 2 | 32877 | Metabolite - 11560 | 201 | 49 | 1.56E−01 | 0.024 | 1.02E−02 |
| 1 | 32753 | Metabolite - 09789_201 | 201 | 193 | 2.42E−01 | 0.058 | 1.03E−02 |
| 2 | 1494 | 5-oxoproline | 200 | 50 | 1.56E−01 | 0.024 | 1.04E−02 |
| 1 | 12774 | Metabolite - 3094 | 50 | 199 | −2.41E−01 | 0.058 | 1.05E−02 |
| 1 | 32635 | Metabolite - 11318 | 201 | 175 | 2.41E−01 | 0.058 | 1.05E−02 |

TABLE 4-continued

Biomarker correlation with Rd

| Study | Comp_ID | Compound Name | Lib_ID | RF_Rank | Correlation | R-square | P-value |
|---|---|---|---|---|---|---|---|
| 1 | 20950 | Metabolite - 7846 | 50 | 162 | −2.40E−01 | 0.058 | 1.07E−02 |
| 1 | 32606 | bilirubin | 201 | 289 | 2.40E−01 | 0.058 | 1.08E−02 |
| 1 | 32752 | Metabolite - 11435 | 201 | 184 | −2.38E−01 | 0.057 | 1.16E−02 |
| 1 | 32754 | Metabolite - 11437 | 201 | 186 | 2.34E−01 | 0.055 | 1.29E−02 |
| 1 | 12129 | beta-hydroxyisovalerate | 50 | 140 | −2.34E−01 | 0.055 | 1.30E−02 |
| 1 | 17028 | Metabolite - 4611 | 50 | 130 | −2.34E−01 | 0.055 | 1.31E−02 |
| 1 | 33132 | Metabolite - 11787 | 200 | 251 | −2.34E−01 | 0.055 | 1.31E−02 |
| 1 | 12067 | undecanoate | 201 | 183 | −2.33E−01 | 0.054 | 1.34E−02 |
| 1 | 542 | 3-hydroxybutyrate (BHBA) | 50 | 206 | −2.33E−01 | 0.054 | 1.35E−02 |
| 2 | 33323 | Metabolite - 11977 | 200 | 51 | −1.49E−01 | 0.022 | 1.41E−02 |
| 1 | 512 | asparagine | 50 | 75 | 2.31E−01 | 0.053 | 1.44E−02 |
| 2 | 54 | tryptophan | 200 | 52 | 1.47E−01 | 0.022 | 1.53E−02 |
| 1 | 22032 | Metabolite - 8766 | 50 | 208 | −2.28E−01 | 0.052 | 1.57E−02 |
| 2 | 32792 | Metabolite - 11475 | 201 | 53 | −1.46E−01 | 0.021 | 1.64E−02 |
| 1 | 32625 | Metabolite - 11308 | 201 | 301 | −2.26E−01 | 0.051 | 1.65E−02 |
| 1 | 32813 | Metabolite - 11496 | 201 | 116 | −2.25E−01 | 0.051 | 1.69E−02 |
| 1 | 18477 | glycodeoxycholate | 201 | 192 | −2.24E−01 | 0.050 | 1.76E−02 |
| 2 | 12795 | Metabolite - 3113 | 50 | 54 | 1.44E−01 | 0.021 | 1.78E−02 |
| 1 | 32553 | Metabolite - 03832_201 | 201 | 256 | −2.23E−01 | 0.050 | 1.82E−02 |
| 2 | 33364 | gamma-glutamylthreonine- | 200 | 56 | 1.43E−01 | 0.020 | 1.88E−02 |
| 2 | 2342 | serotonin (5HT) | 200 | 57 | 1.40E−01 | 0.020 | 2.12E−02 |
| 1 | 32855 | Metabolite - 11538 | 201 | 46 | 2.17E−01 | 0.047 | 2.13E−02 |
| 1 | 32197 | 3-(4-hydroxyphenyl)lactate | 201 | 190 | −2.14E−01 | 0.046 | 2.38E−02 |
| 2 | 2132 | citrulline | 200 | 58 | 1.37E−01 | 0.019 | 2.41E−02 |
| 1 | 21049 | 1,6-anhydroglucose | 50 | 136 | 2.13E−01 | 0.045 | 2.43E−02 |
| 1 | 33362 | gamma-glutamylphenylalanine | 200 | 173 | −2.12E−01 | 0.045 | 2.49E−02 |
| 1 | 32452 | propionylcarnitine | 200 | 252 | −2.12E−01 | 0.045 | 2.51E−02 |
| 1 | 32656 | Metabolite - 11339 | 201 | 142 | 2.11E−01 | 0.045 | 2.55E−02 |
| 2 | 1365 | myristate (14:0) | 201 | 59 | −1.36E−01 | 0.018 | 2.59E−02 |
| 1 | 25532 | Metabolite - 10413 | 50 | 226 | −2.10E−01 | 0.044 | 2.63E−02 |
| 2 | 3141 | betaine | 200 | 60 | 1.35E−01 | 0.018 | 2.64E−02 |
| 1 | 32648 | Metabolite - 11331 | 201 | 132 | 2.10E−01 | 0.044 | 2.66E−02 |
| 1 | 25548 | Metabolite - 10419 | 50 | 128 | 2.08E−01 | 0.043 | 2.76E−02 |
| 1 | 32748 | Metabolite - 11431 | 201 | 178 | −2.08E−01 | 0.043 | 2.79E−02 |
| 1 | 33135 | Metabolite - 11790 | 200 | 138 | −2.07E−01 | 0.043 | 2.84E−02 |
| 1 | 31518 | Metabolite - 10933 | 50 | 152 | −2.07E−01 | 0.043 | 2.85E−02 |
| 1 | 19478 | Metabolite - 6467 | 50 | 118 | −2.06E−01 | 0.042 | 2.95E−02 |
| 2 | 33226 | Metabolite - 11881 | 201 | 65 | 1.32E−01 | 0.018 | 2.97E−02 |
| 1 | 32561 | Metabolite - 11244 | 201 | 243 | −2.05E−01 | 0.042 | 2.98E−02 |
| 1 | 11438 | phosphate | 50 | 273 | −2.05E−01 | 0.042 | 3.02E−02 |
| 2 | 1572 | glycerate | 50 | 66 | 1.31E−01 | 0.017 | 3.10E−02 |
| 2 | 33477 | erythronate- | 50 | 67 | 1.31E−01 | 0.017 | 3.13E−02 |
| 1 | 12781 | Metabolite - 3099 | 50 | 141 | −2.03E−01 | 0.041 | 3.18E−02 |
| 1 | 32732 | Metabolite - 11415 | 201 | 155 | 2.03E−01 | 0.041 | 3.22E−02 |
| 1 | 1299 | tyrosine | 200 | 147 | −2.02E−01 | 0.041 | 3.31E−02 |
| 2 | 27256 | Metabolite - 10500 | 50 | 69 | −1.29E−01 | 0.017 | 3.37E−02 |
| 1 | 32346 | glycochenodeoxycholate | 201 | 202 | −2.00E−01 | 0.040 | 3.45E−02 |
| 1 | 27710 | N-acetylglycine | 50 | 126 | 2.00E−01 | 0.040 | 3.47E−02 |
| 1 | 22842 | cholate | 201 | 165 | −1.99E−01 | 0.040 | 3.56E−02 |
| 1 | 31373 | Metabolite - 10878 | 50 | 274 | 1.98E−01 | 0.039 | 3.59E−02 |
| 2 | 16511 | Metabolite - 4274 | 50 | 72 | 1.27E−01 | 0.016 | 3.71E−02 |
| 2 | 15996 | aspartate | 50 | 73 | 1.27E−01 | 0.016 | 3.72E−02 |
| 1 | 33228 | Metabolite - 11883 | 200 | 332 | 1.97E−01 | 0.039 | 3.72E−02 |
| 1 | 18929 | Metabolite - 5907 | 50 | 172 | −1.96E−01 | 0.039 | 3.80E−02 |
| 2 | 569 | caffeine | 200 | 74 | −1.26E−01 | 0.016 | 3.87E−02 |
| 2 | 32971 | Metabolite - 11654 | 200 | 76 | −1.25E−01 | 0.016 | 3.98E−02 |
| 1 | 32795 | Metabolite - 11478 | 201 | 189 | −1.94E−01 | 0.038 | 4.00E−02 |
| 1 | 32868 | glycocholate | 201 | 225 | −1.93E−01 | 0.037 | 4.12E−02 |
| 2 | 18335 | quinate | 50 | 78 | 1.24E−01 | 0.015 | 4.24E−02 |
| 1 | 32587 | Metabolite - 02249_201 | 201 | 89 | −1.91E−01 | 0.036 | 4.38E−02 |
| 1 | 22548 | Metabolite - 9026 | 50 | 337 | −1.91E−01 | 0.036 | 4.39E−02 |
| 1 | 32829 | Metabolite - 03653_200 | 200 | 102 | 1.90E−01 | 0.036 | 4.48E−02 |
| 1 | 33185 | Metabolite - 11840 | 201 | 104 | −1.90E−01 | 0.036 | 4.49E−02 |
| 1 | 20699 | erythritol | 50 | 133 | −1.90E−01 | 0.036 | 4.50E−02 |
| 1 | 32588 | Metabolite - 01327_201 | 201 | 233 | −1.90E−01 | 0.036 | 4.52E−02 |
| 1 | 32848 | Metabolite - 11531 | 201 | 245 | −1.89E−01 | 0.036 | 4.54E−02 |
| 1 | 17389 | Metabolite - 4796 | 50 | 79 | 1.89E−01 | 0.036 | 4.57E−02 |
| 2 | 1493 | ornithine | 50 | 82 | 1.22E−01 | 0.015 | 4.60E−02 |
| 2 | 32418 | myristoleate*14-1-n-5- | 201 | 84 | −1.21E−01 | 0.015 | 4.68E−02 |
| 2 | 15140 | kynurenine | 200 | 83 | 1.21E−01 | 0.015 | 4.68E−02 |
| 1 | 32596 | Metabolite - 02250_200 | 200 | 151 | −1.88E−01 | 0.035 | 4.69E−02 |
| 1 | 33380 | Metabolite - 12029 | 201 | 68 | 1.87E−01 | 0.035 | 4.78E−02 |
| 1 | 27272 | Metabolite - 10505 | 50 | 393 | 1.86E−01 | 0.035 | 4.96E−02 |
| 1 | 63 | cholesterol | 50 | 212 | −1.86E−01 | 0.035 | 4.96E−02 |

TABLE 4-continued

Biomarker correlation with Rd

| Study | Comp_ID | Compound Name | Lib_ID | RF_Rank | Correlation | R-square | P-value |
|---|---|---|---|---|---|---|---|
| 1 | 33198 | Metabolite - 11853 | 201 | 314 | −1.84E−01 | 0.034 | 5.21E−02 |
| 2 | 15630 | N-acetylornithine | 200 | 87 | 1.17E−01 | 0.014 | 5.52E−02 |
| 2 | 19323 | docosahexaenoate (DHA)22-6-n-3- | 201 | 90 | −1.16E−01 | 0.013 | 5.66E−02 |
| 2 | 32760 | Metabolite - 11443 | 201 | 91 | −1.16E−01 | 0.013 | 5.68E−02 |
| 2 | 18392 | theobromine | 200 | 92 | 1.16E−01 | 0.013 | 5.73E−02 |
| 1 | 32514 | Metabolite - 11200 | 200 | 201 | 1.79E−01 | 0.032 | 5.88E−02 |
| 2 | 16634 | Metabolite - 4357 | 50 | 96 | −1.13E−01 | 0.013 | 6.37E−02 |
| 1 | 32518 | Metabolite - 11204 | 200 | 396 | −1.75E−01 | 0.031 | 6.46E−02 |
| 1 | 33081 | Metabolite - 11736 | 200 | 276 | −1.75E−01 | 0.031 | 6.47E−02 |
| 1 | 32850 | Metabolite - 11533 | 201 | 217 | −1.73E−01 | 0.030 | 6.82E−02 |
| 1 | 32671 | Metabolite - 11354 | 200 | 139 | 1.73E−01 | 0.030 | 6.86E−02 |
| 2 | 32786 | Metabolite - 11469 | 200 | 98 | 1.11E−01 | 0.012 | 6.92E−02 |
| 2 | 25522 | Metabolite - 10407 | 50 | 99 | −1.10E−01 | 0.012 | 7.11E−02 |
| 2 | 1649 | valine | 200 | 100 | −1.10E−01 | 0.012 | 7.21E−02 |
| 1 | 32684 | Metabolite - 11367 | 201 | 224 | −1.70E−01 | 0.029 | 7.23E−02 |
| 1 | 553 | cotinine | 200 | 266 | 1.70E−01 | 0.029 | 7.24E−02 |
| 1 | 33389 | Metabolite - 12038 | 201 | 214 | −1.70E−01 | 0.029 | 7.24E−02 |
| 1 | 1563 | chenodeoxycholate | 201 | 370 | −1.70E−01 | 0.029 | 7.39E−02 |
| 2 | 22481 | Metabolite - 8988 | 50 | 102 | 1.09E−01 | 0.012 | 7.48E−02 |
| 1 | 12593 | Metabolite - 2973 | 50 | 149 | 1.67E−01 | 0.028 | 7.76E−02 |
| 1 | 32793 | Metabolite - 11476 | 200 | 383 | −1.67E−01 | 0.028 | 7.80E−02 |
| 1 | 32564 | Metabolite - 11247 | 201 | 249 | 1.67E−01 | 0.028 | 7.84E−02 |
| 2 | 1508 | pantothenate | 200 | 104 | −1.07E−01 | 0.012 | 7.84E−02 |
| 2 | 16829 | Metabolite - 4503 | 50 | 105 | 1.07E−01 | 0.011 | 7.99E−02 |
| 1 | 32652 | Metabolite - 11335 | 200 | 388 | 1.66E−01 | 0.028 | 8.03E−02 |
| 1 | 15365 | glycerol 3-phosphate (G3P) | 50 | 348 | −1.65E−01 | 0.027 | 8.15E−02 |
| 2 | 32875 | Metabolite - 11558 | 200 | 107 | −1.06E−01 | 0.011 | 8.29E−02 |
| 2 | 15506 | choline | 200 | 108 | 1.06E−01 | 0.011 | 8.32E−02 |
| 2 | 32492 | caprylate-8-0- | 201 | 109 | 1.05E−01 | 0.011 | 8.51E−02 |
| 1 | 16287 | Metabolite - 2800 | 50 | 209 | −1.63E−01 | 0.027 | 8.51E−02 |
| 1 | 1114 | deoxycholate | 201 | 106 | −1.63E−01 | 0.027 | 8.63E−02 |
| 2 | 32619 | Metabolite - 11302 | 201 | 110 | 1.05E−01 | 0.011 | 8.64E−02 |
| 1 | 27275 | Metabolite - 10507 | 50 | 182 | 1.62E−01 | 0.026 | 8.74E−02 |
| 1 | 32718 | Metabolite - 01342_200 | 200 | 167 | −1.61E−01 | 0.026 | 8.94E−02 |
| 2 | 33403 | Metabolite - 12051 | 200 | 112 | −1.03E−01 | 0.011 | 8.96E−02 |
| 1 | 32769 | Metabolite - 11452 | 201 | 278 | −1.59E−01 | 0.025 | 9.31E−02 |
| 2 | 32756 | Metabolite - 02276_201 | 201 | 116 | 1.01E−01 | 0.010 | 9.72E−02 |
| 2 | 33225 | Metabolite - 11880 | 201 | 118 | −1.01E−01 | 0.010 | 9.88E−02 |
| 1 | 32839 | Metabolite - 11522 | 201 | 144 | 1.57E−01 | 0.025 | 9.89E−02 |

2C: Variable Selection with Random Forest for Rd Modeling 50 iterations of a random forest analysis with complete 5-fold cross-validation regressions (for Study 1 this analysis included only baseline data, n=111; while for Study 2 all samples were included, n=402) was carried out as follows:

80% of the data was used as the training set to run 1000 regression random forests, record the importance scores and rank the variables according to their importance scores;

Next, four variables at a time were deleted starting from the lowest ranked variables, then the random forest was run with the remaining variables on the training set to predict the remaining 20% of the data (i.e., test set). The error and R-square for each was recorded.

For each variable, the mean/median importance score and rank across all run was calculated.

Variable selection is more or less stable for the approximately first 30-60 variables.

Figure 1:
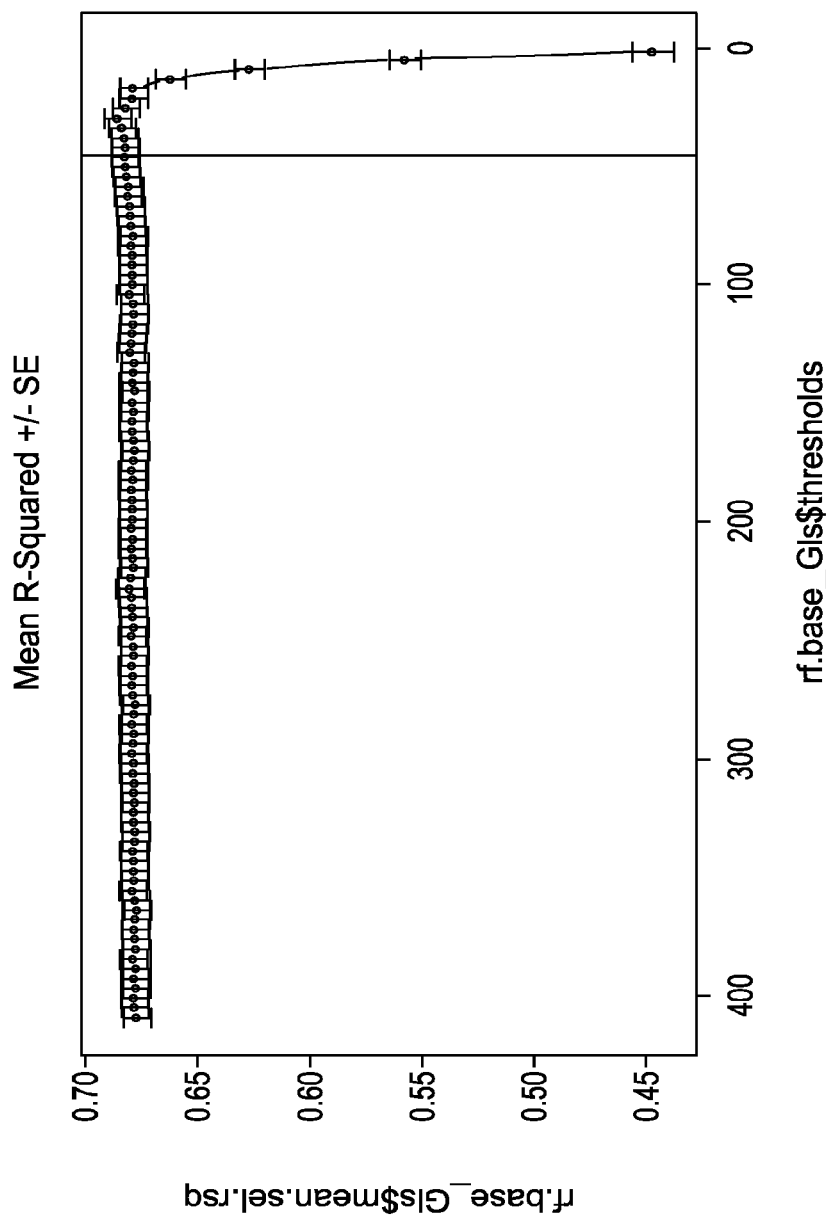
FIG. 1 provides a graph showing the mean $R^2$ values of Rd correlation as a function of the number of metabolites. As the number of compounds increases (from right to left), the r-square value for Rd correlation (Y) increases until it reaches an optimal number (n<30), indicating that variable selection is more or less stable for the approximately first 30 variables.
Figure 2:
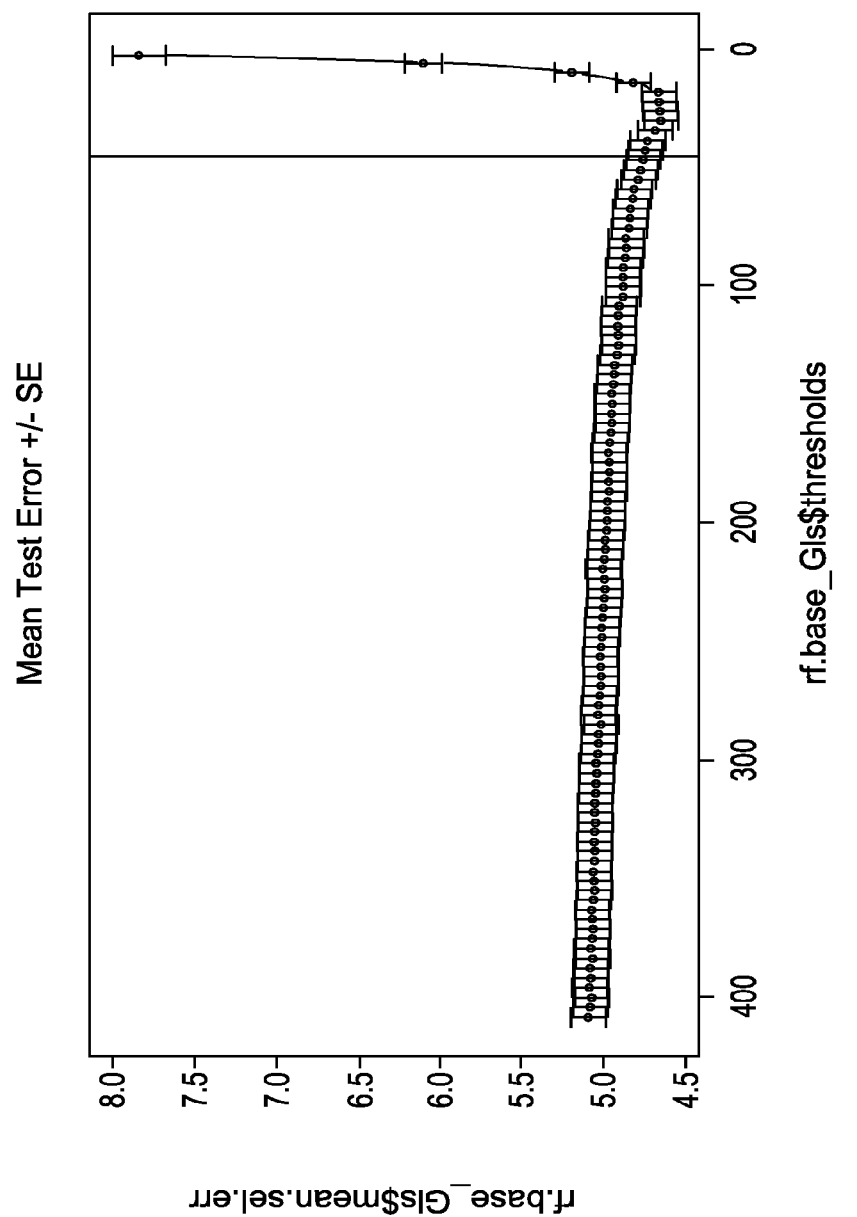
FIG. 2 provides a graph showing the mean $R^2$ values of Rd correlation as a function of the number of metabolites. As the number of compounds increases (from right to left), test error for Rd correlation (Y) decreases until it reach an optimal number (n<30), indicating that variable selection is more or less stable for the approximately first 30 variables.

2D: Estimate of the Number of Metabolites Considered Significant for Rd Correlation The mean R-square values remain constantly high and the corresponding errors remain consistently low as the number of metabolites reaches approximately 30 or more (FIGS. 1 and 2), suggesting that a total of approximately 30 metabolites may be sufficient for construction of an algorithm to correlate with Rd, although it may also be possible to construct an algorithm to correlate with Rd based on a combination of less than seven metabolites. As a result, only the top 30 to 50 cross-validated compounds were selected for regression analyses.

Based on random forest variable selection procedures, the biomarker compounds that are considered reliably significant for construction of an algorithm for Rd correlation were identified. The RF score for each of the biomarker compounds is listed in the column headed "RF_Rank" in Table 4.

2E: Modeling of Rd Correlation with Top Compounds

Figure 3:
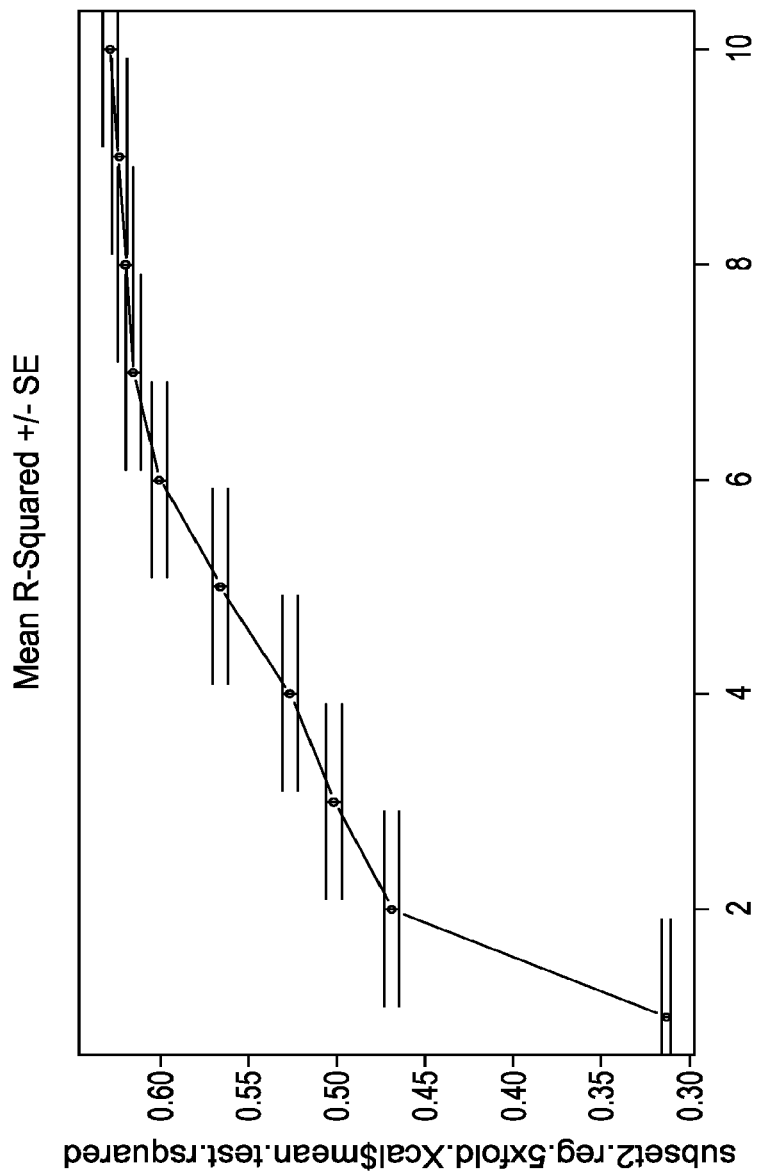
FIG. 3 provides a graph showing the mean R-square values (Y-axis) of Rd correlation as a function of the number of metabolites (X-axis).
Figure 4:
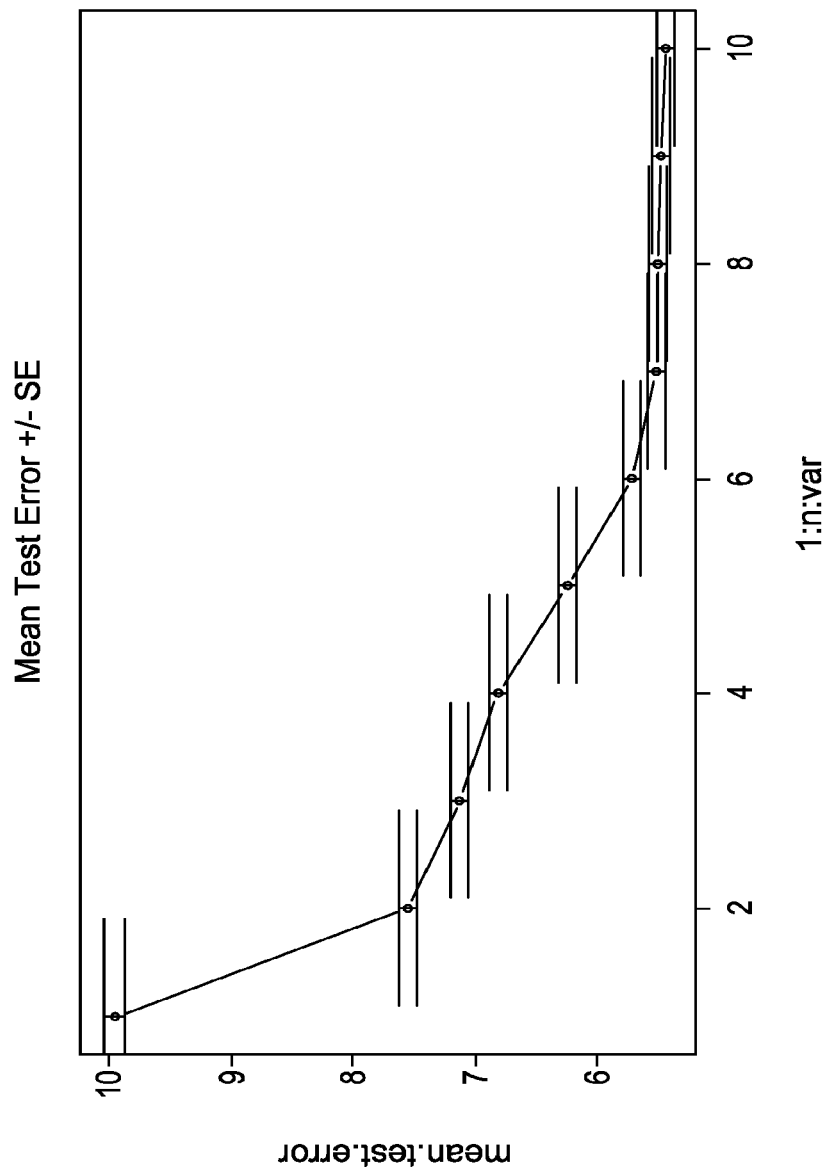
FIG. 4 provides a graph showing the mean test error values (Y-axis) of Rd correlation as a function of the number of metabolites (X-axis).

Based on the modeling experiments, the mean R-square values remain constantly high and the corresponding errors remain consistently low as the number of metabolites reaches seven and above (FIGS. 3 and 4), suggesting that a combination of seven metabolites will be sufficient for construction of an algorithm to correlate with Rd, although it may also be possible to construct an algorithm to correlate with Rd based on a combination of less than seven metabolites.

2F: LASSO Regression

Only cross-validated variables from the random forest analyses above were used for LASSO regression to pick the best combination of variables to predict Rd. The most appropriate transformation of the cross-validated variables was also considered for the LASSO regression.

LASSO regression analysis based upon the cohort in study 1 provided one of the best models of Rd regression with three to nine variables and cross-validated r-square values for the correlation. The best r-square value approaches 0.68 with seven to eight metabolites using the non-transformed data (Table 5) and approaches 0.69-0.70 with the same number of metabolites with appropriate transformation of each variable (Table 6).

TABLE 5

LASSO regression with non-transformed data.

| Number of Variables | 3 | 4 | 5 | 6 | 7 | 8 | 9 |
|---|---|---|---|---|---|---|---|
| LASSO Maximum R-square | 0.355 | 0.422 | 0.600 | 0.643 | 0.670 | 0.720 | 0.779 |
| Cross-Validated R-square | 0.586 | 0.600 | 0.653 | 0.651 | 0.681 | 0.687 | 0.665 |
| 1,5-Anhydro-D-glucitol | ✓ | ✓ | ✓ | ✓ | ✓ | ✓ | ✓ |
| Bradykinin-hydroxyproline | ✓ | ✓ | ✓ | ✓ | ✓ | ✓ | |
| Palmitate | ✓ | ✓ | ✓ | ✓ | ✓ | ✓ | ✓ |
| Metabolite-9727 | | | ✓ | ✓ | ✓ | ✓ | ✓ |
| Glu-Val | | | ✓ | ✓ | ✓ | ✓ | ✓ |
| Threonine | | ✓ | | | ✓ | ✓ | ✓ |
| Dihydroimidazole-4-acetate | | | | | ✓ | ✓ | ✓ |
| Mannose | | | | | | ✓ | |
| 2-Hydroxybutyrate | | | | ✓ | | | |
| Isobar-56** | | | | | | | ✓ |
| Serine | | | | | | | ✓ |

Note:
**Isobar 56 includes DL-pipecolic acid and 1-amino-1-cyclopentanecarboxylic acid that can be separated

TABLE 6

LASSO regression with transformed data.

| Number of Variables | 3 | 4 | 5 | 6 | 7 | 8 | 9 |
|---|---|---|---|---|---|---|---|
| LASSO Maximum R-square | 0.355 | 0.422 | 0.600 | 0.643 | 0.670 | 0.720 | 0.779 |
| Cross-Validated R-square | 0.592 | 0.603 | 0.662 | 0.657 | 0.692 | 0.702 | 0.684 |
| 1,5-Anhydro-D-glucitol | ✓ | ✓ | ✓ | ✓ | ✓ | ✓ | ✓ |
| Bradykinin-hydroxyproline form | ✓ | ✓ | ✓ | ✓ | ✓ | ✓ | ✓ |
| Log(Palmitate) | ✓ | ✓ | ✓ | ✓ | ✓ | ✓ | ✓ |
| Log(Metabolite-9727) | | | ✓ | ✓ | ✓ | ✓ | ✓ |
| Glu-Val | | | ✓ | ✓ | ✓ | ✓ | ✓ |
| Threonine | | ✓ | | | ✓ | ✓ | ✓ |
| Log(Dihydroimidaz-ole-4-acetate) | | | | | ✓ | ✓ | ✓ |
| Log(Mannose) | | | | | | ✓ | |
| Log(2-Hydroxybuty-rate) | | | | ✓ | | | |
| Isobar-56** | | | | | | | ✓ |
| Serine | | | | | | | ✓ |

Note:
**Isobar 56 includes DL-pipecolic acid and 1-amino-1-cyclopentanecarboxylic The R-square for the correlation of Rd with 7-8 metabolites approaches 0.70 with cross-validation in an independent cohort.

LASSO analysis based on the cohort in study 1 provided the best models of Rd regression with 3-9 variables with cross-validated r-square values for the correlation of another set approaching 0.68 with 7-8 metabolites using the non-transformed data as shown in Table 7.

TABLE 7

LASSO regression with non-transformed data.

| | Number of Variables | | | | | | |
|---|---|---|---|---|---|---|---|
| | 3 | 4 | 5 | 6 | 7 | 8 | 9 |
| Cross-Validated R-square | 0.617 | 0.636 | 0.650 | 0.656 | 0.678 | 0.681 | 0.685 |
| 1,5-Anhydro-D-glucitol | ✓ | ✓ | ✓ | ✓ | ✓ | ✓ | ✓ |
| Palmitate | ✓ | ✓ | ✓ | ✓ | ✓ | ✓ | ✓ |
| Glu-Val | ✓ | ✓ | ✓ | ✓ | ✓ | ✓ | ✓ |
| Serine | | ✓ | ✓ | ✓ | ✓ | ✓ | ✓ |
| Margarate | | | ✓ | ✓ | ✓ | ✓ | ✓ |
| X-9727 | | | | | ✓ | ✓ | ✓ |
| X-10511 | | | | | | ✓ | ✓ |
| Etio cholanolone sulfate (X-1345) | | | | | | ✓ | ✓ |
| Gamma tocopherol (X-4276) | | | | | | | ✓ |
| Creatine | | | | | | | ✓ |

2G: Models Predictive of Insulin Resistance.

In study 2, compounds identified as important in building models to predict Rd by Random Forest and Lasso Regression are listed in Table 4. The cross-validated compounds were then selected for regression analysis along with clinical measurements (e.g. fasting insulin, fasting pro-insulin, fasting free fatty acids (FFA), fasting C-peptide, HDL cholesterol, LDL cholesterol, fasting plasma glucose, adiponectin, BMI, PYY, etc.) Each regression method and the Univariate Correlation/Linear Regression method model was then used to predict Rd for each individual, which was in turn used to classify individuals according to the level of glucose utilization as normal, insulin impaired, or insulin resistant. Samples from ninety percent of the subjects were used to build the model and samples from the remaining ten percent of the subjects were used to test the predictive power of the model. Biomarker compounds that are useful to predict Rd and that are positively or negatively correlated with Rd were identified in these analyses. These markers are useful to predict insulin resistance. All of the biomarker compounds are statistically significant ($p<0.05$) in each of the regression models.

The models generated using this analytical approach are summarized in Table 8. The sensitivity, specificity and predictive power (positive, PPV and negative, NPV) of the models are shown in Table 8. The sensitivity of the models ranges from about 54% to about 63% and the specificity ranges from about 63% to greater than 95%. The PPV range is from about 78% to about 94% and the NPV from greater than about 79% to greater than about 83%.

TABLE 8

Metabolite Biomarkers and models that are predictive of Insulin Resistance as determined by glucose disposal rate (Rd).

| Model No. | No. Variables | R-square | Sensitivity | Specificity | PPV | NPV | Variable 1 | Variable 2 | Variable 3 |
|---|---|---|---|---|---|---|---|---|---|
| 1 | 8 | 0.5486 | 59.84 | 95.51 | 87.36 | 82.11 | BMI | Fasting Insulin | Fasting_Proinsulin |
| 2 | 9 | 0.4937 | 55.12 | 95.51 | 86.42 | 80.41 | Fasting Insulin | Oleate | BMI |

TABLE 8-continued

Metabolite Biomarkers and models that are predictive of Insulin Resistance as determined by glucose disposal rate (Rd).

| | | | | | | | | | |
|---|---|---|---|---|---|---|---|---|---|
| 3 | 7 | 0.5398 | 59.06 | 95.10 | 86.21 | 81.75 | BMI | Fasting Insulin | Fasting Proinsulin |
| 4 | 9 | 0.5137 | 56.69 | 95.10 | 85.71 | 80.90 | BMI | Fasting Insulin | 2Hydroxybutyrate |
| 5 | 9 | 0.5308 | 60.63 | 95.10 | 86.52 | 82.33 | Fasting Insulin | Fasting Proinsulin | Glu1.Val |
| 6 | 7 | 0.5122 | 56.69 | 94.69 | 84.71 | 80.84 | BMI | Fasting Insulin | Pyruvate |
| 7 | 8 | 0.5179 | 56.69 | 94.69 | 84.71 | 80.84 | BMI | Fasting Insulin | Pyruvate |
| 8 | 9 | 0.5179 | 56.69 | 94.69 | 84.71 | 80.84 | BMI | Fasting Insulin | Lactate |
| 9 | 7 | 0.5380 | 62.20 | 94.69 | 85.87 | 82.86 | BMI | Fasting Insulin | Fasting Proinsulin |
| 10 | 7 | 0.5458 | 61.42 | 94.69 | 85.71 | 82.56 | BMI | Fasting Insulin | Fasting Proinsulin |
| 11 | 8 | 0.5531 | 60.63 | 94.69 | 85.56 | 82.27 | BMI | Fasting Insulin | Fasting Proinsulin |
| 12 | 8 | 0.5534 | 59.84 | 94.69 | 85.39 | 81.98 | BMI | Fasting Insulin | Fasting Proinsulin |
| 13 | 9 | 0.5596 | 62.99 | 94.69 | 86.02 | 83.15 | BMI | Fasting Insulin | Fasting Proinsulin |
| 14 | 9 | 0.5584 | 59.84 | 94.69 | 85.39 | 81.98 | BMI | Fasting Insulin | Fasting Proinsulin |
| 15 | 9 | 0.5580 | 59.84 | 94.69 | 85.39 | 81.98 | BMI | Fasting Insulin | Fasting Proinsulin |
| 16 | 9 | 0.5223 | 56.69 | 94.69 | 84.71 | 80.84 | BMI | Fasting Insulin | 2Hydroxybutyrate |
| 17 | 9 | 0.5317 | 60.63 | 94.69 | 85.56 | 82.27 | Fasting Insulin | Glu1.Val | BMI |
| 18 | 9 | 0.5106 | 57.48 | 94.29 | 93.91 | 81.05 | BMI | Fasting Insulin | 2Hydroxybutyrate |
| 19 | 9 | 0.5167 | 55.91 | 94.29 | 83.53 | 80.49 | BMI | Fasting Insulin | 2Hydroxybutyrate |
| 20 | 9 | 0.5368 | 61.42 | 94.29 | 84.78 | 82.50 | Fasting Insulin | Fasting Proinsulin | BMI |
| 21 | 9 | 0.5253 | 59.84 | 94.29 | 84.44 | 81.91 | Creatine | Glycine | Fasting Insulin |
| 22 | 9 | 0.5260 | 58.27 | 94.29 | 84.09 | 81.34 | Fasting Insulin | Fasting Proinsulin | Pyruvate |
| 23 | 9 | 0.4943 | 56.69 | 94.29 | 83.72 | 80.77 | Fasting Insulin | BMI | FPG |
| 24 | 9 | 0.4864 | 55.12 | 94.29 | 83.33 | 80.21 | Fasting Insulin | BMI | FPG |
| 25 | 9 | 0.4958 | 54.33 | 94.29 | 83.13 | 79.93 | Triglycerides | Linolenate | Fasting Insulin |
| 26 | 7 | 0.5401 | 57.48 | 94.29 | 83.91 | 81.05 | BMI | Fasting Insulin | Fasting FFA |
| 27 | 8 | 0.5499 | 59.06 | 94.29 | 84.27 | 81.63 | BMI | Fasting Insulin | Fasting Proinsulin |
| 28 | 8 | 0.5492 | 59.06 | 94.29 | 84.27 | 81.63 | BMI | Fasting Insulin | Fasting Proinsulin |
| 29 | 9 | 0.5578 | 62.99 | 94.29 | 85.11 | 83.09 | BMI | Fasting Insulin | Fasting Proinsulin |
| 30 | 9 | 0.5576 | 62.99 | 94.29 | 85.11 | 83.09 | BMI | Fasting Insulin | Fasting Proinsulin |
| 31 | 9 | 0.5615 | 59.84 | 94.29 | 84.44 | 81.91 | BMI | Fasting Insulin | Fasting Proinsulin |
| 32 | 9 | 0.4972 | 60.63 | 93.88 | 83.70 | 82.14 | BMI | Fasting Insulin | 2Hydroxybutyrate |
| 33 | 9 | 0.5060 | 55.91 | 93.88 | 82.56 | 80.42 | BMI | Fasting Insulin | 2Hydroxybutyrate |
| 34 | 9 | 0.5635 | 62.99 | 93.88 | 84.21 | 83.03 | Fasting Insulin | Fasting Proinsulin | Gamma.Glu.Leu |
| 35 | 9 | 0.4996 | 55.12 | 93.88 | 82.35 | 80.14 | Fasting Insulin | Fasting_C_Peptide | Lactate |
| 36 | 9 | 0.4983 | 54.33 | 93.88 | 82.14 | 79.86 | Fasting Insulin | Lactate | BMI |
| 37 | 7 | 0.5136 | 55.12 | 93.88 | 82.35 | 80.14 | BMI | Fasting Insulin | .Betaine |
| 38 | 8 | 0.5177 | 55.91 | 93.88 | 82.56 | 80.42 | BMI | Fasting Insulin | Pyruvate |
| 39 | 8 | 0.5183 | 54.33 | 93.88 | 82.14 | 79.86 | BMI | Fasting Insulin | .Betaine |
| 40 | 9 | 0.5177 | 55.91 | 93.88 | 82.56 | 80.42 | BMI | Fasting Insulin | .Galactonate |
| 41 | 9 | 0.5183 | 54.33 | 93.88 | 82.14 | 79.86 | BMI | Fasting Insulin | Pyruvate |
| 42 | 7 | 0.5390 | 62.99 | 93.88 | 84.21 | 83.03 | BMI | Fasting Insulin | Fasting Proinsulin |
| 43 | 7 | 0.5382 | 62.20 | 93.88 | 84.04 | 82.73 | BMI | Fasting Insulin | Fasting Proinsulin |
| 44 | 8 | 0.5479 | 61.42 | 93.88 | 83.87 | 82.44 | BMI | Fasting Insulin | Fasting Proinsulin |
| 45 | 8 | 0.5513 | 59.84 | 93.88 | 83.52 | 81.85 | BMI | Fasting Insulin | Fasting Proinsulin |
| 46 | 9 | 0.5595 | 61.42 | 93.88 | 83.87 | 82.44 | BMI | Fasting Insulin | Fasting Proinsulin |
| 47 | 9 | 0.5575 | 59.06 | 93.88 | 83.33 | 81.56 | BMI | Fasting Insulin | Fasting Proinsulin |
| 48 | 9 | 0.4936 | 56.69 | 93.47 | 81.82 | 80.63 | BMI | Fasting Insulin | 2Hydroxybutyrate |
| 49 | 9 | 0.5198 | 55.91 | 93.47 | 81.61 | 80.35 | BMI | Fasting Insulin | 2Hydroxybutyrate |

TABLE 8-continued

Metabolite Biomarkers and models that are predictive of Insulin Resistance as determined by glucose disposal rate (Rd).

| | | | | | | | | | |
|---|---|---|---|---|---|---|---|---|---|
| 50 | 9 | 0.5211 | 58.27 | 93.47 | 82.22 | 81.21 | Fasting Insulin | Glutamate | BMI |
| 51 | 9 | 0.5167 | 58.27 | 93.47 | 82.22 | 81.21 | Fasting Insulin | Oleoyl.LPC | Pyruvate |
| 52 | 7 | 0.5148 | 57.48 | 93.47 | 82.02 | 80.92 | BMI | Fasting Insulin | .Gamma.Glu.Leu |
| 53 | 7 | 0.5128 | 55.91 | 93.47 | 81.61 | 80.35 | BMI | Fasting Insulin | .Glu1.Val |
| 54 | 7 | 0.5139 | 55.12 | 93.47 | 81.40 | 80.07 | BMI | Fasting Insulin | .Gamma.Glu.Leu |
| 55 | 8 | 0.5188 | 57.48 | 93.47 | 82.02 | 80.92 | BMI | Fasting Insulin | .Betaine |
| 56 | 8 | 0.5194 | 55.91 | 93.47 | 81.61 | 80.35 | BMI | Fasting Insulin | .Gamma.Glu.Leu |
| 57 | 8 | 0.5178 | 54.33 | 93.47 | 81.18 | 79.79 | BMI | Fasting Insulin | .Betaine |
| 58 | 9 | 0.5188 | 57.48 | 93.47 | 82.02 | 80.92 | BMI | Fasting Insulin | .Betaine |
| 59 | 9 | 0.5194 | 55.91 | 93.47 | 81.61 | 80.35 | BMI | Fasting Insulin | .Betaine |
| 60 | 9 | 0.5178 | 54.33 | 93.47 | 81.18 | 79.79 | BMI | Fasting Insulin | Pyruvate |
| 61 | 7 | 0.5396 | 62.99 | 93.47 | 83.33 | 82.97 | BMI | Fasting Insulin | Fasting Proinsulin |
| 62 | 8 | 0.5547 | 62.99 | 93.47 | 83.33 | 82.97 | BMI | Fasting Insulin | Fasting Proinsulin |
| 63 | 8 | 0.5493 | 62.20 | 93.47 | 83.16 | 82.67 | BMI | Fasting Insulin | Fasting Proinsulin |
| 64 | 8 | 0.5525 | 60.63 | 93.47 | 82.80 | 82.08 | BMI | Fasting Insulin | Fasting Proinsulin |
| 65 | 9 | 0.5615 | 62.20 | 93.47 | 83.16 | 82.67 | BMI | Fasting Insulin | Fasting Proinsulin |
| 66 | 9 | 0.5589 | 61.42 | 93.47 | 82.98 | 82.37 | BMI | Fasting Insulin | Fasting Proinsulin |
| 67 | 7 | 0.5127 | 55.12 | 93.06 | 80.46 | 80.00 | BMI | Fasting Insulin | .Gamma.Glu.Leu |
| 68 | 8 | 0.5179 | 55.91 | 93.06 | 80.68 | 80.28 | BMI | Fasting Insulin | .Betaine |
| 69 | 9 | 0.5179 | 55.91 | 93.06 | 80.68 | 80.28 | BMI | Fasting Insulin | .Gamma.Glu.Leu |
| 70 | 7 | 0.5388 | 57.48 | 93.06 | 81.11 | 80.85 | BMI | Fasting Insulin | Fasting FFA |
| 71 | 9 | 0.5081 | 59.06 | 93.06 | 81.52 | 81.43 | Fasting Insulin | Fasting_C_Peptide | BMI |
| 72 | 7 | 0.5157 | 56.69 | 92.65 | 80.00 | 80.50 | BMI | Fasting Insulin | .Betaine |
| 73 | 7 | 0.5124 | 56.69 | 92.65 | 80.00 | 80.50 | BMI | Fasting Insulin | .Betaine |
| 74 | 7 | 0.5131 | 55.91 | 92.65 | 79.78 | 80.21 | BMI | Fasting Insulin | .Betaine |
| 75 | 7 | 0.5121 | 55.91 | 92.65 | 79.78 | 80.21 | BMI | Fasting Insulin | Pyruvate |
| 76 | 8 | 0.5187 | 58.27 | 92.65 | 80.43 | 81.07 | BMI | Fasting Insulin | .Betaine |
| 77 | 8 | 0.5183 | 55.12 | 92.65 | 79.55 | 79.93 | BMI | Fasting Insulin | Pyruvate |
| 78 | 8 | 0.5176 | 55.12 | 92.65 | 79.55 | 79.93 | BMI | Fasting Insulin | .Betaine |
| 79 | 9 | 0.5187 | 58.27 | 92.65 | 80.43 | 81.07 | BMI | Fasting Insulin | Pyruvate |
| 80 | 9 | 0.5183 | 55.12 | 92.65 | 79.55 | 79.93 | BMI | Fasting Insulin | .Gamma.Glu.Leu |
| 81 | 9 | 0.5176 | 55.12 | 92.65 | 79.55 | 79.93 | BMI | Fasting Insulin | .Betaine |
| 82 | 7 | 0.5383 | 57.48 | 92.65 | 80.22 | 80.78 | BMI | Fasting Insulin | Fasting FFA |
| 83 | 9 | 0.5071 | 55.91 | 92.65 | 79.78 | 80.21 | BMI | Fasting Insulin | 2Hydroxybutyrate |
| 84 | 9 | 0.5137 | 58.27 | 92.65 | 80.43 | 81.07 | Fasting Insulin | Oleoyl.LPC | BMI |
| 85 | 9 | 0.5153 | 53.54 | 92.65 | 79.07 | 79.37 | Fasting Insulin | BMI | Galactonate |
| 86 | 9 | 0.4879 | 56.69 | 92.24 | 79.12 | 80.43 | BMI | Fasting Insulin | 2Hydroxybutyrate |
| 87 | 9 | 0.5032 | 55.91 | 91.84 | 78.02 | 80.07 | Fasting Insulin | Fasting_C_Peptide | Lactate |
| 88 | 9 | 0.4877 | 55.91 | 91.84 | 78.02 | 80.07 | Fasting Insulin | Lactate | Oleate |
| 89 | 7 | 0.5390 | 57.48 | 91.84 | 78.49 | 80.65 | Fasting Insulin | Fasting Insulin | Fasting FFA |
| 90 | 9 | 0.5122 | 52.87 | 62.63 | 86.05 | 81.47 | Fasting Insulin | Fasting Insulin | 2Hydroxybutyrate |

| Model No. | Variable 4 | Variable 5 | Variable 6 | Variable 7 | Variable 8 | Variable 9 |
|---|---|---|---|---|---|---|
| 1 | 57 Fasting FFA | Adiponectin | Glu1Val | Betaine | 2Hydroxybutyrate | |
| 2 | LDL_Cholesterol | FPG | Linoleate | 2Hydroxybutyrate | Linolenate | HDL Cholesterol |
| 3 | Fasting FFA | Adiponectin | Glu1Val | 2Hydroxybutyrate | | |
| 4 | Glu1.Val. | Creatine | Pyruvate | Gluconate | Glycine | Linolenate |
| 5 | BMI | Betaine | 2Hydroxybutyrate | Oleate | Adiponectin | Gluconate |
| 6 | Betaine | .Gamma.Glu.Leu | 2Hydroxybutyrate | Gluconate | | |
| 7 | .Gamma.Glu.Leu | 2Hydroxybutyrate | .Linoyl.LPC | Creatine | Gluconate | |

TABLE 8-continued

Metabolite Biomarkers and models that are predictive of Insulin Resistance as determined by glucose disposal rate (Rd).

| | | | | | | |
|---|---|---|---|---|---|---|
| 8 | Pyruvate | Betaine | .Galactonate | 2Hydroxybutyrate | .Linolyl.LPC | Gluconate |
| 9 | Fasting FFA | HDL Cholesterol | .Gamma.Glu. Leu | 2Hydroxybutyrate | | |
| 10 | Fasting FFA | Adiponectin | .Gamma.Glu. Leu | 2Hydroxybutyrate | | |
| 11 | Fasting FFA | Adiponectin | .Gamma.Glu. Leu | 2Hydroxybutyrate | Creatine | |
| 12 | Fasting FFA | Adiponectin | .Betaine | .Gamma.Glu. Leu | 2Hydroxybutyrate | |
| 13 | Fasting FFA | Adiponectin | .Betaine | .Gamma.Glu. Leu | 2Hydroxybutyrate | Gluconate |
| 14 | Fasting FFA | Adiponectin | .Gamma.Glu. Leu | 2Hydroxybutyrate | Creatine | Gluconate |
| 15 | .LDL_Cholesterol | Fasting FFA | Adiponectin | .Gamma.Glu. Leu | .Linoleate | 2Hydroxybutyrate |
| 16 | Gamma.Glu. Leu | lin__Linolyl.LPC | Betaine | Pyruvate | Gluconate | X9033 |
| 17 | Betaine | Fasting Proinsulin | 2Hydroxybutyrate | Linolyl.LPC | Adiponectin | Gluconate |
| 18 | Pyruvate | Oleoyl.LPC | Gluconate | Oleate | Galactonate | Linoleate |
| 19 | Betaine | Glul.Val | Creatine | Gluconate | lin__Glycine | X9033 |
| 20 | Betaine | Gamma.Glu. Leu | 2Hydroxybutyrate | Oleate | Adiponectin | Gluconate |
| 21 | Fasting Proinsulin | Glul.Val | BMI | 2Hydroxybutyrate | Adiponectin | Gluconate |
| 22 | BMI | FPG | 2Hydroxybutyrate | Lactate | Adiponectin | Gluconate |
| 23 | Linoleate | 2Hydroxybutyrate | Linolenate | HDL Cholesterol | Hepadecenate | Oleate |
| 24 | Galactonate | 1.5.Anhydroglucitol | 2Hydroxybutyrate | Lactate | Oleate | HDL Cholesterol |
| 25 | Lactate | BMI | LDL_Cholesterol | FPG | 1.5.Anhydroglucitol | 2Hydroxybutyrate |
| 26 | Adiponectin | .Gamma.Glu. Leu | 2Hydroxybutyrate | Creatine | | |
| 27 | .FPG | Fasting FFA | Adiponectin | .Gamma.Glu. Leu | 2Hydroxybutyrate | |
| 28 | .LDL_Cholesterol | Fasting FFA | Adiponectin | .Gamma.Glu. Leu | 2Hydroxybutyrate | |
| 29 | Fasting FFA | Adiponectin | .Gamma.Glu. Leu | .Linoleate | 2Hydroxybutyrate | .Linolenate |
| 30 | .FPG | Fasting FFA | Adiponectin | .Gamma.Glu. Leu | .Linoleate | 2Hydroxybutyrate |
| 31 | Fasting FFA | Adiponectin | .Gamma.Glu. Leu | .Linoleate | 2Hydroxybutyrate | Creatine |
| 32 | Gluconate | Glycine | Lactate | Galactonate | Threonine | X1.5.Anhydroglucitol |
| 33 | Glutamate | Pyruvate | Oleoyl.LPC | Gluconate | Glycine | Galactonate |
| 34 | Linoleate | BMI | Fasting FFA | 2Hydroxybutyrate | Adiponectin | Gluconate |
| 35 | BMI | LDL_Cholesterol | FPG | Glycine | Triglycerides | 2Hydroxybutyrate |
| 36 | LDL_Cholesterol | FPG | Glycine | Triglycerides | 1.5.Anhydroglucitol | 2Hydroxybutyrate |
| 37 | .Gamma.Glu. Leu | 2Hydroxybutyrate | Creatine | Gluconate | | |
| 38 | .Betaine | .Galactonate | 2Hydroxybutyrate | .Linolyl.LPC | Gluconate | |
| 39 | .Gamma.Glu. Leu | 2Hydroxybutyrate | .Glycine | Creatine | Gluconate | |
| 40 | .Gamma.Glu. Leu | 2Hydroxybutyrate | .Glycine | .Linolyl.LPC | Creatine | Gluconate |
| 41 | .Gamma.Glu. Leu | 2Hydroxybutyrate | .Glycine | .Linolyl.LPC | Creatine | Gluconate |
| 42 | Fasting FFA | .Gamma.Glu. Leu | 2Hydroxybutyrate | Gluconate | | |
| 43 | Fasting FFA | .Betaine | .Gamma.Glu. Leu | 2Hydroxybutyrate | | |
| 44 | Fasting FFA | Adiponectin | .Glul.Val | .Linoleate | 2Hydroxybutyrate | |
| 45 | Fasting FFA | Adiponectin | .Gamma.Glu. Leu | 2Hydroxybutyrate | .Linolyl.LPC | |
| 46 | Fasting FFA | Adiponectin | .Betaine | .Gamma.Glu. Leu | .Linoleate | 2Hydroxybutyrate |
| 47 | Fasting FFA | Adiponectin | .Betaine | .Gamma.Glu. Leu | 2Hydroxybutyrate | Hepadecenate |
| 48 | Linolenate | Oleate | Hepadecenate | Linoleate | Serine | Threonine |
| 49 | Linolyl.LPC | Betaine | Glul.Val | Pyruvate | Gluconate | Galactonate |
| 50 | 2Hydroxybutyrate | Glycine | Oleate | Adiponectin | Creatine | Gluconate |
| 51 | BMI | Galactonate | 2Hydroxybutyrate | Oleate | Adiponectin | Gluconate |
| 52 | 2Hydroxybutyrate | .Linolyl.LPC | Creatine | Gluconate | | |
| 53 | .Betaine | 2Hydroxybutyrate | .Linolyl.LPC | Gluconate | | |
| 54 | 2Hydroxybutyrate | .Glycine | Creatine | Gluconate | | |
| 55 | .Gamma.Glu. Leu | 2Hydroxybutyrate | .Linolyl.LPC | Creatine | Gluconate | |

TABLE 8-continued

Metabolite Biomarkers and models that are predictive of Insulin Resistance as determined by glucose disposal rate (Rd).

| | | | | | | |
|---|---|---|---|---|---|---|
| 56 | 2Hydroxybutyrate | .Glycine | .Linolyl.LPC | Creatine | Gluconate | |
| 57 | .Gamma.Glu.Leu | 2Hydroxybutyrate | .Linolyl.LPC | Gluconate | Threonine | |
| 58 | .Gamma.Glu.Leu | 2Hydroxybutyrate | .Linolyl.LPC | .Oleate | Gluconate | Hepadecenate |
| 59 | .Gamma.Glu.Leu | 2Hydroxybutyrate | .Glycine | .Linolyl.LPC | Creatine | Gluconate |
| 60 | .Betaine | .Gamma.Glu.Leu | 2Hydroxybutyrate | .Linolyl.LPC | Creatine | Gluconate |
| 61 | Fasting FFA | .Gamma.Glu.Leu | .Linoleate | 2Hydroxybutyrate | | |
| 62 | Fasting FFA | Adiponectin | .Gamma.Glu.Leu | .Linoleate | 2Hydroxybutyrate | |
| 63 | Fasting FFA | Adiponectin | .Gamma.Glu.Leu | 2Hydroxybutyrate | Hepadecenate | |
| 64 | Fasting FFA | Adiponectin | .Gamma.Glu.Leu | 2Hydroxybutyrate | Gluconate | |
| 65 | Fasting FFA | Adiponectin | .Gamma.Glu.Leu | .Linoleate | 2Hydroxybutyrate | Gluconate |
| 66 | Fasting FFA | Adiponectin | .Gamma.Glu.Leu | .Linoleate | 2Hydroxybutyrate | Linolyl.LPC |
| 67 | 2Hydroxybutyrate | .Glycine | .Linolyl.LPC | Creatine | | |
| 68 | .Gamma.Glu.Leu | 2Hydroxybutyrate | .Glycine | .Linolyl.LPC | Gluconate | |
| 69 | 2Hydroxybutyrate | .Glycine | .Linolenate | .Linolyl.LPC | Creatine | Gluconate |
| 70 | Adiponectin | .Betaine | .Gamma.Glu.Leu | 2Hydroxybutyrate | | |
| 71 | LDL Cholesterol | Galactonate | 2Hydroxybutyrate | Oleate | Adiponectin | Gluconate |
| 72 | .Gamma.Glu.Leu | 2Hydroxybutyrate | .Linolyl.LPC | Gluconate | | |
| 73 | .Galactonate | .Gamma.Glu.Leu | 2Hydroxybutyrate | Gluconate | | |
| 74 | .Gamma.Glu.Leu | 2Hydroxybutyrate | .Glycine | Gluconate | | |
| 75 | .Gamma.Glu.Leu | 2Hydroxybutyrate | .Linolyl.LPC | Gluconate | | |
| 76 | .Galactonate | .Gamma.Glu.Leu | 2Hydroxybutrate | .Linolyl.LPC | Gluconate | |
| 77 | .Betaine | .Gamma.Glu.Leu | 2Hydroxybutyrate | .Linolyl.LPC | Gluconate | |
| 78 | .Gamma.Glu.Leu | 2Hydroxybutyrate | .Linolenate | .Linolyl.LPC | Gluconate | |
| 79 | .Betaine | .Galactonate | .Gamma.Glu.Leu | 2Hydroxybutyrate | .Linolyl.LPC | Gluconate |
| 80 | 2Hydroxybutyrate | .Glycine | .Linolyl.LPC | Creatine | Gluconate | Threonine |
| 81 | .Galactonate | .Gamma.Glu.Leu | 2Hydroxybutyrate | .Linolyl.LPC | Creatine | Gluconate |
| 82 | Adiponectin | .Gamma.Glu.Leu | .Linoleate | 2Hydroxybutyrate | | |
| 83 | Oleoyl.LPC | Gluconate | Oleate | Galactonate | Hepadecenate | Linoleate |
| 84 | Galactonate | Linoleate | 2Hydroxybutyrate | Oleate | Adiponectin | Gluconate |
| 85 | Linoleate | 2Hydroxybutyrate | Glutamate | Oleate | Adiponectin | Gluconate |
| 86 | Lactate | Oleate | Arginine | Hepadecenate | Serine | Threonine |
| 87 | BMI | LDL_Cholesterol | Galactonate | Triglycerides | 2Hydroxybutyrate | Gluconate |
| 88 | Serine | BMI | Arginine | 2Hydroxybutyrate | HDL Cholesterol | Threonine |
| 89 | Adiponectin | .Gamma.Glu.Leu | 2Hydroxybutyrate | .Linolyl.LPC | | |
| 90 | Creatine | Glutamate | Pyruvate | Gluconate | Glycine | Galactonate |

Abbreviations:
BMI, Body Mass Index;
FFA, Free Fatty Acids;
FPG, Fasting Plasma Glucose 2H: Correlated Biomarker Compounds:

Many biomarker compounds were correlated as shown in Tables 9A and 9B. Table 9A contains the pair-wise correlation analysis of biomarkers identified in Study 1 and Table 9B contains the pair-wise correlation analysis of biomarkers identified in Study 2. Correlated compounds are often mutually exclusive in regression models and thus can be used (i.e. substituted for a correlated compound) in different models that had similar prediction powers as those shown in Table 8 above. This aspect is useful when developing biochemical assays that are targeted to specific biomarkers since certain biomarkers may be more amenable to assay development than other biomarkers.

TABLE 9A

| Correlated Biomarkers in Study 1. | | | | |
|---|---|---|---|---|
| Pairwise Correlation | N | Correlation | P-value | R-square |
| 1,5-anhydroglucitol-1,5 (AG) *Metabolite-11234 | 112 | −0.5242 | 2.99E−09 | 0.2748 |
| 1,5-anhydroglucitol-1,5 (AG) *Metabolite-11249 | 112 | −0.5041 | 1.46E−08 | 0.2541 |
| 1,5-anhydroglucitol-1,5 (AG) *Metabolite-11252 | 112 | −0.5114 | 8.32E−09 | 0.2615 |
| 1,5-anhydroglucitol-1,5 (AG) *Metabolite-12061 | 112 | −0.5521 | 2.78E−10 | 0.3049 |
| 1,5-anhydroglucitol-1,5 (AG) *Metabolite-12064 | 112 | −0.5046 | 1.40E−08 | 0.2546 |
| 2-hydroxybutyrate (AHB)*1,5-anhydroglucitol-1,5 (AG) | 112 | −0.5413 | 7.19E−10 | 0.2930 |
| 2-hydroxybutyrate (AHB)*2-aminobutyrate | 112 | 0.7651 | <0.000 | 0.5854 |
| 2-hydroxybutyrate (AHB)*3-hydroxybutyrate (BHBA) | 112 | 0.6517 | 7.11E−15 | 0.4247 |
| 2-hydroxybutyrate (AHB)*3-methyl-2-oxobutyrate | 112 | 0.6750 | 2.22E−16 | 0.4557 |
| 2-hydroxybutyrate (AHB)*3-methyl-2-oxovalerate | 112 | 0.5970 | 3.71E−12 | 0.3565 |
| 2-hydroxybutyrate (AHB)*4-methyl-2-oxopentanoate | 112 | 0.6599 | 2.44E−15 | 0.4355 |
| 2-hydroxybutyrate (AHB)*creatine | 112 | 0.5123 | 7.75E−09 | 0.2624 |
| 2-hydroxybutyrate (AHB)*erythrose | 112 | 0.5156 | 5.96E−09 | 0.2659 |
| 2-hydroxybutyrate (AHB)*galactonic acid | 112 | 0.7137 | <0.000 | 0.5094 |
| 2-hydroxybutyrate (AHB)*gluconate | 112 | 0.5427 | 6.35E−10 | 0.2945 |
| 2-hydroxybutyrate (AHB)*gondoate-20-1-n-9- | 112 | 0.5765 | 2.91E−11 | 0.3323 |
| 2-hydroxybutyrate (AHB)*isoleucine | 112 | 0.6025 | 2.09E−12 | 0.3630 |
| 2-hydroxybutyrate (AHB)*leucine | 112 | 0.6472 | 1.27E−14 | 0.4188 |
| 2-hydroxybutyrate (AHB)*mannose | 112 | 0.7043 | <0.000 | 0.4960 |
| 2-hydroxybutyrate (AHB)*margarate (17:0) | 112 | 0.5270 | 2.38E−09 | 0.2777 |
| 2-hydroxybutyrate (AHB)*palmitate (16:0) | 112 | 0.5191 | 4.54E−09 | 0.2694 |
| 2-hydroxybutyrate (AHB)*stearate (18:0) | 112 | 0.5888 | 8.57E−12 | 0.3467 |
| 2-hydroxybutyrate (AHB)*uridine | 112 | 0.5282 | 2.15E−09 | 0.2790 |
| 2-hydroxybutyrate (AHB)*valine* | 112 | 0.6705 | 6.66E−16 | 0.4496 |
| 2-hydroxybutyrate (AHB)*Metabolite-10432 | 112 | 0.6826 | 2.22E−16 | 0.4660 |
| 2-hydroxybutyrate (AHB)*Metabolite-10752 | 112 | 0.5221 | 3.55E−09 | 0.2726 |
| 2-hydroxybutyrate (AHB)*Metabolite-11228 | 112 | 0.5810 | 1.87E−11 | 0.3376 |
| 2-hydroxybutyrate (AHB)*Metabolite-11887 | 112 | 0.5314 | 1.66E−09 | 0.2824 |
| 2-hydroxybutyrate (AHB)*Metabolite-11897 | 112 | 0.5037 | 1.51E−08 | 0.2537 |
| 2-hydroxybutyrate (AHB)*Metabolite-12037 | 112 | 0.5768 | 2.82E−11 | 0.3327 |
| 2-hydroxybutyrate (AHB)*Metabolite-12061 | 112 | 0.5053 | 1.33E−08 | 0.2553 |
| 2-hydroxybutyrate (AHB)*Metabolite-12064 | 112 | 0.8857 | <0.000 | 0.7844 |
| 2-hydroxybutyrate (AHB)*glutamate | 112 | 0.7745 | <0.000 | 0.5998 |
| 2-hydroxybutyrate (AHB)*Metabolite-3100 | 112 | 0.5619 | 1.14E−10 | 0.3158 |
| 2-hydroxybutyrate (AHB)*Metabolite-4055 | 112 | 0.6836 | <0.000 | 0.4672 |
| 2-hydroxybutyrate (AHB)*Metabolite-6488 | 112 | 0.5779 | 2.54E−11 | 0.3339 |
| 2-hydroxybutyrate (AHB)*Metabolite-6627 | 112 | 0.5193 | 4.44E−09 | 0.2697 |
| 2-hydroxybutyrate (AHB)*Metabolite-9033 | 112 | 0.5608 | 1.27E−10 | 0.3145 |
| 2-hydroxybutyrate (AHB)*Metabolite-9043 | 112 | 0.5879 | 9.46E−12 | 0.3456 |
| 2-hydroxybutyrate (AHB)*Metabolite-9727 | 112 | 0.7077 | <0.000 | 0.5009 |
| 3-hydroxybutyrate (BHBA)*glutamate | 112 | 0.5506 | 3.18E−10 | 0.3032 |
| 3-methyl-2-oxobutyrate*palmitate (16:0) | 112 | 0.5683 | 6.31E−11 | 0.3230 |
| 4-methyl-2-oxopentanoate*palmitate (16:0) | 112 | 0.5424 | 6.53E−10 | 0.2942 |
| alpha linolenate (18:3(n-3))*dihomo-alpha-linolenate-20-3-n-3- | 112 | 0.5295 | 1.94E−09 | 0.2804 |
| alpha linolenate (18:3(n-3))*gonodoate-20-1-n-9- | 112 | 0.7264 | <0.000 | 0.5277 |
| alpha linolenate (18:3(n-3))*linoleate (18:2(n-6)) | 112 | 0.7877 | <0.000 | 0.6204 |
| alpha linolenate (18:3(n-3))*n-3-DPA-22-5-n-3- | 112 | 0.5722 | 4.37E−11 | 0.3274 |
| alpha linolenate (18:3(n-3))*oleate (18:1(n-9)) | 112 | 0.7490 | <0.000 | 0.5610 |
| alpha linolenate (18:3(n-3))*palmitate (16:0) | 112 | 0.7354 | <0.000 | 0.5409 |
| alpha linolenate (18:3(n-3))*palmitoleate (16:1(n-7)) | 112 | 0.6224 | 2.36E−13 | 0.3874 |
| alpha linolenate (18:3(n-3))*stearate (18:0) | 112 | 0.6939 | <0.000 | 0.4815 |
| alpha linolenate (18:3(n-3))*Metabolite-11365 | 112 | 0.5054 | 1.32E−08 | 0.2555 |
| alpha linolenate (18:3(n-3))*Metabolite-11379 | 112 | 0.7245 | 0 | 0.5249 |
| alpha linolenate (18:3(n-3))*Metabolite-11653 | 112 | 0.5578 | 1.66E−10 | 0.3112 |
| alpha linolenate (18:3(n-3))*Metabolite-11887 | 112 | 0.7730 | 0 | 0.5975 |
| alpha linolenate (18:3(n-3))*Metabolite-12037 | 112 | 0.6665 | 1.11E−15 | 0.4443 |
| BMI*gamma-glutamylleucine | 112 | 0.5215 | 3.74E−09 | 0.2719 |
| BMI*glutamylvaline | 112 | 0.5425 | 6.47E−10 | 0.2943 |
| bradykinin*bradykinin, hydroxyproline form- | 112 | 0.5212 | 3.83E−09 | 0.2716 |
| creatine*Metabolite-02546_200 | 112 | −0.5849 | 1.27E−11 | 0.3421 |
| dipalmitin*palmitate (16:0) | 112 | 0.5630 | 1.04E−10 | 0.3170 |
| erythrose*1,5-anhydroglucitol-1,5 (AG) | 112 | −0.5099 | 9.35E−09 | 0.2600 |
| erythrose*galactonic acid | 112 | 0.6691 | 6.66E−16 | 0.4476 |
| erythrose*gluconate | 112 | 0.6461 | 1.44E−14 | 0.4174 |
| erythrose*glutamate | 112 | 0.7334 | 0 | 0.5378 |
| fructose*galactonic acid | 112 | 0.6151 | 5.35E−13 | 0.3784 |
| fructose*gluconate | 112 | 0.7100 | 0 | 0.5042 |
| fructose*glutamate | 112 | 0.6623 | 1.78E−15 | 0.4387 |
| galactonic acid*1,5-anhydroglucitol-1,5 (AG) | 112 | −0.6211 | 2.77E−13 | 0.3857 |
| galactonic acid*2-aminobutyrate | 112 | 0.5246 | 2.91E−09 | 0.2752 |
| galactonic acid*3-methyl-2-oxobutyrate | 112 | 0.5517 | 2.89E−10 | 0.3044 |
| galactonic acid*4-methyl-2-oxopentanoate | 112 | 0.5288 | 2.05E−09 | 0.2797 |
| galactonic acid*gluconate | 112 | 0.7653 | 0 | 0.5857 |
| galactonic acid*gondoate-20-1-n-9- | 112 | 0.5981 | 3.33E−12 | 0.3577 |
| galactonic acid*isoleucine | 112 | 0.5461 | 4.74E−10 | 0.2982 |
| galactonic acid*mannose | 112 | 0.8354 | 0 | 0.6978 |

TABLE 9A-continued

Correlated Biomarkers in Study 1.

| Pairwise Correlation | N | Correlation | P-value | R-square |
|---|---|---|---|---|
| galactonic acid*margarate (17:0) | 112 | 0.5473 | 4.26E−10 | 0.2995 |
| galactonic acid*palmitate (16:0) | 112 | 0.5279 | 2.21E−09 | 0.2787 |
| galactonic acid*stearate (18:0) | 112 | 0.5986 | 3.16E−12 | 0.3583 |
| galactonic acid*Metabolite-10360 | 112 | 0.5113 | 8.39E−09 | 0.2614 |
| galactonic acid*Metabolite-10432 | 112 | 0.6635 | 1.55E−15 | 0.4403 |
| galactonic acid*Metabolite-10609 | 112 | 0.5803 | 2.01E−11 | 0.3367 |
| galactonic acid*Metabolite-10750 | 112 | 0.6247 | 1.83E−13 | 0.3903 |
| galactonic acid*Metabolite-10752 | 112 | 0.6833 | 0 | 0.4668 |
| galactonic acid*Metabolite-11228 | 112 | 0.6299 | 9.99E−14 | 0.3968 |
| galactonic acid*Metabolite-11230 | 112 | 0.5353 | 1.19E−09 | 0.2866 |
| galactonic acid*Metabolite-11234 | 112 | 0.7072 | 0 | 0.5002 |
| galactonic acid*Metabolite-11235 | 112 | 0.5168 | 5.43E−09 | 0.2671 |
| galactonic acid*Metabolite-11242 | 112 | 0.5837 | 1.43E−11 | 0.3407 |
| galactonic acid*Metabolite-11249 | 112 | 0.5771 | 2.72E−11 | 0.3331 |
| galactonic acid*Metabolite-11252 | 112 | 0.6003 | 2.65E−12 | 0.3603 |
| galactonic acid*Metabolite-11258 | 112 | 0.5045 | 1.42E−08 | 0.2545 |
| galactonic acid*Metabolite-11387 | 112 | 0.5520 | 2.82E−10 | 0.3047 |
| galactonic acid*Metabolite-11432 | 112 | 0.6147 | 5.64E−13 | 0.3778 |
| galactonic acid*Metabolite-11434 | 112 | 0.6344 | 5.93E−14 | 0.4025 |
| galactonic acid*Metabolite-11628 | 112 | 0.5803 | 2.01E−11 | 0.3367 |
| galactonic acid*Metabolite-11887 | 112 | 0.5451 | 5.16E−10 | 0.2971 |
| galactonic acid*Metabolite-11897 | 112 | 0.6229 | 2.25E−13 | 0.3880 |
| galactonic acid*Metabolite-12037 | 112 | 0.5794 | 2.18E−11 | 0.3357 |
| galactonic acid*Metabolite-12061 | 112 | 0.7387 | 0 | 0.5456 |
| galactonic acid*Metabolite-12064 | 112 | 0.6051 | 1.59E−12 | 0.3662 |
| galactonic acid*glutamate | 112 | 0.9200 | 0 | 0.8464 |
| galactonic acid*Metabolite-3100 | 112 | 0.5343 | 1.30E−09 | 0.2855 |
| galactonic acid*Metabolite-4055 | 112 | 0.6292 | 1.09E−13 | 0.3958 |
| galactonic acid*Metabolite-5847 | 112 | 0.6075 | 1.23E−12 | 0.3690 |
| galactonic acid*Metabolite-6446 | 112 | 0.6367 | 4.53E−14 | 0.4053 |
| galactonic acid*Metabolite-6488 | 112 | 0.5753 | 3.26E−11 | 0.3309 |
| galactonic acid*Metabolite-6506 | 112 | 0.5094 | 9.72E−09 | 0.2595 |
| galactonic acid*Metabolite-9033 | 112 | 0.7427 | 0 | 0.5517 |
| galactonic acid*Metabolite-9043 | 112 | 0.5751 | 3.32E−11 | 0.3307 |
| galactonic acid*Metabolite-9727 | 112 | 0.5195 | 4.37E−09 | 0.2699 |
| gamma-glutamylleucine*glutamylvaline | 112 | 0.9404 | 0 | 0.8844 |
| gamma-glutamylleucine*peptide-HWESASXX | 112 | 0.7379 | 0 | 0.5445 |
| gamma-glutamylleucine*peptide-HWESASXXR | 112 | 0.5766 | 2.87E−11 | 0.3325 |
| gluconate*1,5-anhydroglucitol-1,5 (AG) | 112 | −0.6774 | 2.22E−16 | 0.4588 |
| gluconate*mannose | 112 | 0.7419 | 0 | 0.5504 |
| gluconate*Metabolite-10432 | 112 | 0.6367 | 4.51E−14 | 0.4054 |
| gluconate*Metabolite-10609 | 112 | 0.5759 | 3.08E−11 | 0.3316 |
| gluconate*Metabolite-10610 | 112 | 0.5098 | 9.39E−09 | 0.2599 |
| gluconate*Metabolite-10750 | 112 | 0.7024 | 0 | 0.4934 |
| gluconate*Metabolite-10752 | 112 | 0.6996 | 0 | 0.4894 |
| gluconate*Metabolite-11228 | 112 | 0.6652 | 1.33E−15 | 0.4425 |
| gluconate*Metabolite-11230 | 112 | 0.5881 | 9.21E−12 | 0.3459 |
| gluconate*Metabolite-11231 | 112 | 0.5374 | 1.00E−09 | 0.2888 |
| gluconate*Metabolite-11234 | 112 | 0.7041 | 0 | 0.4958 |
| gluconate*Metabolite-11235 | 112 | 0.5807 | 1.92E−11 | 0.3372 |
| gluconate*Metabolite-11242 | 112 | 0.6321 | 7.75E−14 | 0.3996 |
| gluconate*Metabolite-11249 | 112 | 0.5309 | 1.72E−09 | 0.2819 |
| gluconate*Metabolite-11252 | 112 | 0.5145 | 6.51E−09 | 0.2647 |
| gluconate*Metabolite-11387 | 112 | 0.5015 | 1.78E−08 | 0.2515 |
| gluconate*Metabolite-11432 | 112 | 0.5697 | 5.56E−11 | 0.3245 |
| gluconate*Metabolite-11434 | 112 | 0.6693 | 6.66E−16 | 0.4480 |
| gluconate*Metabolite-11435 | 112 | 0.5294 | 1.96E−09 | 0.2802 |
| gluconate*Metabolite-11628 | 112 | 0.5278 | 2.24E−09 | 0.2785 |
| gluconate*Metabolite-11897 | 112 | 0.6460 | 1.47E−14 | 0.4173 |
| gluconate*Metabolite-12061 | 112 | 0.7448 | 0 | 0.5548 |
| gluconate*Metabolite-12064 | 112 | 0.5160 | 5.78E−09 | 0.2663 |
| gluconate*glutamate | 112 | 0.7895 | 0 | 0.6234 |
| gluconate*Metabolite-3100 | 112 | 0.5649 | 8.70E−11 | 0.3191 |
| gluconate*Metabolite-4055 | 112 | 0.5887 | 8.67E−12 | 0.3466 |
| gluconate*Metabolite-4986 | 112 | 0.5742 | 3.63E−11 | 0.3297 |
| gluconate*Metabolite-5847 | 112 | 0.5735 | 3.88E−11 | 0.3289 |
| gluconate*Metabolite-6446 | 112 | 0.6913 | 0 | 0.4779 |
| gluconate*Metabolite-6488 | 112 | 0.5778 | 2.55E−11 | 0.3339 |
| gluconate*Metabolite-9033 | 112 | 0.7458 | 0 | 0.5562 |
| gluconate*Metabolite-9043 | 112 | 0.5257 | 2.64E−09 | 0.2764 |
| glutamylvaline*peptide-HWESASXX | 112 | 0.7816 | 0 | 0.6109 |
| glutamylvaline*peptide-HWESASXXR | 112 | 0.5946 | 4.75E−12 | 0.3536 |
| glycerate*threonate | 112 | 0.6260 | 1.57E−13 | 0.3919 |
| glycerol*alpha linolenate (18:3(n-3)) | 112 | 0.6345 | 5.86E−14 | 0.4026 |
| glycerol*linoleate (18:2(n-6)) | 112 | 0.7008 | 0 | 0.4911 |
| glycerol*oleate (18:1(n-9)) | 112 | 0.7338 | 0 | 0.5385 |

TABLE 9A-continued

Correlated Biomarkers in Study 1.

| Pairwise Correlation | N | Correlation | P-value | R-square |
|---|---|---|---|---|
| glycerol*palmitate (16:0) | 112 | 0.6943 | 0 | 0.4821 |
| gondoate-20-1-n-9-*linolenate (18:2(n-6)) | 112 | 0.7862 | 0 | 0.6181 |
| gondoate-20-1-n-9-*oleate (18:1(n-9)) | 112 | 0.8756 | 0 | 0.7666 |
| gondoate-20-1-n-9-*palmitate (16:0) | 112 | 0.8128 | 0 | 0.6607 |
| lactate*pyruvate | 112 | 0.7722 | 0 | 0.5963 |
| lactate*Metabolite-4357 | 112 | 0.6960 | 0 | 0.4844 |
| lactate*Metabolite-4360 | 112 | 0.8576 | 0 | 0.7355 |
| lactate*Metabolite-4986 | 112 | 0.6386 | 3.60E−14 | 0.4078 |
| lactate*Metabolite-5348 | 112 | 0.5750 | 3.35E−11 | 0.3306 |
| linoleate (18:2(n-6))*n-3-DPA-22-5-n-3- | 112 | 0.5966 | 3.86E−12 | 0.3560 |
| linoleate (18:2(n-6))*oleate (18:1(n-9)) | 112 | 0.8621 | 0 | 0.7433 |
| linoleate (18:2(n-6))*palmitate (16:0) | 112 | 0.8248 | 0 | 0.6803 |
| linoleate (18:2(n-6))*palmitoleate (16:1(n-7)) | 112 | 0.6826 | 2.22E−16 | 0.4659 |
| linoleate (18:2(n-6))*stearate (18:0) | 112 | 0.7065 | 0 | 0.4991 |
| linoleate (18:2(n-6))*Metabolite-11379 | 112 | 0.7858 | 0 | 0.6175 |
| linoleate (18:2(n-6))*Metabolite-11653 | 112 | 0.5638 | 9.63E−11 | 0.3179 |
| linoleate (18:2(n-6))*Metabolite-11887 | 112 | 0.8301 | 0 | 0.6891 |
| linoleate (18:2(n-6))*Metabolite-12037 | 112 | 0.7066 | 0 | 0.4992 |
| mannose*1,5-anhydroglucitol-1,5 (AG) | 112 | −0.6115 | 8.00E−13 | 0.3739 |
| mannose*margarate (17:0) | 112 | 0.5273 | 2.33E−09 | 0.2780 |
| mannose*glutamate | 112 | 0.8909 | 0 | 0.7937 |
| margarate (17:0)*creatine | 112 | 0.5567 | 1.85E−10 | 0.3099 |
| margarate (17:0)*stearate (18:0) | 112 | 0.5258 | 2.63E−09 | 0.2765 |
| margarate (17:0)*Metabolite-10750 | 112 | 0.5003 | 1.94E−08 | 0.2503 |
| margarate (17:0)*Metabolite-12037 | 112 | 0.5123 | 7.75E−09 | 0.2624 |
| margarate (17:0)*Metabolite-12064 | 112 | 0.5374 | 1.00E−09 | 0.2888 |
| margarate (17:0)*glutamate | 112 | 0.5499 | 3.38E−10 | 0.3024 |
| margarate (17:0)*Metabolite-6446 | 112 | 0.5082 | 1.07E−08 | 0.2582 |
| margarate (17:0)*Metabolite-9033 | 112 | 0.5051 | 1.35E−08 | 0.2551 |
| myristate (14:0)*oleate (18:1(n-9)) | 112 | 0.5118 | 8.05E−09 | 0.2619 |
| myristate (14:0)*palmitate (16:0) | 112 | 0.6230 | 2.22E−13 | 0.3881 |
| n-3-DPA-22-5-n-3-*oleate (18:1(n-9)) | 112 | 0.6538 | 5.55E−15 | 0.4275 |
| n-3-DPA-22-5-n-3-*palmitate (16:0) | 112 | 0.6285 | 1.18E−13 | 0.3950 |
| oleate (18:1(n-9))*palmitate (16:0) | 112 | 0.9032 | 0 | 0.8158 |
| oleate (18:1(n-9))*palmitoleate (16:1(n-7)) | 112 | 0.7218 | 0 | 0.5209 |
| oleate (18:1(n-9))*stearate (18:0) | 112 | 0.7798 | 0 | 0.6081 |
| oleate (18:1(n-9))*Metabolite-11252 | 112 | 0.5052 | 1.34E−08 | 0.2552 |
| oleate (18:1(n-9))*Metabolite-11379 | 112 | 0.8566 | 0 | 0.7337 |
| oleate (18:1(n-9))*Metabolite-11653 | 112 | 0.6108 | 8.61E−13 | 0.3731 |
| oleate (18:1(n-9))*Metabolite-11887 | 112 | 0.8989 | 0 | 0.8081 |
| oleate (18:1(n-9))*Metabolite-12037 | 112 | 0.8335 | 0 | 0.6947 |
| ornithine*EDTA* | 112 | 0.6101 | 9.31E−13 | 0.3722 |
| ornithine*Metabolite-10812 | 112 | 0.5121 | 7.86E−09 | 0.2623 |
| ornithine*Metabolite-3091 | 112 | 0.5529 | 2.59E−10 | 0.3057 |
| ornithine*Metabolite-3103 | 112 | 0.5739 | 3.73E−11 | 0.3293 |
| ornithine*Metabolite-3108 | 112 | 0.5599 | 1.37E−10 | 0.3135 |
| ornithine*Metabolite-4274 | 112 | 0.5198 | 4.29E−09 | 0.2702 |
| palmitate (16:0)*palmitoleate (16:1(n-7)) | 112 | 0.7277 | 0 | 0.5296 |
| palmitate (16:0)*stearate (18:0) | 112 | 0.8313 | 0 | 0.6911 |
| palmitate (16:0)*Metabolite-11252 | 112 | 0.5102 | 9.13E−09 | 0.2603 |
| palmitate (16:0)*Metabolite-11379 | 112 | 0.8594 | 0 | 0.7386 |
| palmitate (16:0)*Metabolite-11653 | 112 | 0.6739 | 4.44E−16 | 0.4542 |
| palmitate (16:0)*Metabolite-11887 | 112 | 0.8789 | 0 | 0.7724 |
| palmitate (16:0)*Metabolite-12037 | 112 | 0.7972 | 0 | 0.6356 |
| palmitate (16:0)*Metabolite-12064 | 112 | 0.5431 | 6.13E−10 | 0.2950 |
| palmitoleate (16:1(n-7))*Metabolite-11379 | 112 | 0.8744 | 0 | 0.7646 |
| stearate (18:0)*Metabolite-11249 | 112 | 0.5247 | 2.88E−09 | 0.2753 |
| stearate (18:0)*Metabolite-11252 | 112 | 0.5606 | 1.30E−10 | 0.3142 |
| stearate (18:0)*Metabolite-11258 | 112 | 0.5185 | 4.74E−09 | 0.2689 |
| stearate (18:0)*Metabolite-11379 | 112 | 0.6025 | 2.10E−12 | 0.3630 |
| stearate (18:0)*Metabolite-11653 | 112 | 0.5560 | 1.97E−10 | 0.3091 |
| stearate (18:0)*Metabolite-11887 | 112 | 0.7628 | 0 | 0.5818 |
| stearate (18:0)*Metabolite-12037 | 112 | 0.7230 | 0 | 0.5228 |
| stearate (18:0)*Metabolite-12064 | 112 | 0.5859 | 1.15E−11 | 0.3433 |
| Metabolite-10432*1,5-anhydroglucitol-1,5 (AG) | 112 | −0.5674 | 6.88E−11 | 0.3220 |
| Metabolite-10432*glutamate | 112 | 0.7402 | 0 | 0.5479 |
| Metabolite-10609*glutamate | 112 | 0.5732 | 3.99E−11 | 0.3285 |
| glycine*Metabolite-3003 | 112 | 0.9861 | 0 | 0.9725 |
| Metabolite-10750*1,5-anhydroglucitol-1,5 (AG) | 112 | −0.5347 | 1.26E−09 | 0.2859 |
| Metabolite-10750*glutamate | 112 | 0.6864 | 0 | 0.4711 |
| Metabolite-10752*1,5-anhydroglucitol-1,5 (AG) | 112 | −0.5387 | 8.96E−10 | 0.2902 |
| Metabolite-10752*glutamate | 112 | 0.7503 | 0 | 0.5629 |
| Metabolite-10814*glutamate | 112 | 0.5121 | 7.85E−09 | 0.2623 |
| serine*Metabolite-3078 | 112 | 0.6279 | 1.26E−13 | 0.3943 |
| serine*Metabolite-3088 | 112 | 0.5175 | 5.15E−09 | 0.2678 |
| serine*Metabolite-4364 | 112 | 0.5899 | 7.72E−12 | 0.3480 |

TABLE 9A-continued

Correlated Biomarkers in Study 1.

| Pairwise Correlation | N | Correlation | P-value | R-square |
|---|---|---|---|---|
| serine*Metabolite-4769 | 112 | 0.6668 | 1.11E−15 | 0.4447 |
| glutamate*1,5-anhydroglucitol-1,5 (AG) | 112 | −0.6945 | 0 | 0.4823 |
| glutamate*2-aminobutyrate | 112 | 0.5296 | 1.92E−09 | 0.2805 |
| glutamate*3-methyl-2-oxobutyrate | 112 | 0.5857 | 1.18E−11 | 0.3430 |
| glutamate*4-methyl-2-oxopentanoate | 112 | 0.5366 | 1.07E−09 | 0.2879 |
| glutamate*gondoate-20-1-n-9- | 112 | 0.5823 | 1.65E−11 | 0.3390 |
| glutamate*isoleucine | 112 | 0.5442 | 5.59E−10 | 0.2961 |
| glutamate*leucine | 112 | 0.5311 | 1.70E−09 | 0.2820 |
| glutamate*palmitate (16:0) | 112 | 0.5134 | 7.08E−09 | 0.2636 |
| glutamate*stearate (18:0) | 112 | 0.5742 | 3.63E−11 | 0.3297 |
| glutamate*valine* | 112 | 0.5511 | 3.04E−10 | 0.3037 |
| glutamate*Metabolite-11228 | 112 | 0.6659 | 1.11E−15 | 0.4435 |
| glutamate*Metabolite-11230 | 112 | 0.5964 | 3.98E−12 | 0.3557 |
| glutamate*Metabolite-11231 | 112 | 0.5182 | 4.85E−09 | 0.2686 |
| glutamate*Metabolite-11234 | 112 | 0.7245 | 0 | 0.5249 |
| glutamate*Metabolite-11235 | 112 | 0.5706 | 5.09E−11 | 0.3256 |
| glutamate*Metabolite-11242 | 112 | 0.6197 | 3.21E−13 | 0.3841 |
| glutamate*Metabolite-11249 | 112 | 0.6040 | 1.80E−12 | 0.3648 |
| glutamate*Metabolite-11252 | 112 | 0.6137 | 6.24E−13 | 0.3767 |
| glutamate*Metabolite-11258 | 112 | 0.5232 | 3.24E−09 | 0.2738 |
| glutamate*Metabolite-11387 | 112 | 0.5860 | 1.14E−11 | 0.3434 |
| glutamate*Metabolite-11432 | 112 | 0.6245 | 1.87E−13 | 0.3900 |
| glutamate*Metabolite-11434 | 112 | 0.6707 | 6.66E−16 | 0.4498 |
| glutamate*Metabolite-11435 | 112 | 0.5301 | 1.84E−09 | 0.2810 |
| glutamate*Metabolite-11628 | 112 | 0.5606 | 1.30E−10 | 0.3142 |
| glutamate*Metabolite-11887 | 112 | 0.5450 | 5.21E−10 | 0.2970 |
| glutamate*Metabolite-11897 | 112 | 0.6695 | 6.66E−16 | 0.4482 |
| glutamate*Metabolite-12037 | 112 | 0.5761 | 3.01E−11 | 0.3319 |
| glutamate*Metabolite-12061 | 112 | 0.7919 | 0 | 0.6271 |
| glutamate*Metabolite-12064 | 112 | 0.6742 | 4.44E−16 | 0.4545 |
| glutamate*Metabolite-3078 | 112 | −0.5143 | 6.62E−09 | 0.2645 |
| glutamate*Metabolite-3100 | 112 | 0.6438 | 1.91E−14 | 0.4145 |
| glutamate*Metabolite-4055 | 112 | 0.7284 | 0 | 0.5305 |
| glutamate*Metabolite-4986 | 112 | 0.5229 | 3.34E−09 | 0.2734 |
| glutamate*Metabolite-5847 | 112 | 0.6457 | 1.51E−14 | 0.4170 |
| glutamate*Metabolite-6446 | 112 | 0.7149 | 0 | 0.5111 |
| glutamate*Metabolite-6488 | 112 | 0.6599 | 2.44E−15 | 0.4355 |
| glutamate*Metabolite-6627 | 112 | 0.5376 | 9.88E−10 | 0.2890 |
| glutamate*Metabolite-9033 | 112 | 0.8164 | 0 | 0.6665 |
| glutamate*Metabolite-9043 | 112 | 0.6741 | 4.44E−16 | 0.4544 |
| glutamate*Metabolite-9299 | 112 | 0.5571 | 1.78E−10 | 0.3103 |
| glutamate*Metabolite-9727 | 112 | 0.5597 | 1.41E−10 | 0.3132 |
| Metabolite-3078*1,5-anhydroglucitol-1,5 (AG) | 112 | 0.5166 | 5.54E−09 | 0.2668 |
| Metabolite-3078*gamma-glutamylglutamine | 112 | 0.5975 | 3.54E−12 | 0.3570 |
| Metabolite-4055*1,5-anhydroglucitol-1,5 (AG) | 112 | −0.5505 | 3.20E−10 | 0.3031 |
| pyruvate*Metabolite-4357 | 112 | 0.5054 | 1.32E−08 | 0.2554 |
| pyruvate*Metabolite-4360 | 112 | 0.7299 | 0 | 0.5328 |
| Metabolite-4769*gamma-glutamylglutamine | 112 | 0.6458 | 1.49E−14 | 0.4171 |
| Metabolite-5847*1,5-anhydroglucitol-1,5 (AG) | 112 | −0.5083 | 1.05E−08 | 0.2584 |
| Metabolite-6446*1,5-anhydroglucitol-1,5 (AG) | 112 | −0.5887 | 8.71E−12 | 0.3465 |
| Metabolite-9033*1,5-anhydroglucitol-1,5 (AG) | 112 | −0.5674 | 6.87E−11 | 0.3220 |
| Metabolite-9033*Metabolite-11228 | 112 | 0.6119 | 7.64E−13 | 0.3744 |
| Metabolite-9033*Metabolite-11230 | 112 | 0.6313 | 8.50E−14 | 0.3986 |
| Metabolite-9033*Metabolite-11231 | 112 | 0.5342 | 1.31E−09 | 0.2854 |
| Metabolite-9033*Metabolite-11234 | 112 | 0.6833 | 0 | 0.4669 |
| Metabolite-9033*Metabolite-11235 | 112 | 0.5267 | 2.44E−09 | 0.2774 |
| Metabolite-9033*Metabolite-11242 | 112 | 0.5712 | 4.84E−11 | 0.3262 |
| Metabolite-9033*Metabolite-11249 | 112 | 0.5127 | 7.51E−09 | 0.2629 |
| Metabolite-9033*Metabolite-11252 | 112 | 0.5285 | 2.10E−09 | 0.2794 |
| Metabolite-9033*Metabolite-11387 | 112 | 0.5259 | 2.60E−09 | 0.2766 |
| Metabolite-9033*Metabolite-11432 | 112 | 0.6192 | 3.42E−13 | 0.3834 |
| Metabolite-9033*Metabolite-11434 | 112 | 0.6631 | 1.55E−15 | 0.4396 |
| Metabolite-9033*Metabolite-11435 | 112 | 0.5165 | 5.56E−09 | 0.2668 |
| Metabolite-9033*Metabolite-11628 | 112 | 0.5228 | 3.36E−09 | 0.2733 |
| Metabolite-9033*Metabolite-11897 | 112 | 0.6761 | 2.22E−16 | 0.4572 |
| Metabolite-9033*Metabolite-12061 | 112 | 0.7544 | 0 | 0.5691 |
| Metabolite-9033*Metabolite-12064 | 112 | 0.5456 | 4.93E−10 | 0.2977 |
| Metabolite-9033*Metabolite-9043 | 112 | 0.5697 | 5.53E−11 | 0.3246 |
| Metabolite-9033*Metabolite-9045 | 112 | 0.5596 | 1.42E−10 | 0.3131 |
| Metabolite-9033*Metabolite-9299 | 112 | 0.6908 | 0 | 0.4772 |

TABLE 9B

Correlated Biomarkers in Study 2.

| Compounds | N | Correlation | R-square | p-values |
|---|---|---|---|---|
| HDL_Cholesterol*Adiponectin | 397 | 0.511148 | 0.261272 | <0.001 |
| Fat_Mass*BMI | 402 | 0.843078 | 0.710781 | <0.001 |
| Weight*BMI | 402 | 0.804681 | 0.647512 | <0.001 |
| Waist*BMI | 398 | 0.800452 | 0.640724 | <0.001 |
| Hip*BMI | 398 | 0.705318 | 0.497473 | <0.001 |
| Fat_Mass_pcnt*BMI | 402 | 0.602829 | 0.363403 | <0.001 |
| BMI*HOMA | 388 | 0.590842 | 0.349094 | <0.001 |
| BMI*Fasting_Insulin | 388 | 0.589749 | 0.347804 | <0.001 |
| BMI*QUICKI | 388 | −0.580267 | 0.336710 | <0.001 |
| RD*BMI | 402 | −0.551166 | 0.303784 | <0.001 |
| BMI*Fasting_C_Peptide | 401 | 0.542661 | 0.294480 | <0.001 |
| Fasting_C_Peptide*HOMA | 388 | 0.829625 | 0.688277 | <0.001 |
| Fasting_Insulin*Fasting_C_Peptide | 388 | 0.828392 | 0.686233 | <0.001 |
| Fasting_C_Peptide*QUICKI | 388 | −0.768811 | 0.591070 | <0.001 |
| Fasting_Proinsulin*Fasting_C_Peptide | 398 | 0.570761 | 0.325768 | <0.001 |
| Fat_Mass*Fasting_C_Peptide | 401 | 0.519632 | 0.270017 | <0.001 |
| RD*Fasting_C_Peptide | 401 | −0.506727 | 0.256773 | <0.001 |
| Waist*Fasting_C_Peptide | 397 | 0.501492 | 0.251495 | <0.001 |
| Fasting_Insulin*HOMA | 388 | 0.979376 | 0.959178 | <0.001 |
| Fasting_Insulin*QUICKI | 388 | −0.880137 | 0.774641 | <0.001 |
| Fasting_Insulin*Fasting_Proinsulin | 386 | 0.509757 | 0.259853 | <0.001 |
| Fat_Mass*Fasting_Insulin | 388 | 0.576818 | 0.332719 | <0.001 |
| Waist*Fasting_Insulin | 384 | 0.502325 | 0.252330 | <0.001 |
| Fasting_Proinsulin*HOMA | 386 | 0.525130 | 0.275761 | <0.001 |
| Fasting_FFA*palmitate (16:0) | 393 | 0.552703 | 0.305480 | <0.001 |
| Fasting_FFA*oleate (18:1(n-9)) | 393 | 0.519978 | 0.270377 | <0.001 |
| Fasting_FFA*linoleate (18:2(n-6)) | 393 | 0.504094 | 0.254111 | <0.001 |
| Fasting_FFA*Heptadecenate | 393 | 0.503364 | 0.253375 | <0.001 |
| 2-aminobutyrate*2-hydroxybutyrate (AHB) | 270 | 0.526705 | 0.277419 | <0.001 |
| alpha linolenate (18:3(n-3))*Isobar-cis-9-cis-11-trans-11-eicosenoate | 270 | 0.634441 | 0.402516 | <0.001 |
| alpha linolenate (18:3(n-3))*linoleate (18:1(n-9)) (18:2(n-6)) | 270 | 0.561647 | 0.315447 | <0.001 |
| alpha linolenate (18:3(n-3))*myristate (14:0) | 270 | 0.656699 | 0.431254 | <0.001 |
| alpha linolenate (18:3(n-3))*myristoleate (18:1(n-9))*14-1-n-5- | 270 | 0.580375 | 0.336836 | <0.001 |
| alpha linolenate (18:3(n-3))*n-3-DPA-22-5-n-3- | 270 | 0.730453 | 0.533562 | <0.001 |
| alpha linolenate (18:3(n-3))*oleate (18:1(n-9)) | 270 | 0.576371 | 0.332204 | <0.001 |
| alpha linolenate (18:3(n-3))*palmitate (16:0) | 270 | 0.656120 | 0.430494 | <0.001 |
| alpha linolenate (18:3(n-3))*palmitoleate (16:1(n-7)) | 270 | 0.631278 | 0.398512 | <0.001 |
| alpha linolenate (18:3(n-3))*stearate (18:0) | 270 | 0.592125 | 0.350612 | <0.001 |
| alpha linolenate (18:3(n-3))*Metabolite-11261 | 270 | 0.545276 | 0.297326 | <0.001 |
| alpha linolenate (18:3(n-3))*Heptadecenate | 270 | 0.645969 | 0.417276 | <0.001 |
| alpha linolenate (18:3(n-3))*Metabolite-11521 | 270 | 0.536472 | 0.287803 | <0.001 |
| 5-oxoproline*gamma-glutamylleucine | 270 | 0.634304 | 0.402341 | <0.001 |
| aspartate*gamma-glutamylleucine | 270 | 0.673200 | 0.453199 | <0.001 |
| erythronate-*gamma-glutamylleucine | 270 | 0.645586 | 0.416781 | <0.001 |
| gamma-glutamylleucine*gamma-glutamylmethionine- | 270 | 0.624245 | 0.389682 | <0.001 |
| gamma-glutamylleucine*gammaglutamylphenylalanine | 270 | 0.797356 | 0.635776 | <0.001 |
| gamma-glutamylleucine*gamma-glutamylthreonine- | 270 | 0.590454 | 0.348635 | <0.001 |
| gamma-glutamylleucine*gamma-glutamyltyrosine | 270 | 0.709135 | 0.502873 | <0.001 |
| gamma-glutamylleucine*glutamine | 270 | −0.589607 | 0.347636 | <0.001 |
| gamma-glutamylleucine*glycerate | 270 | 0.515968 | 0.266223 | <0.001 |
| gamma-glutamylleucine*Metabolite-10814 | 270 | 0.561643 | 0.315442 | <0.001 |
| gamma-glutamylleucine*Metabolite-11505 | 270 | 0.580041 | 0.336448 | <0.001 |
| gamma-glutamylleucine*Metabolite-11560 | 270 | 0.544984 | 0.297008 | <0.001 |
| gamma-glutamylleucine*Metabolite-12055 | 270 | 0.818261 | 0.669551 | <0.001 |
| gamma-glutamylleucine*Metabolite-3078 | 270 | −0.544729 | 0.296730 | <0.001 |
| gamma-glutamylleucine*Metabolite-3114 | 270 | 0.610266 | 0.372424 | <0.001 |
| gamma-glutamylleucine*Glutamate | 402 | 0.813405 | 0.661627 | <0.001 |
| gamma-glutamylleucine*glutamylvaline | 270 | 0.980569 | 0.961516 | <0.001 |
| glucose*mannose | 270 | 0.569026 | 0.323791 | <0.001 |
| glucose*galactonic acid | 270 | 0.612109 | 0.374677 | <0.001 |
| 5-oxoproline*gluconate | 270 | 0.519968 | 0.270367 | <0.001 |
| 5-oxoproline*Glutamate | 270 | 0.598936 | 0.358724 | <0.001 |
| aspartate*Glutamate | 270 | 0.647610 | 0.419399 | <0.001 |
| erythronate-*Glutamate | 270 | 0.577551 | 0.333565 | <0.001 |
| gamma-glutamylleucine*Glutamate | 270 | 0.702612 | 0.493664 | <0.001 |
| gamma-glutamylphenylalanine*Glutamate | 270 | 0.683581 | 0.467283 | <0.001 |
| gamma-glutamylthreonine-*Glutamate | 270 | 0.547683 | 0.299956 | <0.001 |
| gamma-glutamyltyrosine*Glutamate | 270 | 0.656418 | 0.430885 | <0.001 |
| glutamine*Glutamate | 270 | −0.693796 | 0.481352 | <0.001 |
| glycerate*Glutamate | 270 | 0.514091 | 0.264289 | <0.001 |
| Metabolite-10814*Glutamate | 270 | 0.683648 | 0.467375 | <0.001 |
| Metabolite-11505*Glutamate | 270 | 0.565409 | 0.319687 | <0.001 |
| Metabolite-11560*Glutamate | 270 | 0.596566 | 0.355891 | <0.001 |
| Metabolite-12055*Glutamate | 270 | 0.710157 | 0.504322 | <0.001 |

TABLE 9B-continued

Correlated Biomarkers in Study 2.

| Compounds | N | Correlation | R-square | p-values |
|---|---|---|---|---|
| Metabolite-3078*Glutamate | 270 | −0.573092 | 0.328434 | <0.001 |
| Metabolite-3114*Glutamate | 270 | 0.717209 | 0.514389 | <0.001 |
| Glutamate*glutamylvaline | 402 | 0.815543 | 0.665110 | <0.001 |
| 5-oxoproline*glutamylvaline | 270 | 0.567314 | 0.321845 | <0.001 |
| aspartate*glutamylvaline | 270 | 0.650190 | 0.422746 | <0.001 |
| erythronate-*glutamylvaline | 270 | 0.648632 | 0.420723 | <0.001 |
| gamma-glutamylmethionine-*glutamylvaline | 270 | 0.682431 | 0.465712 | <0.001 |
| gammaglutamylphenylalanine*glutamylvaline | 270 | 0.748588 | 0.560384 | <0.001 |
| gamma-glutamylthreonine-*glutamylvaline | 270 | 0.613004 | 0.375774 | <0.001 |
| gamma-glutamyltyrosine*glutamylvaline | 270 | 0.669454 | 0.448169 | <0.001 |
| glutamine*glutamylvaline | 270 | −0.586263 | 0.343704 | <0.001 |
| glycerate*glutamylvaline | 270 | 0.500861 | 0.250862 | <0.001 |
| Metabolite-10814*glutamylvaline | 270 | 0.544487 | 0.296466 | <0.001 |
| Metabolite-11505*glutamylvaline | 270 | 0.571094 | 0.326149 | <0.001 |
| Metabolite-11560*glutamylvaline | 270 | 0.520971 | 0.271411 | <0.001 |
| Metabolite-12055*glutamylvaline | 270 | 0.818203 | 0.669456 | <0.001 |
| Metabolite-3078*glutamylvaline | 270 | −0.536866 | 0.288225 | <0.001 |
| Metabolite-3114*glutamylvaline | 270 | 0.588849 | 0.346744 | <0.001 |
| Docosatetraenate*Heptadecenate | 402 | 0.731992 | 0.535812 | <0.001 |
| Fasting_FFA*Heptadecenate | 393 | 0.503364 | 0.253375 | <0.001 |
| Heptadecenate*palmitate (16:0) | 402 | 0.902155 | 0.813884 | <0.001 |
| Heptadecenate*margarate (17:0) | 402 | 0.827249 | 0.684341 | <0.001 |
| Heptadecenate*stearate (18:0) | 402 | 0.719541 | 0.517740 | <0.001 |
| Heptadecenate*alpha linolenate (18:3(n-3)) | 402 | 0.605486 | 0.366614 | <0.001 |
| Isobar-cis-9-cis-11-trans-11-eicosenoate*Heptadecenate | 270 | 0.717041 | 0.514147 | <0.001 |
| linoleate (18:2(n-6))*Heptadecenate | 270 | 0.696473 | 0.485075 | <0.001 |
| myristate (14:0)*Heptadecenate | 270 | 0.815585 | 0.665178 | <0.001 |
| myristoleate (18:1(n-9))*14-1-n-5-*Heptadecenate | 270 | 0.764373 | 0.584266 | <0.001 |
| n-3-DPA-22-5-n-3-*Heptadecenate | 270 | 0.600981 | 0.361178 | <0.001 |
| oleate (18:1(n-9))*Heptadecenate | 270 | 0.826866 | 0.683707 | <0.001 |
| palmitoleate (16:1(n-7))*Heptadecenate | 270 | 0.891137 | 0.794126 | <0.001 |
| Heptadecenate*Metabolite-11909 | 270 | 0.500849 | 0.250850 | <0.001 |
| Linolyl.LPC*Oleoyl.LPC | 270 | 0.503307 | 0.253318 | <0.001 |
| hypoxanthine*lactate | 270 | 0.521393 | 0.271850 | <0.001 |
| dihomo-alpha-alpha linolenate (18:3(n-3))-20-3-n-3-*linoleate (18:2(n-6)) | 270 | 0.513066 | 0.263237 | <0.001 |
| Isobar-cis-9-cis-11-trans-11-eicosenoate*linoleate (18:2(n-6)) | 270 | 0.614356 | 0.377433 | <0.001 |
| linoleate (18:2(n-6))*myristate (14:0) | 270 | 0.777196 | 0.604033 | <0.001 |
| linoleate (18:2(n-6))*oleate (18:1(n-9)) | 270 | 0.764875 | 0.585034 | <0.001 |
| linoleate (18:2(n-6))*palmitate (16:0) | 270 | 0.591405 | 0.349760 | <0.001 |
| linoleate (18:2(n-6))*palmitoleate (16:1(n-7)) | 270 | 0.667721 | 0.445851 | <0.001 |
| linoleate (18:2(n-6))*stearate (18:0) | 402 | 0.688839 | 0.474500 | <0.001 |
| Docosatetraenate*linoleate (18:2(n-6)) | 402 | 0.718624 | 0.516421 | <0.001 |
| linoleate (18:2(n-6))*margarate (17:0) | 402 | 0.658122 | 0.433124 | <0.001 |
| Docosatetraenate*oleate (18:1(n-9)) | 402 | 0.764928 | 0.585115 | <0.001 |
| margarate (17:0)*oleate (18:1(n-9)) | 270 | 0.510486 | 0.260596 | <0.001 |
| 3-hydroxybutyrate (BHBA)*oleate (18:1(n-9)) | 270 | 0.576371 | 0.332204 | <0.001 |
| alpha linolenate (18:3(n-3))*oleate (18:1(n-9)) | 270 | 0.736518 | 0.542459 | <0.001 |
| Isobar-cis-9-cis-11-trans-11-eicosenoate*oleate (18:1(n-9)) | 270 | 0.777196 | 0.604033 | <0.001 |
| linoleate (18:1(n-9)) (18:2(n-6))*oleate (18:1(n-9)) | 270 | 0.709041 | 0.502739 | <0.001 |
| margarate (17:0)*oleate (18:1(n-9)) | 270 | 0.668674 | 0.447124 | <0.001 |
| myristate (14:0)*oleate (18:1(n-9)) | 270 | 0.587740 | 0.345438 | <0.001 |
| myristoleate (18:1(n-9))*14-1-n-5-*oleate (18:1(n-9)) | 270 | 0.907290 | 0.823175 | <0.001 |
| oleate (18:1(n-9))*palmitate (16:0) | 270 | 0.766301 | 0.587217 | <0.001 |
| oleate (18:1(n-9))*palmitoleate (16:1(n-7)) | 270 | 0.765960 | 0.586695 | <0.001 |
| oleate (18:1(n-9))*stearate (18:0) | 402 | 0.748928 | 0.560893 | <0.001 |
| pyruvate*Metabolite-4357 | 270 | 0.586698 | 0.344214 | <0.001 |
| asparagine*serine | 270 | 0.638729 | 0.407974 | <0.001 |
| ornithine*serine | 270 | 0.656649 | 0.431187 | <0.001 |
| serine*Metabolite-4274 | 270 | 0.578680 | 0.334870 | <0.001 |
| dihomo-alpha-alpha linolenate (18:3(n-3))-20-3-n-3-*palmitate (16:0) | 270 | 0.516782 | 0.267063 | <0.001 |
| Isobar-cis-9-cis-11-trans-11-eicosenoate*palmitate (16:0) | 270 | 0.703264 | 0.494580 | <0.001 |
| margarate (17:0)*palmitate (16:0) | 270 | 0.752390 | 0.566091 | <0.001 |
| myristate (14:0)*palmitate (16:0) | 270 | 0.807589 | 0.652199 | <0.001 |
| myristoleate (18:1(n-9))*14-1-n-5-*palmitate (16:0) | 270 | 0.658236 | 0.433274 | <0.001 |
| n-3-DPA-22-5-n-3-*palmitate (16:0) | 270 | 0.553025 | 0.305836 | <0.001 |
| palmitate (16:0)*palmitoleate (16:1(n-7)) | 270 | 0.784704 | 0.615761 | <0.001 |
| palmitate (16:0)*stearate (18:0) | 270 | 0.843751 | 0.711916 | <0.001 |
| palmitate (16:0)*Heptadecenate | 270 | 0.851782 | 0.725532 | <0.001 |
| palmitate (16:0)*Docosatetraenate | 270 | 0.533851 | 0.284997 | <0.001 |
| Metabolite-9033*Metabolite-10750 | 270 | 0.550669 | 0.303236 | <0.001 |
| bradykinin, hydroxyproline form-*peptide-HWESASXXR | 270 | 0.587635 | 0.345314 | <0.001 |

2I: Predicting and Monitoring Insulin Resistance:

The biomarker panel and algorithm will measure insulin resistance (IR) which is a root cause of type 2 diabetes. The results will be presented as an "IR Score™" which represents the level of insulin resistance of the subject. IR Scores will range from Normal Glucose Tolerance (NGT) through increasing levels (Low, Medium, High) of Impaired Glucose Tolerance (IGT). The IR Score™ will allow the physician to place the patient on the spectrum of glucose tolerance, from normal to high. For example, an IR Score™ of 25 will put the patient in the Low IGT category while an IR Score™ of 80 will put the patient in the High IGT category.

By determining the IR Score on an annual or semi-annual basis, physicians can monitor a patient's progression toward diabetes. For example, an IR score of 25 was obtained at a first time point, an IR Score of 34 was obtained at a second time point, an IR Score of 40 was obtained at a third time point, an IR Score of 40 was obtained at a third time point, an IR Score of 55 was obtained at a fourth time point, and an IR Score of 80 was obtained at a fourth time point indicating an increase in IR and progression of disease from normal to highly impaired glucose tolerance. Using the biomarkers and algorithm of the instant invention for progression monitoring will guide the physician's decision to implement preventative measures such as dietary restrictions, exercise, or early-stage drug treatment. An example of a report demonstrating the use of the IR Score to monitor IR status over time is shown in FIG. 5.

TABLE 10

| IR Score | | |
|---|---|---|
| IR Score | 1 to 100 | ≤25 NGT |
| | | 26 to 50 Low IGT |
| | | 51 to 75 Medium IGT |
| | | 76 to 100 High IGT |
| | | >100 Type 2 Diabetes |

2J: Biomarkers that Correlate with Glucose Tolerance Tests

Another study will be carried out to test the biomarkers discovered in the instant invention with a new cohort and to discover additional biochemical biomarkers that correlate with insulin sensitivity (IS) and insulin resistance (IR) as measured by the hyperinsulinemic euglycemic (HI) clamp (Table 11). Using the following study design, baseline fasting EDTA-plasma samples collected from NGT, IGT, IFG IGT/IFG and diabetic subjects (total=250) will be analyzed.

TABLE 11

| Summary of Study Subjects | |
|---|---|
| Condition | Number of Subjects |
| NGT | 50 |
| IGT | 50 |

TABLE 11-continued

| Summary of Study Subjects | |
|---|---|
| Condition | Number of Subjects |
| IFG | 50 |
| IGT/IFG | 50 |
| T2D | 50 |

Abbreviations
NGT: Normal Glucose Tolerant (OGTT, <140 mg/dL or <7.8 mmol/L)
IGT: Impaired Glucose Tolerant (OGTT, 140-199 mg/dL or 7.8-11.0 mmol/L)
IFG: Impaired Fasting Glucose (Fasting plasma glucose, 100-125 mg/dL or 5.6-6.9 mmol/L)
IGT/IFG: IGT and/or IFG
T2D: Type II Diabetes (OGTT, ≥200 mg/dL or ≥11.1 mmol/L)

Example 3

Biomarkers for Metabolic Syndrome Related Disorders

3A: Biomarkers of Metabolic Syndrome

Biomarkers were discovered by (1) analyzing plasma and serum samples drawn from different groups of subjects to determine the levels of metabolites in the samples and then (2) statistically analyzing the results to determine those metabolites that were differentially present in the two groups.

The samples used for the analysis were obtained from 19 Caucasian males aged 18-39, average age of 25.6, that had been diagnosed with metabolic syndrome and 19 healthy, age-matched, Caucasian males.

T-tests were used to determine differences in the mean levels of metabolites between the two populations (i.e., Metabolic syndrome vs. Healthy controls).

Biomarkers:

As listed below in Tables 12 and 13, biomarkers were discovered that were differentially present between samples from subjects with Metabolic Syndrome and Control (healthy) subjects.

Tables 12 and 13 include, for each listed biomarker, the p-value and q-value determined in the statistical analysis of the data concerning the biomarkers and an indication of the mean level in metabolic syndrome, the mean level in the control, and the percentage difference in the metabolic syndrome mean level as compared to the healthy mean level in plasma (Table 12) and serum (Table 13). The term "Isobar" as used in the tables indicates the compounds that could not be distinguished from each other on the analytical platform used in the analysis (i.e., the compounds in an isobar elute at nearly the same time and have similar (and sometimes exactly the same) quant ions, and thus cannot be distinguished). Comp_ID refers to the compound identification number used as a primary key for that compound in the in-house chemical database. Library indicates the chemical library that was used to identify the compounds. The number 50 refer to the GC library and the number 61 refers to the LC library.

TABLE 12

| Metabolite biomarkers of Metabolic Syndrome in plasma | | | | | | | |
|---|---|---|---|---|---|---|---|
| COMP_ID | COMPOUND | LIB_ID | p-value | q-value | Mean_Metabolic Syndrome | Mean_Ctrl | % Change Met. Syn. vs Control |
| 22290 | 2-propylpentanoic acid | 50 | 0.2189 | 0.329 | 14.75 | 0.89 | 1557% |
| 10715 | Metabolite - 2395 | 61 | 0.3183 | 0.3868 | 6.94 | 0.83 | 736% |

TABLE 12-continued

Metabolite biomarkers of Metabolic Syndrome in plasma

| COMP_ID | COMPOUND | LIB_ID | p-value | q-value | Mean_Metabolic Syndrome | Mean_Ctrl | % Change Met. Syn. vs Control |
|---|---|---|---|---|---|---|---|
| 10327 | Metabolite - 2281 | 61 | 0.0788 | 0.2083 | 1.97 | 0.72 | 174% |
| 10092 | Metabolite - 2250 | 61 | 0.3313 | 0.3919 | 1.84 | 0.74 | 149% |
| 569 | caffeine | 61 | 0.0806 | 0.2083 | 1.92 | 0.78 | 146% |
| 22054 | Metabolite - 8792 | 50 | <0.0001 | 4.00E−04 | 1.71 | 0.76 | 125% |
| 12796 | Metabolite - 3114 | 50 | 0.0559 | 0.1731 | 1.89 | 0.89 | 112% |
| 10286 | Metabolite - 2272 | 61 | 0.0922 | 0.2131 | 2.09 | 1.01 | 107% |
| 12751 | Metabolite - 3073 | 50 | 0.0055 | 0.0575 | 3.09 | 1.6 | 93% |
| 10672 | Metabolite - 2390 | 61 | 0.0045 | 0.0575 | 1.85 | 0.97 | 91% |
| 18369 | gamma-glu-leu | 61 | 0.2496 | 0.3473 | 2.82 | 1.49 | 89% |
| 14715 | Metabolite - 3653 | 61 | 0.5859 | 0.5302 | 2.39 | 1.28 | 87% |
| 11056 | Metabolite - 2568 | 61 | 0.3525 | 0.3951 | 3.38 | 1.84 | 84% |
| 57 | glutamic acid | 50 | 0.0403 | 0.1575 | 2.6 | 1.46 | 78% |
| 9130 | Metabolite - 2139 | 61 | 0.0027 | 0.0473 | 1.62 | 0.94 | 72% |
| 1638 | arginine | 61 | 0.0795 | 0.2083 | 1.53 | 0.9 | 70% |
| 24233 | Metabolite - 9855 | 61 | 0.327 | 0.3896 | 1.59 | 0.95 | 67% |
| 22130 | DL-3-phenyllactic acid | 61 | 0.1899 | 0.3052 | 1.82 | 1.1 | 65% |
| 17492 | Metabolite - 4906 | 61 | 0.1714 | 0.2843 | 1.62 | 0.98 | 65% |
| 21630 | Metabolite - 8402 | 50 | 0.0044 | 0.0575 | 1.48 | 0.9 | 64% |
| 17557 | Metabolite - 4929 | 61 | 0.0132 | 0.0946 | 1.25 | 0.77 | 62% |
| 15253 | Metabolite - 3832 | 61 | 0.4313 | 0.4494 | 2.22 | 1.38 | 61% |
| 20842 | Metabolite - 7765 | 61 | 0.2648 | 0.3613 | 2.17 | 1.35 | 61% |
| 14837 | Metabolite - 3707 | 61 | 0.8263 | 0.605 | 3.14 | 1.97 | 59% |
| 3147 | xanthine | 61 | 0.0204 | 0.1174 | 1.54 | 0.98 | 57% |
| 21127 | monopalmitin | 50 | 0.0025 | 0.0473 | 1.5 | 0.96 | 56% |
| 2734 | gamma-L-glutamyl-L-tyrosine | 61 | 0.1081 | 0.2168 | 1.93 | 1.24 | 56% |
| 6413 | Metabolite - 1342-possible-phenylacetylglutamine- | 61 | 0.2081 | 0.3221 | 1.82 | 1.17 | 56% |
| 2132 | citrulline | 50 | 0.4298 | 0.4494 | 0.34 | 0.22 | 55% |
| 20830 | Metabolite - 7762 | 61 | 0.0195 | 0.1168 | 1.43 | 0.93 | 54% |
| 15996 | aspartate | 50 | 0.2785 | 0.3701 | 2.81 | 1.83 | 54% |
| 18118 | Metabolite - 5346 | 50 | 0.016 | 0.1008 | 1.52 | 0.99 | 54% |
| 15113 | Metabolite - 3783 | 61 | 0.0978 | 0.2144 | 0.85 | 0.56 | 52% |
| 7171 | Metabolite - 1643 | 61 | 0.3158 | 0.3868 | 2.06 | 1.36 | 51% |
| 19377 | Metabolite - 6272 | 50 | 0.0031 | 0.0497 | 1.16 | 0.77 | 51% |
| 16337 | Metabolite - 4167 | 61 | 0.0333 | 0.1436 | 1.41 | 0.94 | 50% |
| 12756 | Metabolite - 3077 | 50 | 4.00E−04 | 0.045 | 1.93 | 1.3 | 48% |
| 17390 | Metabolite - 4806 | 50 | 0.0276 | 0.1362 | 1.23 | 0.83 | 48% |
| 21418 | Isobar-56-includes-DL-pipecolic acid-1-amino-1-cyclopentanecarboxylic acid | 61 | 0.1632 | 0.2797 | 1.78 | 1.21 | 47% |
| 1125 | isoleucine | 50 | 0.0994 | 0.2148 | 1.13 | 0.77 | 47% |
| 6847 | Metabolite - 1496 | 61 | 0.0238 | 0.1264 | 1.45 | 0.99 | 46% |
| 12658 | Metabolite - 3026 | 50 | 0.0062 | 0.0575 | 1.66 | 1.15 | 44% |
| 18392 | theobromine | 61 | 0.4972 | 0.4818 | 1.41 | 0.98 | 44% |
| 13775 | Metabolite - 3370 | 61 | 0.001 | 0.0473 | 1.52 | 1.06 | 43% |
| 7933 | Metabolite - 1911 | 61 | 0.5673 | 0.5208 | 1.44 | 1.01 | 43% |
| 22320 | Metabolite - 8889 | 50 | 0.0244 | 0.1264 | 0.72 | 0.51 | 41% |
| 27278 | Metabolite - 10510 | 50 | 0.0213 | 0.1195 | 1.48 | 1.05 | 41% |
| 11178 | Metabolite - 2608 | 61 | 0.0065 | 0.0575 | 1.24 | 0.88 | 41% |
| 12656 | Metabolite - 3025 | 50 | 0.0025 | 0.0473 | 1.59 | 1.13 | 41% |
| 18882 | taurodeoxycholic acid | 61 | 0.2208 | 0.3294 | 1.87 | 1.33 | 41% |
| 27513 | indole-3-acetic acid | 61 | 0.0439 | 0.1617 | 1.36 | 0.97 | 40% |
| 13214 | Metabolite - 3183-possible-gamma-L-glutamyl-L-phenylalanine | 61 | 0.2025 | 0.3182 | 2.06 | 1.48 | 39% |
| 1481 | inositol-1-phosphate | 50 | 0.0444 | 0.1617 | 1.72 | 1.24 | 39% |
| 60 | leucine | 50 | 0.0726 | 0.2034 | 1.12 | 0.81 | 38% |
| 12780 | Metabolite - 3098 | 50 | 0.0023 | 0.0473 | 1.67 | 1.21 | 38% |
| 12774 | Metabolite - 3094 | 50 | 0.0057 | 0.0575 | 1.19 | 0.87 | 37% |
| 1561 | alpha-tocopherol | 50 | 0.0599 | 0.1774 | 1.31 | 0.96 | 36% |
| 12647 | Metabolite - 3019 | 50 | 0.0024 | 0.0473 | 1.5 | 1.1 | 36% |
| 17068 | Metabolite - 4627 | 61 | 0.8349 | 0.6052 | 1.66 | 1.22 | 36% |
| 12960 | Metabolite - 3134 | 61 | 0.0558 | 0.1731 | 1.25 | 0.92 | 36% |
| 9491 | Metabolite - 2185 | 61 | 0.2076 | 0.3221 | 1.18 | 0.87 | 36% |
| 9172 | Metabolite - 2000 | 61 | 0.0197 | 0.1168 | 1.15 | 0.85 | 35% |
| 1898 | proline | 61 | 0.0309 | 0.1425 | 1.36 | 1.01 | 35% |
| 1299 | tyrosine | 61 | 0.0027 | 0.0473 | 1.3 | 0.97 | 34% |
| 18829 | phenylalanine | 61 | 0.0014 | 0.0473 | 1.51 | 1.13 | 34% |
| 12767 | Metabolite - 3087 | 50 | 0.3192 | 0.3868 | 1.24 | 0.93 | 33% |
| 9905 | Metabolite - 2231 | 61 | 0.0482 | 0.1629 | 1.45 | 1.09 | 33% |
| 19372 | Metabolite - 6269 | 50 | 0.0255 | 0.1288 | 1.01 | 0.76 | 33% |
| 19397 | Metabolite - 6326 | 50 | 0.016 | 0.1008 | 1.38 | 1.04 | 33% |

TABLE 12-continued

Metabolite biomarkers of Metabolic Syndrome in plasma

| COMP_ID | COMPOUND | LIB_ID | p-value | q-value | Mean_Metabolic Syndrome | Mean_Ctrl | % Change Met. Syn. vs Control |
|---|---|---|---|---|---|---|---|
| 1649 | valine | 50 | 0.1994 | 0.3156 | 1.1 | 0.83 | 33% |
| 12222 | Metabolite - 2374 | 50 | 0.0068 | 0.0575 | 1.37 | 1.04 | 32% |
| 15140 | L-kynurenine | 61 | 0.0123 | 0.0912 | 1.33 | 1.01 | 32% |
| 5628 | Metabolite - 1086 | 61 | 0.8915 | 0.6155 | 1.95 | 1.49 | 31% |
| 5687 | Metabolite - 1110 | 61 | 0.6883 | 0.573 | 1.54 | 1.18 | 31% |
| 20699 | meso-erythritol | 50 | 0.0466 | 0.1629 | 1.29 | 0.99 | 30% |
| 15990 | L-alpha-glycerophosphorylcholine | 61 | 0.2682 | 0.3634 | 1.94 | 1.49 | 30% |
| 27718 | creatine | 61 | 0.0922 | 0.2131 | 1.47 | 1.13 | 30% |
| 12609 | Metabolite - 2986 | 50 | 0.0331 | 0.1436 | 1.82 | 1.4 | 30% |
| 18476 | glycocholic acid | 61 | 0.1687 | 0.283 | 1.91 | 1.47 | 30% |
| 18010 | Metabolite - 5231 | 61 | 0.2164 | 0.329 | 1.52 | 1.17 | 30% |
| 12876 | Metabolite - 3125 | 61 | 0.0652 | 0.1905 | 1.22 | 0.94 | 30% |
| 19364 | Metabolite - 6246 | 50 | 0.0105 | 0.0809 | 1.32 | 1.02 | 29% |
| 10245 | Metabolite - 2269- | 61 | 0.84 | 0.6052 | 1.5 | 1.16 | 29% |
| 6266 | Metabolite - 1286 | 61 | 0.092 | 0.2131 | 1.59 | 1.23 | 29% |
| 15506 | choline | 61 | 0.1324 | 0.2451 | 1.71 | 1.33 | 29% |
| 12639 | Metabolite - 3012 | 50 | 0.0024 | 0.0473 | 1.59 | 1.24 | 28% |
| 16518 | Metabolite - 4276 | 50 | 0.1013 | 0.2164 | 1.14 | 0.89 | 28% |
| 17512 | Metabolite - 4912 | 61 | 0.5453 | 0.5139 | 2.99 | 2.34 | 28% |
| 29817 | Metabolite - 10683 | 50 | 0.0151 | 0.1008 | 1.57 | 1.23 | 28% |
| 24076 | Metabolite - 9726 | 50 | 0.0364 | 0.1465 | 1.34 | 1.06 | 26% |
| 584 | mannose | 50 | 0.1042 | 0.2168 | 1.39 | 1.1 | 26% |
| 18524 | 6-hydroxydopamine | 50 | 0.3352 | 0.3923 | 1.06 | 0.84 | 26% |
| 1126 | alanine | 50 | 0.1098 | 0.2168 | 0.97 | 0.77 | 26% |
| 10629 | Metabolite - 2386 | 61 | 0.5698 | 0.5208 | 1.2 | 0.96 | 25% |
| 1301 | lysine | 50 | 0.3451 | 0.3929 | 1.01 | 0.81 | 25% |
| 27256 | Metabolite - 10500 | 50 | 0.0367 | 0.1465 | 1.07 | 0.86 | 24% |
| 9024 | Metabolite - 2111 | 61 | 0.0925 | 0.2131 | 0.98 | 0.79 | 24% |
| 10746 | Isobar-6-includes-valine-betaine | 61 | 0.1592 | 0.2751 | 1.47 | 1.19 | 24% |
| 12768 | Metabolite - 3088 | 50 | 0.1478 | 0.2642 | 1.85 | 1.5 | 23% |
| 1572 | glyceric acid | 50 | 0.2335 | 0.3381 | 1.6 | 1.3 | 23% |
| 12650 | Metabolite - 3022 | 50 | 0.0772 | 0.2083 | 1.45 | 1.18 | 23% |
| 22337 | Metabolite - 8893 | 61 | 0.1269 | 0.2414 | 1.08 | 0.88 | 23% |
| 10087 | Metabolite - 2249 | 61 | 0.3326 | 0.3919 | 1.36 | 1.11 | 23% |
| 1670 | urea | 50 | 0.0445 | 0.1617 | 1.31 | 1.07 | 22% |
| 527 | lactate | 50 | 0.2905 | 0.3718 | 1.54 | 1.26 | 22% |
| 16496 | Metabolite - 4251 | 50 | 0.5501 | 0.5161 | 0.88 | 0.72 | 22% |
| 8336 | Metabolite - 2005 | 61 | 0.2177 | 0.329 | 1.29 | 1.06 | 22% |
| 1303 | malic acid | 50 | 0.754 | 0.5875 | 1.07 | 0.88 | 22% |
| 15737 | hydroxyacetic acid | 50 | 0.0844 | 0.2083 | 1.08 | 0.89 | 21% |
| 16819 | Metabolite - 4496 | 50 | 0.0589 | 0.177 | 1.2 | 0.99 | 21% |
| 1358 | octadecanoic acid | 50 | 0.0073 | 0.0584 | 1.15 | 0.95 | 21% |
| 17665 | p-hydroxybenzaldehyde | 61 | 0.0329 | 0.1436 | 1.84 | 1.52 | 21% |
| 7081 | Metabolite - 1609 | 61 | 0.3512 | 0.3951 | 1.05 | 0.87 | 21% |
| 10737 | Isobar-1-includes-mannose-fructose-glucose-galactose-alpha-L-sorbopyranose-Inositol-D-allose-D--altrose-D-psicone-L--gulose-allo-inositol | 61 | 0.0589 | 0.177 | 1.3 | 1.08 | 20% |
| 13557 | Metabolite - 3323 | 61 | 0.5667 | 0.5208 | 1.26 | 1.05 | 20% |
| 15122 | glycerol | 50 | 0.0822 | 0.2083 | 1.21 | 1.01 | 20% |
| 16511 | Metabolite - 4274 | 50 | 0.4771 | 0.4733 | 1.15 | 0.96 | 20% |
| 1121 | heptadecanoic acid | 50 | 0.0531 | 0.1724 | 1.23 | 1.03 | 19% |
| 11053 | Metabolite - 2567 | 61 | 0.5088 | 0.4907 | 3.1 | 2.6 | 19% |
| 22026 | 1-methylguanidine | 50 | 0.0457 | 0.1629 | 1.19 | 1 | 19% |
| 25609 | Metabolite - 10439 | 50 | 0.3468 | 0.3929 | 1.63 | 1.37 | 19% |
| 12035 | nonanate | 50 | 0.0892 | 0.2131 | 1.47 | 1.24 | 19% |
| 1110 | arachidonic acid | 50 | 0.1038 | 0.2168 | 1.11 | 0.94 | 18% |
| 54 | tryptophan | 61 | 0.0487 | 0.1629 | 1.28 | 1.09 | 17% |
| 15278 | Metabolite - 3843 | 61 | 0.4117 | 0.4378 | 1.15 | 0.98 | 17% |
| 27570 | Metabolite - 10569 | 61 | 0.0063 | 0.0575 | 1.09 | 0.93 | 17% |
| 30178 | Metabolite - 10705 | 61 | 0.7541 | 0.5875 | 1.64 | 1.4 | 17% |
| 63 | cholesterol | 50 | 0.0343 | 0.1446 | 1.17 | 1 | 17% |
| 10551 | Metabolite - 2347 | 61 | 0.6957 | 0.573 | 1.96 | 1.68 | 17% |
| 21188 | 1-stearoyl-rac-glycerol | 50 | 0.4701 | 0.4687 | 1.14 | 0.98 | 16% |
| 1365 | tetradecanoic acid | 50 | 0.071 | 0.2016 | 1.15 | 0.99 | 16% |
| 5426 | Metabolite - 1004 | 61 | 0.3901 | 0.4235 | 1.08 | 0.93 | 16% |
| 19368 | Metabolite - 6267 | 50 | 0.2381 | 0.3381 | 1.59 | 1.37 | 16% |
| 27273 | Metabolite - 10506 | 50 | 0.1692 | 0.283 | 1.38 | 1.19 | 16% |

TABLE 12-continued

Metabolite biomarkers of Metabolic Syndrome in plasma

| COMP_ID | COMPOUND | LIB_ID | p-value | q-value | Mean_Metabolic Syndrome | Mean_Ctrl | % Change Met. Syn. vs Control |
|---|---|---|---|---|---|---|---|
| 7029 | Metabolite - 1597 | 61 | 0.0558 | 0.1731 | 1.77 | 1.53 | 16% |
| 10156 | Metabolite - 2259 | 61 | 0.7281 | 0.5856 | 1.04 | 0.9 | 16% |
| 10700 | Metabolite - 2393 | 61 | 0.6334 | 0.5495 | 2.23 | 1.93 | 16% |
| 13142 | Metabolite - 3165 | 61 | 0.0829 | 0.2083 | 1.34 | 1.16 | 16% |
| 25602 | Metabolite - 10432 | 50 | 0.9349 | 0.6253 | 2.17 | 1.88 | 15% |
| 1431 | p-hydroxyphenyllactic acid | 50 | 0.2345 | 0.3381 | 1.23 | 1.07 | 15% |
| 27271 | Metabolite - 10504 | 50 | 0.2474 | 0.3466 | 1.08 | 0.94 | 15% |
| 6398 | Metabolite - 1335 | 61 | 0.8947 | 0.6155 | 1.89 | 1.66 | 14% |
| 1336 | n-hexadecanoic acid | 50 | 0.1174 | 0.2297 | 1.09 | 0.96 | 14% |
| 27672 | 3-indoxyl-sulfate | 61 | 0.4812 | 0.4752 | 1.3 | 1.15 | 13% |
| 22895 | Metabolite - 9299 | 50 | 0.7239 | 0.5856 | 1.05 | 0.93 | 13% |
| 12129 | beta-hydroxyisovaleric acid | 50 | 0.3035 | 0.3814 | 1.4 | 1.24 | 13% |
| 19282 | Metabolite - 6126 | 61 | 0.8029 | 0.6047 | 1.14 | 1.01 | 13% |
| 21069 | dioctyl-phthalate | 50 | 0.0953 | 0.2144 | 1.07 | 0.95 | 13% |
| 17064 | Metabolite - 4624 | 50 | 0.0925 | 0.2131 | 1.25 | 1.11 | 13% |
| 21128 | 1-octadecanol | 50 | 0.0486 | 0.1629 | 1.08 | 0.96 | 13% |
| 18232 | Metabolite - 5403 | 50 | 0.1348 | 0.2473 | 1.19 | 1.06 | 12% |
| 15529 | Metabolite - 3951 | 61 | 0.1081 | 0.2168 | 1.29 | 1.15 | 12% |
| 27675 | 4-nitrophenol | 61 | 0.3162 | 0.3868 | 1.27 | 1.14 | 11% |
| 9216 | Metabolite - 2168 | 61 | 0.0835 | 0.2083 | 1.2 | 1.08 | 11% |
| 10750 | Isobar-8-includes-anthranilic acid-salicylamide | 61 | 0.2166 | 0.329 | 1.2 | 1.08 | 11% |
| 7601 | Metabolite - 1819 | 61 | 0.5864 | 0.5302 | 1.2 | 1.08 | 11% |
| 1604 | uric acid | 61 | 0.2964 | 0.3747 | 1.04 | 0.94 | 11% |
| 513 | creatinine | 61 | 0.1885 | 0.3052 | 1.06 | 0.96 | 10% |
| 1361 | pentadecanoic acid | 50 | 0.2362 | 0.3381 | 1.17 | 1.06 | 10% |
| 1642 | decanoic acid | 50 | 0.3114 | 0.3866 | 1.39 | 1.26 | 10% |
| 18147 | Metabolite - 5367 | 50 | 0.0753 | 0.2083 | 1.11 | 1.01 | 10% |
| 22803 | Isobar-66-includes-glycochenodeoxycholic acid-glycodeoxycholic acid | 61 | 0.41 | 0.4378 | 1.69 | 1.54 | 10% |
| 20267 | Metabolite - 7187 | 61 | 0.9304 | 0.6243 | 2.16 | 1.97 | 10% |
| 5531 | Metabolite - 1095 | 61 | 0.5242 | 0.5009 | 0.69 | 0.63 | 10% |
| 19363 | Metabolite - 6227 | 50 | 0.3417 | 0.3923 | 1.3 | 1.19 | 9% |
| 1105 | Linoleic acid | 50 | 0.3425 | 0.3923 | 1.07 | 0.98 | 9% |
| 17228 | Metabolite - 4727 | 61 | 0.7215 | 0.5856 | 1.56 | 1.43 | 9% |
| 1643 | fumaric acid | 50 | 0.9687 | 0.6344 | 1.46 | 1.34 | 9% |
| 16782 | Metabolite - 4470 | 61 | 0.9699 | 0.6344 | 1.12 | 1.03 | 9% |
| 1302 | methionine | 61 | 0.2524 | 0.3489 | 1.27 | 1.17 | 9% |
| 13545 | Metabolite - 3322 | 61 | 0.9964 | 0.6461 | 1.93 | 1.78 | 8% |
| 12083 | D-ribose | 50 | 0.6963 | 0.573 | 1.31 | 1.21 | 8% |
| 20950 | Metabolite - 7846 | 50 | 0.4339 | 0.4499 | 1.32 | 1.22 | 8% |
| 5765 | Metabolite - 1142 | 61 | 0.6088 | 0.5395 | 1.21 | 1.12 | 8% |
| 27719 | galactonic acid | 50 | 0.6632 | 0.5631 | 1.08 | 1 | 8% |
| 27409 | oleamide | 50 | 0.5882 | 0.5302 | 0.95 | 0.88 | 8% |
| 1507 | palmitoleic acid | 50 | 0.7754 | 0.5955 | 1.25 | 1.16 | 8% |
| 24077 | Metabolite - 9727 | 50 | 0.5913 | 0.5308 | 1.28 | 1.19 | 8% |
| 20489 | D-glucose | 50 | 0.0349 | 0.1446 | 1.14 | 1.06 | 8% |
| 6422 | Metabolite - 1320 | 61 | 0.1095 | 0.2168 | 1.02 | 0.95 | 7% |
| 19787 | Metabolite - 6746 | 61 | 0.2617 | 0.3594 | 1.17 | 1.09 | 7% |
| 5632 | Metabolite - 1138 | 61 | 0.156 | 0.2741 | 1.03 | 0.96 | 7% |
| 8098 | Metabolite - 1867 | 61 | 0.6653 | 0.5631 | 1.03 | 0.96 | 7% |
| 30273 | Metabolite - 10736 | 50 | 0.6061 | 0.5394 | 1.18 | 1.1 | 7% |
| 19934 | inositol | 50 | 0.6428 | 0.553 | 1.35 | 1.26 | 7% |
| 15676 | 3-methyl-2-oxovaleric acid | 61 | 0.5389 | 0.5102 | 1.21 | 1.13 | 7% |
| 18349 | DL-indole-3-lactic acid | 61 | 0.8534 | 0.6083 | 1.22 | 1.14 | 7% |
| 15765 | ethylmalonic acid | 61 | 0.7431 | 0.5875 | 0.99 | 0.93 | 6% |
| 30282 | Metabolite - 10744 | 50 | 0.4613 | 0.4621 | 1.17 | 1.1 | 6% |
| 16138 | Metabolite - 4080 | 50 | 0.8136 | 0.6047 | 2.4 | 2.27 | 6% |
| 10544 | Metabolite - 2329 | 61 | 0.9173 | 0.6207 | 1.11 | 1.05 | 6% |
| 15500 | carnitine | 61 | 0.6276 | 0.5468 | 0.94 | 0.89 | 6% |
| 12645 | Metabolite - 3017 | 50 | 0.6906 | 0.573 | 1.32 | 1.25 | 6% |
| 16665 | Metabolite - 4364 | 50 | 0.7407 | 0.5875 | 1.16 | 1.1 | 5% |
| 17648 | Metabolite - 5007 | 61 | 0.886 | 0.6154 | 2.2 | 2.09 | 5% |
| 15365 | sn-Glycerol-3-phosphate | 50 | 0.8826 | 0.6154 | 1.8 | 1.71 | 5% |
| 10499 | Metabolite - 2073 | 61 | 0.5624 | 0.5208 | 1.02 | 0.97 | 5% |
| 12638 | Metabolite - 3011 | 50 | 0.9472 | 0.6287 | 1.31 | 1.25 | 5% |
| 12663 | Metabolite - 3030 | 50 | 0.7315 | 0.5856 | 1.55 | 1.48 | 5% |
| 10065 | Metabolite - 2244 | 61 | 0.6638 | 0.5631 | 0.95 | 0.91 | 4% |
| 1645 | n-dodecanoate | 50 | 0.451 | 0.4584 | 1.24 | 1.19 | 4% |
| 6305 | Metabolite - 1254 | 61 | 0.7656 | 0.5901 | 0.82 | 0.79 | 4% |
| 18665 | Metabolite - 5728 | 61 | 0.6202 | 0.5451 | 1.14 | 1.1 | 4% |

TABLE 12-continued

Metabolite biomarkers of Metabolic Syndrome in plasma

| COMP_ID | COMPOUND | LIB_ID | p-value | q-value | Mean_Metabolic Syndrome | Mean_Ctrl | % Change Met. Syn. vs Control |
|---|---|---|---|---|---|---|---|
| 13065 | Metabolite - 3146 | 61 | 0.6037 | 0.5394 | 1.21 | 1.17 | 3% |
| 7127 | Metabolite - 1616 | 61 | 0.9018 | 0.6171 | 0.92 | 0.89 | 3% |
| 12673 | Metabolite - 3040 | 50 | 0.638 | 0.5512 | 1.29 | 1.25 | 3% |
| 59 | histidine | 50 | 0.8614 | 0.6083 | 1 | 0.97 | 3% |
| 27275 | Metabolite - 10507 | 50 | 0.8966 | 0.6155 | 1.36 | 1.32 | 3% |
| 12626 | Metabolite - 3003 | 50 | 0.7594 | 0.5875 | 1.1 | 1.07 | 3% |
| 17627 | Metabolite - 4986 | 50 | 0.8711 | 0.6123 | 1.23 | 1.2 | 2% |
| 13589 | Metabolite - 3327 | 61 | 0.919 | 0.6207 | 1.51 | 1.48 | 2% |
| 12894 | Metabolite - 2456 | 61 | 0.9618 | 0.6331 | 1.05 | 1.03 | 2% |
| 1648 | serine | 50 | 0.8095 | 0.6047 | 1.14 | 1.12 | 2% |
| 20248 | Metabolite - 7177 | 61 | 0.7567 | 0.5875 | 1.23 | 1.21 | 2% |
| 25607 | Metabolite - 10437 | 50 | 0.9076 | 0.6182 | 1.34 | 1.32 | 2% |
| 1564 | citric acid | 50 | 0.4876 | 0.4779 | 0.04 | 0.04 | 0% |
| 12726 | Metabolite - 3058 | 50 | 0.693 | 0.573 | 1.15 | 1.15 | 0% |
| 12593 | Metabolite - 2973 | 50 | 0.7576 | 0.5875 | 0.43 | 0.43 | 0% |
| 14988 | Metabolite - 3756 | 61 | 0.9471 | 0.6287 | 1.1 | 1.1 | 0% |
| 10147 | Metabolite - 2036 | 61 | 0.9971 | 0.6461 | 1.26 | 1.27 | −1% |
| 16829 | Metabolite - 4503 | 50 | 0.8459 | 0.6069 | 1.19 | 1.2 | −1% |
| 27411 | Metabolite - 10547 | 61 | 0.9605 | 0.6331 | 1.04 | 1.05 | −1% |
| 1410 | 1-Hexadecanol | 50 | 0.8407 | 0.6052 | 0.97 | 0.98 | −1% |
| 10655 | Metabolite - 2388 | 61 | 0.7806 | 0.5973 | 1.1 | 1.12 | −2% |
| 17327 | Metabolite - 4767 | 50 | 0.8114 | 0.6047 | 1.09 | 1.11 | −2% |
| 12666 | Metabolite - 3033-possible-threonine-deriv- | 50 | 0.6852 | 0.573 | 1.23 | 1.26 | −2% |
| 1366 | trans-4-hydroxyproline | 50 | 0.9284 | 0.6243 | 1.09 | 1.12 | −3% |
| 21047 | 3-methyl-2-oxobutyric- | 61 | 0.6204 | 0.5451 | 0.99 | 1.02 | −3% |
| 10825 | Metabolite - 2546 | 61 | 0.7995 | 0.6047 | 0.98 | 1.01 | −3% |
| 16070 | Metabolite - 4019 | 50 | 0.7173 | 0.5856 | 1.19 | 1.23 | −3% |
| 22132 | DL-alpha-hydroxyisocaproic acid | 61 | 0.8586 | 0.6083 | 1.17 | 1.21 | −3% |
| 17786 | aldosterone | 61 | 0.8368 | 0.6052 | 1.1 | 1.14 | −4% |
| 30265 | Metabolite - 10732 | 50 | 0.6895 | 0.573 | 2.46 | 2.55 | −4% |
| 19097 | Metabolite - 5969 | 61 | 0.9094 | 0.6182 | 0.83 | 0.87 | −5% |
| 22145 | acetyl-L-carnitine | 61 | 0.7304 | 0.5856 | 1.14 | 1.2 | −5% |
| 1494 | 5-oxoproline | 50 | 0.8287 | 0.605 | 1.33 | 1.4 | −5% |
| 22309 | Metabolite - 8887 | 61 | 0.8136 | 0.6047 | 1.89 | 1.99 | −5% |
| 6571 | Metabolite - 1397 | 61 | 0.7119 | 0.5834 | 0.93 | 0.98 | −5% |
| 16509 | Metabolite - 4273 | 50 | 0.4072 | 0.4378 | 1.3 | 1.37 | −5% |
| 19623 | Metabolite - 6671 | 50 | 0.563 | 0.5208 | 0.33 | 0.35 | −6% |
| 6517 | Metabolite - 1338 | 61 | 0.4487 | 0.4583 | 0.98 | 1.04 | −6% |
| 12162 | Metabolite - 2339 | 50 | 0.427 | 0.4494 | 0.62 | 0.66 | −6% |
| 5733 | Metabolite - 1127 | 61 | 0.4107 | 0.4378 | 1.2 | 1.28 | −6% |
| 27272 | Metabolite - 10505 | 50 | 0.2265 | 0.3355 | 1.38 | 1.48 | −7% |
| 58 | glycine | 50 | 0.4963 | 0.4818 | 0.96 | 1.03 | −7% |
| 12777 | Metabolite - 3097 | 50 | 0.5284 | 0.5025 | 3.1 | 3.33 | −7% |
| 17568 | Metabolite - 4931 | 61 | 0.7564 | 0.5875 | 1.05 | 1.13 | −7% |
| 13038 | Metabolite - 3143 | 61 | 0.2742 | 0.3667 | 1.29 | 1.39 | −7% |
| 20299 | Metabolite - 7266 | 50 | 0.341 | 0.3923 | 0.86 | 0.93 | −8% |
| 12720 | Metabolite - 3056 | 61 | 0.5179 | 0.4971 | 1.1 | 1.19 | −8% |
| 12782 | Metabolite - 3100 | 50 | 0.7853 | 0.5986 | 1.94 | 2.1 | −8% |
| 22609 | Metabolite - 9047 | 50 | 0.8612 | 0.6083 | 1.45 | 1.57 | −8% |
| 2761 | thyroxine | 61 | 0.3227 | 0.3868 | 1.2 | 1.3 | −8% |
| 1284 | threonine | 50 | 0.4887 | 0.4779 | 0.99 | 1.08 | −8% |
| 22548 | Metabolite - 9026 | 50 | 0.8228 | 0.605 | 1.01 | 1.11 | −9% |
| 6851 | Metabolite - 1497 | 61 | 0.7431 | 0.5875 | 0.69 | 0.76 | −9% |
| 7644 | Metabolite - 1831- | 61 | 0.1522 | 0.2697 | 1.05 | 1.16 | −9% |
| 22880 | Metabolite - 9286 | 50 | 0.3811 | 0.4159 | 0.38 | 0.42 | −10% |
| 12533 | Metabolite - 2915 | 50 | 0.0688 | 0.1983 | 0.9 | 1 | −10% |
| 25402 | Metabolite - 10360 | 50 | 0.4214 | 0.4458 | 0.7 | 0.78 | −10% |
| 20676 | maleic acid | 61 | 0.3809 | 0.4159 | 0.62 | 0.7 | −11% |
| 6362 | Metabolite - 1323-possible-p-cresol-sulfate | 61 | 0.8874 | 0.6154 | 1.22 | 1.38 | −12% |
| 22133 | DL-hexanoyl-carnitine | 61 | 0.289 | 0.3718 | 0.53 | 0.6 | −12% |
| 17304 | Metabolite - 4759 | 61 | 0.2874 | 0.3718 | 0.98 | 1.11 | −12% |
| 16468 | Metabolite - 4236 | 61 | 0.1187 | 0.23 | 0.87 | 0.99 | −12% |
| 5618 | Metabolite - 1085 | 61 | 0.3652 | 0.4028 | 0.97 | 1.11 | −13% |
| 30555 | Metabolite - 10781 | 61 | 0.8625 | 0.6083 | 1.28 | 1.47 | −13% |
| 6373 | Metabolite - 1304 | 61 | 0.2945 | 0.3747 | 1.18 | 1.36 | −13% |
| 22175 | l-aspartyl-l-phenylalanine | 61 | 0.8236 | 0.605 | 1.03 | 1.19 | −13% |
| 16071 | Metabolite - 4020 | 50 | 0.1303 | 0.2435 | 0.93 | 1.08 | −14% |
| 19402 | Metabolite - 6346 | 50 | 0.0066 | 0.0575 | 0.97 | 1.13 | −14% |
| 22600 | Metabolite - 9043 | 50 | 0.3407 | 0.3923 | 1.09 | 1.27 | −14% |

TABLE 12-continued

Metabolite biomarkers of Metabolic Syndrome in plasma

| COMP_ID | COMPOUND | LIB_ID | p-value | q-value | Mean_Metabolic Syndrome | Mean_Ctrl | % Change Met. Syn. vs Control |
|---|---|---|---|---|---|---|---|
| 17330 | Metabolite - 4769 | 50 | 0.2308 | 0.3381 | 0.92 | 1.08 | −15% |
| 2342 | serotonin | 61 | 0.4557 | 0.4609 | 0.89 | 1.05 | −15% |
| 3127 | hypoxanthine | 61 | 0.2372 | 0.3381 | 1.54 | 1.82 | −15% |
| 15128 | DL-homocysteine | 61 | 0.0794 | 0.2083 | 0.81 | 0.96 | −16% |
| 16512 | Metabolite - 4275 | 50 | 0.2404 | 0.339 | 1.04 | 1.27 | −18% |
| 17494 | Metabolite - 4907 | 61 | 0.9491 | 0.6287 | 1.53 | 1.87 | −18% |
| 19370 | Metabolite - 6268 | 50 | 0.2874 | 0.3718 | 0.91 | 1.12 | −19% |
| 14672 | Metabolite - 3615 | 61 | 0.984 | 0.6416 | 0.88 | 1.09 | −19% |
| 577 | fructose | 50 | 0.2716 | 0.3657 | 0.96 | 1.19 | −19% |
| 11499 | Metabolite - 2753 | 61 | 0.459 | 0.4619 | 0.69 | 0.86 | −20% |
| 6374 | Metabolite - 1327 | 61 | 0.3602 | 0.4016 | 0.94 | 1.18 | −20% |
| 22053 | 3-hydroxydecanoic acid | 61 | 0.3226 | 0.3868 | 1.04 | 1.31 | −21% |
| 27738 | threonic acid | 50 | 0.1963 | 0.3131 | 1.02 | 1.29 | −21% |
| 542 | 3-hydroxybutanoic acid | 50 | 0.3099 | 0.3866 | 1.24 | 1.57 | −21% |
| 12757 | Metabolite - 3078 | 50 | 0.1683 | 0.283 | 1 | 1.27 | −21% |
| 12781 | Metabolite - 3099 | 50 | 0.2872 | 0.3718 | 2.88 | 3.67 | −22% |
| 24074 | Metabolite - 9706 | 50 | 0.2808 | 0.3708 | 0.85 | 1.1 | −23% |
| 53 | glutamine | 50 | 0.0982 | 0.2144 | 0.71 | 0.92 | −23% |
| 14239 | Metabolite - 3474 | 61 | 0.1845 | 0.3012 | 1.02 | 1.33 | −23% |
| 12625 | Metabolite - 3002 | 50 | 0.0973 | 0.2144 | 0.68 | 0.9 | −24% |
| 19110 | Metabolite - 5978 | 50 | 0.1078 | 0.2168 | 0.64 | 0.85 | −25% |
| 17540 | Metabolite - 4926 | 61 | 0.4366 | 0.4504 | 2.34 | 3.13 | −25% |
| 22570 | Metabolite - 9033 | 50 | 0.1374 | 0.2477 | 0.25 | 0.34 | −26% |
| 10961 | Metabolite - 2561 | 61 | 0.5701 | 0.5208 | 1.31 | 1.81 | −28% |
| 10604 | Metabolite - 2370 | 61 | 0.1251 | 0.2402 | 0.68 | 0.95 | −28% |
| 5657 | Metabolite - 1092 | 61 | 0.6524 | 0.5589 | 3.89 | 5.46 | −29% |
| 18705 | Metabolite - 5768 | 61 | 0.158 | 0.2751 | 1.03 | 1.48 | −30% |
| 16044 | Metabolite - 4005 | 50 | 0.0144 | 0.0992 | 0.55 | 0.81 | −32% |
| 17091 | Metabolite - 4641 | 61 | 0.1742 | 0.2866 | 0.76 | 1.12 | −32% |
| 10066 | Metabolite - 2029 | 61 | 0.4461 | 0.4579 | 1.19 | 1.77 | −33% |
| 22159 | dehydroisoandrosterone-3-sulfate | 61 | 0.0303 | 0.1425 | 0.93 | 1.4 | −34% |
| 22649 | Metabolite - 9108 | 50 | 0.0532 | 0.1724 | 0.66 | 1 | −34% |
| 17306 | Metabolite - 4760 | 61 | 0.098 | 0.2144 | 0.82 | 1.25 | −34% |
| 9165 | Metabolite - 2150 | 61 | 0.1062 | 0.2168 | 0.76 | 1.16 | −34% |
| 6239 | Metabolite - 1264 | 61 | 0.1367 | 0.2477 | 2.92 | 4.84 | −40% |
| 10781 | Metabolite - 2469 | 61 | 0.0231 | 0.126 | 0.89 | 1.51 | −41% |
| 10304 | Metabolite - 2276 | 61 | 0.8813 | 0.6154 | 1.28 | 2.19 | −42% |
| 5280 | biliverdin | 61 | 0.0289 | 0.1395 | 1.19 | 2.14 | −44% |
| 18871 | Metabolite - 5848 | 61 | 0.0069 | 0.0575 | 1.03 | 1.88 | −45% |
| 18702 | Metabolite - 5767 | 61 | 0.0017 | 0.0473 | 0.76 | 1.45 | −48% |
| 12478 | Metabolite - 2898 | 61 | 0.1285 | 0.2421 | 0.86 | 1.71 | −50% |
| 27710 | N-acetylglycine | 50 | 0.0049 | 0.0575 | 0.78 | 1.64 | −52% |
| 17495 | Metabolite - 4908 | 61 | 0.044 | 0.1617 | 0.94 | 1.99 | −53% |
| 10177 | Metabolite - 2039 | 61 | 0.0067 | 0.0575 | 0.83 | 1.86 | −55% |
| 12306 | Metabolite - 2869 | 61 | 0.627 | 0.5468 | 1.18 | 2.72 | −57% |

TABLE 13

Metabolite biomarkers of Metabolic Syndrome in serum.

| COMP_ID | COMPOUND | LIB_ID | p-value | q-value | Mean_Metabolic Syndrome | Mean_Control | % Change Met. Syn. vs Control |
|---|---|---|---|---|---|---|---|
| 19402 | Metabolite - 6346 | 50 | 0 | 9.00E−04 | 0.88 | 1.07 | −18% |
| 22054 | Metabolite - 8792 | 50 | 0 | 9.00E−04 | 1.29 | 0.56 | 130% |
| 12663 | Metabolite - 3030 | 50 | 4.00E−04 | 0.0304 | 0.61 | 0.83 | −27% |
| 27710 | N-acetylglycine | 50 | 6.00E−04 | 0.0335 | 0.56 | 1.28 | −56% |
| 18829 | phenylalanine | 61 | 0.0015 | 0.0629 | 0.95 | 0.71 | 34% |
| 13257 | Metabolite - 3218 | 61 | 0.0019 | 0.0675 | 0.94 | 0.57 | 65% |
| 9172 | Metabolite - 2000 | 61 | 0.0023 | 0.0675 | 1.24 | 0.86 | 44% |
| 17390 | Metabolite - 4806 | 50 | 0.0032 | 0.0827 | 1.2 | 0.69 | 74% |
| 20830 | Metabolite - 7762 | 61 | 0.005 | 0.1061 | 1.21 | 0.69 | 75% |
| 10672 | Metabolite - 2390 | 61 | 0.0051 | 0.1061 | 1.05 | 0.63 | 67% |
| 13142 | Metabolite - 3165 | 61 | 0.0066 | 0.1177 | 0.99 | 0.78 | 27% |
| 18147 | Metabolite - 5367 | 50 | 0.0068 | 0.1177 | 1.05 | 0.9 | 17% |

TABLE 13-continued

Metabolite biomarkers of Metabolic Syndrome in serum.

| COMP_ID | COMPOUND | LIB_ID | p-value | q-value | Mean_Metabolic Syndrome | Mean_Control | % Change Met. Syn. vs Control |
|---|---|---|---|---|---|---|---|
| 19110 | Metabolite - 5978 | 50 | 0.0075 | 0.1206 | 1.08 | 1.66 | −35% |
| 16337 | Metabolite - 4167 | 61 | 0.0087 | 0.1269 | 1.33 | 0.8 | 66% |
| 27570 | Metabolite - 10569 | 61 | 0.0095 | 0.1269 | 1.15 | 0.94 | 22% |
| 6422 | Metabolite - 1320 | 61 | 0.0098 | 0.1269 | 1.07 | 0.97 | 10% |
| 21630 | Metabolite - 8402 | 50 | 0.0104 | 0.1269 | 1.17 | 0.76 | 54% |
| 1299 | tyrosine | 61 | 0.0113 | 0.1304 | 1.26 | 0.87 | 45% |
| 9491 | Metabolite - 2185 | 61 | 0.0119 | 0.1304 | 1.14 | 0.77 | 48% |
| 18702 | Metabolite - 5767 | 61 | 0.013 | 0.132 | 0.75 | 1.31 | −43% |
| 13775 | Metabolite - 3370 | 61 | 0.0138 | 0.132 | 0.93 | 0.68 | 37% |
| 10177 | Metabolite - 2039 | 61 | 0.014 | 0.132 | 0.82 | 1.59 | −48% |
| 7081 | Metabolite - 1609 | 61 | 0.0171 | 0.1442 | 1.02 | 0.84 | 21% |
| 18871 | Metabolite - 5848 | 61 | 0.0171 | 0.1442 | 0.86 | 1.32 | −35% |
| 12658 | Metabolite - 3026 | 50 | 0.0178 | 0.1442 | 0.98 | 0.79 | 24% |
| 12647 | Metabolite - 3019 | 50 | 0.0191 | 0.1442 | 0.92 | 0.79 | 16% |
| 12656 | Metabolite - 3025 | 50 | 0.0193 | 0.1442 | 0.88 | 0.75 | 17% |
| 18118 | Metabolite - 5346 | 50 | 0.0194 | 0.1442 | 1.16 | 0.86 | 35% |
| 17786 | aldosterone | 61 | 0.0209 | 0.1498 | 1.14 | 0.91 | 25% |
| 27273 | Metabolite - 10506 | 50 | 0.0239 | 0.1655 | 0.77 | 0.91 | −15% |
| 17665 | p-hydroxybenzaldehyde | 61 | 0.0265 | 0.1775 | 0.7 | 0.53 | 32% |
| 6374 | Metabolite - 1327 | 61 | 0.0277 | 0.1781 | 1.23 | 1.92 | −36% |
| 7029 | Metabolite - 1597 | 61 | 0.0305 | 0.1781 | 0.67 | 0.5 | 34% |
| 21188 | 1-stearoyl-rac-glycerol | 50 | 0.0308 | 0.1781 | 1.16 | 0.76 | 53% |
| 16044 | Metabolite - 4005 | 50 | 0.0317 | 0.1781 | 1.01 | 1.55 | −35% |
| 5727 | Metabolite - 1126 | 61 | 0.0341 | 0.1781 | 1.19 | 0.96 | 24% |
| 10737 | Isobar-1-includes-mannose-fructose-glucose-galactose-alpha-L-sorbopyranose-Inositol-D-allose-D--altrose-D-psicone-L--gulose-allo-inositol | 61 | 0.0343 | 0.1781 | 0.93 | 0.75 | 24% |
| 1303 | malic acid | 50 | 0.0353 | 0.1781 | 1.05 | 1.23 | −15% |
| 57 | glutamic acid | 50 | 0.0361 | 0.1781 | 1.86 | 1 | 86% |
| 14491 | Metabolite - 3530 | 61 | 0.0362 | 0.1781 | 0.66 | 1.02 | −35% |
| 12478 | Metabolite - 2898 | 61 | 0.0364 | 0.1781 | 0.64 | 1.64 | −61% |
| 6266 | Metabolite - 1286 | 61 | 0.0369 | 0.1781 | 1.01 | 0.79 | 28% |
| 1638 | arginine | 61 | 0.0374 | 0.1781 | 1.49 | 0.81 | 84% |
| 63 | cholesterol | 50 | 0.0378 | 0.1781 | 1.11 | 0.93 | 19% |
| 15529 | Metabolite - 3951 | 61 | 0.0386 | 0.1781 | 0.98 | 0.84 | 17% |
| 15278 | Metabolite - 3843 | 61 | 0.0403 | 0.181 | 1.17 | 0.8 | 46% |
| 27275 | Metabolite - 10507 | 50 | 0.0417 | 0.181 | 0.6 | 0.78 | −23% |
| 22159 | dehydroisoandrosterone-3-sulfate | 61 | 0.0422 | 0.181 | 0.8 | 1.11 | −28% |
| 19397 | Metabolite - 6326 | 50 | 0.0427 | 0.181 | 1.12 | 0.9 | 24% |
| 12609 | Metabolite - 2986 | 50 | 0.044 | 0.1812 | 0.88 | 0.7 | 26% |
| 10087 | Metabolite - 2249 | 61 | 0.0468 | 0.1812 | 1.21 | 0.84 | 44% |
| 19377 | Metabolite - 6272 | 50 | 0.0472 | 0.1812 | 1.24 | 0.95 | 31% |
| 1604 | uric acid | 61 | 0.0485 | 0.1812 | 1.12 | 0.96 | 17% |
| 54 | tryptophan | 61 | 0.0501 | 0.1812 | 0.98 | 0.82 | 20% |
| 15140 | L-kynurenine | 61 | 0.0507 | 0.1812 | 1.11 | 0.85 | 31% |
| 12666 | Metabolite - 3033-possible-threonine-deriv- | 50 | 0.051 | 0.1812 | 0.82 | 0.95 | −14% |
| 21127 | monopalmitin | 50 | 0.0517 | 0.1812 | 1.31 | 0.82 | 60% |
| 10629 | Metabolite - 2386 | 61 | 0.0529 | 0.1812 | 1.08 | 0.82 | 32% |
| 1125 | isoleucine | 50 | 0.0533 | 0.1812 | 1.57 | 1.05 | 50% |
| 12035 | nonanate | 50 | 0.0542 | 0.1812 | 0.75 | 0.58 | 29% |
| 60 | leucine | 50 | 0.0543 | 0.1812 | 1.36 | 1 | 36% |
| 12751 | Metabolite - 3073 | 50 | 0.0549 | 0.1812 | 0.74 | 0.64 | 16% |
| 12781 | Metabolite - 3099 | 50 | 0.0549 | 0.1812 | 0.52 | 0.75 | −31% |
| 12774 | Metabolite - 3094 | 50 | 0.0566 | 0.1828 | 1.11 | 0.89 | 25% |
| 24076 | Metabolite - 9726 | 50 | 0.059 | 0.1828 | 1.09 | 0.9 | 21% |
| 6571 | Metabolite - 1397 | 61 | 0.0593 | 0.1828 | 1.18 | 0.94 | 26% |
| 10499 | Metabolite - 2073 | 61 | 0.0594 | 0.1828 | 1.22 | 0.96 | 27% |
| 27278 | Metabolite - 10510 | 50 | 0.0598 | 0.1828 | 1.05 | 0.82 | 28% |
| 513 | creatinine | 61 | 0.0623 | 0.1875 | 1.15 | 0.93 | 24% |
| 18665 | Metabolite - 5728 | 61 | 0.0632 | 0.1878 | 0.97 | 0.85 | 14% |
| 18369 | gamma-glu-leu | 61 | 0.0679 | 0.1978 | 1.96 | 1.02 | 92% |
| 19370 | Metabolite - 6268 | 50 | 0.0685 | 0.1978 | 0.79 | 0.97 | −19% |

TABLE 13-continued

Metabolite biomarkers of Metabolic Syndrome in serum.

| COMP_ID | COMPOUND | LIB_ID | p-value | q-value | Mean_Metabolic Syndrome | Mean_Control | % Change Met. Syn. vs Control |
|---|---|---|---|---|---|---|---|
| 20699 | meso-erythritol | 50 | 0.0697 | 0.1986 | 1.15 | 0.89 | 29% |
| 9130 | Metabolite - 2139 | 61 | 0.0709 | 0.1991 | 1.31 | 0.92 | 42% |
| 18392 | theobromine | 61 | 0.0727 | 0.2015 | 1.24 | 0.69 | 80% |
| 1649 | valine | 50 | 0.074 | 0.2015 | 1.5 | 1.08 | 39% |
| 18882 | taurodeoxycholic acid | 61 | 0.0747 | 0.2015 | 2.13 | 1.13 | 88% |
| 27718 | creatine | 61 | 0.0798 | 0.2098 | 1.28 | 0.94 | 36% |
| 27513 | indole-3-acetic acid | 61 | 0.0815 | 0.2098 | 1.17 | 0.84 | 39% |
| 9216 | Metabolite - 2168 | 61 | 0.0832 | 0.2098 | 1.02 | 0.84 | 21% |
| 9905 | Metabolite - 2231 | 61 | 0.0833 | 0.2098 | 1.08 | 0.86 | 26% |
| 19414 | Metabolite - 6350 | 50 | 0.0838 | 0.2098 | 1.33 | 1.08 | 23% |
| 20092 | Metabolite - 7050 | 61 | 0.0844 | 0.2098 | 0.59 | 0.84 | −30% |
| 6435 | Metabolite - 1348 | 61 | 0.0848 | 0.2098 | 2.07 | 0.99 | 109% |
| 1648 | serine | 50 | 0.09 | 0.22 | 0.91 | 1.09 | −17% |
| 13214 | Metabolite - 3183-possible-gamma-L-glutamyl-L-phenylalanine | 61 | 0.0918 | 0.2214 | 1.4 | 0.97 | 44% |
| 22649 | Metabolite - 9108 | 50 | 0.0927 | 0.2214 | 0.93 | 1.17 | −21% |
| 30689 | Metabolite - 10790 | 61 | 0.0939 | 0.2217 | 0.97 | 1.07 | −9% |
| 22548 | Metabolite - 9026 | 50 | 0.0989 | 0.2309 | 2.37 | 0.98 | 142% |
| 1358 | octadecanoic acid | 50 | 0.1003 | 0.2317 | 1.04 | 0.89 | 17% |
| 16512 | Metabolite - 4275 | 50 | 0.1067 | 0.2438 | 0.71 | 0.93 | −24% |
| 21069 | dioctyl-phthalate | 50 | 0.1079 | 0.2438 | 1.34 | 0.88 | 52% |
| 12960 | Metabolite - 3134 | 61 | 0.1094 | 0.2446 | 1.27 | 1.05 | 21% |
| 22609 | Metabolite - 9047 | 50 | 0.1248 | 0.272 | 0.89 | 0.42 | 112% |
| 1898 | proline | 61 | 0.1257 | 0.272 | 1.12 | 0.88 | 27% |
| 1642 | decanoic acid | 50 | 0.1266 | 0.272 | 0.85 | 0.74 | 15% |
| 12726 | Metabolite - 3058 | 50 | 0.1269 | 0.272 | 0.81 | 0.97 | −16% |
| 11974 | Metabolite - 2827 | 61 | 0.1311 | 0.2779 | 1.03 | 1.24 | −17% |
| 20842 | Metabolite - 7765 | 61 | 0.1349 | 0.2833 | 1.61 | 0.97 | 66% |
| 17304 | Metabolite - 4759 | 61 | 0.1386 | 0.2872 | 1.47 | 0.92 | 60% |
| 15737 | hydroxyacetic acid | 50 | 0.1396 | 0.2872 | 2.37 | 0.81 | 193% |
| 18010 | Metabolite - 5231 | 61 | 0.1433 | 0.2919 | 1.16 | 0.83 | 40% |
| 59 | histidine | 50 | 0.1489 | 0.2956 | 0.87 | 1.03 | −16% |
| 16665 | Metabolite - 4364 | 50 | 0.1496 | 0.2956 | 0.78 | 0.93 | −16% |
| 12757 | Metabolite - 3078 | 50 | 0.15 | 0.2956 | 0.67 | 0.89 | −25% |
| 1640 | ascorbic acid | 50 | 0.1509 | 0.2956 | 1.02 | 1.65 | −38% |
| 21418 | Isobar-56-includes-DL-pipecolic acid-1-amino-1-cyclopentanecarboxylic acid | 61 | 0.1522 | 0.2956 | 1.17 | 0.74 | 58% |
| 10327 | Metabolite - 2281 | 61 | 0.1573 | 0.3028 | 1.44 | 0.85 | 69% |
| 10700 | Metabolite - 2393 | 61 | 0.1613 | 0.3032 | 1 | 0.8 | 25% |
| 10961 | Metabolite - 2561 | 61 | 0.1674 | 0.3032 | 0.91 | 0.72 | 26% |
| 2734 | gamma-L-glutamyl-L-tyrosine | 61 | 0.1684 | 0.3032 | 1.26 | 0.85 | 48% |
| 27409 | oleamide | 50 | 0.169 | 0.3032 | 2.13 | 1.09 | 95% |
| 6847 | Metabolite - 1496 | 61 | 0.169 | 0.3032 | 1.27 | 1 | 27% |
| 18705 | Metabolite - 5768 | 61 | 0.1693 | 0.3032 | 0.68 | 0.97 | −30% |
| 27742 | aconitate | 61 | 0.1696 | 0.3032 | 1.92 | 1.06 | 81% |
| 19368 | Metabolite - 6267 | 50 | 0.1697 | 0.3032 | 0.71 | 0.8 | −11% |
| 30265 | Metabolite - 10732 | 50 | 0.1716 | 0.3032 | 0.65 | 0.85 | −24% |
| 542 | 3-hydroxybutanoic acid | 50 | 0.1728 | 0.3032 | 0.91 | 1.24 | −27% |
| 21128 | 1-octadecanol | 50 | 0.174 | 0.3032 | 1.93 | 0.91 | 112% |
| 1126 | alanine | 50 | 0.175 | 0.3032 | 1.28 | 1.11 | 15% |
| 9165 | Metabolite - 2150 | 61 | 0.1811 | 0.3111 | 0.7 | 0.95 | −26% |
| 8098 | Metabolite - 1867 | 61 | 0.1854 | 0.3159 | 1.15 | 0.93 | 24% |
| 20299 | Metabolite - 7266 | 50 | 0.1953 | 0.3285 | 0.92 | 1.04 | −12% |
| 12129 | beta-hydroxyisovaleric acid | 50 | 0.196 | 0.3285 | 0.75 | 0.67 | 12% |
| 12626 | Metabolite - 3003 | 50 | 0.1999 | 0.3315 | 0.94 | 1.04 | −10% |
| 18476 | glycocholic acid | 61 | 0.201 | 0.3315 | 1.75 | 1.57 | 11% |
| 12222 | Metabolite - 2374 | 50 | 0.2083 | 0.3378 | 1.04 | 0.91 | 14% |
| 1361 | pentadecanoic acid | 50 | 0.2083 | 0.3378 | 2.3 | 0.96 | 140% |
| 53 | glutamine | 50 | 0.2096 | 0.3378 | 1.02 | 1.23 | −17% |
| 22026 | 1-methylguanidine | 50 | 0.2146 | 0.3408 | 1.01 | 0.92 | 10% |
| 7127 | Metabolite - 1616 | 61 | 0.2149 | 0.3408 | 1.02 | 1.28 | −20% |
| 10746 | Isobar-6-includes-valine-betaine | 61 | 0.217 | 0.3408 | 0.88 | 0.49 | 80% |

TABLE 13-continued

Metabolite biomarkers of Metabolic Syndrome in serum.

| COMP_ID | COMPOUND | LIB_ID | p-value | q-value | Mean_Metabolic Syndrome | Mean_Control | % Change Met. Syn. vs Control |
|---|---|---|---|---|---|---|---|
| 5426 | Metabolite - 1004 | 61 | 0.2181 | 0.3408 | 1.97 | 1.02 | 93% |
| 1302 | methionine | 61 | 0.2235 | 0.3428 | 0.91 | 0.83 | 10% |
| 1121 | heptadecanoic acid | 50 | 0.2248 | 0.3428 | 1.5 | 0.94 | 60% |
| 6373 | Metabolite - 1304 | 61 | 0.2252 | 0.3428 | 0.77 | 1.32 | −42% |
| 25602 | Metabolite - 10432 | 50 | 0.226 | 0.3428 | 0.64 | 0.8 | −20% |
| 22145 | acetyl-L-carnitine | 61 | 0.2282 | 0.343 | 1.07 | 1.24 | −14% |
| 18232 | Metabolite - 5403 | 50 | 0.2307 | 0.343 | 1.02 | 0.93 | 10% |
| 1365 | tetradecanoic acid | 50 | 0.231 | 0.343 | 1.31 | 0.86 | 52% |
| 10750 | Isobar-8-includes-anthranilic acid-salicylamide | 61 | 0.2353 | 0.346 | 0.93 | 0.81 | 15% |
| 24233 | Metabolite - 9855 | 61 | 0.238 | 0.346 | 1.27 | 0.75 | 69% |
| 6305 | Metabolite - 1254 | 61 | 0.2381 | 0.346 | 2.42 | 1.05 | 130% |
| 30555 | Metabolite - 10781 | 61 | 0.2409 | 0.3476 | 0.45 | 0.67 | −33% |
| 569 | caffeine | 61 | 0.2479 | 0.3553 | 1.57 | 0.79 | 99% |
| 12162 | Metabolite - 2339 | 50 | 0.2496 | 0.3554 | 1.41 | 1.48 | −5% |
| 16829 | Metabolite - 4503 | 50 | 0.2514 | 0.3554 | 0.83 | 0.96 | −14% |
| 15113 | Metabolite - 3783 | 61 | 0.2569 | 0.3592 | 1.97 | 1.34 | 47% |
| 13211 | Metabolite - 3182 | 61 | 0.2592 | 0.3592 | 1.63 | 1.05 | 55% |
| 8336 | Metabolite - 2005 | 61 | 0.261 | 0.3592 | 1.07 | 0.89 | 20% |
| 17330 | Metabolite - 4769 | 50 | 0.261 | 0.3592 | 0.79 | 0.91 | −13% |
| 12645 | Metabolite - 3017 | 50 | 0.2635 | 0.3603 | 0.81 | 0.91 | −11% |
| 21047 | 3-methyl-2-oxobutyric- | 61 | 0.2676 | 0.3635 | 1 | 0.86 | 16% |
| 5733 | Metabolite - 1127 | 61 | 0.2766 | 0.3705 | 0.84 | 0.92 | −9% |
| 1670 | urea | 50 | 0.2793 | 0.3705 | 0.99 | 0.89 | 11% |
| 1572 | glyceric acid | 50 | 0.2799 | 0.3705 | 0.9 | 0.69 | 30% |
| 1507 | palmitoleic acid | 50 | 0.2804 | 0.3705 | 0.86 | 1.07 | −20% |
| 1110 | arachidonic acid | 50 | 0.2843 | 0.3716 | 1.03 | 0.91 | 13% |
| 1561 | alpha-tocopherol | 50 | 0.2874 | 0.3733 | 1.07 | 0.8 | 34% |
| 19364 | Metabolite - 6246 | 50 | 0.2912 | 0.3759 | 0.91 | 0.79 | 15% |
| 5765 | Metabolite - 1142 | 61 | 0.2932 | 0.3761 | 0.99 | 0.86 | 15% |
| 6405 | Metabolite - 1338 | 61 | 0.3015 | 0.3844 | 2.63 | 0.96 | 174% |
| 16071 | Metabolite - 4020 | 50 | 0.3073 | 0.3884 | 0.92 | 1 | −8% |
| 16496 | Metabolite - 4251 | 50 | 0.3085 | 0.3884 | 1.54 | 1.24 | 24% |
| 12533 | Metabolite - 2915 | 50 | 0.3102 | 0.3884 | 1.1 | 1.01 | 9% |
| 10286 | Metabolite - 2272 | 61 | 0.316 | 0.3933 | 1.45 | 1 | 45% |
| 8469 | Metabolite - 2036-possible-Heme | 61 | 0.3184 | 0.3939 | 0.88 | 0.55 | 60% |
| 10065 | Metabolite - 2244 | 61 | 0.325 | 0.3991 | 1.02 | 0.95 | 7% |
| 19623 | Metabolite - 6671 | 50 | 0.3265 | 0.3991 | 2.43 | 2.77 | −12% |
| 27411 | Metabolite - 10547 | 61 | 0.3324 | 0.4023 | 0.52 | 0.68 | −24% |
| 12777 | Metabolite - 3097 | 50 | 0.3329 | 0.4023 | 0.53 | 0.7 | −24% |
| 18394 | theophylline | 61 | 0.3355 | 0.4031 | 0.97 | 0.71 | 37% |
| 2761 | thyroxine | 61 | 0.3418 | 0.4082 | 0.86 | 0.93 | −8% |
| 18254 | paraxanthine | 61 | 0.3437 | 0.4082 | 0.97 | 0.58 | 67% |
| 7933 | Metabolite - 1911 | 61 | 0.3458 | 0.4083 | 1.13 | 0.77 | 47% |
| 15996 | aspartate | 50 | 0.3567 | 0.417 | 0.63 | 0.49 | 29% |
| 7601 | Metabolite - 1819 | 61 | 0.3571 | 0.417 | 0.77 | 0.72 | 7% |
| 1336 | n-hexadecanoic acid | 50 | 0.3594 | 0.4174 | 1.07 | 0.92 | 16% |
| 10147 | Metabolite - 2036 | 61 | 0.3626 | 0.4186 | 0.9 | 0.99 | −9% |
| 5618 | Metabolite - 1085 | 61 | 0.3702 | 0.4251 | 1.35 | 1.06 | 27% |
| 15500 | carnitine | 61 | 0.377 | 0.429 | 1.07 | 0.97 | 10% |
| 6413 | Metabolite - 1342-possible-phenylacetylglutamine- | 61 | 0.3778 | 0.429 | 1.1 | 0.94 | 17% |
| 27738 | threonic acid | 50 | 0.3822 | 0.4317 | 0.89 | 0.96 | −7% |
| 22132 | DL-alpha-hydroxyisocaproic acid | 61 | 0.3947 | 0.4428 | 1 | 0.88 | 14% |
| 17306 | Metabolite - 4760 | 61 | 0.3968 | 0.4428 | 0.74 | 1.09 | −32% |
| 20267 | Metabolite - 7187 | 61 | 0.399 | 0.4428 | 2.07 | 1.37 | 51% |
| 14368 | Metabolite - 3489 | 61 | 0.4005 | 0.4428 | 0.84 | 0.94 | −11% |
| 10825 | Metabolite - 2546 | 61 | 0.405 | 0.4454 | 1.13 | 1.02 | 11% |
| 6546 | Metabolite - 1391 | 61 | 0.4074 | 0.4456 | 1.12 | 1.02 | 10% |
| 27675 | 4-nitrophenol | 61 | 0.4103 | 0.4465 | 0.96 | 0.88 | 9% |
| 17064 | Metabolite - 4624 | 50 | 0.4189 | 0.4534 | 0.88 | 0.92 | −4% |
| 20489 | D-glucose | 50 | 0.4214 | 0.4538 | 0.93 | 0.95 | −2% |
| 20676 | maleic acid | 61 | 0.4265 | 0.4553 | 1.18 | 1.33 | −11% |
| 13557 | Metabolite - 3323 | 61 | 0.4306 | 0.4553 | 1.3 | 1.02 | 27% |
| 10551 | Metabolite - 2347 | 61 | 0.4307 | 0.4553 | 1.97 | 1.41 | 40% |

TABLE 13-continued

Metabolite biomarkers of Metabolic Syndrome in serum.

| COMP_ID | COMPOUND | LIB_ID | p-value | q-value | Mean_Metabolic Syndrome | Mean_Control | % Change Met. Syn. vs Control |
|---|---|---|---|---|---|---|---|
| 15990 | L-alpha-glycerophosphorylcholine | 61 | 0.4316 | 0.4553 | 0.71 | 0.58 | 22% |
| 6517 | Metabolite - 1338 | 61 | 0.4377 | 0.4591 | 0.86 | 0.8 | 8% |
| 19097 | Metabolite - 5969 | 61 | 0.4396 | 0.4591 | 0.98 | 1.08 | −9% |
| 22803 | Isobar-66-includes-glycochenodeoxycholic acid-glycodeoxycholic acid | 61 | 0.442 | 0.4593 | 1.63 | 1.38 | 18% |
| 1410 | 1-Hexadecanol | 50 | 0.4484 | 0.4635 | 2.68 | 1.01 | 165% |
| 15765 | ethylmalonic acid | 61 | 0.4505 | 0.4635 | 0.95 | 0.81 | 17% |
| 5280 | biliverdin | 61 | 0.4559 | 0.4663 | 0.86 | 1.01 | −15% |
| 1284 | threonine | 50 | 0.4577 | 0.4663 | 1.14 | 1.24 | −8% |
| 30273 | Metabolite - 10736 | 50 | 0.4611 | 0.4675 | 0.89 | 1 | −11% |
| 16518 | Metabolite - 4276 | 50 | 0.4687 | 0.4717 | 0.86 | 0.72 | 19% |
| 12756 | Metabolite - 3077 | 50 | 0.4698 | 0.4717 | 0.73 | 0.68 | 7% |
| 12639 | Metabolite - 3012 | 50 | 0.4752 | 0.4748 | 0.79 | 0.73 | 8% |
| 12650 | Metabolite - 3022 | 50 | 0.4937 | 0.4894 | 0.84 | 0.77 | 9% |
| 10544 | Metabolite - 2329 | 61 | 0.4945 | 0.4894 | 1.05 | 1.4 | −25% |
| 22337 | Metabolite - 8893 | 61 | 0.5005 | 0.493 | 1.07 | 1.14 | −6% |
| 18524 | 6-hydroxydopamine | 50 | 0.5075 | 0.4953 | 1.13 | 1.2 | −6% |
| 13065 | Metabolite - 3146 | 61 | 0.5076 | 0.4953 | 1.01 | 0.97 | 4% |
| 15506 | choline | 61 | 0.5148 | 0.5 | 1.02 | 0.75 | 36% |
| 14988 | Metabolite - 3756 | 61 | 0.5198 | 0.5007 | 0.68 | 0.74 | −8% |
| 12894 | Metabolite - 2456 | 61 | 0.5228 | 0.5007 | 0.9 | 0.94 | −4% |
| 22880 | Metabolite - 9286 | 50 | 0.5255 | 0.5007 | 1.33 | 1.25 | 6% |
| 7171 | Metabolite - 1643 | 61 | 0.5279 | 0.5007 | 2.54 | 2.05 | 24% |
| 14715 | Metabolite - 3653 | 61 | 0.5332 | 0.5007 | 1.92 | 1.07 | 79% |
| 15000 | Metabolite - 3758 | 61 | 0.5332 | 0.5007 | 0.96 | 0.91 | 5% |
| 29817 | Metabolite - 10683 | 50 | 0.5335 | 0.5007 | 0.84 | 0.79 | 6% |
| 19372 | Metabolite - 6269 | 50 | 0.535 | 0.5007 | 1.09 | 1.13 | −4% |
| 18091 | Metabolite - 5306 | 61 | 0.5372 | 0.5007 | 1.06 | 0.96 | 10% |
| 15676 | 3-methyl-2-oxovaleric acid | 61 | 0.554 | 0.5065 | 0.93 | 0.89 | 4% |
| 16468 | Metabolite - 4236 | 61 | 0.5544 | 0.5065 | 1.1 | 0.98 | 12% |
| 22053 | 3-hydroxydecanoic acid | 61 | 0.5575 | 0.5065 | 0.92 | 1.07 | −14% |
| 10781 | Metabolite - 2469 | 61 | 0.5584 | 0.5065 | 0.8 | 1 | −20% |
| 17568 | Metabolite - 4931 | 61 | 0.5585 | 0.5065 | 0.89 | 1.05 | −15% |
| 12625 | Metabolite - 3002 | 50 | 0.5605 | 0.5065 | 1.74 | 1.78 | −2% |
| 1643 | fumaric acid | 50 | 0.5626 | 0.5065 | 0.88 | 0.96 | −8% |
| 27272 | Metabolite - 10505 | 50 | 0.5629 | 0.5065 | 0.72 | 0.74 | −3% |
| 19363 | Metabolite - 6227 | 50 | 0.5725 | 0.5111 | 0.83 | 0.79 | 5% |
| 10655 | Metabolite - 2388 | 61 | 0.5733 | 0.5111 | 0.93 | 1 | −7% |
| 58 | glycine | 50 | 0.5779 | 0.5111 | 0.9 | 0.98 | −8% |
| 15128 | DL-homocysteine | 61 | 0.5816 | 0.5111 | 1.27 | 1.36 | −7% |
| 17068 | Metabolite - 4627 | 61 | 0.5821 | 0.5111 | 1.35 | 0.76 | 78% |
| 1494 | 5-oxoproline | 50 | 0.5828 | 0.5111 | 0.99 | 0.86 | 15% |
| 6531 | Metabolite - 1385 | 61 | 0.5892 | 0.5145 | 1.09 | 1.14 | −4% |
| 19282 | Metabolite - 6126 | 61 | 0.605 | 0.5238 | 1.38 | 1.03 | 34% |
| 22130 | DL-3-phenyllactic acid | 61 | 0.6056 | 0.5238 | 2.23 | 1.36 | 64% |
| 1301 | lysine | 50 | 0.6074 | 0.5238 | 1.53 | 1.32 | 16% |
| 6851 | Metabolite - 1497 | 61 | 0.616 | 0.5277 | 1.55 | 1.46 | 6% |
| 6398 | Metabolite - 1335 | 61 | 0.6169 | 0.5277 | 1.34 | 1.56 | −14% |
| 27256 | Metabolite - 10500 | 50 | 0.6227 | 0.5304 | 1.1 | 1.05 | 5% |
| 21841 | Metabolite - 8577 | 61 | 0.6366 | 0.54 | 1.08 | 0.99 | 9% |
| 5687 | Metabolite - 1110 | 61 | 0.6394 | 0.5402 | 0.96 | 0.94 | 2% |
| 12306 | Metabolite - 2869 | 61 | 0.6482 | 0.5455 | 2.58 | 1.89 | 37% |
| 12767 | Metabolite - 3087 | 50 | 0.6549 | 0.5488 | 1.44 | 1.18 | 22% |
| 12638 | Metabolite - 3011 | 50 | 0.6612 | 0.5519 | 0.91 | 0.99 | −8% |
| 5489 | Metabolite - 1057 | 61 | 0.6673 | 0.5547 | 1.03 | 1.05 | −2% |
| 19462 | Metabolite - 6446 | 50 | 0.6727 | 0.5556 | 1.08 | 1.04 | 4% |
| 10604 | Metabolite - 2370 | 61 | 0.676 | 0.5556 | 0.86 | 0.88 | −2% |
| 15121 | Metabolite - 3786 | 61 | 0.6764 | 0.5556 | 0.86 | 0.89 | −3% |
| 10092 | Metabolite - 2250 | 61 | 0.6803 | 0.5561 | 1.63 | 0.76 | 114% |
| 22320 | Metabolite - 8889 | 50 | 0.6822 | 0.5561 | 1.69 | 1.77 | −5% |
| 1645 | n-dodecanoate | 50 | 0.6858 | 0.5567 | 0.82 | 0.79 | 4% |
| 527 | lactate | 50 | 0.6911 | 0.5589 | 0.99 | 0.91 | 9% |
| 3127 | hypoxanthine | 61 | 0.7003 | 0.5629 | 0.54 | 0.51 | 6% |
| 24077 | Metabolite - 9727 | 50 | 0.7015 | 0.5629 | 0.92 | 0.97 | −5% |

TABLE 13-continued

Metabolite biomarkers of Metabolic Syndrome in serum.

| COMP_ID | COMPOUND | LIB_ID | p-value | q-value | Mean_Metabolic Syndrome | Mean_Control | % Change Met. Syn. vs Control |
|---|---|---|---|---|---|---|---|
| 1366 | trans-4-hydroxyproline | 50 | 0.7106 | 0.568 | 1.14 | 1.08 | 6% |
| 11499 | Metabolite - 2753 | 61 | 0.7138 | 0.5684 | 1.31 | 0.8 | 64% |
| 18349 | DL-indole-3-lactic acid | 61 | 0.7229 | 0.5722 | 0.91 | 0.86 | 6% |
| 7644 | Metabolite - 1831- | 61 | 0.7346 | 0.5751 | 0.88 | 0.89 | −1% |
| 5531 | Metabolite - 1095 | 61 | 0.7348 | 0.5751 | 1.34 | 1.34 | 0% |
| 12768 | Metabolite - 3088 | 50 | 0.736 | 0.5751 | 0.65 | 0.68 | −4% |
| 1431 | p-hydroxyphenyllactic acid | 50 | 0.7405 | 0.5764 | 1.19 | 0.91 | 31% |
| 12673 | Metabolite - 3040 | 50 | 0.7654 | 0.5878 | 0.75 | 0.82 | −9% |
| 2132 | citrulline | 50 | 0.7659 | 0.5878 | 3.41 | 3.29 | 4% |
| 22309 | Metabolite - 8887 | 61 | 0.7694 | 0.5878 | 0.58 | 0.54 | 7% |
| 30282 | Metabolite - 10744 | 50 | 0.7699 | 0.5878 | 0.89 | 0.87 | 2% |
| 14672 | Metabolite - 3615 | 61 | 0.7721 | 0.5878 | 0.82 | 0.89 | −8% |
| 25607 | Metabolite - 10437 | 50 | 0.7765 | 0.589 | 0.76 | 0.87 | −13% |
| 6820 | Metabolite - 1554 | 61 | 0.7865 | 0.5944 | 1.06 | 1 | 6% |
| 14239 | Metabolite - 3474 | 61 | 0.7901 | 0.5949 | 1 | 0.9 | 11% |
| 20248 | Metabolite - 7177 | 61 | 0.7984 | 0.5973 | 1.04 | 1.02 | 2% |
| 27326 | Metabolite - 10527 | 50 | 0.799 | 0.5973 | 1.16 | 1.12 | 4% |
| 25402 | Metabolite - 10360 | 50 | 0.8093 | 0.6029 | 1.29 | 1.3 | −1% |
| 19934 | inositol | 50 | 0.8135 | 0.6038 | 0.68 | 0.68 | 0% |
| 12593 | Metabolite - 2973 | 50 | 0.8339 | 0.6152 | 1.66 | 1.66 | 0% |
| 23462 | Metabolite - 9693 | 61 | 0.8348 | 0.6152 | 1.15 | 1.15 | 0% |
| 16819 | Metabolite - 4496 | 50 | 0.8463 | 0.6215 | 0.88 | 0.85 | 4% |
| 16138 | Metabolite - 4080 | 50 | 0.8667 | 0.6297 | 0.53 | 0.51 | 4% |
| 25609 | Metabolite - 10439 | 50 | 0.8668 | 0.6297 | 0.72 | 0.66 | 9% |
| 584 | mannose | 50 | 0.87 | 0.6297 | 0.93 | 0.84 | 11% |
| 15122 | glycerol | 50 | 0.8737 | 0.6297 | 0.93 | 0.89 | 4% |
| 22570 | Metabolite - 9033 | 50 | 0.875 | 0.6297 | 1.52 | 1.51 | 1% |
| 20888 | Metabolite - 7806 | 61 | 0.8756 | 0.6297 | 0.97 | 0.99 | −2% |
| 13038 | Metabolite - 3143 | 61 | 0.8833 | 0.6316 | 1.32 | 1.14 | 16% |
| 16509 | Metabolite - 4273 | 50 | 0.8851 | 0.6316 | 0.69 | 0.7 | −1% |
| 16511 | Metabolite - 4274 | 50 | 0.8873 | 0.6316 | 1.1 | 1.08 | 2% |
| 13589 | Metabolite - 3327 | 61 | 0.8935 | 0.6338 | 1.19 | 1.06 | 12% |
| 5628 | Metabolite - 1086 | 61 | 0.9002 | 0.6364 | 1.73 | 1.6 | 8% |
| 10245 | Metabolite - 2269- | 61 | 0.9081 | 0.6398 | 1.08 | 0.87 | 24% |
| 6362 | Metabolite - 1323-possible-p-cresol-sulfate | 61 | 0.9178 | 0.6429 | 1.08 | 1.02 | 6% |
| 5632 | Metabolite - 1138 | 61 | 0.9201 | 0.6429 | 1.03 | 1.05 | −2% |
| 15365 | sn-Glycerol-3-phosphate | 50 | 0.9265 | 0.6429 | 0.82 | 0.82 | 0% |
| 10304 | Metabolite - 2276 | 61 | 0.9274 | 0.6429 | 1.36 | 1.77 | −23% |
| 10156 | Metabolite - 2259 | 61 | 0.9281 | 0.6429 | 1.06 | 1.03 | 3% |
| 27719 | galactonic acid | 50 | 0.9386 | 0.6449 | 1.13 | 1.1 | 3% |
| 22895 | Metabolite - 9299 | 50 | 0.9394 | 0.6449 | 1.05 | 1.05 | 0% |
| 15253 | Metabolite - 3832 | 61 | 0.9468 | 0.6449 | 1.48 | 1.41 | 5% |
| 1105 | Linoleic acid | 50 | 0.9483 | 0.6449 | 0.95 | 0.94 | 1% |
| 12780 | Metabolite - 3098 | 50 | 0.9494 | 0.6449 | 0.87 | 0.83 | 5% |
| 10441 | Metabolite - 2308 | 61 | 0.9506 | 0.6449 | 0.92 | 0.88 | 5% |
| 27672 | 3-indoxyl-sulfate | 61 | 0.9527 | 0.6449 | 0.98 | 0.95 | 3% |
| 22133 | DL-hexanoyl-carnitine | 61 | 0.9585 | 0.646 | 1.36 | 1.35 | 1% |
| 16070 | Metabolite - 4019 | 50 | 0.9631 | 0.646 | 0.85 | 0.85 | 0% |
| 12720 | Metabolite - 3056 | 61 | 0.9635 | 0.646 | 0.9 | 0.92 | −2% |
| 24074 | Metabolite - 9706 | 50 | 0.9711 | 0.6479 | 1.12 | 1.11 | 1% |
| 13545 | Metabolite - 3322 | 61 | 0.9736 | 0.6479 | 1.49 | 1.34 | 11% |
| 1564 | citric acid | 50 | 0.9794 | 0.6479 | 3.72 | 3.73 | 0% |
| 17327 | Metabolite - 4767 | 50 | 0.9803 | 0.6479 | 1.32 | 1.03 | 28% |
| 20950 | Metabolite - 7846 | 50 | 0.982 | 0.6479 | 0.93 | 0.97 | −4% |
| 14837 | Metabolite - 3707 | 61 | 0.99 | 0.6511 | 2.12 | 1.66 | 28% |

Figure 8:
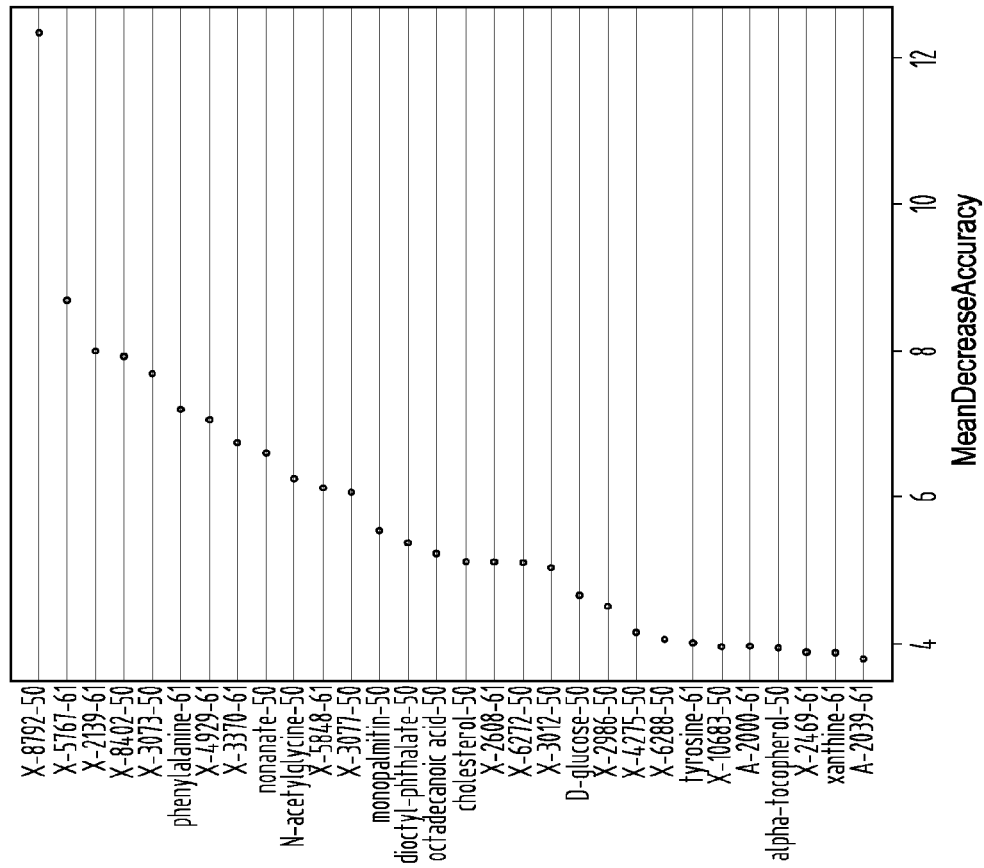
FIG. 8 provides a Random Forest Analysis Importance Plot of one embodiment of serum metabolites that are useful biomarkers for predicting metabolic syndrome.
Figure 9:
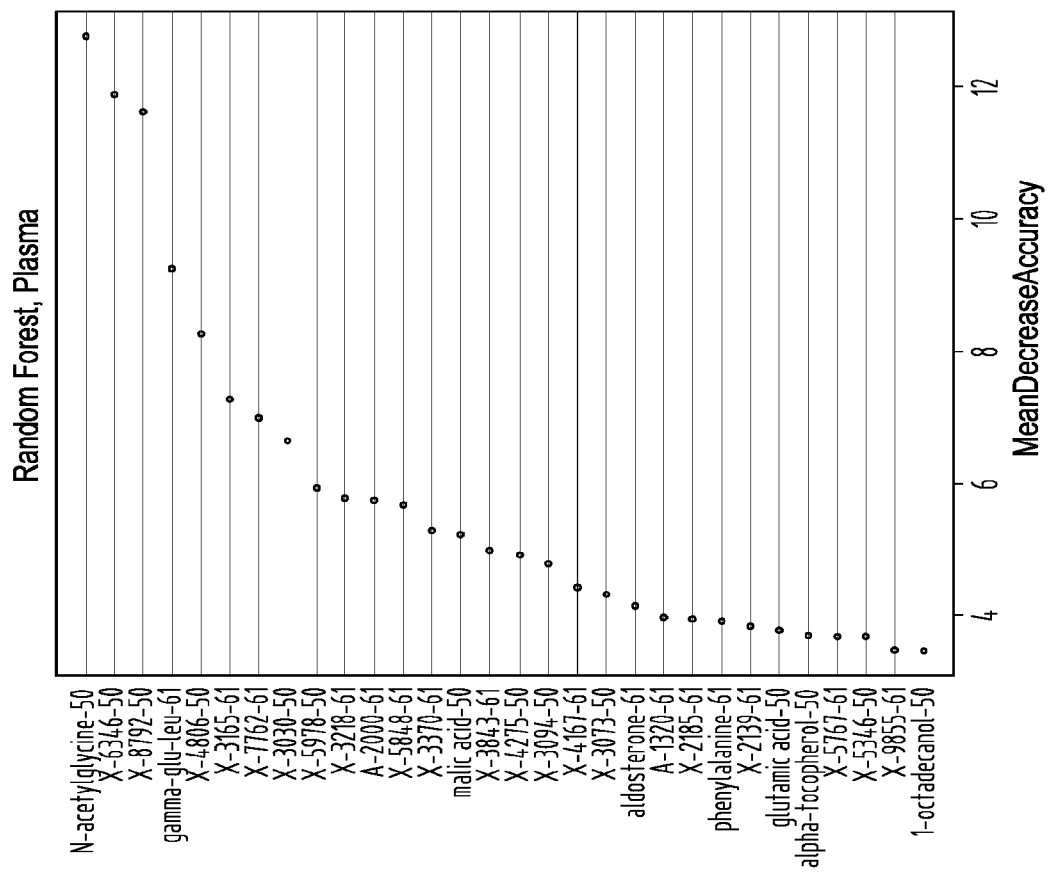
FIG. 9 provides a Random Forest Analysis Importance Plot of one embodiment of plasma metabolites that are useful biomarkers for predicting metabolic syndrome.

Random forests were generated for plasma and serum biomarkers. The models for the serum biomarkers correctly classified 81.5% of the subjects as either being healthy or having metabolic syndrome; 83% of the healthy subjects were classified correctly and 77% of the subjects having metabolic syndrome were correctly classified. For the models based on the biomarkers from plasma, the 89% of the subjects were correctly classified as either being healthy or having metabolic syndrome; 100% of the healthy subjects were correctly classified and 77% of the metabolic syndrome subjects were correctly classified. The most important biomarkers are shown in the importance plot in FIG. 8 (Serum) and FIG. 9 (Plasma).

3B: Biomarkers of Atherosclerosis

Biomarkers were discovered by (1) analyzing plasma, aorta and liver samples drawn from subjects with atherosclerosis and healthy subjects to determine the levels of metabolites in the samples and then (2) statistically analyzing the results to determine those metabolites that were differentially present in the two groups.

The samples used for the analysis were from wild-type and transgenic mice, C57BL/6 and LDb, respectively. The transgenic LDb mice provide a model for atherosclerosis in human subjects. Previous studies have shown that LDb transgenic mice in a C57BL/6 background have about 5-fold higher plasma cholesterol and triglyceride levels than C57BL/6 wild-type mice and start to develop atherosclerotic lesions at about 3 months of age. Plasma, ascending and descending aorta tissues and liver tissue from each group of mice at 2, 5 or 8 months were subjected to metabolomic analysis. These collection time points represent early (initiation), mid and late stage for atherosclerosis in the transgenic model.

T-tests were used to determine differences in the mean levels of metabolites between the two populations (i.e., LDb vs. C57BL/6). Classification analysis was carried out using recursive partitioning and random forest analyses to uncover the biomarkers that can best differentiate the 2 groups of mice. Recursive partitioning relates a 'dependent' variable (Y) to a collection of independent ('predictor') variables (X) in order to uncover—or simply understand—the elusive relationship, Y=f(X). It was performed with the JMP program (SAS) to generate a decision tree. The statistical significance of the "split" of the data can be placed on a more quantitative footing by computing p-values, which discern the quality of a split relative to a random event. The significance level of each "split" of data into the nodes or branches of the tree was computed as p-values, which discern the quality of the split relative to a random event. It was given as LogWorth, which is the negative log 10 of a raw p-value. Statistical analyses were performed with the program "R" available on the worldwide web at the website cran.r-project.org.

Random forests give an estimate of how well individuals can be classified in a new data set into each group, in contrast to a t-test, which tests whether the unknown means for two populations are different or not. Random forests create a set of classification trees based on continual sampling of the experimental units and compounds. Then each observation is classified based on the majority votes from all the classification trees. Statistical analyses were performed with the program "R" available on the worldwide web at the website cran.r-project.org.

Biomarkers:

As listed below in Tables 14, 15 and 16, biomarkers were discovered that were differentially present between samples from LDb (atherosclerotic) subjects and C57BL/6 (healthy) subjects.

Tables 14, 15 and 16 include, for each listed biomarker, the p-value and q-value determined in the statistical analysis of the data concerning the biomarkers and an indication of the percentage difference in the atherosclerotic mean level as compared to the healthy mean level in plasma (Table 14), aorta (Table 15) and liver (Table 16). The term "Isobar" as used in the tables indicates the compounds that could not be distinguished from each other on the analytical platform used in the analysis (i.e., the compounds in an isobar elute at nearly the same time and have similar (and sometimes exactly the same) quant ions, and thus cannot be distinguished). Comp_ID refers to the compound identification number used as a primary key for that compound in the in-house chemical database. Library indicates the chemical library that was used to identify the compounds. The number 50 refer to the GC library and the number 61 refers to the LC library.

TABLE 14

Metabolite biomarkers of Atherosclerosis in plasma.

| COMP_ID | COMPOUND | LIB_ID | p-value | q-value | % Change in LDb |
|---|---|---|---|---|---|
| 21415 | Metabolite - 8209 | 50 | 4.25E−07 | 2.40E−06 | 497% |
| 21012 | Metabolite - 7889 | 50 | 1.12E−22 | 6.95E−21 | 494% |
| 21011 | Metabolite - 7888 | 50 | 8.87E−24 | 8.25E−22 | 482% |
| 25649 | Metabolite - 10450 | 50 | 4.17E−15 | 7.76E−14 | 442% |
| 18619 | Metabolite - 5669 | 61 | 5.95E−06 | 2.84E−05 | 423% |
| 27279 | Metabolite - 10511 | 50 | 1.81E−19 | 6.74E−18 | 404% |
| 63 | cholesterol | 50 | 1.56E−24 | 2.90E−22 | 400% |
| 8469 | Metabolite - 2036-possible-Heme | 61 | 1.00E−04 | 4.00E−04 | 371% |
| 27278 | Metabolite - 10510 | 50 | 5.00E−19 | 1.33E−17 | 351% |
| 22993 | Metabolite - 9448 | 50 | 4.73E−15 | 8.00E−14 | 350% |
| 25366 | Metabolite - 10286 | 61 | 1.65E−05 | 1.00E−04 | 339% |
| 21631 | Metabolite - 8403 | 50 | 9.85E−21 | 4.58E−19 | 306% |
| 27414 | beta-sitosterol | 50 | 1.11E−12 | 1.29E−11 | 302% |
| 21013 | Metabolite - 7890 | 50 | 6.00E−14 | 7.73E−13 | 237% |
| 12785 | Metabolite - 3103 | 50 | 0.0011 | 0.0026 | 236% |
| 16831 | Metabolite - 4504 | 50 | 2.00E−04 | 5.00E−04 | 234% |
| 18155 | Metabolite - 5386 | 61 | 2.55E−05 | 1.00E−04 | 223% |
| 8159 | Metabolite - 1971 | 61 | 0.0026 | 0.0054 | 213% |
| 27256 | Metabolite - 10500 | 50 | 2.49E−19 | 7.72E−18 | 209% |
| 21127 | monopalmitin | 50 | 6.23E−14 | 7.73E−13 | 204% |
| 21184 | 1-oleoyl-rac-glycerol | 50 | 6.14E−08 | 4.17E−07 | 196% |
| 6380 | Metabolite - 1330 | 61 | 0.0963 | 0.0914 | 177% |

TABLE 14-continued

Metabolite biomarkers of Atherosclerosis in plasma.

| COMP_ID | COMPOUND | LIB_ID | p-value | q-value | % Change in LDb |
|---|---|---|---|---|---|
| 21188 | 1-stearoyl-rac-glycerol | 50 | 5.43E−12 | 5.94E−11 | 177% |
| 22032 | Metabolite - 8766 | 50 | 1.79E−14 | 2.78E−13 | 163% |
| 1561 | alpha-tocopherol | 50 | 4.00E−04 | 0.001 | 161% |
| 6266 | Metabolite - 1286 | 61 | 6.00E−04 | 0.0015 | 130% |
| 19323 | Docosahexaenoic-Acid | 50 | 2.43E−17 | 5.65E−16 | 126% |
| 27890 | Metabolite - 10611 | 50 | 2.81E−09 | 2.26E−08 | 126% |
| 6130 | Metabolite - 1208 | 61 | 1.04E−05 | 4.62E−05 | 124% |
| 6362 | p-cresol-sulfate | 61 | 2.77E−05 | 1.00E−04 | 123% |
| 9172 | Metabolite - 2000 | 61 | 1.43E−15 | 2.96E−14 | 121% |
| 15991 | L-alpha-glycerophosphorylcholine | 61 | 0.0014 | 0.0032 | 117% |
| 9905 | Metabolite - 2231 | 61 | 1.00E−04 | 2.00E−04 | 116% |
| 15611 | Metabolite - 3971 | 61 | 3.71E−06 | 1.82E−05 | 115% |
| 24205 | Metabolite - 9841 | 61 | 1.98E−06 | 1.02E−05 | 111% |
| 12604 | Metabolite - 2981 | 50 | 6.77E−09 | 5.04E−08 | 111% |
| 27888 | Metabolite - 10609 | 50 | 0.0116 | 0.0181 | 110% |
| 27728 | glycerol-2-phosphate | 50 | 8.04E−06 | 3.65E−05 | 107% |
| 12035 | nonanate | 50 | 3.95E−05 | 2.00E−04 | 104% |
| 17251 | Metabolite - 4732 | 61 | 0.0089 | 0.0147 | 103% |
| 23079 | Metabolite - 9647 | 61 | 1.18E−05 | 1.00E−04 | 101% |
| 1110 | arachidonic acid | 50 | 0.0015 | 0.0032 | 100% |
| 15753 | hippuric acid | 61 | 1.00E−04 | 2.00E−04 | 97% |
| 17800 | cortodoxone | 61 | 1.00E−04 | 4.00E−04 | 92% |
| 27773 | Isobar-71[1] | 61 | 0.0301 | 0.0379 | 92% |
| 1359 | oleic acid | 50 | 0.0669 | 0.0711 | 90% |
| 1358 | octadecanoic acid | 50 | 4.62E−14 | 6.61E−13 | 88% |
| 12774 | Metabolite - 3094 | 50 | 2.92E−09 | 2.26E−08 | 86% |
| 12767 | Metabolite - 3087 | 50 | 0.007 | 0.0124 | 85% |
| 24330 | Metabolite - 10126 | 61 | 1.00E−09 | 8.46E−09 | 84% |
| 21150 | sinapic acid | 61 | 1.10E−10 | 9.75E−10 | 84% |
| 20136 | Metabolite - 7062 | 61 | 3.65E−05 | 1.00E−04 | 80% |
| 10782 | Metabolite - 2486 | 61 | 0.0854 | 0.0837 | 80% |
| 6171 | Metabolite - 1244 | 61 | 0.003 | 0.0059 | 78% |
| 16138 | Metabolite - 4080 | 50 | 3.02E−07 | 1.76E−06 | 77% |
| 21418 | Isobar-56[2] | 61 | 6.28E−08 | 4.17E−07 | 77% |
| 1105 | linoleic acid | 50 | 3.36E−11 | 3.29E−10 | 75% |
| 1336 | n-hexadecanoic acid | 50 | 3.99E−11 | 3.71E−10 | 73% |
| 12112 | Metabolite - 2314 | 61 | 1.47E−06 | 7.82E−06 | 72% |
| 57 | glutamic acid | 50 | 0.0083 | 0.0141 | 71% |
| 22586 | Metabolite - 9039 | 61 | 1.00E−04 | 3.00E−04 | 70% |
| 21828 | Metabolite - 8574 | 61 | 0.0027 | 0.0055 | 68% |
| 26444 | Metabolite - 10465 | 61 | 2.89E−11 | 2.99E−10 | 66% |
| 5475 | Metabolite - 1033 | 61 | 1.01E−07 | 6.06E−07 | 63% |
| 10700 | Metabolite - 2393 | 61 | 0.0101 | 0.0162 | 61% |
| 22259 | Isobar-59[3] | 61 | 0.0013 | 0.003 | 58% |
| 16992 | Metabolite - 4603 | 61 | 0.0237 | 0.031 | 57% |
| 18691 | Metabolite - 5749 | 61 | 0.0854 | 0.0837 | 57% |
| 19934 | inositol | 50 | 0.0067 | 0.012 | 55% |
| 12609 | Metabolite - 2986 | 50 | 0.0013 | 0.0029 | 55% |
| 15365 | sn-Glycerol-3-phosphate | 50 | 8.00E−04 | 0.0018 | 53% |
| 11499 | Metabolite - 2753 | 61 | 0.0071 | 0.0125 | 51% |
| 16074 | Metabolite - 2758 | 50 | 6.00E−04 | 0.0016 | 49% |
| 15670 | 2-methylhippuric acid | 61 | 6.00E−04 | 0.0016 | 49% |
| 8210 | Metabolite - 1981 | 61 | 0.017 | 0.0238 | 47% |
| 1121 | heptadecanoic acid | 50 | 8.42E−09 | 6.03E−08 | 46% |
| 17488 | Metabolite - 4887 | 61 | 2.00E−04 | 6.00E−04 | 45% |
| 1493 | ornithine | 50 | 0.0482 | 0.0557 | 42% |
| 6851 | Metabolite - 1497 | 61 | 0.0676 | 0.0711 | 42% |
| 22895 | Metabolite - 9299 | 50 | 0.0133 | 0.0195 | 39% |
| 13038 | Metabolite - 3143 | 61 | 0.0117 | 0.0181 | 39% |
| 5699 | Metabolite - 1157 | 61 | 0.0036 | 0.0068 | 37% |
| 18015 | Metabolite - 3113 | 61 | 1.00E−04 | 4.00E−04 | 36% |
| 24076 | Metabolite - 9726 | 50 | 3.00E−04 | 0.001 | 36% |
| 20031 | Metabolite - 7007 | 61 | 0.0011 | 0.0026 | 36% |
| 20488 | D-glucose | 50 | 2.00E−04 | 7.00E−04 | 34% |
| 10401 | Metabolite - 2058 | 61 | 0.0015 | 0.0032 | 34% |
| 1507 | palmitoleic acid | 50 | 0.0168 | 0.0236 | 34% |
| 1670 | urea | 50 | 4.00E−04 | 0.001 | 34% |
| 15948 | S-adenosyl-l-homocysteine | 61 | 0.023 | 0.0303 | 33% |
| 5465 | Metabolite - 1029 | 61 | 8.00E−04 | 0.002 | 33% |
| 2849 | guanosine-5-monophosphate | 61 | 0.0418 | 0.0499 | 33% |
| 1494 | 5-oxoproline | 50 | 0.0039 | 0.0073 | 32% |
| 11923 | Metabolite - 2821 | 61 | 0.0089 | 0.0147 | 32% |
| 18969 | Metabolite - 5920 | 61 | 0.0033 | 0.0063 | 32% |

TABLE 14-continued

Metabolite biomarkers of Atherosclerosis in plasma.

| COMP_ID | COMPOUND | LIB_ID | p-value | q-value | % Change in LDb |
|---|---|---|---|---|---|
| 20830 | Metabolite - 7762 | 61 | 0.056 | 0.0621 | 31% |
| 2832 | adenosine-5-monophosphate | 61 | 0.0137 | 0.0199 | 30% |
| 17083 | Metabolite - 4634 | 50 | 0.0718 | 0.0742 | 28% |
| 15996 | aspartate | 50 | 0.1053 | 0.0995 | 27% |
| 14639 | Metabolite - 3603 | 61 | 0.0225 | 0.0302 | 26% |
| 25514 | Metabolite - 10404 | 61 | 0.0747 | 0.0768 | 26% |
| 17747 | D-sphingosine | 50 | 0.0239 | 0.0311 | 26% |
| 27137 | Metabolite - 10498 | 50 | 0.0511 | 0.0576 | 26% |
| 30128 | Metabolite - 10687 | 61 | 1.00E−04 | 4.00E−04 | 25% |
| 16244 | Isobar-21[4] | 61 | 0.0038 | 0.0072 | 25% |
| 15053 | sorbitol | 50 | 0.0718 | 0.0742 | 25% |
| 15122 | glycerol | 50 | 0.0019 | 0.004 | 25% |
| 14387 | Metabolite - 3490 | 61 | 0.0754 | 0.0771 | 23% |
| 1642 | decanoic acid | 50 | 0.0455 | 0.0536 | 23% |
| 20675 | 1,5-anhydro-D-glucitol | 50 | 0.1081 | 0.1016 | 22% |
| 11438 | phosphate | 50 | 0.0022 | 0.0045 | 21% |
| 584 | mannose | 50 | 0.0128 | 0.0191 | 19% |
| 2129 | L-5-Hydroxytryptophan | 61 | 0.0809 | 0.0806 | 19% |
| 9491 | Metabolite - 2185 | 61 | 0.0162 | 0.023 | 18% |
| 605 | uracil | 50 | 0.0468 | 0.0544 | 18% |
| 10655 | Metabolite - 2388 | 61 | 0.0112 | 0.0177 | 18% |
| 17665 | p-hydroxybenzaldehyde | 61 | 0.0121 | 0.0186 | 18% |
| 10746 | Isobar-6[5] | 61 | 0.0564 | 0.0621 | 16% |
| 19372 | Metabolite - 6269 | 50 | 0.0117 | 0.0181 | 16% |
| 9216 | Metabolite - 2168 | 61 | 0.0464 | 0.0543 | 15% |
| 15113 | Metabolite - 3783 | 61 | 0.0126 | 0.019 | 14% |
| 27718 | creatine | 61 | 0.0245 | 0.0312 | 14% |
| 1113 | isocitrate | 61 | 0.0132 | 0.0195 | 14% |
| 18232 | Metabolite - 5403 | 50 | 0.0493 | 0.0562 | 14% |
| 10737 | Isobar-1[6] | 61 | 0.0229 | 0.0303 | 13% |
| 7175 | Metabolite - 1655 | 61 | 0.0099 | 0.016 | 13% |
| 19402 | Metabolite - 6346 | 50 | 0.0411 | 0.0496 | 10% |
| 15677 | 3-methyl-L-histidine | 61 | 0.0795 | 0.0799 | −8% |
| 9324 | Metabolite - 2173 | 61 | 0.0842 | 0.0834 | −9% |
| 54 | tryptophan | 61 | 0.0808 | 0.0806 | −11% |
| 17007 | Metabolite - 4609 | 61 | 0.0957 | 0.0914 | −11% |
| 1574 | histamine | 61 | 0.0574 | 0.0629 | −12% |
| 5765 | Metabolite - 1142 | 61 | 0.0951 | 0.0913 | −14% |
| 27672 | 3-indoxyl-sulfate | 61 | 0.0514 | 0.0576 | −15% |
| 10667 | Metabolite - 2389 | 61 | 0.0939 | 0.0906 | −15% |
| 15765 | ethylmalonic acid | 61 | 0.0241 | 0.0311 | −17% |
| 16705 | Metabolite - 4428 | 61 | 0.0153 | 0.0219 | −17% |
| 15529 | Metabolite - 3951 | 61 | 0.0125 | 0.019 | −18% |
| 11053 | Metabolite - 2567 | 61 | 0.0053 | 0.0098 | −18% |
| 24213 | Metabolite - 9845 | 61 | 0.0189 | 0.0261 | −19% |
| 20950 | Metabolite - 7846 | 50 | 0.0915 | 0.0887 | −19% |
| 13065 | Metabolite - 3146 | 61 | 0.0021 | 0.0045 | −20% |
| 1643 | fumaric acid | 50 | 0.0485 | 0.0558 | −20% |
| 1512 | picolinic acid | 50 | 0.0322 | 0.0396 | −21% |
| 24197 | Metabolite - 9838 | 61 | 0.0675 | 0.0711 | −22% |
| 12724 | Metabolite - 3057 | 61 | 0.0174 | 0.0241 | −22% |
| 27130 | Metabolite - 10493 | 61 | 0.0087 | 0.0146 | −22% |
| 15676 | 3-methyl-2-oxovaleric acid | 61 | 0.0716 | 0.0742 | −23% |
| 18871 | Metabolite - 5848 | 61 | 0.0385 | 0.0468 | −24% |
| 13328 | Metabolite - 3238 | 61 | 0.0194 | 0.0266 | −24% |
| 6253 | Metabolite - 1283 | 61 | 0.0595 | 0.0644 | −25% |
| 10347 | Metabolite - 2285 | 61 | 0.0015 | 0.0032 | −25% |
| 16712 | Metabolite - 4432 | 61 | 0.0081 | 0.0139 | −26% |
| 14786 | Metabolite - 3697 | 61 | 0.0795 | 0.0799 | −27% |
| 15683 | 4-methyl-2-oxopentanoate | 61 | 0.0128 | 0.0191 | −28% |
| 8644 | Metabolite - 2051 | 61 | 0.0413 | 0.0496 | −28% |
| 7650 | Metabolite - 1834 | 61 | 7.29E−08 | 4.52E−07 | −28% |
| 6398 | Metabolite - 1335 | 61 | 0.0617 | 0.0664 | −29% |
| 1412 | 2'-deoxyuridine | 61 | 4.00E−04 | 0.001 | −30% |
| 19405 | Metabolite - 6347 | 50 | 0.0877 | 0.0855 | −31% |
| 22130 | DL-3-phenyllactic acid | 61 | 0.0441 | 0.0522 | −34% |
| 26449 | Metabolite - 10467 | 61 | 0.0777 | 0.079 | −34% |
| 25584 | Metabolite - 10425 | 50 | 0.0078 | 0.0136 | −34% |
| 18929 | Metabolite - 5907 | 50 | 0.0253 | 0.032 | −35% |
| 28059 | Metabolite - 10650 | 50 | 1.00E−04 | 5.00E−04 | −36% |
| 5466 | Metabolite - 1030 | 61 | 0.0098 | 0.016 | −37% |
| 20169 | Metabolite - 7092 | 61 | 0.0582 | 0.0633 | −37% |
| 25459 | Metabolite - 10395 | 50 | 0.0542 | 0.0604 | −38% |
| 17091 | Metabolite - 4641 | 61 | 8.22E−07 | 4.50E−06 | −38% |

TABLE 14-continued

Metabolite biomarkers of Atherosclerosis in plasma.

| COMP_ID | COMPOUND | LIB_ID | p-value | q-value | % Change in LDb |
|---|---|---|---|---|---|
| 19968 | Metabolite - 6930 | 50 | 0.0318 | 0.0395 | −39% |
| 11299 | Metabolite - 2706 | 61 | 6.83E−08 | 4.38E−07 | −39% |
| 25505 | Metabolite - 10402 | 61 | 4.00E−04 | 0.0012 | −39% |
| 16653 | Metabolite - 4361 | 50 | 0.0032 | 0.0063 | −41% |
| 18968 | Metabolite - 5919 | 61 | 4.00E−04 | 0.0011 | −41% |
| 11292 | Metabolite - 2703 | 61 | 0.0059 | 0.0107 | −41% |
| 13534 | Metabolite - 3320 | 61 | 0.0055 | 0.01 | −43% |
| 6297 | Metabolite - 1304 | 61 | 0.0334 | 0.0409 | −43% |
| 19367 | Metabolite - 6266 | 50 | 0.0035 | 0.0068 | −44% |
| 16071 | Metabolite - 4020 | 50 | 1.00E−04 | 4.00E−04 | −45% |
| 24206 | Metabolite - 9842 | 61 | 0.0142 | 0.0204 | −47% |
| 25602 | Metabolite - 10432 | 50 | 8.00E−04 | 0.0018 | −52% |
| 25598 | Metabolite - 10428 | 50 | 0.0665 | 0.0711 | −58% |
| 25597 | Metabolite - 10427 | 50 | 0.0028 | 0.0056 | −58% |
| 25599 | Metabolite - 10429 | 50 | 0.0319 | 0.0395 | −59% |
| 22548 | Metabolite - 9026 | 50 | 0.0202 | 0.0274 | −61% |
| 19362 | Metabolite - 6226 | 50 | 0.0243 | 0.0312 | −65% |
| 16650 | Metabolite - 4360 | 50 | 0.008 | 0.0138 | −66% |
| 25538 | Metabolite - 10415 | 61 | 0.0495 | 0.0562 | −66% |
| 25546 | Metabolite - 10418 | 61 | 0.0018 | 0.0038 | −73% |
| 25527 | Metabolite - 10410 | 61 | 2.00E−04 | 5.00E−04 | −78% |
| 22566 | Metabolite - 9029 | 61 | 2.00E−04 | 6.00E−04 | −80% |
| 25529 | Metabolite - 10411 | 61 | 3.00E−04 | 0.001 | −81% |
| 25517 | Metabolite - 10406 | 61 | 6.00E−04 | 0.0016 | −83% |
| 10148 | Metabolite - 2257 | 61 | 1.00E−04 | 5.00E−04 | −84% |
| 21651 | Metabolite - 8410 | 61 | 6.66E−06 | 3.10E−05 | −87% |
| 25541 | Metabolite - 10417 | 61 | 2.84E−05 | 1.00E−04 | −91% |
| 25539 | Metabolite - 10416 | 61 | 3.59E−06 | 1.81E−05 | −93% |

[1] Isobar-71 includes conduritol-beta-epoxide-3-deoxyglucosone
[2] Isobar-56 includes DL-pipecolic acid-1-amino-1-cyclopentanecarboxylic acid
[3] Isobar-59 includes N-6-trimethyl-L-lysine-H-homoarg-OH
[4] Isobar-21-includes gamma-aminobutyryl-L-histidine-L-anserine
[5] Isobar-6 includes valine-betaine
[6] Isobar-1 includes mannose, fructose, glucose, galactose, alpha-L-sorbopyranose, Inositol, D-allose, D-altrose, D-psicone, L-gulose, allo-inositol

TABLE 15

Metabolite biomarkers of Atherosclerosis in aorta.

| COMP_ID | COMPOUND | LIB_ID | p-value | q-value | % Change in LDb |
|---|---|---|---|---|---|
| 63 | cholesterol | 50 | 7.16E−07 | 8.78E−06 | 569% |
| 22993 | Metabolite - 9448 | 50 | 1.06E−05 | 1.00E−04 | 565% |
| 10655 | Metabolite - 2388 | 61 | 2.34E−07 | 4.83E−06 | 287% |
| 25548 | Metabolite - 10419 | 50 | 1.00E−04 | 3.00E−04 | 277% |
| 22320 | Metabolite - 8889 | 50 | 0.0015 | 0.0018 | 244% |
| 15991 | L-alpha-glycerophosphorylcholine | 61 | 0.0174 | 0.0135 | 227% |
| 27256 | Metabolite - 10500 | 50 | 6.36E−07 | 8.78E−06 | 190% |
| 19383 | Metabolite - 6286 | 50 | 6.00E−04 | 0.001 | 125% |
| 9137 | Metabolite - 2141 | 61 | 0.0026 | 0.0028 | 121% |
| 16028 | Metabolite - 3998 | 50 | 0.0012 | 0.0015 | 110% |
| 10739 | Metabolite - 2407 | 61 | 0.0057 | 0.0053 | 94% |
| 17987 | Metabolite - 5228 | 50 | 0.0087 | 0.0078 | 92% |
| 22675 | Metabolite - 9126 | 61 | 9.00E−04 | 0.0013 | 89% |
| 1481 | inositol-1-phosphate | 50 | 0.0149 | 0.0117 | 78% |
| 30173 | Metabolite - 10701 | 61 | 0.002 | 0.0022 | 70% |
| 12774 | Metabolite - 3094 | 50 | 0.0252 | 0.0186 | 66% |
| 21421 | Metabolite - 8214 | 50 | 0.0482 | 0.0321 | 63% |
| 22032 | Metabolite - 8766 | 50 | 0.0017 | 0.0019 | 62% |
| 12604 | Metabolite - 2981 | 50 | 0.0027 | 0.0028 | 54% |
| 16002 | Metabolite - 3992 [1] | 61 | 1.71E−05 | 1.00E−04 | 37% |
| 20360 | Metabolite - 7326 | 61 | 0.0352 | 0.0243 | −14% |
| 7601 | Metabolite - 1819 | 61 | 0.0351 | 0.0243 | −14% |
| 18829 | phenylalanine | 61 | 0.0303 | 0.0216 | −16% |
| 1604 | uric acid | 50 | 0.0331 | 0.0234 | −17% |
| 13505 | Metabolite - 3313 | 61 | 0.0337 | 0.0237 | −17% |
| 19787 | Metabolite - 6746 | 61 | 0.0143 | 0.0115 | −18% |
| 16235 | Isobar-19[2] | 61 | 0.0433 | 0.0292 | −18% |
| 10743 | Isobar-4[3] | 61 | 0.0428 | 0.0292 | −18% |

TABLE 15-continued

Metabolite biomarkers of Atherosclerosis in aorta.

| COMP_ID | COMPOUND | LIB_ID | p-value | q-value | % Change in LDb |
|---|---|---|---|---|---|
| 54 | tryptophan | 61 | 0.0217 | 0.0164 | −19% |
| 3147 | xanthine | 61 | 0.0234 | 0.0175 | −19% |
| 27570 | Metabolite - 10569 | 61 | 0.0177 | 0.0135 | −20% |
| 15529 | Metabolite - 3951 | 61 | 0.0468 | 0.0313 | −20% |
| 1125 | isoleucine | 50 | 0.0109 | 0.0092 | −22% |
| 1648 | serine | 50 | 0.0071 | 0.0065 | −23% |
| 605 | uracil | 50 | 0.0416 | 0.0286 | −23% |
| 7029 | Metabolite - 1597 | 61 | 0.0045 | 0.0043 | −24% |
| 1299 | tyrosine | 61 | 0.008 | 0.0073 | −24% |
| 1592 | N-acetylneuraminic acid | 61 | 0.0087 | 0.0078 | −24% |
| 1508 | pantothenic acid | 61 | 0.0105 | 0.0089 | −24% |
| 13810 | Metabolite - 3379 | 61 | 0.0146 | 0.0116 | −24% |
| 24076 | Metabolite - 9726 | 50 | 1.00E−04 | 3.00E−04 | −26% |
| 8336 | Metabolite - 2005 | 61 | 0.0019 | 0.0021 | −26% |
| 22258 | Isobar-58[4] | 61 | 0.0292 | 0.0211 | −26% |
| 60 | leucine | 50 | 0.0045 | 0.0043 | −28% |
| 30128 | Metabolite - 10687 | 61 | 0.0114 | 0.0095 | −28% |
| 17048 | Metabolite - 4617 | 61 | 0.0014 | 0.0017 | −29% |
| 17960 | Metabolite - 5207 | 50 | 0.0015 | 0.0018 | −29% |
| 15677 | 3-methyl-L-histidine | 61 | 5.00E−04 | 0.001 | −30% |
| 1431 | (p-Hydroxyphenyl)lactic acid | 50 | 0.001 | 0.0013 | −30% |
| 1649 | valine | 50 | 0.0039 | 0.004 | −30% |
| 1898 | proline | 50 | 0.0042 | 0.0042 | −30% |
| 1284 | threonine | 50 | 0.0047 | 0.0045 | −31% |
| 15948 | S-adenosyl-l-homocysteine | 61 | 0.0101 | 0.0088 | −31% |
| 26456 | Metabolite - 10470 | 61 | 0.0134 | 0.011 | −31% |
| 1302 | methionine | 61 | 0.0161 | 0.0125 | −31% |
| 22185 | n-acetyl-l-aspartic acid | 61 | 9.00E−04 | 0.0013 | −32% |
| 1414 | 3-phospho-d-glycerate | 61 | 0.002 | 0.0022 | −32% |
| 1643 | fumaric acid | 50 | 0.0042 | 0.0042 | −33% |
| 10890 | Metabolite - 2554 | 61 | 0.0029 | 0.003 | −34% |
| 10746 | Isobar-6[5] | 61 | 0.0283 | 0.0208 | −35% |
| 15253 | Metabolite - 3832-possible-phenol-sulfate | 61 | 0.0292 | 0.0211 | −35% |
| 5821 | 3-phospho-l-serine | 61 | 7.00E−04 | 0.0012 | −36% |
| 12102 | o-phosphoethanolamine | 50 | 0.0014 | 0.0018 | −36% |
| 8404 | Metabolite - 2027 | 61 | 0.0019 | 0.0021 | −36% |
| 1123 | inosine | 61 | 2.00E−04 | 5.00E−04 | −37% |
| 3127 | hypoxanthine | 61 | 8.00E−04 | 0.0012 | −37% |
| 6771 | Metabolite - 1460 | 61 | 0.0015 | 0.0018 | −37% |
| 14311 | Metabolite - 3481 | 61 | 0.0198 | 0.015 | −37% |
| 16233 | Isobar-13[6] | 61 | 6.00E−04 | 0.001 | −38% |
| 11222 | Metabolite - 2688 | 61 | 5.00E−04 | 0.001 | −38% |
| 1638 | arginine | 61 | 8.00E−04 | 0.0012 | −38% |
| 15497 | arginino-succinate | 61 | 0.0012 | 0.0015 | −38% |
| 15506 | choline | 61 | 2.00E−04 | 5.00E−04 | −39% |
| 16705 | Metabolite - 4428 | 61 | 0.0012 | 0.0016 | −39% |
| 8991 | Metabolite - 2105 | 61 | 0.0096 | 0.0085 | −39% |
| 514 | cytidine | 61 | 5.00E−04 | 9.00E−04 | −40% |
| 13018 | Metabolite - 3138 | 61 | 5.00E−04 | 0.001 | −40% |
| 527 | lactate | 50 | 7.00E−04 | 0.0012 | −40% |
| 23051 | Metabolite - 9566 | 61 | 0.001 | 0.0014 | −40% |
| 28131 | Metabolite - 10670 | 61 | 4.00E−04 | 8.00E−04 | −41% |
| 1494 | 5-oxoproline | 50 | 9.00E−04 | 0.0013 | −41% |
| 606 | uridine | 61 | 5.00E−04 | 0.001 | −42% |
| 18374 | methionine-sulfoxide | 61 | 1.00E−04 | 4.00E−04 | −43% |
| 57 | glutamic acid | 50 | 6.00E−04 | 0.001 | −44% |
| 15996 | aspartate | 50 | 8.00E−04 | 0.0012 | −44% |
| 20489 | D-glucose | 50 | 0.0051 | 0.0048 | −44% |
| 18348 | 3-hydroxy-3methylglutaryl-coenzyme-A | 61 | 0.01 | 0.0087 | −44% |
| 27718 | creatine | 61 | 2.00E−04 | 5.00E−04 | −45% |
| 1303 | malic acid | 61 | 7.00E−04 | 0.0011 | −45% |
| 1412 | 2'-deoxyuridine | 61 | 1.02E−06 | 1.09E−05 | −46% |
| 21430 | Metabolite - 8266 | 61 | 2.00E−04 | 6.00E−04 | −47% |
| 11544 | Metabolite - 2766 | 61 | 0.0013 | 0.0016 | −47% |
| 19372 | Metabolite - 6269 | 50 | 0.0027 | 0.0028 | −47% |
| 22145 | acetyl-L-carnitine | 61 | 2.00E−04 | 5.00E−04 | −48% |
| 10737 | Isobar-1[7] | 61 | 3.00E−04 | 6.00E−04 | −48% |
| 14247 | Metabolite - 3475 | 61 | 0.0146 | 0.0116 | −48% |
| 19110 | Metabolite - 5978 | 50 | 3.00E−04 | 7.00E−04 | −49% |
| 22730 | Metabolite - 9186 | 61 | 8.00E−04 | 0.0012 | −49% |
| 11777 | glycine | 50 | 5.00E−04 | 0.001 | −50% |
| 16228 | Isobar-22[8] | 61 | 1.00E−04 | 3.00E−04 | −51% |

TABLE 15-continued

Metabolite biomarkers of Atherosclerosis in aorta.

| COMP_ID | COMPOUND | LIB_ID | p-value | q-value | % Change in LDb |
|---|---|---|---|---|---|
| 16843 | Metabolite - 4510 | 50 | 1.00E-04 | 3.00E-04 | -51% |
| 53 | glutamine | 50 | 2.00E-04 | 6.00E-04 | -51% |
| 19708 | Metabolite - 6711 | 61 | 0.0124 | 0.0103 | -51% |
| 1416 | GABA | 50 | 1.38E-08 | 1.18E-06 | -52% |
| 15500 | carnitine | 61 | 5.00E-04 | 9.00E-04 | -52% |
| 2125 | taurine | 61 | 0.0017 | 0.002 | -52% |
| 22475 | Metabolite - 8986 | 61 | 0.0044 | 0.0043 | -52% |
| 28059 | Metabolite - 10650 | 50 | 1.87E-05 | 1.00E-04 | -54% |
| 20361 | Metabolite - 7327 | 61 | 3.32E-05 | 2.00E-04 | -54% |
| 17971 | Metabolite - 5210 | 50 | 1.00E-04 | 3.00E-04 | -54% |
| 22494 | Metabolite - 8994 | 50 | 4.00E-04 | 9.00E-04 | -54% |
| 7650 | Metabolite - 1834 | 61 | 2.06E-07 | 4.83E-06 | -55% |
| 27738 | threonic acid | 50 | 1.00E-04 | 3.00E-04 | -55% |
| 27678 | Metabolite - 10584 | 50 | 3.00E-04 | 7.00E-04 | -55% |
| 12459 | Isobar-10[9] | 61 | 3.43E-05 | 2.00E-04 | -56% |
| 15125 | (2-Aminoethyl)phosphonate | 61 | 1.00E-04 | 3.00E-04 | -56% |
| 19934 | inositol | 50 | 3.00E-04 | 7.00E-04 | -56% |
| 16860 | Metabolite - 4517 | 50 | 1.00E-04 | 3.00E-04 | -57% |
| 17064 | Metabolite - 4624 | 50 | 1.00E-04 | 4.00E-04 | -57% |
| 1107 | allantoin | 50 | 5.00E-04 | 0.001 | -57% |
| 1573 | guanosine | 61 | 4.00E-06 | 3.69E-05 | -58% |
| 1670 | urea | 50 | 1.00E-04 | 3.00E-04 | -58% |
| 27727 | glutathione-oxidized | 61 | 1.00E-04 | 4.00E-04 | -61% |
| 1519 | sucrose | 50 | 0.0104 | 0.0089 | -62% |
| 22702 | Metabolite - 9127 | 61 | 4.30E-06 | 3.69E-05 | -63% |
| 15336 | tartaric acid | 61 | 6.92E-08 | 2.97E-06 | -66% |
| 6172 | Metabolite - 1245 | 61 | 2.82E-07 | 4.83E-06 | -70% |
| 17975 | Metabolite - 5211 | 50 | 1.04E-05 | 1.00E-04 | -70% |
| 27773 | Isobar-71[10] | 61 | 3.00E-04 | 7.00E-04 | -71% |

[1] Possibly Cl-adduct of Formate dimmer
[2] Isobar-19 includes 1,5-anhydro-D-glucitol, 2'-deoxy-D-galactose, 2'-deoxy-D-glucose, L-fucose, L-rhamnose
[3] Isobar-4 includes Gluconic acid, DL-arabinose, D-ribose, L-xylose, DL-lyxose, D-xylulose, galactonic acid
[4] Isobar-58 includes bicine, 2-methylaminomethyl-tartronic acid
[5] Isobar-6 includes valine-betaine
[6] Isobar-13 includes 5-keto-D-gluconic acid, 2-keto-L-gulonic acid, D-glucuronic acid, D-galacturonic acid
[7] Isobar-1 includes mannose, fructose, glucose, galactose, alpha-L-sorbopyranose, Inositol, D-allose, D-altrose, D-psicone, L-gulose, allo-inositol
[8] Isobar-22-includes-glutamic acid-O-acetyl-L-serine
[9] Isobar-10-includes-glutamine-H-beta-ala-gly-OH-1-methylguanine-H-Gly-Sar-OH-lysine
[10] Isobar-71 includes conduritol-beta-epoxide-3-deoxyglucosone

TABLE 16

Metabolite biomarkers of Atherosclerosis in liver.

| COMP_ID | COMPOUND | LIB_ID | p-value | q-value | % Change in LDb |
|---|---|---|---|---|---|
| 19788 | Metabolite - 6747 | 61 | 6.49E-06 | 0.001 | 895% |
| 1564 | citric acid | 50 | 0.0069 | 0.0454 | 399% |
| 9117 | Metabolite - 2135 | 61 | 0.0173 | 0.0851 | 206% |
| 25626 | Metabolite - 10443 | 61 | 0.021 | 0.0964 | 180% |
| 19597 | Metabolite - 6648 | 50 | 0.0055 | 0.0452 | 162% |
| 15685 | 5-hydroxylysine | 61 | 0.0049 | 0.0452 | 159% |
| 16655 | Metabolite - 4362 | 50 | 0.0064 | 0.0454 | 131% |
| 21418 | Isobar-56[1] | 61 | 1.36E-05 | 0.0011 | 129% |
| 22475 | Metabolite - 8986 | 61 | 0.0012 | 0.0191 | 129% |
| 15803 | maltose | 50 | 0.0224 | 0.0992 | 128% |
| 18344 | D-xyulose | 50 | 1.00E-04 | 0.0071 | 126% |
| 27678 | Metabolite - 10584 | 50 | 0.0083 | 0.049 | 126% |
| 22020 | Metabolite - 8749 | 50 | 6.00E-04 | 0.0168 | 124% |
| 30204 | Metabolite - 10713 | 61 | 0.0138 | 0.0703 | 122% |
| 30203 | Metabolite - 10712 | 61 | 9.00E-04 | 0.0186 | 113% |
| 15053 | sorbitol | 50 | 0.0048 | 0.0452 | 105% |
| 1640 | ascorbic acid | 50 | 0.0032 | 0.0375 | 104% |
| 19753 | Metabolite - 6718 | 61 | 0.0073 | 0.046 | 97% |
| 21650 | Metabolite - 8409 | 61 | 0.0185 | 0.0866 | 91% |
| 1516 | sarcosine | 50 | 0.0124 | 0.0659 | 85% |
| 22309 | Metabolite - 8887 | 61 | 0.001 | 0.0191 | 85% |
| 27299 | Metabolite - 10520 | 61 | 4.00E-04 | 0.0136 | 83% |
| 1118 | eicosanoic acid | 50 | 0.0015 | 0.0191 | 78% |
| 25429 | Metabolite - 10369 | 50 | 0.0045 | 0.0452 | 72% |

TABLE 16-continued

Metabolite biomarkers of Atherosclerosis in liver.

| COMP_ID | COMPOUND | LIB_ID | p-value | q-value | % Change in LDb |
|---|---|---|---|---|---|
| 8669 | Metabolite - 2055 | 61 | 0.0087 | 0.0498 | 69% |
| 8210 | Metabolite - 1981 | 61 | 0.023 | 0.0992 | 65% |
| 20488 | D-glucose | 50 | 0.0073 | 0.046 | 55% |
| 15606 | Metabolite - 3968 | 61 | 0.0069 | 0.0454 | 51% |
| 11379 | Metabolite - 2725 | 61 | 0.0224 | 0.0992 | 50% |
| 11484 | Metabolite - 2752 | 61 | 7.00E−04 | 0.0168 | 50% |
| 11292 | Metabolite - 2703 | 61 | 0.0133 | 0.0694 | 49% |
| 8457 | Metabolite - 2035 [2] | 61 | 0.0066 | 0.0454 | 47% |
| 16859 | Metabolite - 4516 | 50 | 0.0066 | 0.0454 | 44% |
| 554 | adenine | 50 | 0.0076 | 0.0463 | 44% |
| 7081 | Metabolite - 1609 | 61 | 0.0039 | 0.0412 | 41% |
| 20795 | Metabolite - 7747 | 61 | 0.0033 | 0.0375 | 40% |
| 16229 | Isobar-24[3] | 61 | 0.0055 | 0.0452 | 39% |
| 18388 | Metabolite - 5491 | 50 | 0.0057 | 0.0452 | 39% |
| 24360 | Metabolite - 10206 | 50 | 0.0178 | 0.086 | 38% |
| 12080 | D-ribose | 50 | 0.0104 | 0.0575 | 37% |
| 22993 | Metabolite - 9448 | 50 | 0.0156 | 0.0782 | 36% |
| 10737 | Isobar-1[4] | 61 | 0.0084 | 0.049 | 36% |
| 16060 | Metabolite - 4014 | 50 | 0.0181 | 0.0862 | 36% |
| 24285 | Metabolite - 10026 | 61 | 0.0229 | 0.0992 | 23% |
| 63 | cholesterol | 50 | 0.0104 | 0.0575 | 15% |
| 22414 | Metabolite - 8933 | 61 | 0.0037 | 0.0406 | −29% |
| 1827 | riboflavine | 61 | 0.0052 | 0.0452 | −29% |
| 22320 | Metabolite - 8889 | 50 | 0.0056 | 0.0452 | −29% |
| 9002 | Metabolite - 2107 | 61 | 0.0012 | 0.0191 | −31% |
| 3138 | pyridoxamine-phosphate | 61 | 0.0054 | 0.0452 | −34% |
| 15964 | D-arabitol | 50 | 2.00E−04 | 0.0098 | −34% |
| 7432 | Metabolite - 1735 | 61 | 0.0014 | 0.0191 | −35% |
| 22185 | n-acetyl-l-aspartic acid | 61 | 0.0068 | 0.0454 | −36% |
| 23024 | Metabolite - 9458 | 61 | 0.0011 | 0.0191 | −37% |
| 21296 | glucosamine-6-sulfate | 61 | 0.0014 | 0.0191 | −39% |
| 7650 | Metabolite - 1834 | 61 | 7.40E−06 | 0.001 | −41% |
| 9468 | Metabolite - 2183 | 61 | 8.00E−04 | 0.0182 | −46% |
| 6530 | Metabolite - 1384 | 61 | 0.0115 | 0.0621 | −57% |
| 25561 | Metabolite - 10421 | 61 | 0.0069 | 0.0454 | −58% |
| 597 | phosphoenolpyruvate | 61 | 0.0014 | 0.0191 | −59% |
| 1414 | 3-phospho-d-glycerate | 50 | 1.57E−05 | 0.0011 | −60% |
| 10148 | Metabolite - 2257 | 61 | 0.003 | 0.037 | −68% |
| 27794 | Metabolite - 10587 | 61 | 4.00E−04 | 0.0127 | −69% |
| 6146 | alpha-amino-adipate | 50 | 2.00E−04 | 0.0098 | −73% |

[1]Isobar-56 includes DL-pipecolic acid-1-amino-1-cyclopentanecarboxylic acid
[2] Possible 5-methyl-deoxycytidine-monophosphate
[3]Isobar-24 includes L-arabitol, adonitol, xylitol
[4]Isobar-1 includes mannose, fructose, glucose, galactose, alpha-L-sorbopyranose, Inositol, D-allose, D-altrose, D-psicone, L-gulose, allo-inositol Identification of plasma biomarkers indicative of initiation and/or progression of atherosclerosis would help diagnosis and treatment of human patients with this disease. Recursive partitioning of plasma metabolites identified cholesterol as a biomarker that could differentiate the LDb and C57BL/6 mice perfectly, as expected. Three other metabolites were also identified by recursive partitioning to differentiate the LDb and C57BL/6 mice (Table 17). Plasma levels of these metabolites, like plasma cholesterol, were higher in LDb mice even at 2 months of age and remained consistently higher during the following 6 months, suggesting that earlier buildup of these metabolites is likely involved in the development of atherosclerosis and provide biomarkers for progression (FIGS. 13, 14, 15, and 16).

TABLE 17

Atherosclerosis biomarkers in plasma that differentiate Atherosclerosis subjects (LDb) and healthy control subjects (C57BL/6 mice) without error.

| Cmpd_ID | Compound | Atherosclerosis level | Control level | R-Square | LogWorth |
|---|---|---|---|---|---|
| 19323 | Docosahexaenoic-Acid | ≥528666 | <528666 | 1.000 | 21.11 |
| 21011 | Metabolite - 7888 | ≥2523794 | <2523794 | 1.000 | 21.11 |
| 21631 | Metabolite - 8403 | ≥238349 | <238349 | 1.000 | 21.11 |

Metabolite-1834 did not segregate LDb and C57BL/6 groups in 2-month-old mice, but started to segregate the 5-month-olds and segregated 8-month-old mice perfectly (FIG. 17). This metabolite is one of the biomarkers for atherosclerosis progression.

Figure 19:
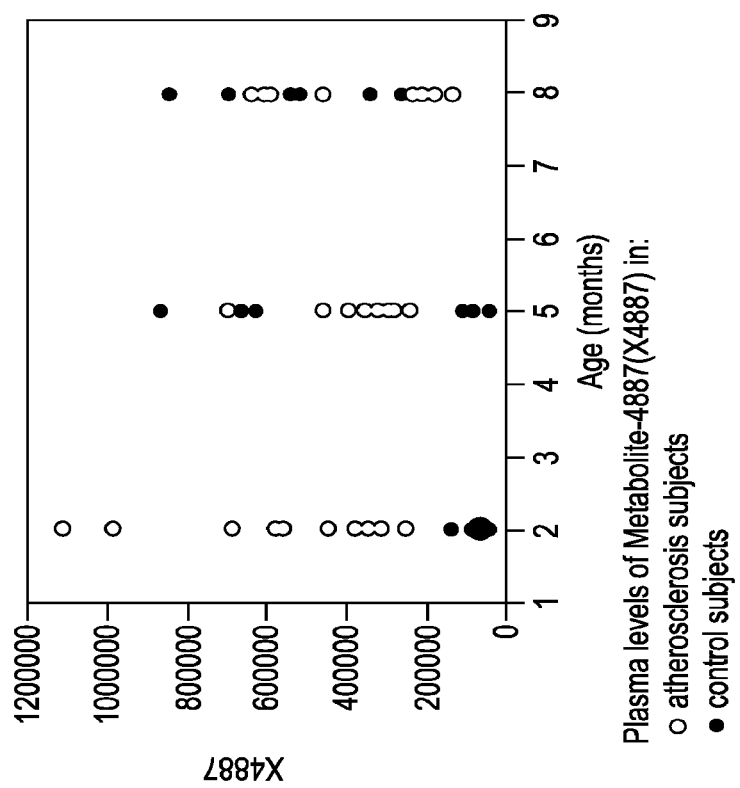
FIG. 19 provides an example of plasma levels of Metabolite-4887 in atherosclerosis subjects and control subjects at different ages.

Several metabolites (p-cresol-sulfate, Metabolite-4887, Metabolite-5386) classified subjects as LDb or C57BL/6 very well in 2-month-old mice, but the power of differentiation diminished as the mice aged, with no segregation in 8-month-old mice (FIGS. 18 and 19). These metabolites are biomarkers for atherosclerosis initiation.

Random forest results show that the samples can be classified correctly with varying degrees of accuracy using the biomarkers. The confusion matrices demonstrate that LDb subjects can be distinguished from C57BL/6 subjects using plasma (Table 18), aorta (Table 19) and liver (Table 20) samples. The "Out-of-Bag" (OOB) Error rate gives an estimate of how accurately new observations can be predicted using the random forest model (e.g., whether a sample is from a subject having atherosclerosis or a control subject).

TABLE 18

Random Forest Confusion Matrices for Atherosclerosis in Plasma
Plasma

| | Control | Atherosclerosis | Error |
|---|---|---|---|
| Age Collected: 2 months | | | |
| Control | 10 | 0 | 0 |
| Atherosclerosis | 0 | 10 | 0 |
| OOB Error | 0 | 0% | |
| Age Collected: 5 months | | | |
| Control | 10 | 0 | 0 |
| Atherosclerosis | 2 | 9 | 0 |
| OOB Error | 0 | 0% | |
| Age Collected: 8 months | | | |
| Control | 8 | 0 | 0 |
| Atherosclerosis | 0 | 8 | 0 |
| OOB Error | 0 | 0% | |
| ALL | | | |
| Control | 28 | 0 | 0 |
| Atherosclerosis | 0 | 27 | 0 |
| OOB Error | 0 | 0% | |

TABLE 19

Random Forest Confusion Matrices for Atherosclerosis
in Aorta Tissues
Aorta Tissue

| | Control | Atherosclerosis | Error |
|---|---|---|---|
| Age Collected: 2 months | | | |
| Control | 6 | 1 | 0.14 |
| Atherosclerosis | 2 | 2 | 0.5 |
| OOB Error | 3/11 = 0.27 | 27% | |
| Age Collected: 5 months | | | |
| Control | 7 | 0 | 0 |
| Atherosclerosis | 2 | 4 | 0.33 |
| OOB Error | 2/13 = 0.15 | 15% | |
| Age Collected: 8 months | | | |
| Control | 6 | 0 | 0 |
| Atherosclerosis | 0 | 4 | 0 |
| OOB Error | 0/10 = 0.00 | 0% | |
| ALL | | | |
| Control | 18 | 2 | 0.1 |
| Atherosclerosis | 3 | 11 | 0.21 |
| OOB Error | 5/34 = 0.15 | 15% | |

TABLE 20

Random Forest Confusion Matrices for Atherosclerosis in Liver
Liver

| | Control | Atherosclerosis | Error |
|---|---|---|---|
| Age Collected: 2 months | | | |
| Control | 7 | 1 | 0.13 |
| Atherosclerosis | 1 | 3 | 0.25 |
| OOB Error | 2/12 = 0.17 | 17% | |
| Age Collected: 5 months | | | |
| Control | 3 | 1 | 0.25 |
| Atherosclerosis | 3 | 3 | 0.5 |
| OOB Error | 4/10 = 0.4 | 40% | |
| Age Collected: 8 months | | | |
| Control | 5 | 0 | 0 |
| Atherosclerosis | 1 | 5 | 0.17 |
| OOB Error | 1/11 = 0.09 | 9% | |
| ALL | | | |
| Control | 15 | 2 | 0.12 |
| Atherosclerosis | 3 | 13 | 0.19 |
| OOB Error | 5/33 = 0.15 | 15% | |

In addition, a study was carried out on human subjects suffering from atherosclerosis (n=15) or healthy subjects (n=14). The biomarkers 3-methylhistidine, p-cresol sulfate, mannose, glucose, and gluconate showed the same alterations in human plasma from disease vs. healthy subjects as seen in the mouse model. Thus, these compounds were identified as important biomarkers useful to distinguish individuals with atherosclerosis from healthy subjects.

3C: Biomarkers of Cardiomyopathy

Biomarkers were discovered by (1) analyzing cardiac tissue samples (Table 21) or plasma samples (Table 22) from different groups of mouse subjects to determine the levels of metabolites in the samples and then (2) statistically analyzing the results to determine those metabolites that were differentially present in the two groups. These subjects provide an animal (mouse) model for human DCM.

Two groups of subjects were used. One group consisted of eight subjects exhibiting cardiac dilatation and depressed left ventricular systolic function (ejection fraction of less than 0.40), as determined by echocardiography (cTnT-W141 transgenic mice). Thirteen age- and gender-matched subjects (non-transgenic (wild-type background strain) mice) served as controls. All mice were 7-19 months old and weighed 23-40 gm.

T-tests were used to determine differences in the mean levels of metabolites between the two populations (i.e., Dilated Cardiomyopathy, DCM vs. Healthy control). Classification analysis was carried out using recursive partitioning and random forest analyses to uncover the biomarkers that can best differentiate the two groups. Recursive partitioning relates a 'dependent' variable (Y) to a collection of independent ('predictor') variables (X) in order to uncover—or simply understand—the elusive relationship, Y=f(X). It was performed with the JMP program (SAS) to generate a decision tree. The statistical significance of the "split" of the data can be placed on a more quantitative footing by computing p-values, which discern the quality of a split relative to a random event. The significance level of each "split" of data into the nodes or branches of the tree was computed as p-values, which discern the quality of the split relative to a random event. It was given as LogWorth, which is the negative log 10 of a raw p-value.

Biomarkers:

As listed below in Tables 21 and 22, biomarkers were discovered that were differentially present between cardiac tissue and plasma samples, respectively, collected from dilated cardiomyopathy subjects and healthy subjects.

Tables 21 and 22 include, for each listed biomarker, the p-value and q-value determined in the statistical analysis of the data concerning the biomarkers and an indication of the percentage difference in the dilated cardiomyopathy mean level as compared to the healthy mean level in cardiac tissue (Table 21) or plasma (Table 22). The term "Isobar" as used in the tables indicates the compounds that could not be distinguished from each other on the analytical platform used in the analysis (i.e., the compounds in an isobar elute at nearly the same time and have similar (and sometimes exactly the same) quant ions, and thus cannot be distinguished). Comp_ID refers to the compound identification number used as a primary key for that compound in the in-house chemical database. Library indicates the chemical library that was used to identify the compounds. The number 50 refer to the GC library and the number 61 refers to the LC library.

TABLE 21

Metabolite biomarkers of dilated cardiomyopathy (DCM) in cardiac tissues.

| COMP_ID | COMPOUND | LIB_ID | p-value | q-value | % Change in DCM |
|---|---|---|---|---|---|
| 22185 | n-acetyl-l-aspartic acid | 61 | 0.0044 | 0.0144 | 100% |
| 15996 | aspartate | 50 | 0.0002 | 0.0022 | 64% |
| 1414 | 3-phospho-d-glycerate | 50 | 0.0742 | 0.0888 | 52% |
| 1898 | proline | 61 | 3.64E−05 | 0.0007 | 52% |
| 1648 | serine | 50 | 0.0009 | 0.0057 | 49% |
| 1299 | tyrosine | 61 | 3.36E−05 | 0.0007 | 39% |
| 1284 | threonine | 50 | 0.0054 | 0.0173 | 28% |
| 54 | tryptophan | 61 | 0.0383 | 0.0571 | 20% |
| 1649 | valine | 50 | 0.0081 | 0.0227 | 19% |
| 1125 | isoleucine | 50 | 0.0041 | 0.014 | 16% |
| 11777 | glycine | 50 | 0.0109 | 0.0255 | 15% |
| 13179 | creatine | 61 | 0.0011 | 0.0061 | −17% |
| 590 | hypotaurine | 61 | 0.0728 | 0.0879 | −21% |
| 5278 | beta-nicotinamide adenine dinucleotide | 61 | 0.0092 | 0.0239 | −27% |
| 15500 | carnitine | 61 | 0.0331 | 0.0509 | −32% |
| 2127 | glutathione, reduced | 61 | 0.0033 | 0.0125 | −62% |
| 12080 | D-ribose | 50 | 0.0033 | 0.0125 | 39% |
| 15122 | glycerol | 50 | 0.0663 | 0.0819 | −16% |
| 19934 | inositol | 50 | 0.0225 | 0.0417 | −22% |
| 18882 | taurodeoxycholic acid | 61 | 0.0584 | 0.0754 | 72% |
| 15365 | sn-Glycerol 3-phosphate | 50 | 0.0109 | 0.0255 | 41% |
| 63 | cholesterol | 50 | 0.011 | 0.0255 | 14% |
| 1121 | heptadecanoic acid | 50 | 0.0594 | 0.0761 | −15% |
| 21127 | monopalmitin | 50 | 0.0149 | 0.0324 | −23% |
| 1336 | n-hexadecanoic acid | 50 | 0.0014 | 0.0072 | −24% |
| 19323 | docosahexaenoic acid | 50 | 0.0009 | 0.0057 | −24% |
| 1600 | o-phosphoethanolamine | 50 | 0.0253 | 0.0435 | −30% |
| 1365 | tetradecanoic acid | 50 | 0.0516 | 0.0691 | −31% |
| 1570 | oleic acid | 50 | 0.0269 | 0.0446 | −31% |
| 1105 | linoleic acid | 50 | 0.0014 | 0.0072 | −32% |
| 1518 | squalene | 50 | 0.0013 | 0.0072 | −43% |
| 15504 | phosphopantheine | 61 | 0.0186 | 0.0367 | −49% |
| 1827 | riboflavine | 61 | 0.0037 | 0.0129 | 85% |
| 594 | niacinamide | 50 | 0.0091 | 0.0239 | −17% |
| 3138 | pyridoxamine phosphate | 61 | 0.0047 | 0.0153 | −19% |
| 1508 | pantothenic acid | 61 | 0.0093 | 0.0239 | −32% |
| 3127 | hypoxanthine | 50 | 0.0112 | 0.0255 | 92% |
| 606 | uridine | 61 | 0.0262 | 0.0445 | 56% |
| 1107 | allantoin | 50 | 0.0207 | 0.0398 | 39% |
| 514 | cytidine | 61 | 0.0034 | 0.0126 | 33% |
| 1573 | guanosine | 61 | 0.0326 | 0.0507 | 32% |
| 605 | uracil | 50 | 0.0291 | 0.0457 | 27% |
| 21031 | hydroxyurea | 61 | 0.0069 | 0.0204 | −47% |
| 2856 | uridine 5'-monophosphate | 61 | 0.0005 | 0.004 | −68% |
| 18360 | adenylosuccinic acid | 61 | 9.02E−06 | 0.0004 | −85% |
| 555 | adenosine | 61 | 0.0007 | 0.0051 | −87% |
| 2832 | adenosine 5'-monophosphate | 61 | 4.53E−06 | 0.0004 | −90% |
| 2849 | guanosine 5'-monophosphate | 61 | 2.06E−05 | 0.0006 | −94% |
| 20701 | malitol | 50 | 0.0167 | 0.0343 | −32% |
| 8469 | Metabolite - 2036 | 61 | 0.0144 | 0.0319 | 525% |
| 10781 | Metabolite - 2469 | 61 | 0.007 | 0.0204 | 355% |
| 10604 | Metabolite - 2370 | 61 | 0.0089 | 0.0239 | 213% |
| 10401 | Metabolite - 2058 | 61 | 0.0006 | 0.0048 | 203% |
| 5597 | Metabolite - 1073 | 61 | 0.0178 | 0.0357 | 203% |
| 14639 | Metabolite - 3603 | 61 | 5.89E−05 | 0.001 | 194% |
| 16019 | Metabolite - 3995 | 61 | 0.0001 | 0.0017 | 156% |
| 22480 | Metabolite - 8987 | 50 | 1.78E−05 | 0.0006 | 150% |
| 6130 | Metabolite - 1208 | 61 | 0.0277 | 0.0454 | 144% |

TABLE 21-continued

Metabolite biomarkers of dilated cardiomyopathy (DCM) in cardiac tissues.

| COMP_ID | COMPOUND | LIB_ID | p-value | q-value | % Change in DCM |
|---|---|---|---|---|---|
| 9137 | Metabolite - 2141 | 61 | 0.0174 | 0.0353 | 127% |
| 21418 | Isobar-56[1] | 61 | 0.0015 | 0.0072 | 122% |
| 18015 | Metabolite - 3113 | 61 | 0.0015 | 0.0072 | 122% |
| 22414 | Metabolite - 8933 | 61 | 0.0903 | 0.0028 | 108% |
| 6122 | Metabolite - 1206 [2] | 61 | 0.0414 | 0.058 | 104% |
| 9024 | Metabolite - 2111 | 61 | 0.0241 | 0.0432 | 104% |
| 18073 | Metabolite - 5270 | 61 | 0.0159 | 0.0337 | 92% |
| 12711 | Metabolite - 3053 | 61 | 0.0574 | 0.0752 | 89% |
| 13512 | Metabolite - 3315 | 61 | 0.028 | 0.0454 | 89% |
| 16471 | Metabolite - 4238 | 61 | 0.046 | 0.0627 | 89% |
| 5618 | Metabolite - 1085 [3] | 61 | 0.0371 | 0.0558 | 85% |
| 7654 | Metabolite - 1836 | 61 | 0.002 | 0.0085 | 82% |
| 16860 | Metabolite - 4517 | 50 | 0.0027 | 0.011 | 79% |
| 14715 | Metabolite - 3653 [4] | 61 | 0.0037 | 0.0129 | 72% |
| 21410 | Isobar-52[5] | 61 | 0.0018 | 0.008 | 69% |
| 17885 | Metabolite - 5147 | 61 | 0.0155 | 0.0332 | 56% |
| 22494 | Metabolite - 8994 | 50 | 0.0003 | 0.003 | 56% |
| 10850 | Metabolite - 2548 [6] | 61 | 0.0668 | 0.0819 | 52% |
| 15213 | Metabolite - 3808 | 61 | 5.92E−06 | 0.0004 | 52% |
| 21415 | Metabolite - 8209 | 50 | 0.011 | 0.0255 | 52% |
| 6266 | Metabolite - 1286 | 61 | 9.64E−05 | 0.0013 | 49% |
| 7127 | Metabolite - 1616 | 61 | 0.0019 | 0.0084 | 49% |
| 7272 | Metabolite - 1679 | 61 | 0.0562 | 0.0746 | 45% |
| 8509 | Metabolite - 2041 | 61 | 0.0104 | 0.0255 | 45% |
| 9313 | Metabolite - 2172 | 61 | 0.0246 | 0.0432 | 45% |
| 9905 | Metabolite - 2231 | 61 | 0.0167 | 0.0343 | 43% |
| 16071 | Metabolite - 4020 | 50 | 0.002 | 0.0085 | 41% |
| 22441 | Metabolite - 8950 | 61 | 0.0798 | 0.0925 | 39% |
| 19273 | Metabolite - 6108 | 61 | 0.0405 | 0.058 | 37% |
| 16233 | Isobar-13[7] | 61 | 0.0126 | 0.0282 | 33% |
| 9324 | Metabolite - 2173 | 61 | 0.0577 | 0.0752 | 33% |
| 19787 | Metabolite - 6746 | 61 | 0.0244 | 0.0432 | 30% |
| 20299 | Metabolite - 7266 | 50 | 0.0212 | 0.0402 | 30% |
| 9122 | Metabolite - 2137 | 61 | 0.0836 | 0.0961 | 28% |
| 21404 | Isobar-48[8] | 61 | 0.0487 | 0.0658 | 27% |
| 21011 | Metabolite - 7888 | 50 | 0.0031 | 0.012 | 27% |
| 13142 | Metabolite - 3165 | 61 | 0.0412 | 0.058 | 18% |
| 19372 | Metabolite - 6269 | 50 | 0.0192 | 0.0374 | 16% |
| 16285 | Metabolite - 2798 | 50 | 0.045 | 0.062 | 15% |
| 13505 | Metabolite - 3313 | 61 | 0.0338 | 0.0514 | 11% |
| 17064 | Metabolite - 4624 | 50 | 0.0619 | 0.0779 | −15% |
| 19599 | Metabolite - 6649 | 50 | 0.0287 | 0.0457 | −18% |
| 16074 | Metabolite - 2758 | 50 | 0.0417 | 0.058 | −19% |
| 20361 | Metabolite - 7327 | 61 | 0.0008 | 0.0056 | −20% |
| 7081 | Metabolite - 1609 | 61 | 0.0604 | 0.0767 | −21% |
| 17919 | Metabolite - 5187 | 61 | 0.0072 | 0.0208 | −22% |
| 17978 | Metabolite - 5213 | 50 | 0.0689 | 0.0838 | −23% |
| 18273 | Metabolite - 5420 | 50 | 0.0784 | 0.0916 | −23% |
| 16984 | Metabolite - 4599 | 50 | 0.0624 | 0.0779 | −24% |
| 11545 | Metabolite - 2767 | 61 | 0.0412 | 0.058 | −25% |
| 22509 | Metabolite - 9011 | 61 | 0.0063 | 0.0191 | −29% |
| 12856 | Metabolite - 3123 | 61 | 0.0768 | 0.0904 | −32% |
| 16060 | Metabolite - 4014 | 50 | 0.0253 | 0.0435 | −32% |
| 16843 | Metabolite - 4510 | 50 | 0.0289 | 0.0457 | −34% |
| 17960 | Metabolite - 5207 | 50 | 0.0003 | 0.003 | −35% |
| 16116 | Metabolite - 4051 | 50 | 0.0226 | 0.0417 | −36% |
| 14595 | Metabolite - 3576 | 61 | 0.0106 | 0.0255 | −36% |
| 8176 | Metabolite - 1974 | 61 | 0.0008 | 0.0056 | −37% |
| 15085 | Metabolite - 3776 | 61 | 0.0093 | 0.0239 | −39% |
| 16705 | Metabolite - 4428 | 61 | 0.0059 | 0.0182 | −40% |
| 19505 | Metabolite - 6547 | 61 | 0.0267 | 0.0446 | −41% |
| 11056 | Metabolite - 2568 | 61 | 0.075 | 0.0891 | −43% |
| 22507 | Metabolite - 9010 | 50 | 0.0396 | 0.0578 | −46% |
| 9130 | Metabolite - 2139 | 61 | 0.001 | 0.006 | −48% |
| 22381 | Metabolite - 8908 | 61 | 0.0389 | 0.0574 | −50% |
| 18702 | Metabolite - 5767 | 61 | 0.0234 | 0.0428 | −56% |
| 11379 | Metabolite - 2725 | 61 | 6.71E−05 | 0.001 | −69% |

TABLE 21-continued

Metabolite biomarkers of dilated cardiomyopathy (DCM) in cardiac tissues.

| COMP_ID | COMPOUND | LIB_ID | p-value | q-value | % Change in DCM |
|---|---|---|---|---|---|
| 22501 | Metabolite - 9007 | 61 | 0.0007 | 0.0052 | −79% |
| 22534 | Metabolite - 9016 | 61 | 2.36E−05 | 0.0006 | −86% |

[1] Isobar-56 includes DL-pipecolic acid, 1-amino-1-cyclopentanecarboxylic acid.
[2] Possible methyltestosterone and others.
[3] Possible isolobinine or 4-aminoestra-1,3,5(10)-triene-3,17beta-diol.
[4] Possible stachydrine.
[5] Isobar-52 includes iminodiacetic acid, L-aspartic acid.
[6] Possible Cl adduct of uric acid.
[7] Isobar 13 includes 5-keto-D-gluconic acid, 2-keto-L-gulonic acid, D-glucuronic acid, D(+)-galacturonic acid.
[8] Isobar 48 includes Serine-2,2-amino-2-methyl-1,3-propanediol,diethanolamine.

TABLE 22

Metabolite biomarkers of dilated cardiomyopathy (DCM) in plasma.

| COMP_ID | COMPOUND | LIB_ID | p-value | q-value | % Change in DCM | TG/NTG |
|---|---|---|---|---|---|---|
| 17007 | Metabolite - 4609 | 61 | 0.0003 | 0.0895 | 83% | 1.83 |
| 1299 | tyrosine | 61 | 0.0005 | 0.0895 | 83% | 1.83 |
| 20161 | Metabolite - 7088 | 61 | 0.0008 | 0.0895 | 239% | 3.39 |
| 19787 | Metabolite - 6746 | 61 | 0.0010 | 0.0895 | 62% | 1.62 |
| 20699 | meso-erythritol | 50 | 0.0013 | 0.0895 | 46% | 1.46 |
| 18968 | Metabolite - 5919 | 61 | 0.0014 | 0.0895 | 100% | 2.00 |
| 1107 | allantoin | 50 | 0.0017 | 0.0901 | 54% | 1.54 |
| 1431 | (p-Hydroxyphenyl)lactic acid | 61 | 0.0028 | 0.1283 | 114% | 2.14 |
| 584 | mannose | 50 | 0.0034 | 0.1411 | −41% | 0.59 |
| 15632 | Metabolite - 3980 | 61 | 0.0054 | 0.1997 | 64% | 1.64 |
| 396 | glutarate | 61 | 0.0069 | 0.2328 | 181% | 2.81 |
| 11292 | Metabolite - 2703 | 61 | 0.0080 | 0.2473 | 124% | 2.24 |
| 18829 | phenylalanine | 61 | 0.0098 | 0.2547 | 39% | 1.39 |
| 15286 | Metabolite - 3848 | 61 | 0.0103 | 0.2547 | 92% | 1.92 |
| 13575 | Metabolite - 3324 | 61 | 0.0112 | 0.2547 | 250% | 3.50 |
| 14786 | Metabolite - 3697 | 61 | 0.0121 | 0.2547 | 52% | 1.52 |
| 22597 | Metabolite - 9041 | 61 | 0.0130 | 0.2547 | −70% | 0.30 |
| 15611 | Metabolite - 3971 | 61 | 0.0132 | 0.2547 | 66% | 1.66 |
| 11813 | Metabolite - 2809 | 61 | 0.0137 | 0.2547 | −28% | 0.72 |
| 6571 | Metabolite - 1397 | 61 | 0.0139 | 0.2547 | 75% | 1.75 |
| 21418 | Isobar 56 includes DL-pipecolic acid, 1-amino-1-cyclopentanecarboxylic acid | 61 | 0.0151 | 0.2547 | 38% | 1.38 |
| 11299 | Metabolite - 2706 | 61 | 0.0159 | 0.2547 | 65% | 1.65 |
| 6305 | Metabolite - A-1254 | 61 | 0.0163 | 0.2547 | 64% | 1.64 |
| 19857 | Metabolite - 6783 | 61 | 0.0165 | 0.2547 | 135% | 2.35 |
| 21044 | (s)-2-hydroxybutyric acid | 50 | 0.0186 | 0.2722 | 105% | 2.05 |
| 16016 | Metabolite - 3994 | 61 | 0.0209 | 0.2722 | 92% | 1.92 |
| 5440 | Metabolite - A-1014 | 61 | 0.0221 | 0.2722 | 41% | 1.41 |
| 22555 | Metabolite - 9027 | 50 | 0.0223 | 0.2722 | −53% | 0.47 |
| 10737 | Isobar 1 includes mannose, fructose, glucose, galactose, alpha-L-sorbopyranose, Inositol, D-allose, D-(+)-altrose, D-psicone, L-(+)-gulose, allo-inositol | 61 | 0.0227 | 0.2722 | −33% | 0.67 |
| 20830 | Metabolite - 7762 | 61 | 0.0231 | 0.2722 | 48% | 1.48 |
| 14961 | Metabolite - 3752 | 61 | 0.0234 | 0.2722 | −46% | 0.54 |
| 15670 | 2-methylhippuric acid | 61 | 0.0234 | 0.2722 | 53% | 1.53 |
| 13142 | Metabolite - 3165 | 61 | 0.0285 | 0.3038 | 37% | 1.37 |
| 605 | uracil | 50 | 0.0286 | 0.3038 | 217% | 3.17 |
| 21011 | Metabolite - 7888 | 50 | 0.0298 | 0.3038 | 37% | 1.37 |
| 8959 | Metabolite - 2100 | 61 | 0.0305 | 0.3038 | −29% | 0.71 |
| 20169 | Metabolite - 7092 | 61 | 0.0320 | 0.3038 | 88% | 1.88 |
| 5776 | Metabolite - A-1194 | 61 | 0.0322 | 0.3038 | 89% | 1.89 |
| 6126 | Metabolite - 1207 | 61 | 0.0326 | 0.3038 | 52% | 1.52 |
| 12459 | Isobar 10 includes glutamine, H-beta-ala-gly-OH, 1-methylguanine, H-Gly-Sar-OH lysine | 61 | 0.0327 | 0.3038 | −31% | 0.69 |

TABLE 22-continued

Metabolite biomarkers of dilated cardiomyopathy (DCM) in plasma.

| COMP_ID | COMPOUND | LIB_ID | p-value | q-value | % Change in DCM | TG/NTG |
|---|---|---|---|---|---|---|
| 3155 | 3-ureidopropionic acid | 61 | 0.0351 | 0.3093 | 60% | 1.60 |
| 15541 | Metabolite - 3957 | 61 | 0.0360 | 0.3093 | 43% | 1.43 |
| 1303 | malic acid | 50 | 0.0388 | 0.3093 | 108% | 2.08 |
| 15737 | hydroxyacetic acid | 50 | 0.0392 | 0.3093 | 38% | 1.38 |
| 527 | lactate | 50 | 0.0399 | 0.3093 | 65% | 1.65 |
| 1670 | urea | 50 | 0.0410 | 0.3093 | 23% | 1.23 |
| 15949 | 2'-deoxycytidine | 61 | 0.0413 | 0.3093 | 24% | 1.24 |
| 7272 | Metabolite - 1679 | 61 | 0.0415 | 0.3093 | 251% | 3.51 |
| 12011 | Metabolite - 2848 | 61 | 0.0425 | 0.3093 | 53% | 1.53 |
| 1643 | fumaric acid | 50 | 0.0437 | 0.3093 | 70% | 1.70 |
| 1574 | histamine | 61 | 0.0452 | 0.3093 | 74% | 1.74 |
| 22566 | Metabolite - 9029 | 61 | 0.0458 | 0.3093 | −63% | 0.37 |
| 15140 | L-kynurenine | 61 | 0.0458 | 0.3093 | 49% | 1.49 |
| 22026 | 1-methylguanidine hydrochloride | 50 | 0.0462 | 0.3093 | 19% | 1.19 |
| 7127 | Metabolite - 1616 | 61 | 0.0473 | 0.3093 | −38% | 0.62 |
| 1604 | uric acid | 50 | 0.0478 | 0.3093 | 146% | 2.46 |
| 7429 | Metabolite - 1733 | 61 | 0.0492 | 0.3093 | 37% | 1.37 |
| 12626 | Metabolite - 3003 | 50 | 0.0500 | 0.3093 | 51% | 1.51 |
| 2849 | guanosine 5'-monophosphate | 61 | 0.0509 | 0.3093 | −58% | 0.42 |
| 16327 | Metabolite - 4161 | 61 | 0.0514 | 0.3093 | 35% | 1.35 |
| 14715 | Metabolite - 3653-Possible stachydrine | 61 | 0.0521 | 0.3093 | 29% | 1.29 |
| 1507 | palmitoleic acid | 50 | 0.0522 | 0.3093 | −54% | 0.46 |
| 9491 | Metabolite - 2185 | 61 | 0.0525 | 0.3093 | 97% | 1.97 |
| 2734 | gamma-L-glutamyl-L-tyrosine | 61 | 0.0541 | 0.3112 | 34% | 1.34 |
| 11235 | Metabolite - 2690 | 61 | 0.0548 | 0.3112 | −34% | 0.66 |
| 13775 | Metabolite - 3370 | 61 | 0.0561 | 0.3112 | 38% | 1.38 |
| 17960 | Metabolite - 5207 | 50 | 0.0569 | 0.3112 | −32% | 0.68 |
| 1587 | N-acetyl-L-leucine | 61 | 0.0577 | 0.3112 | 75% | 1.75 |
| 20798 | Metabolite - 7748 | 61 | 0.0581 | 0.3112 | −41% | 0.59 |
| 2832 | adenosine 5'-monophosphate | 61 | 0.0589 | 0.3112 | −80% | 0.20 |
| 19294 | Metabolite - 6134 | 61 | 0.0596 | 0.3112 | 31% | 1.31 |
| 15278 | Metabolite - 3843 | 61 | 0.0603 | 0.3112 | −31% | 0.69 |
| 15255 | Metabolite - 3833 | 61 | 0.0614 | 0.3127 | 74% | 1.74 |
| 16468 | Metabolite - 4236 | 61 | 0.0644 | 0.3224 | −31% | 0.69 |
| 10309 | Metabolite - 2277 | 61 | 0.0651 | 0.3224 | 35% | 1.35 |
| 1302 | methionine | 61 | 0.0705 | 0.3425 | 21% | 1.21 |
| 17885 | Metabolite - 5147 | 61 | 0.0710 | 0.3425 | 76% | 1.76 |
| 13038 | Metabolite - 3143 | 61 | 0.0726 | 0.3440 | 53% | 1.53 |
| 11411 | Metabolite - 2746 | 61 | 0.0732 | 0.3440 | 79% | 1.79 |
| 6373 | Metabolite - A-1304 | 61 | 0.0749 | 0.3454 | −25% | 0.75 |
| 22259 | Isobar 59 includes N('6)-trimethyl-L-lysine, H-homoarg-OH | 61 | 0.0756 | 0.3454 | −29% | 0.71 |
| 7081 | Metabolite - 1609 | 61 | 0.0762 | 0.3454 | 67% | 1.67 |
| 2856 | uridine 5'-monophosphate | 61 | 0.0807 | 0.3484 | −54% | 0.46 |
| 16983 | Metabolite - 4598 | 50 | 0.0813 | 0.3484 | 34% | 1.34 |
| 20092 | Metabolite - 7050 | 61 | 0.0818 | 0.3484 | −22% | 0.78 |
| 14439 | Metabolite - 3498 | 61 | 0.0833 | 0.3484 | 26% | 1.26 |
| 12682 | Metabolite - 3044 | 61 | 0.0841 | 0.3484 | 77% | 1.77 |
| 18281 | 2-hydroxyhippuric acid | 61 | 0.0843 | 0.3484 | 21% | 1.21 |
| 12129 | beta-hydroxyisovaleric acid | 50 | 0.0864 | 0.3484 | 17% | 1.17 |
| 14117 | Metabolite - 3441 | 61 | 0.0867 | 0.3484 | −20% | 0.80 |
| 20488 | D-glucose | 50 | 0.0874 | 0.3484 | −25% | 0.75 |
| 9216 | Metabolite - 2168 | 61 | 0.0884 | 0.3484 | −21% | 0.79 |
| 19596 | Metabolite - 6647 | 50 | 0.0885 | 0.3484 | 28% | 1.28 |
| 16819 | Metabolite - 4496 | 50 | 0.0909 | 0.3484 | 19% | 1.19 |
| 22584 | Metabolite - 9038 | 61 | 0.0910 | 0.3484 | −55% | 0.45 |
| 21650 | Metabolite - 8409 | 61 | 0.0910 | 0.3484 | −38% | 0.62 |
| 22598 | Metabolite - 9042 | 61 | 0.0920 | 0.3484 | −65% | 0.35 |
| 54 | tryptophan | 61 | 0.0927 | 0.3484 | 19% | 1.19 |
| 16655 | Metabolite - 4362 | 50 | 0.0946 | 0.3484 | −37% | 0.63 |
| 19402 | Metabolite - 6346 | 50 | 0.0969 | 0.3484 | −21% | 0.79 |
| 11661 | indole-3-pyruvic acid | 61 | 0.0972 | 0.3484 | 60% | 1.60 |
| 1561 | alpha-tocopherol | 50 | 0.0974 | 0.3484 | 38% | 1.38 |
| 8180 | Metabolite - 1975 | 61 | 0.0982 | 0.3484 | 35% | 1.35 |
| 16666 | Metabolite - 4365 | 50 | 0.0983 | 0.3484 | −28% | 0.72 |
| 2132 | citrulline | 50 | 0.0985 | 0.3484 | 51% | 1.51 |
| 1508 | pantothenic acid | 61 | 0.1014 | 0.3489 | 37% | 1.37 |
| 1572 | glyceric acid | 50 | 0.1017 | 0.3489 | 14% | 1.14 |
| 21732 | Metabolite - 8475 | 61 | 0.1020 | 0.3489 | −38% | 0.62 |
| 9130 | Metabolite - 2139 | 61 | 0.1024 | 0.3489 | 105% | 2.05 |

TABLE 22-continued

Metabolite biomarkers of dilated cardiomyopathy (DCM) in plasma.

| COMP_ID | COMPOUND | LIB_ID | p-value | q-value | % Change in DCM | TG/NTG |
|---|---|---|---|---|---|---|
| 21654 | Metabolite - 8413 | 61 | 0.1043 | 0.3522 | −25% | 0.75 |
| 10461 | Metabolite - 2313 | 61 | 0.1057 | 0.3534 | −27% | 0.73 |
| 16511 | Metabolite - 4274 | 50 | 0.1072 | 0.3534 | 69% | 1.69 |
| 1638 | arginine | 50 | 0.1075 | 0.3534 | 128% | 2.28 |
| 13345 | Metabolite - 3244 | 61 | 0.1087 | 0.3543 | 24% | 1.24 |
| 1493 | ornithine | 50 | 0.1183 | 0.3823 | 105% | 2.05 |
| 5809 | 3-indoxyl sulfate | 61 | 0.1251 | 0.3991 | 80% | 1.80 |
| 1648 | serine | 50 | 0.1261 | 0.3991 | 73% | 1.73 |
| 1826 | folic acid | 61 | 0.1268 | 0.3991 | −66% | 0.34 |
| 512 | asparagine | 50 | 0.1357 | 0.4181 | 64% | 1.64 |
| 514 | cytidine | 61 | 0.1358 | 0.4181 | 69% | 1.69 |
| 16244 | Isobar 21 includes gamma-aminobutyryl-L-histidine, L-anserine | 61 | 0.1365 | 0.4181 | −31% | 0.69 |
| 1598 | N-tigloylglycine | 61 | 0.1373 | 0.4181 | 16% | 1.16 |
| 17091 | Metabolite - 4641 | 61 | 0.1396 | 0.4217 | 40% | 1.40 |
| 17665 | p-hydroxybenzaldehyde | 61 | 0.1424 | 0.4242 | 18% | 1.18 |
| 1494 | 5-oxoproline | 50 | 0.1430 | 0.4242 | 24% | 1.24 |
| 8336 | Metabolite - 2005 | 61 | 0.1439 | 0.4242 | 82% | 1.82 |
| 13214 | Metabolite - 3183-possible gamma-L-glutamyl-L-phenylalanine. | 61 | 0.1516 | 0.4351 | 28% | 1.28 |
| 1336 | n-hexadecanoic acid | 50 | 0.1518 | 0.4351 | −14% | 0.86 |
| 21701 | Metabolite - 8454 | 61 | 0.1537 | 0.4351 | −34% | 0.66 |
| 10141 | Metabolite - A-2035 | 61 | 0.1540 | 0.4351 | −15% | 0.85 |
| 17028 | Metabolite - 4611 | 50 | 0.1542 | 0.4351 | 19% | 1.19 |
| 1432 | alphahydroxybenzeneacetic acid | 61 | 0.1546 | 0.4351 | −27% | 0.73 |
| 6771 | Metabolite - 1460 | 61 | 0.1581 | 0.4415 | −25% | 0.75 |
| 12774 | Metabolite - 3094 | 50 | 0.1632 | 0.4513 | −13% | 0.87 |
| 20084 | Metabolite - 7047 | 61 | 0.1656 | 0.4513 | 17% | 1.17 |
| 1651 | pyridoxal | 61 | 0.1692 | 0.4513 | 24% | 1.24 |
| 12924 | Metabolite - 3131 | 61 | 0.1702 | 0.4513 | 20% | 1.20 |
| 8072 | Metabolite - 1958 | 61 | 0.1703 | 0.4513 | 17% | 1.17 |
| 1126 | alanine | 50 | 0.1714 | 0.4513 | 61% | 1.61 |
| 22567 | Metabolite - 9030 | 61 | 0.1721 | 0.4513 | −51% | 0.49 |
| 6413 | Metabolite - 1342-possible phenylacetylglutamine or formyl-N-acetyl-5-methoxykynurenamine | 61 | 0.1724 | 0.4513 | 29% | 1.29 |
| 9137 | Metabolite - 2141 | 61 | 0.1725 | 0.4513 | 23% | 1.23 |
| 18232 | Metabolite - 5403 | 50 | 0.1746 | 0.4537 | 16% | 1.16 |
| 19372 | Metabolite - 6269 | 50 | 0.1776 | 0.4565 | 19% | 1.19 |
| 542 | 3-hydroxybutanoic acid | 50 | 0.1785 | 0.4565 | 50% | 1.50 |
| 11323 | Metabolite - 2711 | 61 | 0.1806 | 0.4565 | 72% | 1.72 |
| 606 | uridine | 61 | 0.1806 | 0.4565 | 93% | 1.93 |
| 21631 | Metabolite - 8403 | 50 | 0.1955 | 0.4908 | 24% | 1.24 |
| 15118 | Metabolite - 3784 | 61 | 0.2010 | 0.4996 | 22% | 1.22 |
| 22572 | Metabolite - 9034 | 50 | 0.2035 | 0.4996 | 28% | 1.28 |
| 15121 | Metabolite - 3786 | 61 | 0.2050 | 0.4996 | −53% | 0.47 |
| 20950 | Metabolite - 7846 | 50 | 0.2054 | 0.4996 | −19% | 0.81 |
| 1649 | valine | 50 | 0.2076 | 0.4996 | 55% | 1.55 |
| 1284 | threonine | 50 | 0.2098 | 0.4996 | 61% | 1.61 |
| 16992 | Metabolite - 4603 | 61 | 0.2133 | 0.4996 | 38% | 1.38 |
| 7650 | Metabolite - 1834 | 61 | 0.2138 | 0.4996 | −19% | 0.81 |
| 14753 | Metabolite - 3663 | 61 | 0.2148 | 0.4996 | 19% | 1.19 |
| 17627 | Metabolite - 4986 | 50 | 0.2153 | 0.4996 | 41% | 1.41 |
| 19919 | Metabolite - 6832 | 61 | 0.2160 | 0.4996 | −34% | 0.66 |
| 18969 | Metabolite - 5920 | 61 | 0.2161 | 0.4996 | 46% | 1.46 |
| 22320 | Metabolite - 8889 | 50 | 0.2165 | 0.4996 | 38% | 1.38 |
| 12907 | cGMP | 61 | 0.2214 | 0.5078 | 27% | 1.27 |
| 14759 | Metabolite - 3667 | 61 | 0.2265 | 0.5163 | 10% | 1.10 |
| 6379 | Metabolite - 1329 | 61 | 0.2343 | 0.5308 | 28% | 1.28 |
| 15872 | malonic acid | 61 | 0.2395 | 0.5345 | 46% | 1.46 |
| 10825 | Metabolite - 2546 | 61 | 0.2406 | 0.5345 | −7% | 0.93 |
| 14988 | Metabolite - 3756 | 61 | 0.2407 | 0.5345 | −10% | 0.90 |
| 15990 | L-alpha-glycerophosphorylcholine | 61 | 0.2436 | 0.5345 | −35% | 0.65 |
| 12780 | Metabolite - 3098 | 50 | 0.2443 | 0.5345 | 72% | 1.72 |
| 9002 | Metabolite - 2107 | 61 | 0.2446 | 0.5345 | −33% | 0.67 |
| 16044 | Metabolite - 4005 | 50 | 0.2553 | 0.5546 | 58% | 1.58 |
| 60 | leucine | 50 | 0.2579 | 0.5570 | 47% | 1.47 |
| 1827 | riboflavine | 61 | 0.2609 | 0.5573 | 44% | 1.44 |
| 22032 | Metabolite - 8766 | 50 | 0.2610 | 0.5573 | −13% | 0.87 |

TABLE 22-continued

Metabolite biomarkers of dilated cardiomyopathy (DCM) in plasma.

| COMP_ID | COMPOUND | LIB_ID | p-value | q-value | % Change in DCM | TG/NTG |
|---|---|---|---|---|---|---|
| 16070 | Metabolite - 4019 | 50 | 0.2653 | 0.5613 | −15% | 0.85 |
| 1301 | lysine | 50 | 0.2661 | 0.5613 | 72% | 1.72 |
| 6253 | Metabolite - 1283 | 61 | 0.2689 | 0.5613 | 58% | 1.58 |
| 14043 | Metabolite - 3428 | 61 | 0.2689 | 0.5613 | −26% | 0.74 |
| 19513 | Metabolite - 6552 | 61 | 0.2776 | 0.5731 | −31% | 0.69 |
| 1708 | 7,8-dihydrofolic acid | 61 | 0.2791 | 0.5731 | −32% | 0.68 |
| 8649 | Metabolite - 2053 | 61 | 0.2796 | 0.5731 | −15% | 0.85 |
| 15753 | hippuric acid | 61 | 0.2839 | 0.5731 | 29% | 1.29 |
| 16232 | Isobar 17 includes arginine, N-alpha-acetyl-ornithine | 61 | 0.2839 | 0.5731 | 21% | 1.21 |
| 1591 | N-acetyl-L-valine | 61 | 0.2857 | 0.5731 | 42% | 1.42 |
| 19374 | Metabolite - 6270 | 50 | 0.2867 | 0.5731 | −20% | 0.80 |
| 15122 | glycerol | 50 | 0.2870 | 0.5731 | 26% | 1.26 |
| 15412 | Metabolite - 3910 | 61 | 0.2889 | 0.5739 | −34% | 0.66 |
| 2342 | serotonin | 61 | 0.2920 | 0.5770 | −54% | 0.46 |
| 13512 | Metabolite - 3315 | 61 | 0.2938 | 0.5776 | 22% | 1.22 |
| 22590 | Metabolite - 9040 | 61 | 0.2957 | 0.5782 | −55% | 0.45 |
| 12789 | Metabolite - 3107 | 50 | 0.3012 | 0.5859 | 39% | 1.39 |
| 16138 | Metabolite - 4080 | 50 | 0.3045 | 0.5893 | −18% | 0.82 |
| 15681 | 4-Guanidinobutanoic acid | 61 | 0.3070 | 0.5908 | 36% | 1.36 |
| 1125 | isoleucine | 50 | 0.3094 | 0.5908 | 43% | 1.43 |
| 14502 | Metabolite - 3539 | 61 | 0.3109 | 0.5908 | 46% | 1.46 |
| 14406 | Metabolite - 3493 | 61 | 0.3119 | 0.5908 | −16% | 0.84 |
| 1898 | proline | 61 | 0.3133 | 0.5908 | 10% | 1.10 |
| 2129 | oxitryptan | 61 | 0.3172 | 0.5952 | −17% | 0.83 |
| 15125 | (2-Aminoethyl)phosphonate | 61 | 0.3212 | 0.5961 | −23% | 0.77 |
| 16226 | Isobar 28 includes L-threonine, L-allothreonine, L-homoserine, (S)-(−)-4-amino 2-hydroxybutyric acid | 61 | 0.3213 | 0.5961 | −15% | 0.85 |
| 6104 | tryptamine | 50 | 0.3225 | 0.5961 | 26% | 1.26 |
| 12719 | Metabolite - 3055-possible NH3 adduct of hippuric acid | 61 | 0.3251 | 0.5980 | 32% | 1.32 |
| 15113 | Metabolite - 3783 | 61 | 0.3303 | 0.6045 | −17% | 0.83 |
| 16821 | Metabolite - 4498 | 50 | 0.3358 | 0.6098 | 11% | 1.11 |
| 15743 | N,N-dimethylarginine | 61 | 0.3377 | 0.6098 | 72% | 1.72 |
| 12782 | Metabolite - 3100 | 50 | 0.3397 | 0.6098 | 57% | 1.57 |
| 22570 | Metabolite - 9033 | 50 | 0.3430 | 0.6098 | −24% | 0.76 |
| 10147 | Metabolite - A-2036 | 61 | 0.3459 | 0.6098 | −12% | 0.88 |
| 21046 | digalacturonic acid | 61 | 0.3472 | 0.6098 | −25% | 0.75 |
| 12773 | Metabolite - 3093 | 50 | 0.3483 | 0.6098 | 24% | 1.24 |
| 18330 | 5-methyltetrahydrofolic acid | 61 | 0.3499 | 0.6098 | −21% | 0.79 |
| 20035 | Metabolite - 7008 | 61 | 0.3521 | 0.6098 | −13% | 0.87 |
| 22154 | bradykinin | 61 | 0.3530 | 0.6098 | −45% | 0.55 |
| 22133 | DL-hexanoyl-carnitine | 61 | 0.3547 | 0.6098 | 50% | 1.50 |
| 5628 | Metabolite - 1086 | 61 | 0.3567 | 0.6098 | −33% | 0.67 |
| 10743 | Isobar 4 includes Gluconic acid, DL-arabinose, D-ribose, L-xylose, DL-lyxose, D-xylulose, galactonic acid | 61 | 0.3597 | 0.6098 | 13% | 1.13 |
| 16985 | Metabolite - 4600 | 61 | 0.3606 | 0.6098 | 32% | 1.32 |
| 1476 | glucarate | 50 | 0.3609 | 0.6098 | 18% | 1.18 |
| 17860 | Metabolite - 5127 | 61 | 0.3632 | 0.6098 | 28% | 1.28 |
| 5466 | Metabolite - A-1030 | 61 | 0.3635 | 0.6098 | 23% | 1.23 |
| 17845 | Metabolite - 5108 | 61 | 0.3684 | 0.6098 | 17% | 1.17 |
| 20308 | Metabolite - 7270 | 61 | 0.3690 | 0.6098 | 19% | 1.19 |
| 18761 | Metabolite - 5793 | 61 | 0.3694 | 0.6098 | 57% | 1.57 |
| 10476 | Metabolite - 2316 | 61 | 0.3710 | 0.6098 | −15% | 0.85 |
| 15382 | Metabolite - 3898 | 61 | 0.3722 | 0.6098 | 17% | 1.17 |
| 18467 | cis-5,8,11,14,17-eicosapentaenoic acid | 61 | 0.3728 | 0.6098 | 32% | 1.32 |
| 15529 | Metabolite - 3951 | 61 | 0.3733 | 0.6098 | 14% | 1.14 |
| 15336 | tartaric acid | 61 | 0.3743 | 0.6098 | 16% | 1.16 |
| 21012 | Metabolite - 7889 | 50 | 0.3786 | 0.6098 | 16% | 1.16 |
| 12533 | Metabolite - 2915 | 50 | 0.3809 | 0.6098 | −14% | 0.86 |
| 10700 | Metabolite - 2393 | 61 | 0.3831 | 0.6098 | 26% | 1.26 |
| 12753 | Metabolite - 3074 | 50 | 0.3842 | 0.6098 | 15% | 1.15 |
| 10357 | Metabolite - A-2055 | 61 | 0.3856 | 0.6098 | −24% | 0.76 |
| 21763 | Metabolite - 8507 | 61 | 0.3862 | 0.6098 | −10% | 0.90 |
| 15074 | Metabolite - 3774 | 61 | 0.3893 | 0.6098 | 18% | 1.18 |
| 10286 | Metabolite - 2272 | 61 | 0.3909 | 0.6098 | 47% | 1.47 |
| 14480 | Metabolite - 3521 | 61 | 0.3909 | 0.6098 | −42% | 0.58 |
| 13872 | Metabolite - 3393 | 61 | 0.3933 | 0.6098 | 52% | 1.52 |
| 8300 | Metabolite - 1988 | 61 | 0.3934 | 0.6098 | −13% | 0.87 |

TABLE 22-continued

Metabolite biomarkers of dilated cardiomyopathy (DCM) in plasma.

| COMP_ID | COMPOUND | LIB_ID | p-value | q-value | % Change in DCM | TG/NTG |
|---|---|---|---|---|---|---|
| 22586 | Metabolite - 9039 | 61 | 0.3939 | 0.6098 | −48% | 0.52 |
| 13920 | Metabolite - 3404 | 61 | 0.3967 | 0.6107 | 16% | 1.16 |
| 12645 | Metabolite - 3017 | 50 | 0.3978 | 0.6107 | 24% | 1.24 |
| 18369 | gamma-glu-leu | 61 | 0.3997 | 0.6111 | 11% | 1.11 |
| 19368 | Metabolite - 6267 | 50 | 0.4016 | 0.6115 | 29% | 1.29 |
| 19613 | Metabolite - 6670 | 61 | 0.4043 | 0.6131 | −20% | 0.80 |
| 12756 | Metabolite - 3077 | 50 | 0.4130 | 0.6237 | 25% | 1.25 |
| 7644 | Metabolite - 1831 | 61 | 0.4185 | 0.6289 | 18% | 1.18 |
| 12639 | Metabolite - 3012 | 50 | 0.4198 | 0.6289 | 46% | 1.46 |
| 6130 | Metabolite - 1208 | 61 | 0.4239 | 0.6324 | −41% | 0.59 |
| 11053 | Metabolite - 2567 | 61 | 0.4256 | 0.6324 | 10% | 1.10 |
| 17390 | Metabolite - 4806 | 50 | 0.4286 | 0.6335 | −7% | 0.93 |
| 14247 | Metabolite - 3475 | 61 | 0.4319 | 0.6335 | 14% | 1.14 |
| 20234 | Metabolite - 7170 | 61 | 0.4326 | 0.6335 | 25% | 1.25 |
| 17327 | Metabolite - 4767 | 50 | 0.4364 | 0.6335 | 13% | 1.13 |
| 17359 | Metabolite - 4791 | 50 | 0.4383 | 0.6335 | −21% | 0.79 |
| 22163 | EDTA | 50 | 0.4387 | 0.6335 | 47% | 1.47 |
| 8176 | Metabolite - 1974 | 61 | 0.4407 | 0.6335 | −16% | 0.84 |
| 1647 | glutamine | 50 | 0.4446 | 0.6335 | 44% | 1.44 |
| 17614 | Metabolite - 4966 | 50 | 0.4467 | 0.6335 | −29% | 0.71 |
| 5430 | Metabolite - A-1008 | 61 | 0.4497 | 0.6335 | −5% | 0.95 |
| 19462 | Metabolite - 6446 | 50 | 0.4509 | 0.6335 | −9% | 0.91 |
| 6398 | Metabolite - 1335 | 61 | 0.4510 | 0.6335 | −19% | 0.81 |
| 15639 | Metabolite - 3984 | 61 | 0.4520 | 0.6335 | 54% | 1.54 |
| 12777 | Metabolite - 3097 | 50 | 0.4558 | 0.6335 | 25% | 1.25 |
| 15805 | maltose | 50 | 0.4590 | 0.6335 | 25% | 1.25 |
| 1366 | trans-4-hydroxyproline | 50 | 0.4603 | 0.6335 | 31% | 1.31 |
| 4966 | xylitol | 50 | 0.4612 | 0.6335 | 10% | 1.10 |
| 1419 | 5'-s-methyl-5'-thioadenosine | 61 | 0.4617 | 0.6335 | 18% | 1.18 |
| 11777 | glycine | 50 | 0.4623 | 0.6335 | 36% | 1.36 |
| 22020 | Metabolite - 8749 | 50 | 0.4627 | 0.6335 | 9% | 1.09 |
| 21047 | 3-methyl-2-oxobutyric | 61 | 0.4640 | 0.6335 | −12% | 0.88 |
| 16290 | Metabolite - 4133 | 50 | 0.4655 | 0.6335 | −7% | 0.93 |
| 12803 | Metabolite - A-2441 | 50 | 0.4671 | 0.6335 | −12% | 0.88 |
| 8527 | Metabolite - A-1931 | 61 | 0.4700 | 0.6335 | −3% | 0.97 |
| 19013 | Metabolite - 5931 | 61 | 0.4701 | 0.6335 | 7% | 1.07 |
| 22568 | Metabolite - 9031 | 61 | 0.4758 | 0.6335 | −43% | 0.57 |
| 12783 | Metabolite - 3101 | 50 | 0.4760 | 0.6335 | 27% | 1.27 |
| 5533 | Metabolite - A-1096 | 61 | 0.4762 | 0.6335 | 29% | 1.29 |
| 16805 | Metabolite - 4488 | 61 | 0.4772 | 0.6335 | 21% | 1.21 |
| 22132 | DL-alpha-hydroxyisocaproic acid | 61 | 0.4774 | 0.6335 | 15% | 1.15 |
| 16071 | Metabolite - 4020 | 50 | 0.4818 | 0.6360 | 7% | 1.07 |
| 22439 | Metabolite - 8949 | 61 | 0.4839 | 0.6360 | 17% | 1.17 |
| 5765 | Metabolite - 1142-possible 5-hydroxypentanoate or beta-hydroxyisovaleric acid | 61 | 0.4877 | 0.6360 | −13% | 0.87 |
| 1481 | inositol 1-phosphate | 50 | 0.4879 | 0.6360 | −13% | 0.87 |
| 13217 | Metabolite - 3184 | 61 | 0.4913 | 0.6360 | 15% | 1.15 |
| 5689 | Metabolite - 1111-possible methylnitronitrosoguanidine or ethyl thiocarbamoylacetate | 61 | 0.4925 | 0.6360 | −19% | 0.81 |
| 22166 | glu-glu | 61 | 0.4985 | 0.6360 | 29% | 1.29 |
| 21127 | monopalmitin | 50 | 0.4987 | 0.6360 | −10% | 0.90 |
| 22601 | Metabolite - 9044 | 50 | 0.4990 | 0.6360 | 25% | 1.25 |
| 18384 | Metabolite - 5487 | 50 | 0.5030 | 0.6360 | −12% | 0.88 |
| 18943 | Metabolite - 5912 | 61 | 0.5031 | 0.6360 | −13% | 0.87 |
| 22145 | acetyl-L-carnitine | 61 | 0.5078 | 0.6360 | 20% | 1.20 |
| 17486 | Metabolite - 4886 | 61 | 0.5102 | 0.6360 | −14% | 0.86 |
| 14639 | Metabolite - 3603 | 61 | 0.5123 | 0.6360 | 16% | 1.16 |
| 12785 | Metabolite - 3103 | 50 | 0.5144 | 0.6360 | 38% | 1.38 |
| 9016 | Metabolite - 2109 | 61 | 0.5147 | 0.6360 | −6% | 0.94 |
| 10136 | Metabolite - A-2034 | 61 | 0.5160 | 0.6360 | 4% | 1.04 |
| 1417 | kynurenic acid | 61 | 0.5187 | 0.6360 | 12% | 1.12 |
| 16893 | Metabolite - 4530 | 61 | 0.5188 | 0.6360 | 107% | 2.07 |
| 1564 | citric acid | 50 | 0.5189 | 0.6360 | 12% | 1.12 |
| 22001 | 3-hydroxyoctanoic acid | 61 | 0.5214 | 0.6360 | 19% | 1.19 |
| 18349 | DL-indole-3-lactic acid | 61 | 0.5214 | 0.6360 | 13% | 1.13 |
| 16080 | Metabolite - 4026 | 61 | 0.5228 | 0.6360 | −26% | 0.74 |
| 15197 | 1-methylnicotinamide-1 | 61 | 0.5243 | 0.6360 | 24% | 1.24 |
| 18172 | Metabolite - 5391 | 61 | 0.5247 | 0.6360 | −13% | 0.87 |
| 2240 | homogentisate | 61 | 0.5248 | 0.6360 | −6% | 0.94 |
| 15063 | Metabolite - 3772 | 61 | 0.5263 | 0.6360 | 17% | 1.17 |

TABLE 22-continued

Metabolite biomarkers of dilated cardiomyopathy (DCM) in plasma.

| COMP_ID | COMPOUND | LIB_ID | p-value | q-value | % Change in DCM | TG/NTG |
|---|---|---|---|---|---|---|
| 5618 | Metabolite - 1085-possible isolobinine or 4-aminoestra-1,3,5(10)-triene-3,17beta-diol | 61 | 0.5287 | 0.6360 | −8% | 0.92 |
| 59 | histidine | 61 | 0.5290 | 0.6360 | −8% | 0.92 |
| 5478 | Metabolite - A-1036 | 61 | 0.5339 | 0.6394 | −7% | 0.93 |
| 21013 | Metabolite - 7890 | 50 | 0.5363 | 0.6394 | −15% | 0.85 |
| 22262 | Isobar 61 includes 4-methyl-2-oxovaleric acid, 3-methyl-2-oxovaleric acid | 61 | 0.5381 | 0.6394 | −10% | 0.90 |
| 10850 | Metabolite - 2548-possible Cl adduct of uric acid | 61 | 0.5398 | 0.6394 | 21% | 1.21 |
| 22360 | Metabolite - 8901 | 61 | 0.5414 | 0.6394 | 16% | 1.16 |
| 5475 | Metabolite - A-1033 | 61 | 0.5423 | 0.6394 | 12% | 1.12 |
| 8509 | Metabolite - 2041 | 61 | 0.5445 | 0.6394 | 7% | 1.07 |
| 20694 | oxalic acid | 61 | 0.5456 | 0.6394 | −7% | 0.93 |
| 18010 | Metabolite - 5231 | 61 | 0.5487 | 0.6411 | 33% | 1.33 |
| 2183 | thymidine | 61 | 0.5516 | 0.6423 | 10% | 1.10 |
| 2150 | pyridoxamine | 61 | 0.5544 | 0.6432 | −4% | 0.96 |
| 19708 | Metabolite - 6711 | 61 | 0.5558 | 0.6432 | −9% | 0.91 |
| 22130 | DL-3-phenyllactic acid | 61 | 0.5598 | 0.6457 | −16% | 0.84 |
| 16711 | Metabolite - 4431 | 61 | 0.5614 | 0.6457 | −15% | 0.85 |
| 20391 | Metabolite - 7334 | 61 | 0.5785 | 0.6615 | −13% | 0.87 |
| 16189 | Metabolite - 4097 | 61 | 0.5787 | 0.6615 | 9% | 1.09 |
| 7177 | Metabolite - 1656 | 61 | 0.5817 | 0.6623 | 36% | 1.36 |
| 10655 | Metabolite - 2388 | 61 | 0.5830 | 0.6623 | 11% | 1.11 |
| 16506 | Metabolite - 4271 | 50 | 0.5872 | 0.6651 | 26% | 1.26 |
| 18146 | Metabolite - 5366 | 50 | 0.5890 | 0.6651 | −14% | 0.86 |
| 19494 | Metabolite - 6506 | 50 | 0.6032 | 0.6752 | −11% | 0.89 |
| 18109 | isocitrate | 61 | 0.6041 | 0.6752 | 20% | 1.20 |
| 1110 | arachidonic acid | 50 | 0.6062 | 0.6752 | 8% | 1.08 |
| 17283 | Metabolite - 4750 | 61 | 0.6064 | 0.6752 | −15% | 0.85 |
| 13211 | Metabolite - 3182 | 61 | 0.6084 | 0.6752 | −13% | 0.87 |
| 12726 | Metabolite - 3058 | 50 | 0.6104 | 0.6752 | 25% | 1.25 |
| 15996 | aspartate | 50 | 0.6134 | 0.6752 | 27% | 1.27 |
| 16705 | Metabolite - 4428 | 61 | 0.6135 | 0.6752 | 13% | 1.13 |
| 16865 | Metabolite - 4522 | 50 | 0.6143 | 0.6752 | 6% | 1.06 |
| 12648 | Metabolite - 3020 | 50 | 0.6166 | 0.6755 | −6% | 0.94 |
| 6266 | Metabolite - 1286 | 61 | 0.6183 | 0.6755 | 6% | 1.06 |
| 1105 | Linoleic acid | 50 | 0.6208 | 0.6755 | −6% | 0.94 |
| 15730 | suberic acid | 61 | 0.6219 | 0.6755 | 19% | 1.19 |
| 12650 | Metabolite - 3022 | 50 | 0.6242 | 0.6761 | 24% | 1.24 |
| 20031 | Metabolite - 7007 | 61 | 0.6307 | 0.6811 | −10% | 0.90 |
| 16860 | Metabolite - 4517 | 50 | 0.6346 | 0.6815 | −9% | 0.91 |
| 17064 | Metabolite - 4624 | 50 | 0.6349 | 0.6815 | 19% | 1.19 |
| 19934 | inositol | 50 | 0.6365 | 0.6815 | 11% | 1.11 |
| 12663 | Metabolite - 3030 | 50 | 0.6414 | 0.6836 | 29% | 1.29 |
| 20866 | Metabolite - 7786 | 61 | 0.6422 | 0.6836 | 4% | 1.04 |
| 22602 | Metabolite - 9045 | 50 | 0.6447 | 0.6843 | −13% | 0.87 |
| 12593 | Metabolite - 2973 | 50 | 0.6526 | 0.6907 | 3% | 1.03 |
| 15500 | carnitine | 61 | 0.6619 | 0.6957 | −5% | 0.95 |
| 7595 | Metabolite - 1817 | 61 | 0.6633 | 0.6957 | 5% | 1.05 |
| 19364 | Metabolite - 6246 | 50 | 0.6655 | 0.6957 | 13% | 1.13 |
| 20248 | Metabolite - 7177 | 61 | 0.6667 | 0.6957 | 10% | 1.10 |
| 14054 | Metabolite - 3430-possible gly-leu, acetyl-lys, ala-val | 61 | 0.6670 | 0.6957 | 4% | 1.04 |
| 11438 | phosphate | 50 | 0.6686 | 0.6957 | 5% | 1.05 |
| 19511 | Metabolite - 6551 | 61 | 0.6777 | 0.7032 | 6% | 1.06 |
| 20192 | Metabolite - 7146 | 61 | 0.6833 | 0.7061 | −9% | 0.91 |
| 16949 | Metabolite - 4592 | 61 | 0.6842 | 0.7061 | −7% | 0.93 |
| 2137 | biliverdin | 61 | 0.6893 | 0.7093 | −18% | 0.82 |
| 19961 | Metabolite - 6913 | 50 | 0.6913 | 0.7093 | 2% | 1.02 |
| 7107 | Metabolite - A-1664 | 61 | 0.6945 | 0.7093 | −22% | 0.78 |
| 18756 | Metabolite - 5791 | 61 | 0.6950 | 0.7093 | −8% | 0.92 |
| 12768 | Metabolite - 3088 | 50 | 0.7007 | 0.7125 | 14% | 1.14 |
| 19362 | Metabolite - 6226 | 50 | 0.7030 | 0.7125 | −10% | 0.90 |
| 12791 | Metabolite - 3109 | 50 | 0.7038 | 0.7125 | 18% | 1.18 |
| 528 | alpha-keto-glutarate | 61 | 0.7155 | 0.7217 | 17% | 1.17 |
| 10746 | Isobar 6 includes valine, betaine | 61 | 0.7178 | 0.7217 | 10% | 1.10 |
| 10304 | Metabolite - 2276 | 61 | 0.7191 | 0.7217 | 24% | 1.24 |
| 19377 | Metabolite - 6272 | 50 | 0.7207 | 0.7217 | 9% | 1.09 |
| 18929 | Metabolite - 5907 | 50 | 0.7249 | 0.7239 | −9% | 0.91 |
| 9060 | Metabolite - A-1994 | 61 | 0.7284 | 0.7248 | 16% | 1.16 |
| 22577 | Metabolite - 9035 | 50 | 0.7323 | 0.7248 | 17% | 1.17 |

TABLE 22-continued

Metabolite biomarkers of dilated cardiomyopathy (DCM) in plasma.

| COMP_ID | COMPOUND | LIB_ID | p-value | q-value | % Change in DCM | TG/NTG |
|---|---|---|---|---|---|---|
| 1121 | heptadecanoic acid | 50 | 0.7328 | 0.7248 | 4% | 1.04 |
| 14840 | Metabolite - 3708 | 61 | 0.7359 | 0.7248 | 5% | 1.05 |
| 16712 | Metabolite - 4432 | 61 | 0.7373 | 0.7248 | −3% | 0.97 |
| 16285 | Metabolite - A-2798 | 50 | 0.7393 | 0.7248 | −11% | 0.89 |
| 1584 | methyl indole-3-acetate | 61 | 0.7401 | 0.7248 | −13% | 0.87 |
| 18868 | Metabolite - 5847 | 50 | 0.7421 | 0.7248 | 13% | 1.13 |
| 16843 | Metabolite - 4510 | 50 | 0.7452 | 0.7248 | 15% | 1.15 |
| 19800 | Metabolite - 6750 | 61 | 0.7544 | 0.7248 | 24% | 1.24 |
| 12457 | Metabolite - 2892 | 61 | 0.7565 | 0.7248 | −9% | 0.91 |
| 15677 | 3-methyl-L-histidine | 61 | 0.7568 | 0.7248 | −4% | 0.96 |
| 57 | glutamic acid | 50 | 0.7577 | 0.7248 | 18% | 1.18 |
| 21762 | Metabolite - 8506 | 61 | 0.7591 | 0.7248 | 7% | 1.07 |
| 12770 | Metabolite - 3090 | 50 | 0.7605 | 0.7248 | 7% | 1.07 |
| 19367 | Metabolite - 6266 | 50 | 0.7620 | 0.7248 | −6% | 0.94 |
| 11770 | Metabolite - 2806 | 61 | 0.7646 | 0.7248 | 5% | 1.05 |
| 10148 | Metabolite - 2257 | 61 | 0.7649 | 0.7248 | 13% | 1.13 |
| 10570 | Metabolite - 2366 | 61 | 0.7663 | 0.7248 | −6% | 0.94 |
| 20267 | Metabolite - 7187 | 61 | 0.7675 | 0.7248 | 14% | 1.14 |
| 577 | fructose | 50 | 0.7684 | 0.7248 | −7% | 0.93 |
| 16308 | Metabolite - 4147 | 50 | 0.7687 | 0.7248 | 7% | 1.07 |
| 6362 | Metabolite - 1323-possible p-cresol sulfate | 61 | 0.7707 | 0.7249 | 22% | 1.22 |
| 12112 | Metabolite - A-2314 | 61 | 0.7740 | 0.7261 | 6% | 1.06 |
| 12647 | Metabolite - 3019 | 50 | 0.7767 | 0.7268 | 18% | 1.18 |
| 13104 | Metabolite - 3160 | 61 | 0.7839 | 0.7295 | −5% | 0.95 |
| 17060 | Metabolite - 4622 | 61 | 0.7853 | 0.7295 | 7% | 1.07 |
| 1365 | tetradecanoic acid | 50 | 0.7859 | 0.7295 | −5% | 0.95 |
| 1512 | picolinic acid | 50 | 0.7875 | 0.7295 | −5% | 0.95 |
| 12673 | Metabolite - 3040 | 50 | 0.7915 | 0.7315 | 7% | 1.07 |
| 12876 | Metabolite - 3125 | 61 | 0.7960 | 0.7338 | −8% | 0.92 |
| 18892 | Metabolite - 5866 | 61 | 0.8003 | 0.7360 | −5% | 0.95 |
| 12035 | nonanate | 50 | 0.8032 | 0.7368 | 5% | 1.05 |
| 18678 | Metabolite - 5730 | 61 | 0.8065 | 0.7371 | −7% | 0.93 |
| 19955 | Metabolite - 6907 | 50 | 0.8075 | 0.7371 | 7% | 1.07 |
| 19323 | Docosahexaenoic Acid | 50 | 0.8175 | 0.7428 | 3% | 1.03 |
| 12656 | Metabolite - 3025 | 50 | 0.8225 | 0.7428 | 13% | 1.13 |
| 12751 | Metabolite - 3073 | 50 | 0.8227 | 0.7428 | −10% | 0.90 |
| 18706 | Metabolite - 5769 | 61 | 0.8236 | 0.7428 | −6% | 0.94 |
| 15064 | Metabolite - 3773 | 61 | 0.8252 | 0.7428 | 10% | 1.10 |
| 12666 | Metabolite - 3033-possible threonine deriv- | 50 | 0.8278 | 0.7428 | 10% | 1.10 |
| 16829 | Metabolite - 4503 | 50 | 0.8286 | 0.7428 | −3% | 0.97 |
| 12771 | Metabolite - 3091 | 50 | 0.8298 | 0.7428 | 7% | 1.07 |
| 21188 | 1-stearoyl-rac-glycerol | 50 | 0.8452 | 0.7498 | 3% | 1.03 |
| 16509 | Metabolite - 4273 | 50 | 0.8458 | 0.7498 | −8% | 0.92 |
| 10544 | Metabolite - 2329 | 61 | 0.8460 | 0.7498 | −9% | 0.91 |
| 15625 | Metabolite - 3976 | 61 | 0.8476 | 0.7498 | 3% | 1.03 |
| 6461 | Metabolite - A-1329 | 61 | 0.8499 | 0.7498 | 7% | 1.07 |
| 17207 | Metabolite - 4707 | 61 | 0.8507 | 0.7498 | 4% | 1.04 |
| 12008 | Metabolite - 2847 | 61 | 0.8532 | 0.7498 | 6% | 1.06 |
| 17389 | Metabolite - 4796 | 50 | 0.8537 | 0.7498 | −14% | 0.86 |
| 597 | phosphoenolpyruvate | 61 | 0.8558 | 0.7499 | −4% | 0.96 |
| 10111 | Metabolite - A-2033 | 61 | 0.8587 | 0.7506 | −5% | 0.95 |
| 8796 | Metabolite - 2074 | 61 | 0.8687 | 0.7575 | 5% | 1.05 |
| 7029 | Metabolite - 1597 | 61 | 0.8755 | 0.7601 | 2% | 1.02 |
| 15253 | Metabolite - 3832-possible phenol sulfate | 61 | 0.8757 | 0.7601 | 6% | 1.06 |
| 20194 | Metabolite - 7147 | 61 | 0.8787 | 0.7607 | −2% | 0.98 |
| 15535 | Metabolite - 3955 | 61 | 0.8805 | 0.7607 | 6% | 1.06 |
| 15129 | D-alanyl-D-alanine | 50 | 0.8826 | 0.7608 | 3% | 1.03 |
| 12658 | Metabolite - 3026 | 50 | 0.8933 | 0.7650 | 8% | 1.08 |
| 10604 | Metabolite - 2370 | 61 | 0.8961 | 0.7650 | −4% | 0.96 |
| 13179 | creatine | 61 | 0.8973 | 0.7650 | −4% | 0.96 |
| 10781 | Metabolite - 2469 | 61 | 0.8992 | 0.7650 | 5% | 1.05 |
| 1358 | octadecanoic acid | 50 | 0.9002 | 0.7650 | 1% | 1.01 |
| 15365 | sn-Glycerol 3-phosphate | 50 | 0.9018 | 0.7650 | 3% | 1.03 |
| 9172 | Metabolite - A-2000 | 61 | 0.9060 | 0.7650 | −1% | 0.99 |
| 15227 | trans-aconitic acid-1 | 61 | 0.9063 | 0.7650 | 3% | 1.03 |
| 5702 | choline | 61 | 0.9074 | 0.7650 | −4% | 0.96 |
| 12625 | Metabolite - 3002 | 50 | 0.9081 | 0.7650 | 2% | 1.02 |
| 19860 | Metabolite - 6784 | 61 | 0.9194 | 0.7716 | 1% | 1.01 |
| 12781 | Metabolite - 3099 | 50 | 0.9201 | 0.7716 | 4% | 1.04 |
| 13273 | Metabolite - 3224 | 61 | 0.9344 | 0.7759 | 3% | 1.03 |
| 21025 | iminodiacetic acid | 50 | 0.9345 | 0.7759 | 2% | 1.02 |

TABLE 22-continued

Metabolite biomarkers of dilated cardiomyopathy (DCM) in plasma.

| COMP_ID | COMPOUND | LIB_ID | p-value | q-value | % Change in DCM | TG/NTG |
|---|---|---|---|---|---|---|
| 12912 | Metabolite - 3129 | 61 | 0.9367 | 0.7759 | −1% | 0.99 |
| 6131 | Metabolite - 1209 | 61 | 0.9387 | 0.7759 | −3% | 0.97 |
| 6380 | Metabolite - 1330 | 61 | 0.9399 | 0.7759 | −2% | 0.98 |
| 2125 | taurine | 61 | 0.9400 | 0.7759 | −3% | 0.97 |
| 18118 | Metabolite - 5346 | 50 | 0.9423 | 0.7759 | −3% | 0.97 |
| 19291 | Metabolite - 6132 | 61 | 0.9430 | 0.7759 | −2% | 0.98 |
| 12667 | Metabolite - 3034 | 50 | 0.9440 | 0.7759 | 1% | 1.01 |
| 20927 | Metabolite - 7815 | 61 | 0.9519 | 0.7796 | −1% | 0.99 |
| 16665 | Metabolite - 4364 | 50 | 0.9529 | 0.7796 | −2% | 0.98 |
| 20228 | Metabolite - 7169 | 61 | 0.9548 | 0.7796 | −2% | 0.98 |
| 15600 | Metabolite - 3964 | 61 | 0.9639 | 0.7799 | −1% | 0.99 |
| 9905 | Metabolite - 2231 | 61 | 0.9664 | 0.7799 | 0% | 1.00 |
| 16496 | Metabolite - 4251 | 50 | 0.9670 | 0.7799 | 1% | 1.01 |
| 513 | creatinine | 61 | 0.9687 | 0.7799 | −1% | 0.99 |
| 22581 | Metabolite - 9037 | 61 | 0.9712 | 0.7799 | 2% | 1.02 |
| 18882 | taurodeoxycholic acid | 61 | 0.9715 | 0.7799 | 2% | 1.02 |
| 12754 | Metabolite - 3075 | 50 | 0.9801 | 0.7799 | 1% | 1.01 |
| 13018 | Metabolite - 3138 | 61 | 0.9829 | 0.7799 | 1% | 1.01 |
| 8196 | Metabolite - 1979-Cl adduct of isobar 19 | 61 | 0.9833 | 0.7799 | 0% | 1.00 |
| 19397 | Metabolite - 6326 | 50 | 0.9846 | 0.7799 | −1% | 0.99 |
| 13288 | Metabolite - 3228 | 61 | 0.9860 | 0.7799 | 0% | 1.00 |
| 19490 | Metabolite - 6488 | 50 | 0.9863 | 0.7799 | 1% | 1.01 |
| 12757 | Metabolite - 3078 | 50 | 0.9867 | 0.7799 | −1% | 0.99 |
| 12790 | Metabolite - 3108 | 50 | 0.9880 | 0.7799 | 1% | 1.01 |
| 16512 | Metabolite - 4275 | 50 | 0.9908 | 0.7799 | 0% | 1.00 |
| 17330 | Metabolite - 4769 | 50 | 0.9910 | 0.7799 | 0% | 1.00 |
| 19363 | Metabolite - 6227 | 50 | 0.9929 | 0.7799 | 0% | 1.00 |
| 63 | cholesterol | 50 | 0.9929 | 0.7799 | 0% | 1.00 |
| 10782 | Metabolite - 2486 | 61 | 0.9967 | 0.7812 | 0% | 1.00 |
| 22548 | Metabolite - 9026 | 50 | 0.9988 | 0.7812 | 0% | 1.00 |

Figure 20:
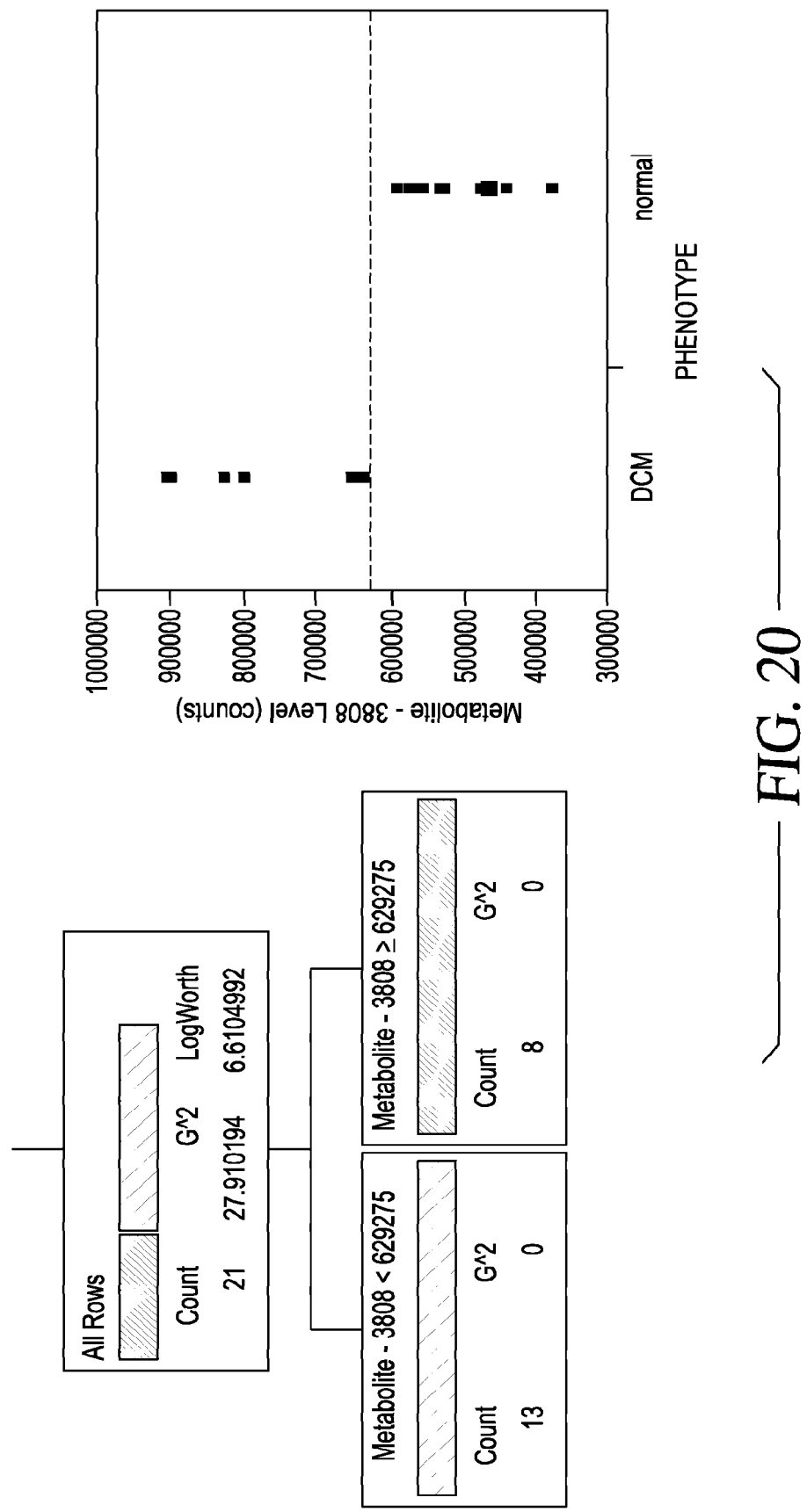
FIG. 20 provides an example of recursive partitioning of DCM biomarker metabolites.

Recursive partitioning statistical analysis of all the metabolites in cardiac tissue between normal and DCM subjects identified Metabolite-3808 (Metabolite-3808) as a compound that separated both groups of subjects perfectly (LogWorth=6.61). Specifically, all subjects with DCM phenotype had levels of Metabolite-3808 above the cutoff value of 629275 while all the subjects with a normal phenotype had Metabolite-3808 levels below the cutoff value (FIG. 20). The cutoff value in the graph in FIG. 20 is indicated by a broken line.

To evaluate the biomarkers discovered in the mouse model of DCM, analysis of human subjects was performed. Biomarkers were discovered by (1) analyzing plasma samples from different groups of human subjects to determine the levels of metabolites in the samples and then (2) statistically analyzing the results to determine those metabolites that were differentially present in the two groups.

Two groups of subjects were used. One group consisted of 39 subjects (18 male, 21 female) with dilated cardiomyopathy (DCM). The second group consisted of 31 healthy control subjects (14 male, 17 male). Subjects were balanced for age and gender; mean age of control females was 50.1+/−10.1 and DCM females was 50.0+/−11.3 while the mean age of control males was 42.7+/−11.3 and DCM males was 45.8+/−10.9.

T-tests (Table 23) were used to determine differences in the mean levels of metabolites between the two populations (i.e., Dilated Cardiomyopathy, DCM vs. Healthy control). Classification analysis was carried out using random forest analyses to uncover the biomarkers that can best differentiate the two groups. The results of the Random forest analysis are shown in Table 24 and the most important biomarkers useful to classify subjects as healthy or DCM are listed in Table 25. Biomarkers:

As listed below in Table 23, biomarkers were discovered that were differentially present between plasma samples collected from dilated cardiomyopathy subjects and healthy subjects.

Table 23 includes, for each listed biomarker, the p-value and q-value determined in the statistical analysis of the data concerning the biomarkers and an indication of the percentage difference in the dilated cardiomyopathy mean level as compared to the healthy mean level in plasma. "ID" refers to the compound identification number used as a primary key for that compound in the in-house chemical database. "Library" indicates the chemical library that was used to identify the compounds. The number 50 refers to the GC library and the numbers 200 and 201 refer to the LC library. "Mouse" indicates the compounds that were also biomarkers discovered in the mouse model of DCM.

TABLE 23

Biomarkers for DCM

| ID | Library | Compound | p-value | q-value | % Change in DCM | Mouse |
|---|---|---|---|---|---|---|
| 32873 | 201 | Metabolite - 11556 | 5.943E−07 | 0.0001 | −10% | |
| 1558 | 200 | 4-acetamidobutanoate | 6.339E−06 | 0.0005 | 7% | |

TABLE 23-continued

| | | Biomarkers for DCM | | | | |
|---|---|---|---|---|---|---|
| ID | Library | Compound | p-value | q-value | % Change in DCM | Mouse |
| 32709 | 200 | Metabolite - 03056 | 1.925E−05 | 0.001 | 73% | |
| 33510 | 200 | Metabolite - 12095 | 2.318E−05 | 0.001 | −9% | |
| 33442 | 200 | pseudouridine | 3.734E−05 | 0.0012 | 1% | |
| 32425 | 201 | dehydroisoandrosterone sulfate (DHEA-S) | 0.0001 | 0.0012 | 4% | |
| 32519 | 200 | Metabolite - 11205 | 0.0001 | 0.0012 | 14% | |
| 32637 | 201 | Metabolite - 11320 | 0.0001 | 0.0012 | 6% | |
| 16866 | 50 | Metabolite - 04523 | 0.0001 | 0.0015 | 9% | |
| 1114 | 201 | deoxycholate | 0.0001 | 0.0017 | 11% | |
| 1284 | 200 | threonine | 0.0001 | 0.0017 | 1% | Yes |
| 32675 | 200 | Metabolite - 03951 | 0.0001 | 0.0017 | 12% | |
| 15506 | 200 | choline | 0.0002 | 0.002 | 29% | Yes |
| 32652 | 200 | Metabolite - 11335 | 0.0002 | 0.0029 | −31% | |
| 32197 | 201 | 3-(4-hydroxyphenyl)lactate | 0.0003 | 0.0035 | −4% | Yes |
| 33515 | 200 | Metabolite - 12100 | 0.0003 | 0.0036 | 31% | |
| 18929 | 50 | Metabolite - 05907 | 0.0004 | 0.004 | −3% | |
| 32405 | 200 | 3-indolepropionate | 0.0004 | 0.004 | −13% | |
| 19934 | 50 | myo-inositol | 0.0006 | 0.0051 | 17% | Yes |
| 33453 | 50 | alpha-ketoglutarate | 0.0006 | 0.0055 | 2% | |
| 1712 | 200 | cortisol | 0.0007 | 0.006 | −53% | |
| 32807 | 201 | Metabolite - 11490 | 0.0012 | 0.0094 | −12% | |
| 25607 | 50 | Metabolite - 10437 | 0.0013 | 0.0097 | 4% | |
| 25459 | 50 | Metabolite - 10395 | 0.0015 | 0.0104 | −3% | |
| 33477 | 50 | erythronate* | 0.0016 | 0.0106 | −25% | |
| 32635 | 201 | Metabolite - 11318 | 0.0018 | 0.0117 | 17% | |
| 57 | 50 | glutamate | 0.002 | 0.0126 | −5% | Yes |
| 18254 | 200 | paraxanthine | 0.0021 | 0.0126 | −3% | |
| 33973 | 201 | epiandrosterone sulfate | 0.0021 | 0.0126 | 51% | |
| 32560 | 201 | Metabolite - 07765 | 0.0025 | 0.0142 | −4% | |
| 20699 | 50 | erythritol | 0.0026 | 0.0144 | −19% | Yes |
| 32590 | 201 | Metabolite - 11273 | 0.003 | 0.0154 | −18% | |
| 32619 | 201 | Metabolite - 11302 | 0.003 | 0.0154 | −11% | |
| 22602 | 50 | Metabolite - 09045 | 0.0033 | 0.0161 | −6% | |
| 32829 | 200 | Metabolite - 03653 | 0.0033 | 0.0161 | −4% | |
| 32910 | 201 | Metabolite - 11593 | 0.0035 | 0.0168 | −8% | |
| 32599 | 201 | Metabolite - 11282 | 0.0037 | 0.017 | 3% | |
| 16653 | 50 | Metabolite - 04361 | 0.004 | 0.0176 | 2% | |
| 18232 | 50 | Metabolite - 05403 | 0.004 | 0.0176 | 30% | |
| 15677 | 201 | 3-methylhistidine | 0.0048 | 0.0206 | 120% | Yes |
| 12770 | 50 | Metabolite - 03090 | 0.0055 | 0.0225 | 13% | |
| 31591 | 201 | androsterone sulfate | 0.0055 | 0.0225 | −78% | |
| 584 | 50 | mannose | 0.0063 | 0.0248 | 16% | Yes |
| 15140 | 200 | kynurenine | 0.0067 | 0.0258 | 22% | Yes |
| 33206 | 201 | Metabolite - 11861 | 0.0068 | 0.0258 | −17% | |
| 33144 | 200 | Metabolite - 11799 | 0.007 | 0.026 | −13% | |
| 33507 | 200 | Metabolite - 12092 | 0.0076 | 0.0278 | −3% | |
| 32740 | 201 | Metabolite - 11423 | 0.0078 | 0.0278 | −27% | |
| 33652 | 201 | Metabolite - 12230 | 0.008 | 0.0279 | −3% | |
| 53 | 200 | glutamine | 0.0082 | 0.028 | 2% | Yes |
| 32808 | 201 | Metabolite - 11491 | 0.0087 | 0.0289 | 39% | |
| 33516 | 200 | Metabolite - 12101 | 0.0089 | 0.0289 | 80% | |
| 3147 | 50 | xanthine | 0.009 | 0.0289 | 20% | |
| 12753 | 50 | Metabolite - 03074 | 0.0099 | 0.0309 | −5% | |
| 1303 | 50 | malate | 0.0101 | 0.0309 | 3% | Yes |
| 32762 | 201 | Metabolite - 11445 | 0.0101 | 0.0309 | 4% | |
| 2734 | 200 | gamma-glutamyltyrosine | 0.0115 | 0.0339 | −4% | Yes |
| 32718 | 200 | Metabolite - 01342 | 0.0116 | 0.0339 | 26% | |
| 32644 | 200 | Metabolite - 11327 | 0.0117 | 0.0339 | −25% | |
| 32654 | 200 | Metabolite - 11337 | 0.012 | 0.0341 | 9% | |
| 33937 | 201 | alpha-hydroxyisovalerate | 0.0127 | 0.0355 | 38% | |
| 12017 | 200 | 3-methoxytyrosine | 0.0134 | 0.0369 | 7% | |
| 32753 | 201 | Metabolite - 09789 | 0.0154 | 0.0418 | −9% | |
| 32587 | 201 | Metabolite - 02249 | 0.016 | 0.0427 | 44% | |
| 59 | 201 | histidine | 0.0179 | 0.047 | −1% | Yes |
| 22548 | 50 | Metabolite - 09026 | 0.0188 | 0.0486 | 28% | |
| 16959 | 50 | Metabolite - 04595 | 0.0191 | 0.0488 | 21% | |
| 33422 | 200 | gammaglutamylphenylalanine | 0.0197 | 0.0494 | 30% | |
| 64 | 200 | phenylalanine | 0.0211 | 0.0522 | −4% | Yes |
| 32110 | 50 | Metabolite - 11086 | 0.0227 | 0.055 | 8% | |
| 33132 | 200 | Metabolite - 11787 | 0.0229 | 0.055 | 132% | |
| 32859 | 200 | Metabolite - 11542 | 0.0236 | 0.0557 | −19% | |
| 32672 | 200 | Metabolite - 02546 | 0.024 | 0.0557 | −5% | |
| 21044 | 50 | 2-hydroxybutyrate (AHB) | 0.0244 | 0.0557 | 3% | Yes |
| 1356 | 201 | nonadecanoate (19:0) | 0.025 | 0.0557 | −1% | |
| 32198 | 200 | acetylcarnitine | 0.025 | 0.0557 | −44% | Yes |

TABLE 23-continued

Biomarkers for DCM

| ID | Library | Compound | p-value | q-value | % Change in DCM | Mouse |
|---|---|---|---|---|---|---|
| 32830 | 200 | Metabolite - 11513 | 0.0251 | 0.0557 | 1% | |
| 599 | 50 | pyruvate | 0.0261 | 0.0571 | −7% | |
| 1358 | 201 | stearate (18:0) | 0.0269 | 0.0576 | −13% | Yes |
| 32701 | 200 | urate* | 0.027 | 0.0576 | −2% | Yes |
| 32393 | 200 | glutamylvaline | 0.0276 | 0.0576 | 11% | |
| 24077 | 50 | Metabolite - 09727 | 0.0277 | 0.0576 | −12% | |
| 24076 | 50 | Metabolite - 09726 | 0.0285 | 0.0586 | −31% | |
| 1299 | 200 | tyrosine | 0.0288 | 0.0587 | −3% | Yes |
| 27718 | 200 | creatine | 0.0294 | 0.059 | −29% | Yes |
| 12757 | 50 | Metabolite - 03078 | 0.0299 | 0.0594 | 19% | |
| 1769 | 200 | cortisone | 0.0308 | 0.0604 | 33% | |
| 32836 | 200 | HWESASXX* | 0.0315 | 0.0612 | 11% | |
| 33028 | 200 | Metabolite - 01497 | 0.0325 | 0.0624 | −8% | |
| 33961 | 200 | 1-stearoylglycerophosphocholine | 0.0329 | 0.0624 | 4% | |
| 33157 | 200 | Metabolite - 11812 | 0.0334 | 0.0624 | 27% | |
| 32606 | 201 | bilirubin* | 0.0336 | 0.0624 | 2% | |
| 33939 | 201 | N-acetylthreonine | 0.0358 | 0.0659 | 7% | |
| 25609 | 50 | Metabolite - 10439 | 0.0363 | 0.066 | 75% | |
| 19368 | 50 | Metabolite - 06267 | 0.0367 | 0.066 | −7% | |
| 12789 | 50 | Metabolite - 03107 | 0.0384 | 0.0683 | 17% | Yes |
| 33441 | 200 | isobutyrylcarnitine | 0.0391 | 0.0684 | −13% | |
| 34035 | 201 | linolenate [alpha or gamma; (18:3(n-3 or 6))] | 0.0394 | 0.0684 | −2% | |
| 33363 | 200 | gamma-glutamylmethionine* | 0.0396 | 0.0684 | −17% | |
| 30257 | 50 | Metabolite - 10729 | 0.0417 | 0.0712 | 3% | |
| 33821 | 200 | Metabolite - 12393 | 0.0431 | 0.0724 | 0% | |
| 33389 | 201 | Metabolite - 12038 | 0.0432 | 0.0724 | 3% | |
| 21047 | 201 | 3-methyl-2-oxobutyrate | 0.0464 | 0.077 | 15% | Yes |
| 18349 | 200 | indolelactate | 0.0472 | 0.0775 | −55% | Yes |
| 12110 | 200 | isocitrate | 0.0478 | 0.0775 | 11% | |
| 33405 | 200 | Metabolite - 12053 | 0.0481 | 0.0775 | 0% | |
| 32497 | 201 | 10c-undecenoate | 0.0496 | 0.0792 | 17% | |
| 33738 | 201 | Metabolite - 12316 | 0.0502 | 0.0794 | −14% | |
| 19402 | 50 | Metabolite - 06346 | 0.0518 | 0.0812 | 53% | |
| 33964 | 200 | [H]HWESASLLR[OH] | 0.0523 | 0.0813 | 26% | |
| 12795 | 50 | Metabolite - 03113 | 0.0535 | 0.0824 | 6% | |
| 32754 | 201 | Metabolite - 11437 | 0.0542 | 0.0827 | −13% | |
| 18497 | 201 | taurocholate | 0.055 | 0.0831 | −9% | |
| 1508 | 200 | pantothenate | 0.0565 | 0.0847 | 25% | Yes |
| 32625 | 201 | Metabolite - 11308 | 0.0609 | 0.0904 | −50% | |
| 32729 | 200 | Metabolite - 11412 | 0.0621 | 0.0915 | −26% | |
| 31555 | 201 | pyridoxate | 0.0648 | 0.0946 | 18% | |
| 33960 | 200 | 1-oleoylglycerophosphocholine | 0.0664 | 0.0961 | 9% | |
| 1642 | 201 | caprate (10:0) | 0.068 | 0.0976 | −5% | |
| 31454 | 50 | cystine | 0.0697 | 0.0985 | −11% | |
| 18477 | 200 | glycodeoxycholate | 0.07 | 0.0985 | −44% | |
| 32850 | 201 | Metabolite - 11533 | 0.0711 | 0.0985 | 155% | |
| 22895 | 50 | Metabolite - 09299 | 0.0717 | 0.0985 | −15% | |
| 31618 | 50 | Metabolite - 10964 | 0.0718 | 0.0985 | −25% | |
| 34007 | 50 | Metabolite - 12502 | 0.072 | 0.0985 | −12% | |
| 1638 | 200 | arginine | 0.0748 | 0.1014 | −14% | Yes |
| 33852 | 200 | Metabolite - 12424 | 0.0767 | 0.1031 | −20% | |
| 33420 | 50 | gamma-tocopherol* | 0.0798 | 0.1058 | −17% | |
| 32398 | 200 | sebacate | 0.0799 | 0.1058 | −9% | |
| 33403 | 200 | Metabolite - 12051 | 0.082 | 0.1077 | −10% | |
| 33957 | 200 | 1-heptadecanoylglycerophosphocholine | 0.0838 | 0.1085 | −1% | |
| 32518 | 200 | Metabolite - 11204 | 0.0849 | 0.1091 | 27% | |
| 1361 | 201 | pentadecanoate (15:0) | 0.0887 | 0.1131 | 69% | |
| 1645 | 201 | laurate (12:0) | 0.0906 | 0.1141 | 10% | |
| 32620 | 201 | Metabolite - 11303 | 0.0908 | 0.1141 | 3% | |
| 15990 | 200 | glycerophosphorylcholine (GPC) | 0.0928 | 0.1158 | −9% | Yes |
| 27531 | 201 | hyodeoxycholate | 0.0956 | 0.1184 | 2% | |
| 1105 | 201 | linoleate (18:2(n-6)) | 0.0969 | 0.1184 | 66% | Yes |
| 33140 | 200 | Metabolite - 11795 | 0.097 | 0.1184 | −1% | |
| 16308 | 50 | Metabolite - 04147 | 0.099 | 0.1193 | 38% | |
| 33927 | 200 | Metabolite - 12481 | 0.0994 | 0.1193 | 18% | |
| 19363 | 50 | Metabolite - 06227 | 0.0998 | 0.1193 | 16% | |
| 31509 | 50 | Metabolite - 10931 | 0.1008 | 0.1196 | 31% | |
| 32561 | 201 | Metabolite - 11244 | 0.1052 | 0.1239 | −11% | |
| 32846 | 201 | Metabolite - 11529 | 0.1091 | 0.1257 | 253% | |
| 21630 | 50 | Metabolite - 08402 | 0.1098 | 0.1257 | 2% | |
| 32550 | 201 | Metabolite - 02272 | 0.1102 | 0.1257 | 21% | |
| 1107 | 50 | allantoin | 0.1104 | 0.1257 | −13% | Yes |
| 32867 | 201 | Metabolite - 11550 | 0.1104 | 0.1257 | 5% | |
| 32549 | 201 | Metabolite - 02269 | 0.1157 | 0.1309 | 8% | |

TABLE 23-continued

Biomarkers for DCM

| ID | Library | Compound | p-value | q-value | % Change in DCM | Mouse |
|---|---|---|---|---|---|---|
| 32786 | 200 | Metabolite - 11469 | 0.1181 | 0.1321 | 8% | |
| 32501 | 201 | dihomo-alpha-linolenate (20:3(n-3)) | 0.1188 | 0.1321 | 24% | |
| 21128 | 50 | octadecanol | 0.1191 | 0.1321 | 11% | |
| 16819 | 50 | Metabolite - 04496 | 0.12 | 0.1323 | −7% | |
| 33209 | 201 | Metabolite - 11864 | 0.121 | 0.1324 | −21% | |
| 32778 | 200 | Metabolite - 11461 | 0.1216 | 0.1324 | −6% | |
| 32839 | 201 | Metabolite - 11522 | 0.1284 | 0.1389 | 20% | |
| 32868 | 201 | glycocholate* | 0.1304 | 0.1401 | −28% | |
| 33969 | 201 | stearidonate (18:4(n-3)) | 0.1388 | 0.146 | 89% | |
| 12783 | 50 | Metabolite - 03101 | 0.1405 | 0.146 | 21% | |
| 31453 | 50 | cysteine | 0.141 | 0.146 | 16% | |
| 33103 | 50 | Metabolite - 11758 | 0.1417 | 0.146 | 26% | |
| 32758 | 201 | Metabolite - 11441 | 0.1421 | 0.146 | 24% | |
| 33935 | 200 | piperine | 0.1422 | 0.146 | −26% | |
| 33472 | 200 | Metabolite - 12085 | 0.1426 | 0.146 | 3% | |
| 32978 | 200 | Metabolite - 11656 | 0.1427 | 0.146 | −26% | |
| 32504 | 201 | n-3 DPA (22:5(n-3)) | 0.1448 | 0.1463 | −3% | |
| 32877 | 201 | Metabolite - 11560 | 0.1463 | 0.1463 | 47% | |
| 27273 | 50 | Metabolite - 10506 | 0.1465 | 0.1463 | 36% | |
| 19370 | 50 | Metabolite - 06268 | 0.149 | 0.1472 | 2% | |
| 1572 | 50 | glycerate | 0.1506 | 0.1472 | 1% | Yes |
| 32346 | 201 | glycochenodeoxycholate | 0.1506 | 0.1472 | 13% | |
| 32769 | 201 | Metabolite - 11452 | 0.1513 | 0.1472 | −17% | |
| 11777 | 50 | glycine | 0.1564 | 0.1508 | −3% | Yes |
| 32759 | 201 | Metabolite - 11442 | 0.1572 | 0.1508 | 79% | |
| 513 | 200 | creatinine | 0.161 | 0.1537 | −2% | Yes |
| 32452 | 200 | propionylcarnitine | 0.163 | 0.1547 | 9% | |
| 20675 | 201 | 1,5-anhydroglucitol (1,5-AG) | 0.1674 | 0.1573 | 5% | |
| 22600 | 50 | Metabolite - 09043 | 0.1677 | 0.1573 | 56% | |
| 33380 | 201 | Metabolite - 12029 | 0.1692 | 0.1573 | −5% | |
| 25532 | 50 | Metabolite - 10413 | 0.1695 | 0.1573 | −7% | |
| 15335 | 50 | mannitol | 0.173 | 0.1598 | 2% | |
| 32952 | 201 | Metabolite - 02277 | 0.1747 | 0.1605 | −13% | |
| 27275 | 50 | Metabolite - 10507 | 0.1777 | 0.1617 | −8% | |
| 25522 | 50 | Metabolite - 10407 | 0.178 | 0.1617 | 37% | |
| 18335 | 50 | quinate | 0.1831 | 0.1648 | 17% | |
| 1670 | 50 | urea | 0.1833 | 0.1648 | −2% | Yes |
| 31266 | 50 | fructose | 0.1853 | 0.1652 | 11% | |
| 32401 | 200 | trigonelline (N'-methylnicotinate) | 0.1856 | 0.1652 | 30% | |
| 33228 | 200 | Metabolite - 11883 | 0.1941 | 0.1718 | −4% | |
| 32776 | 200 | Metabolite - 11459 | 0.1997 | 0.1754 | −13% | |
| 1121 | 201 | margarate (17:0) | 0.2008 | 0.1754 | 12% | Yes |
| 33955 | 200 | 1-palmitoylglycerophosphocholine | 0.2012 | 0.1754 | −25% | |
| 11438 | 50 | phosphate | 0.2028 | 0.1759 | −7% | Yes |
| 32756 | 201 | Metabolite - 02276 | 0.205 | 0.1769 | −23% | |
| 21127 | 50 | 1-palmitoylglycerol (1-monopalmitin) | 0.212 | 0.182 | −40% | Yes |
| 1359 | 201 | oleate(18:1(n-9)) | 0.2134 | 0.1823 | −20% | |
| 16665 | 50 | Metabolite - 04364 | 0.2221 | 0.1888 | 63% | |
| 33662 | 200 | Metabolite - 12240 | 0.2242 | 0.1896 | 17% | |
| 32572 | 200 | Metabolite - 11255 | 0.2263 | 0.1899 | 12% | |
| 32814 | 201 | Metabolite - 11497 | 0.2274 | 0.1899 | 16% | |
| 12774 | 50 | Metabolite - 03094 | 0.2288 | 0.1899 | −11% | |
| 33774 | 201 | Metabolite - 12349 | 0.2289 | 0.1899 | 33% | |
| 33386 | 50 | Metabolite - 12035 | 0.233 | 0.1905 | 10% | |
| 33415 | 201 | Metabolite - 12063 | 0.2331 | 0.1905 | 21% | |
| 33846 | 200 | indoleacetate* | 0.2365 | 0.1909 | −16% | |
| 21049 | 50 | 1,6-anhydroglucose | 0.2368 | 0.1909 | −27% | |
| 16650 | 50 | Metabolite - 04360 | 0.2369 | 0.1909 | −40% | |
| 15365 | 50 | glycerol 3-phosphate (G3P) | 0.2384 | 0.1913 | 12% | Yes |
| 22189 | 200 | palmitoylcarnitine | 0.2412 | 0.1926 | 22% | |
| 30821 | 50 | Metabolite - 10812 | 0.2425 | 0.1927 | −47% | |
| 33620 | 200 | Metabolite - 12199 | 0.2445 | 0.1934 | 16% | |
| 12129 | 200 | beta-hydroxyisovalerate | 0.2499 | 0.1967 | −3% | Yes |
| 33408 | 200 | Metabolite - 12056 | 0.2568 | 0.1992 | 7% | |
| 31373 | 50 | Metabolite - 10878 | 0.2571 | 0.1992 | −10% | |
| 32792 | 201 | Metabolite - 11475 | 0.2573 | 0.1992 | −17% | |
| 18392 | 200 | theobromine | 0.2577 | 0.1992 | −10% | |
| 19323 | 201 | docosahexaenoate (DHA; 22:6(n-3)) | 0.2666 | 0.2052 | −14% | Yes |
| 18394 | 201 | theophylline | 0.2846 | 0.218 | −6% | |
| 32795 | 201 | Metabolite - 11478 | 0.2895 | 0.2208 | −10% | |
| 32698 | 200 | Metabolite - 11381 | 0.2935 | 0.2219 | −26% | |
| 32412 | 200 | butyrylcarnitine | 0.2945 | 0.2219 | 0% | |
| 32800 | 201 | Metabolite - 11483 | 0.296 | 0.2219 | 0% | |
| 33198 | 201 | Metabolite - 11853 | 0.2979 | 0.2219 | −50% | |
| 33254 | 201 | Metabolite - 11909 | 0.2988 | 0.2219 | −26% | |

TABLE 23-continued

Biomarkers for DCM

| ID | Library | Compound | p-value | q-value | % Change in DCM | Mouse |
|---|---|---|---|---|---|---|
| 22842 | 200 | cholate | 0.2993 | 0.2219 | 38% | |
| 33390 | 201 | Metabolite - 12039 | 0.3001 | 0.2219 | −22% | |
| 12626 | 50 | Metabolite - 03003 | 0.3038 | 0.2237 | 13% | |
| 12261 | 201 | taurodeoxycholic acid | 0.3087 | 0.2264 | −46% | |
| 32578 | 200 | Metabolite - 11261 | 0.3152 | 0.2301 | −18% | |
| 18868 | 50 | Metabolite - 05847 | 0.3218 | 0.2328 | −1% | |
| 32735 | 200 | Metabolite - 01911 | 0.3229 | 0.2328 | −12% | |
| 27719 | 50 | galactonic acid | 0.3253 | 0.233 | −14% | |
| 15122 | 50 | glycerol | 0.3269 | 0.233 | 16% | Yes |
| 33204 | 201 | Metabolite - 11859 | 0.3274 | 0.233 | 3% | |
| 32328 | 200 | hexanoylcarnitine | 0.3294 | 0.2334 | −17% | |
| 1898 | 200 | proline | 0.3309 | 0.2334 | −41% | Yes |
| 21421 | 50 | Metabolite - 08214 | 0.3322 | 0.2334 | 2% | |
| 32813 | 201 | Metabolite - 11496 | 0.335 | 0.2334 | −4% | |
| 32697 | 200 | Metabolite - 11380 | 0.3352 | 0.2334 | 74% | |
| 22320 | 50 | Metabolite - 08889 | 0.3383 | 0.2334 | 48% | |
| 32634 | 201 | Metabolite - 11317 | 0.3387 | 0.2334 | 41% | |
| 33194 | 201 | Metabolite - 11849 | 0.3388 | 0.2334 | −34% | |
| 527 | 50 | lactate | 0.3402 | 0.2335 | 95% | Yes |
| 33154 | 200 | Metabolite - 11809 | 0.3458 | 0.2356 | −18% | |
| 32492 | 201 | caprylate (8:0) | 0.3467 | 0.2356 | 4% | |
| 32838 | 200 | Metabolite - 11521 | 0.3511 | 0.2371 | −6% | |
| 32616 | 201 | Metabolite - 11299 | 0.3571 | 0.2402 | −26% | |
| 22154 | 200 | bradykinin | 0.3614 | 0.2422 | −4% | Yes |
| 32875 | 200 | Metabolite - 11558 | 0.3753 | 0.2495 | −33% | |
| 32971 | 200 | Metabolite - 11654 | 0.3753 | 0.2495 | −11% | |
| 16634 | 50 | Metabolite - 04357 | 0.3868 | 0.2551 | 2% | |
| 19576 | 50 | Metabolite - 06627 | 0.3898 | 0.2562 | −1% | |
| 33570 | 200 | Metabolite - 12154 | 0.3919 | 0.2565 | 99% | |
| 2137 | 200 | biliverdin | 0.3952 | 0.2577 | 27% | Yes |
| 32854 | 200 | Metabolite - 11537 | 0.4062 | 0.2638 | −3% | |
| 17747 | 200 | sphingosine | 0.4125 | 0.2669 | −20% | |
| 1365 | 201 | myristate (14:0) | 0.4169 | 0.2683 | 66% | Yes |
| 32511 | 201 | EDTA* | 0.4192 | 0.2683 | 63% | |
| 32767 | 201 | Metabolite - 11450 | 0.4192 | 0.2683 | 7% | |
| 32847 | 201 | Metabolite - 11530 | 0.4303 | 0.2743 | 10% | |
| 17805 | 201 | dihomolinolenate (20:2(n-6)) | 0.4331 | 0.2743 | 15% | |
| 32793 | 200 | Metabolite - 11476 | 0.4346 | 0.2743 | 88% | |
| 12781 | 50 | Metabolite - 03099 | 0.4351 | 0.2743 | 64% | |
| 1648 | 50 | serine | 0.4384 | 0.2753 | −10% | Yes |
| 32557 | 201 | Metabolite - 06126 | 0.4398 | 0.2753 | −3% | |
| 1301 | 50 | lysine | 0.4438 | 0.2767 | 24% | Yes |
| 1126 | 50 | alanine | 0.4497 | 0.2786 | 2% | Yes |
| 569 | 200 | caffeine | 0.4501 | 0.2786 | 25% | |
| 32732 | 201 | Metabolite - 11415 | 0.4532 | 0.2788 | −2% | |
| 33089 | 50 | Metabolite - 11744 | 0.4537 | 0.2788 | 64% | |
| 21184 | 200 | oleoylglycerol (monoolein) | 0.4564 | 0.2795 | 150% | |
| 22481 | 50 | Metabolite - 08988 | 0.4648 | 0.2828 | −24% | |
| 18369 | 200 | gamma-glutamylleucine | 0.4651 | 0.2828 | −9% | Yes |
| 20299 | 50 | Metabolite - 07266 | 0.4717 | 0.2858 | 14% | |
| 33882 | 201 | Metabolite - 12440 | 0.4802 | 0.2895 | 13% | |
| 1336 | 201 | palmitate (16:0) | 0.4822 | 0.2895 | 6% | Yes |
| 20489 | 50 | glucose | 0.4829 | 0.2895 | 46% | |
| 12764 | 50 | Metabolite - 03084 | 0.4883 | 0.2907 | −66% | |
| 1493 | 200 | ornithine | 0.4906 | 0.2911 | −6% | Yes |
| 32595 | 200 | Metabolite - 08893 | 0.4954 | 0.2929 | 40% | |
| 33968 | 201 | 5-dodecenoate (12:1(n-7)) | 0.4994 | 0.2942 | −1% | |
| 12761 | 50 | Metabolite - 03081 | 0.5076 | 0.298 | 20% | |
| 19374 | 50 | Metabolite - 06270 | 0.5136 | 0.2988 | 14% | |
| 22116 | 201 | 4-methyl-2-oxopentanoate | 0.5162 | 0.2988 | −52% | |
| 33447 | 201 | palmitoleate (16:1(n-7)) | 0.5171 | 0.2988 | −12% | |
| 32656 | 201 | Metabolite - 11339 | 0.5186 | 0.2988 | −3% | |
| 32669 | 200 | Metabolite - 11352 | 0.5188 | 0.2988 | −11% | |
| 542 | 200 | 3-hydroxybutyrate (BHBA) | 0.5194 | 0.2988 | 1% | Yes |
| 31401 | 50 | Metabolite - 10892 | 0.5325 | 0.3049 | 16% | |
| 32319 | 50 | trans-4-hydroxyproline | 0.5336 | 0.3049 | 137% | |
| 1302 | 200 | methionine | 0.5401 | 0.3068 | 142% | Yes |
| 32855 | 201 | Metabolite - 11538 | 0.543 | 0.3068 | 10% | |
| 12785 | 50 | Metabolite - 03103 | 0.5441 | 0.3068 | 18% | |
| 32553 | 201 | Metabolite - 03832 | 0.5469 | 0.3073 | 0% | |
| 32869 | 200 | Metabolite - 11552 | 0.5508 | 0.308 | 103% | |
| 12782 | 50 | Metabolite - 03100 | 0.553 | 0.308 | 38% | |
| 2730 | 200 | gamma-glutamylglutamine | 0.5534 | 0.308 | 71% | |
| 1564 | 50 | citrate | 0.5579 | 0.3089 | 18% | Yes |
| 32761 | 201 | Metabolite - 11444 | 0.5587 | 0.3089 | 15% | |

TABLE 23-continued

Biomarkers for DCM

| ID | Library | Compound | p-value | q-value | % Change in DCM | Mouse |
|---|---|---|---|---|---|---|
| 32632 | 200 | Metabolite - 11315 | 0.561 | 0.3092 | 37% | |
| 1605 | 201 | ursodeoxycholate | 0.5703 | 0.3124 | 2% | |
| 12593 | 50 | Metabolite - 02973 | 0.5707 | 0.3124 | 44% | |
| 32885 | 200 | Metabolite - 11568 | 0.5732 | 0.3124 | −4% | |
| 32564 | 201 | Metabolite - 11247 | 0.5743 | 0.3124 | −9% | |
| 3127 | 200 | hypoxanthine | 0.5759 | 0.3124 | 28% | |
| 1444 | 200 | pipecolate | 0.5811 | 0.3138 | −7% | |
| 1644 | 201 | heptanoate | 0.5823 | 0.3138 | −11% | |
| 33227 | 201 | Metabolite - 11882 | 0.5902 | 0.3171 | 13% | |
| 54 | 200 | tryptophan | 0.598 | 0.3203 | −7% | Yes |
| 32418 | 201 | myristoleate (14:1(n-5)) | 0.6043 | 0.3215 | 95% | |
| 15753 | 201 | hippurate | 0.6049 | 0.3215 | 0% | Yes |
| 32774 | 200 | Metabolite - 11457 | 0.6122 | 0.3215 | −49% | |
| 32648 | 201 | Metabolite - 11331 | 0.6136 | 0.3215 | −4% | |
| 27710 | 50 | N-acetylglycine | 0.615 | 0.3215 | −19% | |
| 606 | 201 | uridine | 0.6154 | 0.3215 | −4% | Yes |
| 32797 | 201 | Metabolite - 11480 | 0.6159 | 0.3215 | 35% | |
| 31787 | 201 | 3-carboxy-4-methyl-5-propyl-2-furanpropanoate (CMPF) | 0.6206 | 0.3215 | −60% | |
| 32586 | 200 | Metabolite - 01327 | 0.6213 | 0.3215 | −1% | |
| 32348 | 200 | 2-aminobutyrate | 0.6217 | 0.3215 | 17% | |
| 31489 | 50 | Metabolite - 10914 | 0.6229 | 0.3215 | 8% | |
| 32748 | 201 | Metabolite - 11431 | 0.6286 | 0.3235 | −21% | |
| 32815 | 201 | Metabolite - 11498 | 0.6324 | 0.3235 | −9% | |
| 33138 | 200 | Metabolite - 11793 | 0.6362 | 0.3245 | 32% | |
| 12790 | 50 | Metabolite - 03108 | 0.6404 | 0.3249 | −8% | |
| 12035 | 201 | pelargonate (9:0) | 0.6409 | 0.3249 | 28% | Yes |
| 27722 | 50 | erythrose | 0.6483 | 0.3277 | −6% | |
| 33901 | 201 | Metabolite - 12456 | 0.6545 | 0.3298 | −12% | |
| 15500 | 200 | carnitine | 0.6744 | 0.3389 | 136% | Yes |
| 33195 | 201 | Metabolite - 11850 | 0.6796 | 0.3405 | −9% | |
| 594 | 201 | nicotinamide | 0.6834 | 0.3406 | −26% | |
| 33638 | 201 | Metabolite - 12217 | 0.6867 | 0.3406 | 31% | |
| 32593 | 200 | Metabolite - 02036 | 0.6873 | 0.3406 | −13% | |
| 16511 | 50 | Metabolite - 04274 | 0.6879 | 0.3406 | −1% | |
| 17627 | 50 | Metabolite - 04986 | 0.6934 | 0.3409 | −3% | |
| 12767 | 50 | Metabolite - 03087 | 0.696 | 0.3409 | −5% | |
| 20694 | 50 | oxalate (ethanedioate) | 0.6974 | 0.3409 | −8% | Yes |
| 27672 | 201 | 3-indoxyl sulfate | 0.6979 | 0.3409 | 82% | |
| 15676 | 201 | 3-methyl-2-oxovalerate | 0.6983 | 0.3409 | −9% | |
| 1561 | 50 | alpha-tocopherol | 0.7092 | 0.3442 | −6% | Yes |
| 32458 | 200 | oleamide | 0.7112 | 0.3442 | 8% | |
| 32342 | 200 | adenosine 5'-monophosphate (AMP) | 0.7171 | 0.3458 | −12% | |
| 33131 | 200 | Metabolite - 11786 | 0.7186 | 0.3458 | 4% | |
| 33941 | 200 | decanoylcarnitine | 0.7205 | 0.3458 | 19% | |
| 27278 | 50 | Metabolite - 10510 | 0.7254 | 0.3472 | 3% | |
| 32970 | 201 | Metabolite - 11653 | 0.7333 | 0.35 | −12% | |
| 32562 | 201 | Metabolite - 11245 | 0.736 | 0.3503 | 27% | |
| 21631 | 50 | Metabolite - 08403 | 0.7389 | 0.3507 | −20% | |
| 33230 | 200 | Metabolite - 11885 | 0.7422 | 0.3513 | −24% | |
| 587 | 50 | gluconate | 0.7493 | 0.3526 | −38% | |
| 16508 | 50 | Metabolite - 04272 | 0.7548 | 0.3526 | −8% | |
| 33587 | 201 | eicosenoate [9 or 11, cis or trans] | 0.7575 | 0.3526 | 1446% | |
| 24074 | 50 | Metabolite - 09706 | 0.7579 | 0.3526 | 45% | |
| 15737 | 50 | glycolate (hydroxyacetate) | 0.7599 | 0.3526 | 15% | Yes |
| 32489 | 201 | caproate (6:0) | 0.7624 | 0.3526 | −24% | |
| 32636 | 201 | Metabolite - 11319 | 0.7652 | 0.3526 | 24% | |
| 33833 | 201 | Metabolite - 12405 | 0.7667 | 0.3526 | 52% | |
| 32863 | 201 | Metabolite - 11546 | 0.77 | 0.3526 | 55% | |
| 27738 | 50 | threonate | 0.7742 | 0.3526 | 23% | |
| 63 | 50 | cholesterol | 0.7753 | 0.3526 | 104% | Yes |
| 33402 | 200 | Metabolite - 12050 | 0.7784 | 0.3526 | 40% | |
| 32651 | 200 | Metabolite - 11334 | 0.7794 | 0.3526 | 37% | |
| 33265 | 200 | Metabolite - 11920 | 0.7797 | 0.3526 | 1% | |
| 32757 | 201 | Metabolite - 11440 | 0.78 | 0.3526 | 71% | |
| 512 | 50 | asparagine | 0.7878 | 0.3551 | 65% | Yes |
| 32857 | 200 | Metabolite - 11540 | 0.7901 | 0.3552 | 54% | |
| 31617 | 50 | Metabolite - 10963 | 0.7929 | 0.3555 | 61% | |
| 32738 | 200 | Metabolite - 11421 | 0.8008 | 0.3571 | −28% | |
| 27256 | 50 | Metabolite - 10500 | 0.8059 | 0.3571 | −4% | |
| 32558 | 201 | p-cresol sulfate* | 0.8079 | 0.3571 | 2% | |
| 27447 | 201 | linoleoylglycerol (monolinolein) | 0.808 | 0.3571 | 20% | |
| 1125 | 200 | isoleucine | 0.8081 | 0.3571 | −11% | Yes |
| 16837 | 50 | Metabolite - 04507 | 0.8101 | 0.3571 | −42% | |
| 60 | 200 | leucine | 0.8141 | 0.3572 | −5% | Yes |

TABLE 23-continued

Biomarkers for DCM

| ID | Library | Compound | p-value | q-value | % Change in DCM | Mouse |
|---|---|---|---|---|---|---|
| 1494 | 200 | 5-oxoproline | 0.8154 | 0.3572 | 31% | Yes |
| 33520 | 200 | Metabolite - 12105 | 0.819 | 0.3579 | −2% | |
| 1110 | 201 | arachidonate (20:4(n-6)) | 0.8245 | 0.3594 | −14% | Yes |
| 33972 | 201 | 10-nonadecenoate (19:1(n-9)) | 0.8354 | 0.3613 | 17% | |
| 16666 | 50 | Metabolite - 04365 | 0.8692 | 0.3741 | 5% | |
| 33971 | 201 | 10-heptadecenoate (17:1(n-7)) | 0.8763 | 0.3761 | −16% | |
| 27264 | 50 | Metabolite - 10503 | 0.8865 | 0.3786 | −14% | |
| 22570 | 50 | Metabolite - 09033 | 0.8891 | 0.3788 | 2% | |
| 12771 | 50 | Metabolite - 03091 | 0.8928 | 0.3794 | 74% | |
| 19490 | 50 | Metabolite - 06488 | 0.8965 | 0.3801 | 108% | |
| 32548 | 201 | Metabolite - 11231 | 0.9079 | 0.383 | 2% | |
| 21188 | 50 | stearoylglycerol (monostearin) | 0.909 | 0.383 | 49% | Yes |
| 33488 | 50 | lathosterol | 0.9118 | 0.383 | 24% | |
| 15630 | 200 | N-acetylornithine | 0.9125 | 0.383 | −5% | |
| 21011 | 50 | Metabolite - 07888 | 0.9175 | 0.3837 | −5% | |
| 32848 | 201 | Metabolite - 11531 | 0.9202 | 0.3837 | −11% | |
| 33163 | 200 | Metabolite - 11818 | 0.9209 | 0.3837 | −11% | |
| 15996 | 50 | aspartate | 0.9274 | 0.3855 | −15% | Yes |
| 1649 | 200 | valine | 0.9428 | 0.391 | 61% | Yes |
| 2132 | 200 | citrulline | 0.9557 | 0.3939 | 31% | Yes |
| 25602 | 50 | Metabolite - 10432 | 0.9562 | 0.3939 | −21% | |
| 32760 | 201 | Metabolite - 11443 | 0.9578 | 0.3939 | 9% | |
| 33936 | 200 | octanoylcarnitine | 0.9591 | 0.3939 | −2% | |
| 33369 | 50 | Metabolite - 12023 | 0.9705 | 0.3976 | −35% | |
| 3141 | 200 | betaine | 0.9845 | 0.4022 | −18% | |
| 32520 | 200 | Metabolite - 11206 | 0.9863 | 0.4022 | −21% | |

Pathway trend analysis showed strong differentiation of DCM patients in energy and lipid pathways, suggesting TCA cycle inhibition, glucogenic amino acid mobilization, and β-oxidation increases. Adrenergic steroids (cortisol, cortisone) were increased, consistent with general stress, and androgen metabolites (DHEA-S) were strongly diminished in DCM patients, resulting in an apparent metabolic "feminization" of DCM males.

Comparison to the previous transgenic mouse DCM model plasma study showed that eight compounds, including urate, malate, tyrosine, phenylalanine, erythritol, and others exhibited similar responses and were strongly significant in both studies. Another 16 that were strongly significant in the human study trended in a similar manner in the mouse study. These included α-ketoglutarate, isocitrate, pantothenate, myo-inositol, and glutamate. The data confirm that metabolomic profiles of plasma reflect the disease state in human DCM patients, and that the transgenic mouse model shares many of the biomarker alterations associated with human disease.

T-tests are used to determine if the population means are different, but do not tell us about individual observations. Random Forest analysis is a multivariate technique for identifying compounds that distinguish the Groups. Random forests are used to classify individuals. Random forests are based on a consensus of a large number of decision trees; it is an extremely effective multivariate technique, being resistant to outliers, insensitive to method of normalization, and possesses highly predictive ability for new samples. Shown in Table 24 are results of using the biomarkers listed in Table 23 to classify the subjects as "Healthy" or "DCM". The subjects are correctly classified as Healthy (Control) 81% of the time and correctly classified as having DCM 72% of the time. Subjects are correctly classified with >75% accuracy overall.

TABLE 24

Random Forest Classification of DCM and Healthy subjects

| | Control | DCM | error |
|---|---|---|---|
| Control | 25 | 6 | 19% |
| DCM | 11 | 28 | 28% |

OOB estimate of error rate: 24.29%

The biomarkers that are most important to correctly classify subjects are shown in Table 25 and the Importance plot is shown in Figure #.

TABLE 25

Important DCM biomarkers

Metabolite - 11556
4-acetamidobutanoate
Metabolite - 03951
Choline
Metabolite - 03056
Metabolite - 11335
Metabolite - 4523
erythronate
Metabolite - 11593
pseudouridine
Metabolite - 10395
Metabolite - 12095
myo-inositol
3-indolepropionate
deoxycholate
Metabolite - 11320
Metabolite - 3090
Metabolite - 5907
3-(4-hydroxyphenyl)lactate
Metabolite - 11490
paraxanthine
Metabolite - 11542
cortisol
Metabolite - 4361
creatine TABLE 25-continued Important DCM biomarkers Metabolite - 03653
Metabolite - 11282
kynurenine 3D: Biomarkers of Obesity; Metabolites that are Differentially Present in Lean Compared to Obese Subjects Biomarkers were discovered by (1) analyzing blood samples drawn from different groups of human subjects to determine the levels of metabolites in the samples and then (2) statistically analyzing the results to determine those metabolites that were differentially present in the two groups.

The plasma samples used for the analysis were from 40 lean subjects (BMI<25) and 40 obese subjects (BMI>30) that had been matched for age and gender. After the levels of metabolites were determined, the data was analyzed using univariate T-tests (i.e., Welch's T-test).

T-tests were used to determine differences in the mean levels of metabolites between the two populations (i.e., Obese vs. Lean).

Biomarkers:

As listed below in Table 26, biomarkers were discovered that were differentially present between samples from obese subjects and lean subjects.

Table 26 includes, for each listed biomarker, the p-value and q-value determined in the statistical analysis of the data concerning the biomarkers and an indication of the obese mean level, lean mean level, and the ratio of obese mean level to lean mean level (Table 26). The term "Isobar" as used in the table indicates the compounds that could not be distinguished from each other on the analytical platform used in the analysis (i.e., the compounds in an isobar elute at nearly the same time and have similar (and sometimes exactly the same) quant ions, and thus cannot be distinguished). Comp_ID refers to the compound identification number used as a primary key for that compound in the in-house chemical database. Library indicates the chemical library that was used to identify the compounds. The number 50 refers to the GC library and the number 61 refers to the LC library.

TABLE 26

Metabolite biomarkers that are differentially present in obese compared to lean subjects.

| COMP_ID | Library | COMPOUND | p-value | q-value | Obese/Lean | Mean LEAN | Mean OBESE |
|---|---|---|---|---|---|---|---|
| 584 | 50 | mannose | <0.0001 | <0.0001 | 1.873 | 0.71 | 1.33 |
| 20489 | 50 | D-glucose | <0.0001 | <0.0001 | 1.500 | 0.78 | 1.17 |
| 18369 | 61 | gamma-glu-leu | <0.0001 | <0.0001 | 1.407 | 0.86 | 1.21 |
| 20675 | 50 | 1-5-anhydro-D-glucitol | <0.0001 | <0.0001 | 0.629 | 1.24 | 0.78 |
| 1494 | 50 | 5-oxoproline | <0.0001 | <0.0001 | 0.433 | 1.57 | 0.68 |
| 15365 | 50 | sn-glycerol-3-phosphate | <0.0001 | <0.0001 | 0.330 | 1.85 | 0.61 |
| 527 | 50 | lactate | <0.0001 | <0.0001 | 0.263 | 1.86 | 0.49 |
| 22803 | 61 | Isobar-66-includes- | <0.0001 | 1.00E−04 | 0.207 | 3.92 | 0.81 |
| 3127 | 61 | hypoxanthine | <0.0001 | 1.00E−04 | 0.166 | 2.9 | 0.48 |
| 25402 | 50 | Metabolite - 10360 | <0.0001 | <0.0001 | 2.544 | 0.57 | 1.45 |
| 5652 | 61 | Metabolite - 1090 | <0.0001 | <0.0001 | 0.200 | 1.7 | 0.34 |
| 7650 | 61 | Metabolite - 1834 | <0.0001 | <0.0001 | 0.311 | 1.8 | 0.56 |
| 8959 | 61 | Metabolite - 2100 | <0.0001 | <0.0001 | 0.202 | 5.09 | 1.03 |
| 10087 | 61 | Metabolite - 2249 | <0.0001 | <0.0001 | 1.841 | 0.82 | 1.51 |
| 11053 | 61 | Metabolite - 2567 | <0.0001 | <0.0001 | 1.457 | 0.81 | 1.18 |
| 12667 | 50 | Metabolite - 3034 | <0.0001 | <0.0001 | 0.524 | 1.03 | 0.54 |
| 12969 | 61 | Metabolite - 3135 | <0.0001 | 1.00E−04 | 0.197 | 4.01 | 0.79 |
| 15278 | 61 | Metabolite - 3843 | <0.0001 | <0.0001 | 1.547 | 0.75 | 1.16 |
| 16655 | 50 | Metabolite - 4362 | <0.0001 | <0.0001 | 2.185 | 0.65 | 1.42 |
| 16848 | 50 | Metabolite - 4511 | <0.0001 | <0.0001 | 0.460 | 1.13 | 0.52 |
| 17028 | 50 | Metabolite - 4611 | <0.0001 | <0.0001 | 0.782 | 1.1 | 0.86 |
| 18871 | 61 | Metabolite - 5848 | <0.0001 | <0.0001 | 0.380 | 2.21 | 0.84 |
| 21701 | 61 | Metabolite - 8454 | <0.0001 | <0.0001 | 5.638 | 0.47 | 2.65 |
| 21107 | 61 | 5-sulfosalicylate | <0.0001 | <0.0001 | 4.667 | 0.24 | 1.12 |
| 15686 | 50 | beta-hydroxypyruvate | <0.0001 | <0.0001 | 1.506 | 0.77 | 1.16 |
| 541 | 61 | 4-hydroxyphenylacetate | <0.0001 | <0.0001 | 0.730 | 1.15 | 0.84 |
| 1303 | 50 | malate | <0.0001 | <0.0001 | 0.407 | 1.94 | 0.79 |
| 8649 | 61 | Metabolite - 2053 | <0.0001 | <0.0001 | 1.407 | 0.81 | 1.14 |
| 10433 | 61 | Metabolite - 2293 | <0.0001 | <0.0001 | 10.000 | 0.13 | 1.3 |
| 11094 | 61 | Metabolite - 2589 | <0.0001 | <0.0001 | 8.727 | 0.11 | 0.96 |
| 15000 | 61 | Metabolite - 3758 | <0.0001 | <0.0001 | 14.091 | 0.11 | 1.55 |
| 16821 | 50 | Metabolite - 4498 | <0.0001 | <0.0001 | 0.613 | 0.93 | 0.57 |
| 17667 | 61 | Metabolite - 5026 | <0.0001 | <0.0001 | 259.000 | 0.01 | 2.59 |
| 18010 | 61 | Metabolite - 5231 | <0.0001 | <0.0001 | 0.425 | 1.53 | 0.65 |
| 19291 | 61 | Metabolite - 6132 | <0.0001 | <0.0001 | 3.920 | 0.25 | 0.98 |
| 19377 | 50 | Metabolite - 6272 | <0.0001 | <0.0001 | 0.532 | 1.26 | 0.67 |
| 19508 | 61 | Metabolite - 6549 | <0.0001 | <0.0001 | 4.781 | 0.32 | 1.53 |
| 19969 | 50 | Metabolite - 6931 | <0.0001 | <0.0001 | 1.605 | 0.76 | 1.22 |
| 21586 | 50 | Metabolite - 8359 | <0.0001 | <0.0001 | 2.200 | 0.5 | 1.1 |
| 21644 | 61 | Metabolite - 8406 | <0.0001 | <0.0001 | 12.917 | 0.12 | 1.55 |
| 21648 | 61 | Metabolite - 8407 | <0.0001 | <0.0001 | 11.636 | 0.11 | 1.28 |
| 21650 | 61 | Metabolite - 8409 | <0.0001 | <0.0001 | 10.500 | 0.12 | 1.26 |
| 21651 | 61 | Metabolite - 8410 | <0.0001 | <0.0001 | 22.600 | 0.05 | 1.13 |
| 21652 | 61 | Metabolite - 8411 | <0.0001 | <0.0001 | 50.400 | 0.05 | 2.52 |
| 21653 | 61 | Metabolite - 8412 | <0.0001 | <0.0001 | 249.000 | 0.02 | 4.98 |
| 21657 | 61 | Metabolite - 8416 | <0.0001 | <0.0001 | 15.000 | 0.09 | 1.35 |
| 21731 | 61 | Metabolite - 8474 | <0.0001 | 1.00E−04 | 11.929 | 0.14 | 1.67 |

TABLE 26-continued

Metabolite biomarkers that are differentially present in obese compared to lean subjects.

| COMP_ID | Library | COMPOUND | p-value | q-value | Obese/Lean | Mean LEAN | Mean OBESE |
|---|---|---|---|---|---|---|---|
| 22880 | 50 | Metabolite - 9286 | <0.0001 | <0.0001 | 1.329 | 0.82 | 1.09 |
| 2150 | 61 | pyridoxamine | 1.00E−04 | 1.00E−04 | 1.274 | 0.84 | 1.07 |
| 24285 | 61 | Metabolite - 10026 | 1.00E−04 | 2.00E−04 | 1.333 | 0.87 | 1.16 |
| 5702 | 61 | Metabolite - 1114 | 1.00E−04 | 1.00E−04 | 0.466 | 1.16 | 0.54 |
| 21630 | 50 | Metabolite - 8402 | 1.00E−04 | 1.00E−04 | 1.422 | 0.83 | 1.18 |
| 22590 | 61 | Metabolite - 9040 | 1.00E−04 | 2.00E−04 | 3.783 | 0.69 | 2.61 |
| 25459 | 50 | Metabolite - 10395 | 1.00E−04 | 1.00E−04 | 0.671 | 1.4 | 0.94 |
| 10049 | 61 | Metabolite - 2238 | 1.00E−04 | 2.00E−04 | 6.308 | 0.39 | 2.46 |
| 12109 | 61 | Metabolite - 2853 | 1.00E−04 | 1.00E−04 | 0.475 | 1.62 | 0.77 |
| 14117 | 61 | Metabolite - 3441 | 1.00E−04 | 2.00E−04 | 0.364 | 2.64 | 0.96 |
| 16506 | 50 | Metabolite - 4271 | 1.00E−04 | 1.00E−04 | 0.382 | 1.57 | 0.6 |
| 17151 | 61 | Metabolite - 4656 | 1.00E−04 | 1.00E−04 | 5.833 | 0.24 | 1.4 |
| 21654 | 61 | Metabolite - 8413 | 1.00E−04 | 1.00E−04 | >100 | 0.001 | 1.92 |
| 2832 | 61 | adenosine-5-monophosphate | 2.00E−04 | 2.00E−04 | 0.291 | 2.23 | 0.65 |
| 1670 | 50 | urea | 4.00E−04 | 5.00E−04 | 1.311 | 0.9 | 1.18 |
| 20769 | 61 | maltotriitol | 4.00E−04 | 4.00E−04 | 0.454 | 2.18 | 0.99 |
| 10299 | 61 | Metabolite - 2274 | 4.00E−04 | 4.00E−04 | 6.146 | 0.41 | 2.52 |
| 63 | 50 | cholesterol | 6.00E−04 | 5.00E−04 | 1.161 | 0.93 | 1.08 |
| 1110 | 50 | arachidonic acid | 6.00E−04 | 5.00E−04 | 0.685 | 1.27 | 0.87 |
| 19405 | 50 | Metabolite - 6347 | 6.00E−04 | 6.00E−04 | 1.679 | 0.81 | 1.36 |
| 9016 | 61 | Metabolite - 2109 | 7.00E−04 | 6.00E−04 | 1.695 | 0.95 | 1.61 |
| 1577 | 50 | 2-amino-butyrate | 8.00E−04 | 8.00E−04 | 1.418 | 0.91 | 1.29 |
| 12625 | 50 | Metabolite - 3002 | 8.00E−04 | 8.00E−04 | 1.482 | 0.83 | 1.23 |
| 5800 | 61 | Metabolite - 1188 | 0.001 | 9.00E−04 | 0.271 | 2.47 | 0.67 |
| 19397 | 50 | Metabolite - 6326 | 0.001 | 9.00E−04 | 1.295 | 0.95 | 1.23 |
| 12726 | 50 | Metabolite - 3058 | 0.001 | 9.00E−04 | 0.752 | 1.21 | 0.91 |
| 6161 | 61 | Phthalate-possible | 0.0011 | 0.001 | 1.781 | 0.96 | 1.71 |
| 15683 | 50 | 4-methyl-2-oxopentanoate | 0.0012 | 0.0011 | 1.283 | 0.92 | 1.18 |
| 18232 | 50 | Metabolite - 5403 | 0.0013 | 0.0011 | 1.250 | 0.92 | 1.15 |
| 18882 | 61 | taurodeoxycholic acid | 0.0018 | 0.0015 | 0.305 | 2.46 | 0.75 |
| 8509 | 61 | Metabolite - 2041 | 0.0018 | 0.0015 | 1.140 | 0.93 | 1.06 |
| 21188 | 50 | 1-stearoyl-rac-glycerol | 0.0019 | 0.0016 | 1.753 | 0.77 | 1.35 |
| 19490 | 50 | Metabolite - 6488 | 0.0019 | 0.0016 | 2.033 | 0.6 | 1.22 |
| 12644 | 50 | Metabolite - 3016 | 0.002 | 0.0016 | 1.242 | 0.91 | 1.13 |
| 25548 | 50 | Metabolite - 10419 | 0.0021 | 0.0017 | 0.865 | 1.11 | 0.96 |
| 12459 | 61 | Isobar-10-includes-glutamine-H-beta-ala-gly-OH-1-methylguanine-H-Gly-Sar-OH-lysine | 0.0028 | 0.0022 | 1.168 | 0.95 | 1.11 |
| 1413 | 61 | 3-hydroxyphenylacetate | 0.003 | 0.0024 | 1.198 | 0.91 | 1.09 |
| 21047 | 61 | 3-methyl-2-oxobutyrate | 0.0032 | 0.0025 | 1.519 | 0.81 | 1.23 |
| 16903 | 61 | Metabolite - 4547 | 0.0033 | 0.0025 | 1.505 | 0.97 | 1.46 |
| 22132 | 61 | DL-alpha-hydroxyisocaproic acid | 0.0037 | 0.0028 | 0.566 | 1.22 | 0.69 |
| 21011 | 50 | Metabolite - 7888 | 0.0039 | 0.0029 | 1.508 | 0.65 | 0.98 |
| 10825 | 61 | Metabolite - 2546 | 0.0041 | 0.003 | 0.565 | 1.84 | 1.04 |
| 12912 | 61 | Metabolite - 3129 | 0.0046 | 0.0033 | 1.589 | 0.95 | 1.51 |
| 16893 | 61 | Metabolite - 4530 | 0.0046 | 0.0034 | 0.508 | 1.3 | 0.66 |
| 599 | 61 | pyruvate | 0.0052 | 0.0037 | 0.494 | 1.78 | 0.88 |
| 1604 | 61 | uric acid | 0.0054 | 0.0038 | 1.095 | 0.95 | 1.04 |
| 17068 | 61 | Metabolite - 4627 | 0.0056 | 0.0039 | 0.286 | 2.69 | 0.77 |
| 17614 | 50 | Metabolite - 4966 | 0.006 | 0.0042 | 1.454 | 0.97 | 1.41 |
| 19934 | 50 | inositol | 0.0062 | 0.0043 | 0.831 | 1.18 | 0.98 |
| 12673 | 50 | Metabolite - 3040 | 0.0063 | 0.0043 | 0.592 | 1.79 | 1.06 |
| 10551 | 61 | Metabolite - 2347 | 0.007 | 0.0048 | 0.235 | 3.27 | 0.77 |
| 22189 | 61 | palmitoyl-carnitine | 0.0076 | 0.0051 | 0.725 | 1.31 | 0.95 |
| 22020 | 50 | Metabolite - 8749 | 0.0077 | 0.0052 | 0.406 | 2.34 | 0.95 |
| 9491 | 61 | Metabolite - 2185 | 0.0081 | 0.0054 | 1.277 | 0.94 | 1.2 |
| 22602 | 50 | Metabolite - 9045 | 0.0097 | 0.0064 | 0.673 | 1.07 | 0.72 |
| 16071 | 50 | Metabolite - 4020 | 0.0103 | 0.0067 | 0.826 | 1.21 | 1 |
| 15677 | 61 | 3-methyl-L-histidine | 0.0107 | 0.007 | 1.289 | 0.9 | 1.16 |
| 18476 | 61 | glycocholic acid | 0.0107 | 0.007 | 0.223 | 3.37 | 0.75 |
| 16496 | 50 | Metabolite - 4251 | 0.0122 | 0.0078 | 0.798 | 1.19 | 0.95 |
| 597 | 61 | phosphoenolpyruvate | 0.0127 | 0.008 | 0.735 | 1.02 | 0.75 |
| 6851 | 61 | Metabolite - 1497 | 0.0128 | 0.008 | 1.242 | 0.91 | 1.13 |
| 15650 | 61 | 1-methyladenosine | 0.015 | 0.0093 | 1.117 | 0.94 | 1.05 |
| 22026 | 50 | 1-methylguanidine-hydrochloride | 0.0151 | 0.0093 | 1.158 | 0.95 | 1.1 |
| 12774 | 50 | Metabolite - 3094 | 0.0173 | 0.0106 | 0.842 | 1.14 | 0.96 |
| 7944 | 61 | Metabolite - 1915 | 0.0176 | 0.0107 | 2.514 | 1.38 | 3.47 |
| 14837 | 61 | Metabolite - 3707 | 0.0179 | 0.0108 | 1.911 | 1.12 | 2.14 |
| 13589 | 61 | Metabolite - 3327 | 0.0182 | 0.0109 | 0.374 | 2.97 | 1.11 |
| 9905 | 61 | Metabolite - 2231 | 0.0183 | 0.0109 | 1.195 | 0.87 | 1.04 |
| 12648 | 50 | Metabolite - 3020 | 0.0192 | 0.0115 | 0.745 | 1.41 | 1.05 |

TABLE 26-continued

Metabolite biomarkers that are differentially present in obese compared to lean subjects.

| COMP_ID | Library | COMPOUND | p-value | q-value | Obese/Lean | Mean LEAN | Mean OBESE |
|---|---|---|---|---|---|---|---|
| 10604 | 61 | Metabolite - 2370 | 0.0231 | 0.0136 | 0.719 | 1.35 | 0.97 |
| 17389 | 50 | Metabolite - 4796 | 0.0238 | 0.014 | 0.332 | 2.65 | 0.88 |
| 14715 | 61 | Stachydrine-possible | 0.0257 | 0.015 | 0.345 | 3.54 | 1.22 |
| 1574 | 61 | histamine | 0.0264 | 0.0152 | 0.841 | 1.07 | 0.9 |
| 15113 | 61 | Metabolite - 3783 | 0.0268 | 0.0153 | 1.268 | 0.97 | 1.23 |
| 19514 | 61 | Metabolite - 6553 | 0.0272 | 0.0155 | 1.620 | 0.5 | 0.81 |
| 20842 | 61 | Metabolite - 7765 | 0.0288 | 0.0162 | 0.513 | 2.32 | 1.19 |
| 20194 | 61 | Metabolite - 7147 | 0.0289 | 0.0162 | 0.887 | 1.06 | 0.94 |
| 5577 | 61 | Metabolite - 1065 | 0.0323 | 0.0179 | 2.106 | 1.41 | 2.97 |
| 15227 | 61 | Metabolite - 3816 | 0.0323 | 0.0179 | 0.767 | 1.29 | 0.99 |
| 15140 | 61 | L-kynurenine | 0.0329 | 0.0182 | 1.143 | 0.98 | 1.12 |
| 9748 | 61 | Metabolite - 2212 | 0.034 | 0.0187 | 0.723 | 1.41 | 1.02 |
| 5765 | 61 | 5-hydroxypentanoate-or-beta-hydroxyisovaleric acid-possible | 0.036 | 0.0197 | 0.562 | 2.01 | 1.13 |
| 19372 | 50 | Metabolite - 6269 | 0.038 | 0.0207 | 0.857 | 0.98 | 0.84 |
| 11111 | 61 | Metabolite - 2592 | 0.0404 | 0.0216 | 2.600 | 0.9 | 2.34 |
| 20166 | 61 | Metabolite - 7091 | 0.0415 | 0.0219 | 1.443 | 1.06 | 1.53 |
| 22133 | 61 | DL-hexanoyl-carnitine | 0.0429 | 0.0224 | 1.240 | 1 | 1.24 |
| 10629 | 61 | Metabolite - 2386 | 0.0467 | 0.0242 | 1.289 | 0.83 | 1.07 |
| 15122 | 50 | glycerol | 0.048 | 0.0248 | 1.175 | 0.97 | 1.14 |
| 1643 | 50 | fumarate | 0.051 | 0.0262 | 0.903 | 1.03 | 0.93 |
| 22337 | 61 | Metabolite - 8893 | 0.0518 | 0.0265 | 1.153 | 0.98 | 1.13 |
| 8469 | 61 | Metabolite - 2036 | 0.0521 | 0.0265 | 6.559 | 1.11 | 7.28 |
| 5687 | 61 | Metabolite - 1110 | 0.0547 | 0.0274 | 1.648 | 1.25 | 2.06 |
| 15500 | 61 | carnitine | 0.0591 | 0.0294 | 0.821 | 1.17 | 0.96 |
| 17048 | 61 | Metabolite - 4617 | 0.0614 | 0.0303 | 1.083 | 0.96 | 1.04 |
| 1105 | 50 | Linoleic acid | 0.0647 | 0.0316 | 0.882 | 1.1 | 0.97 |
| 20699 | 50 | meso-erythritol | 0.0703 | 0.0341 | 0.901 | 1.11 | 1 |
| 21763 | 61 | Metabolite - 8507 | 0.0712 | 0.0342 | 0.779 | 1.04 | 0.81 |
| 7941 | 61 | Metabolite - 1914 | 0.0724 | 0.0346 | 1.549 | 0.82 | 1.27 |
| 1336 | 50 | n-hexadecanoic acid | 0.0795 | 0.0379 | 0.885 | 1.13 | 1 |
| 9130 | 61 | Metabolite - 2139 | 0.0815 | 0.0386 | 1.212 | 0.99 | 1.2 |
| 12720 | 61 | Metabolite - 3056 | 0.0891 | 0.0421 | 0.847 | 1.18 | 1 |
| 17783 | 61 | trans-2-3-4-trimethoxycinnamic acid | 0.0906 | 0.0425 | 1.525 | 0.8 | 1.22 |
| 16226 | 61 | Isobar-28-includes-L-threonine-L-allothreonine-L-homoserine-S-4-amino-2-hydroxybutyric acid | 0.0908 | 0.0425 | 0.871 | 1.16 | 1.01 |
| 1358 | 50 | octadecanoic acid | 0.099 | 0.0461 | 0.916 | 1.07 | 0.98 |
| 542 | 50 | 3-hydroxybutanoic acid | 0.1004 | 0.0466 | 0.624 | 1.97 | 1.23 |
| 6266 | 61 | Metabolite - 1286 | 0.1007 | 0.0466 | 1.052 | 0.97 | 1.02 |
| 18392 | 61 | theobromine | 0.1072 | 0.0494 | 1.629 | 1.05 | 1.71 |
| 20950 | 50 | Metabolite - 7846 | 0.1136 | 0.0521 | 0.579 | 2.35 | 1.36 |
| 18349 | 61 | DL-indole-3-lactic acid | 0.1144 | 0.0522 | 0.857 | 1.19 | 1.02 |
| 10245 | 61 | Metabolite - 2269- | 0.1162 | 0.0522 | 1.487 | 1.13 | 1.68 |
| 17304 | 61 | Metabolite - 4759 | 0.1162 | 0.0522 | 1.233 | 0.9 | 1.11 |
| 18034 | 61 | Metabolite - 5234 | 0.1162 | 0.0522 | 1.295 | 1.12 | 1.45 |
| 22001 | 61 | 3-hydroxyoctanoate | 0.1208 | 0.0541 | 0.773 | 1.32 | 1.02 |
| 1572 | 50 | glyceric acid | 0.126 | 0.0555 | 0.874 | 1.11 | 0.97 |
| 12856 | 61 | Metabolite - 3123 | 0.1261 | 0.0555 | 2.924 | 0.79 | 2.31 |
| 6497 | 61 | Metabolite - 1374 | 0.1277 | 0.056 | 1.402 | 1.02 | 1.43 |
| 16650 | 50 | Metabolite - 4360 | 0.1292 | 0.0565 | 0.713 | 1.29 | 0.92 |
| 10286 | 61 | Metabolite - 2272 | 0.1333 | 0.0578 | 0.625 | 1.68 | 1.05 |
| 18657 | 61 | Metabolite - 5726 | 0.1363 | 0.0588 | 0.816 | 1.14 | 0.93 |
| 15681 | 61 | 4-Guanidinobutanoic acid | 0.1368 | 0.0588 | 0.896 | 1.06 | 0.95 |
| 8176 | 61 | Metabolite - 1974 | 0.1394 | 0.0595 | 1.260 | 0.96 | 1.21 |
| 21418 | 61 | Isobar-56-includes-DL-pipecolic acid-1-amino-1-cyclopentanecarboxylic acid | 0.1529 | 0.0643 | 0.768 | 1.64 | 1.26 |
| 12710 | 61 | Metabolite - 3052 | 0.1538 | 0.0644 | 0.920 | 1 | 0.92 |
| 13545 | 61 | Metabolite - 3322 | 0.1626 | 0.0673 | 0.730 | 1.78 | 1.3 |
| 10715 | 61 | Metabolite - 2395 | 0.163 | 0.0673 | 1.527 | 1.29 | 1.97 |
| 17478 | 61 | Metabolite - 4873 | 0.1635 | 0.0673 | 1.481 | 0.81 | 1.2 |
| 19097 | 61 | Metabolite - 5969 | 0.1709 | 0.0698 | 1.174 | 0.92 | 1.08 |
| 18963 | 61 | Metabolite - 5918 | 0.1718 | 0.0699 | 2.337 | 1.01 | 2.36 |
| 24076 | 50 | Metabolite - 9726 | 0.1767 | 0.0714 | 1.110 | 1 | 1.11 |
| 17093 | 61 | Metabolite - 4642 | 0.1812 | 0.0729 | 1.146 | 0.96 | 1.1 |
| 10746 | 61 | Isobar-6-includes-valine-betaine | 0.1889 | 0.0757 | 1.148 | 0.88 | 1.01 |
| 6362 | 61 | p-cresol-sulfate | 0.1896 | 0.0758 | 0.822 | 1.18 | 0.97 |
| 10092 | 61 | Metabolite - 2250 | 0.1908 | 0.0759 | 0.636 | 2.06 | 1.31 |

TABLE 26-continued

Metabolite biomarkers that are differentially present in obese compared to lean subjects.

| COMP_ID | Library | COMPOUND | p-value | q-value | Obese/Lean | Mean LEAN | Mean OBESE |
|---|---|---|---|---|---|---|---|
| 22261 | 61 | Isobar-60-includes-s-2-hydroxybutyrate-2-hydroxyisobutyrate | 0.1987 | 0.0785 | 1.288 | 0.73 | 0.94 |
| 5733 | 61 | Metabolite - 1127 | 0.201 | 0.0792 | 0.884 | 1.12 | 0.99 |
| 20830 | 61 | Metabolite - 7762 | 0.2051 | 0.0802 | 1.357 | 0.98 | 1.33 |
| 10700 | 61 | Metabolite - 2393 | 0.2053 | 0.0802 | 0.928 | 1.11 | 1.03 |
| 22120 | 61 | 6-gamma-gamma-dimethylallyl-amino-purine | 0.2065 | 0.0802 | 0.951 | 1.03 | 0.98 |
| 16518 | 50 | Metabolite - 4276 | 0.2065 | 0.0802 | 1.154 | 0.91 | 1.05 |
| 18829 | 61 | phenylalanine | 0.2149 | 0.0832 | 0.952 | 1.05 | 1 |
| 14439 | 61 | Metabolite - 3498 | 0.2271 | 0.0876 | 1.072 | 0.97 | 1.04 |
| 8300 | 61 | Metabolite - 1988 | 0.2284 | 0.0878 | 1.165 | 1.03 | 1.2 |
| 6421 | 61 | Metabolite - 1345 | 0.2299 | 0.088 | 1.341 | 1.23 | 1.65 |
| 1508 | 61 | pantothenic acid | 0.2315 | 0.0884 | 1.167 | 1.02 | 1.19 |
| 15121 | 61 | Metabolite - 3786 | 0.2338 | 0.0889 | 0.763 | 1.18 | 0.9 |
| 18394 | 61 | theophylline | 0.2362 | 0.0893 | 1.420 | 1.19 | 1.69 |
| 12626 | 50 | Metabolite - 3003 | 0.2364 | 0.0893 | 0.901 | 1.01 | 0.91 |
| 6492 | 61 | Metabolite - 1371 | 0.2409 | 0.0907 | 1.369 | 1.11 | 1.52 |
| 6413 | 61 | phenylacetylglutamine-or-formyl-N-acetyl-5-methoxykynurenamine-possible | 0.2441 | 0.0916 | 0.836 | 1.28 | 1.07 |
| 16662 | 61 | Metabolite - 4363 | 0.2586 | 0.0967 | 0.787 | 1.41 | 1.11 |
| 24077 | 50 | Metabolite - 9727 | 0.2726 | 0.1016 | 0.789 | 1.47 | 1.16 |
| 22259 | 61 | Isobar-59-includes-N-6-trimethyl-L-lysine-H-homoarg-OH | 0.281 | 0.1041 | 1.106 | 0.94 | 1.04 |
| 15676 | 50 | 3-methyl-2-oxovaleric acid | 0.283 | 0.1041 | 0.912 | 0.91 | 0.83 |
| 13208 | 61 | Metabolite - 3181 | 0.2918 | 0.107 | 0.904 | 1.04 | 0.94 |
| 10787 | 61 | Metabolite - 2507 | 0.2989 | 0.1092 | 1.308 | 1.04 | 1.36 |
| 18705 | 61 | Metabolite - 5768 | 0.3012 | 0.1097 | 0.822 | 1.35 | 1.11 |
| 16865 | 50 | Metabolite - 4522 | 0.314 | 0.1133 | 1.041 | 0.97 | 1.01 |
| 12756 | 50 | Metabolite - 3077 | 0.3211 | 0.1151 | 1.059 | 1.01 | 1.07 |
| 16909 | 61 | Metabolite - 4549 | 0.3323 | 0.1179 | 0.716 | 1.41 | 1.01 |
| 18702 | 61 | Metabolite - 5767 | 0.3381 | 0.1196 | 1.118 | 0.93 | 1.04 |
| 569 | 61 | caffeine | 0.3393 | 0.1196 | 0.683 | 3.82 | 2.61 |
| 1507 | 50 | palmitoleic acid | 0.34 | 0.1196 | 0.826 | 1.21 | 1 |
| 20248 | 61 | Metabolite - 7177 | 0.3483 | 0.1217 | 1.317 | 1.01 | 1.33 |
| 15253 | 61 | Metabolite - 3832-possible-phenol-sulfate | 0.3576 | 0.1246 | 1.341 | 1.64 | 2.2 |
| 1645 | 50 | n-dodecanoate | 0.3717 | 0.1291 | 0.922 | 1.16 | 1.07 |
| 22577 | 50 | Metabolite - 9035 | 0.384 | 0.1329 | 0.897 | 1.16 | 1.04 |
| 20267 | 61 | Metabolite - 7187 | 0.3923 | 0.1352 | 1.296 | 1.15 | 1.49 |
| 7933 | 61 | Metabolite - 1911 | 0.4027 | 0.1377 | 0.702 | 2.25 | 1.58 |
| 17066 | 61 | Metabolite - 4626 | 0.4028 | 0.1377 | 0.935 | 1.08 | 1.01 |
| 15529 | 61 | Metabolite - 3951 | 0.4084 | 0.1391 | 0.962 | 1.05 | 1.01 |
| 513 | 61 | creatinine | 0.413 | 0.1399 | 0.971 | 1.04 | 1.01 |
| 8072 | 61 | Metabolite - 1958 | 0.4193 | 0.1416 | 0.971 | 1.02 | 0.99 |
| 1564 | 50 | citric acid | 0.4489 | 0.1507 | 0.912 | 1.13 | 1.03 |
| 15737 | 50 | hydroxyacetic acid | 0.4522 | 0.1514 | 0.953 | 1.06 | 1.01 |
| 18015 | 61 | Metabolite - A-3113 | 0.4749 | 0.1567 | 0.879 | 1.07 | 0.94 |
| 13142 | 61 | Metabolite - 3165 | 0.4763 | 0.1567 | 0.962 | 1.05 | 1.01 |
| 24233 | 61 | Metabolite - 9855 | 0.4766 | 0.1567 | 0.760 | 2.04 | 1.55 |
| 15663 | 61 | 2-3-dihydroxybenzoic acid | 0.4858 | 0.1583 | 0.875 | 1.36 | 1.19 |
| 21421 | 50 | Metabolite - 8214 | 0.487 | 0.1583 | 1.040 | 1.01 | 1.05 |
| 16070 | 50 | Metabolite - 4019 | 0.487 | 0.1583 | 0.960 | 1.01 | 0.97 |
| 12478 | 61 | Metabolite - 2898 | 0.4959 | 0.16 | 1.384 | 1.51 | 2.09 |
| 17271 | 61 | Metabolite - 4746 | 0.4968 | 0.16 | 1.052 | 0.97 | 1.02 |
| 1417 | 61 | Kynurenic acid | 0.5074 | 0.162 | 1.066 | 1.06 | 1.13 |
| 11438 | 50 | phosphate | 0.5236 | 0.1667 | 0.980 | 1 | 0.98 |
| 14840 | 61 | Metabolite - 3708 | 0.5402 | 0.171 | 0.887 | 1.15 | 1.02 |
| 17665 | 61 | p-hydroxybenzaldehyde | 0.5451 | 0.1711 | 1.020 | 1 | 1.02 |
| 54 | 61 | tryptophan | 0.5459 | 0.1711 | 0.981 | 1.03 | 1.01 |
| 15017 | 61 | Metabolite - 3761 | 0.5464 | 0.1711 | 0.934 | 1.06 | 0.99 |
| 13179 | 61 | Metabolite - 3176-possible-creatine | 0.5563 | 0.1732 | 0.936 | 1.1 | 1.03 |
| 14961 | 61 | Metabolite - 3752 | 0.5662 | 0.1758 | 1.064 | 0.94 | 1 |
| 17298 | 61 | Metabolite - 4756 | 0.571 | 0.1768 | 1.071 | 0.98 | 1.05 |
| 22053 | 61 | 3-hydroxydecanoic acid | 0.5741 | 0.1773 | 0.917 | 1.08 | 0.99 |
| 10317 | 61 | Metabolite - 2279 | 0.5777 | 0.1779 | 0.849 | 1.39 | 1.18 |
| 7029 | 61 | Metabolite - 1597 | 0.5816 | 0.1786 | 1.020 | 1 | 1.02 |
| 16244 | 61 | Isobar-21-includes-gamma-aminobutyryl-L-histidine-L-anserine | 0.5964 | 0.1816 | 0.952 | 1.05 | 1 |

TABLE 26-continued

Metabolite biomarkers that are differentially present in obese compared to lean subjects.

| COMP_ID | Library | COMPOUND | p-value | q-value | Obese/Lean | Mean LEAN | Mean OBESE |
|---|---|---|---|---|---|---|---|
| 21044 | 50 | Metabolite - s-2-hydroxybutyric acid | 0.6118 | 0.1857 | 1.064 | 1.09 | 1.16 |
| 10501 | 61 | Metabolite - 2321 | 0.6132 | 0.1857 | 1.099 | 1.21 | 1.33 |
| 19787 | 61 | Metabolite - 6746 | 0.62 | 0.187 | 0.981 | 1.05 | 1.03 |
| 1301 | 50 | lysine | 0.6207 | 0.187 | 0.922 | 1.29 | 1.19 |
| 16939 | 61 | Metabolite - 4586 | 0.6303 | 0.1889 | 1.032 | 0.93 | 0.96 |
| 19906 | 61 | Metabolite - 6827 | 0.6345 | 0.1896 | 1.071 | 1.12 | 1.2 |
| 10304 | 61 | Metabolite - 2276 | 0.6399 | 0.1897 | 1.164 | 1.34 | 1.56 |
| 22145 | 61 | O-acetyl-L-carnitine-hydrochloride | 0.6448 | 0.19 | 1.029 | 1.04 | 1.07 |
| 5809 | 61 | 3-indoxyl-sulfate | 0.646 | 0.19 | 0.936 | 1.1 | 1.03 |
| 18706 | 61 | Metabolite - 5769 | 0.6599 | 0.1935 | 0.963 | 1.08 | 1.04 |
| 12604 | 50 | Metabolite - 2981 | 0.6621 | 0.1936 | 1.020 | 0.99 | 1.01 |
| 17488 | 61 | Metabolite - 4887 | 0.6822 | 0.1975 | 0.966 | 0.89 | 0.86 |
| 1299 | 61 | tyrosine | 0.7135 | 0.2055 | 1.020 | 1.01 | 1.03 |
| 22154 | 61 | bradykinin | 0.7224 | 0.2069 | 0.925 | 1.46 | 1.35 |
| 606 | 61 | uridine | 0.7239 | 0.2069 | 1.020 | 1.01 | 1.03 |
| 12035 | 50 | nonanate | 0.7322 | 0.2087 | 0.990 | 0.99 | 0.98 |
| 6144 | 61 | Metabolite - 1215 | 0.7562 | 0.2145 | 0.861 | 3.88 | 3.34 |
| 21762 | 61 | Metabolite - 8506 | 0.785 | 0.222 | 0.939 | 1.65 | 1.55 |
| 1506 | 61 | orotidine-5-phosphate | 0.789 | 0.2226 | 0.971 | 1.03 | 1 |
| 13038 | 61 | Metabolite - 3143 | 0.7911 | 0.2227 | 0.943 | 1.23 | 1.16 |
| 2734 | 61 | gamma-L-glutamyl-L-tyrosine | 0.8158 | 0.2262 | 1.021 | 0.97 | 0.99 |
| 12924 | 61 | Metabolite - 3131 | 0.8273 | 0.2288 | 1.033 | 1.22 | 1.26 |
| 1642 | 50 | decanoic acid | 0.8396 | 0.2305 | 1.022 | 0.93 | 0.95 |
| 22895 | 50 | Metabolite - 9299 | 0.8504 | 0.2323 | 1.023 | 0.86 | 0.88 |
| 16016 | 61 | Metabolite - 3994 | 0.8777 | 0.2388 | 1.024 | 0.84 | 0.86 |
| 15255 | 61 | Metabolite - 3833 | 0.8785 | 0.2388 | 1.040 | 1.24 | 1.29 |
| 13146 | 61 | Metabolite - 3166 | 0.8821 | 0.2392 | 0.970 | 0.99 | 0.96 |
| 17033 | 61 | Metabolite - 4613 | 0.8939 | 0.2412 | 1.021 | 0.95 | 0.97 |
| 15753 | 61 | hippuric acid | 0.9065 | 0.2441 | 1.022 | 1.38 | 1.41 |
| 15612 | 61 | Metabolite - 3972 | 0.9499 | 0.2546 | 1.000 | 0.97 | 0.97 |
| 18254 | 61 | 1-7-dimethylxanthine | 0.9503 | 0.2546 | 1.026 | 1.94 | 1.99 |
| 594 | 61 | niacinamide | 0.9552 | 0.2548 | 1.024 | 0.83 | 0.85 |
| 15326 | 61 | Metabolite - 3879 | 0.9567 | 0.2548 | 0.985 | 1.31 | 1.29 |
| 15765 | 61 | ethylmalonic acid | 0.9909 | 0.2611 | 1.000 | 0.96 | 0.96 |
| 1570 | 50 | oleic acid | 0.9978 | 0.2623 | 1.000 | 1.03 | 1.03 |

3E: Algorithms (Models) for Diagnosing Metabolic Syndrome and Pre-Disposition to Metabolic Syndrome (Insulin Sensitivity).

Models were developed to test the ability to predict insulin sensitivity (Rd) and metabolic syndrome using the biomarker metabolites alone and/or in combination with clinical measures of metabolic syndrome (e.g. BMI, Rd). The plasma samples used for the analysis were from subjects with various rates of glucose disposal (Rd).

Algorithms for determining insulin sensitivity were developed by multiple iterations of regression analysis of glucose utilization rate (i.e. Rd) in combination with measurements of metabolite biomarkers. The samples were divided into two groups. The first group was used as a 'training' set and the second group was used as a 'test' set. Then a model was developed using the training set and the predictive power of the resulting model was determined using the test set. Several models were developed to identify the most important biomarker metabolites for predicting insulin sensitivity and thereby demonstrating the utility of this approach and these biomarker metabolites.

A model was developed to predict insulin sensitivity (i.e. Rd) using plasma samples collected from a cohort with varying levels of insulin sensitivity and BMI less than 27.9 and BMI greater than 27.9. For this model the training group included half of the plasma samples and was balanced for BMI and Rd. The model was then tested using a test group that included the other half of the samples and was also balanced for BMI and Rd. The results of this analysis showed that the best model for predicting insulin sensitivity includes: BMI and the biomarker metabolites glucose, 3-methyl-2-oxobutyric acid, 1,5-anhydroglucitol and metabolite-6268.

Another model was developed to predict insulin sensitivity (i.e. Rd) using plasma samples collected from a cohort with varying levels of insulin sensitivity and BMI less than 27.9. For this model the training group included half of the plasma samples and was balanced for insulin sensitivity (Rd). The model was then tested using a test group that included the other half of the plasma samples and was also balanced for Rd. The results of this analysis showed that the best model for predicting insulin sensitivity includes the biomarker metabolites: glucose, metabolite-2546, metabolite-2853, metabolite-2370 and metabolite-2386.

Yet another model was developed to predict insulin sensitivity (i.e. Rd) using plasma samples collected from a cohort with varying levels of insulin sensitivity and BMI greater than 27.9. For this model the training group included half of the plasma samples and was balanced for insulin sensitivity (Rd). The model was then tested using a test group that included the other half of the plasma samples and was also balanced for Rd. The results of this analysis showed that the best model for predicting insulin sensitivity includes the biomarker metabolites: 3-methyl-2-oxobutyric, metabolite-3097, metabolite-4020, metabolite-3056 and metabolite-1831.

Figure 21:
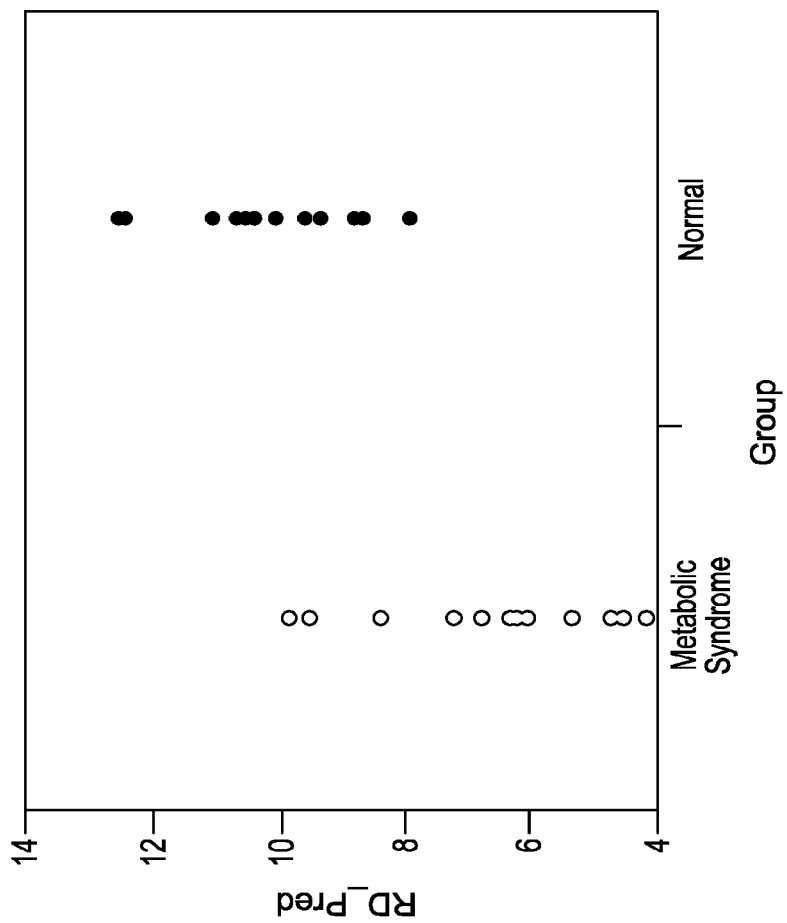
FIG. 21 provides an example of model validation using plasma from metabolic syndrome and healthy subjects.
Figure 22:
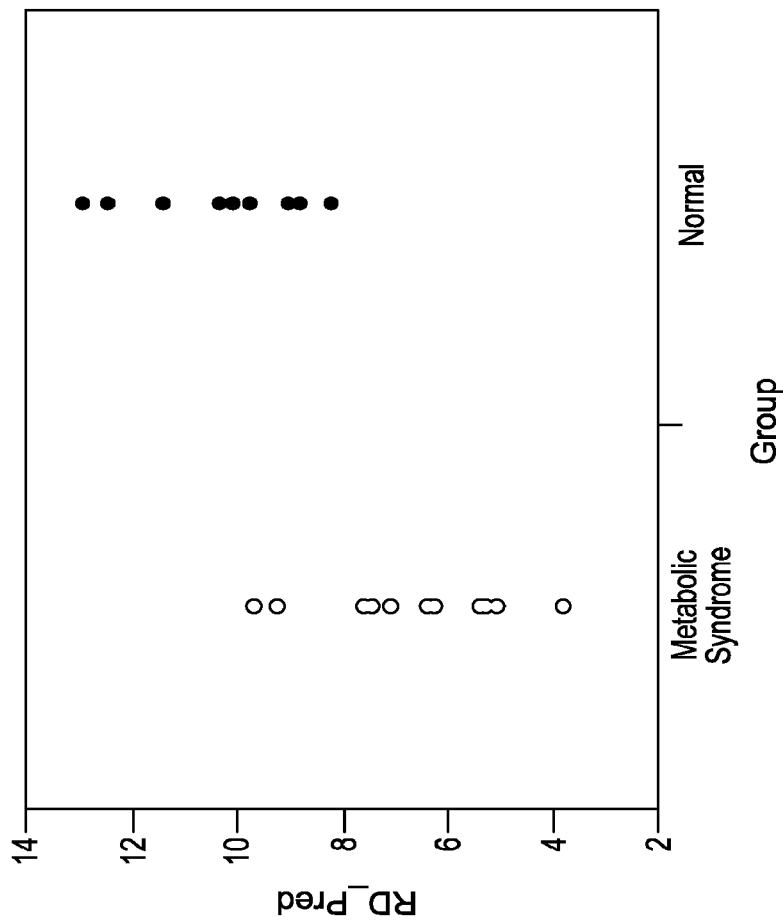
FIG. 22 provides an example of a model validation using serum from metabolic syndrome and healthy subjects.
Figure 23:
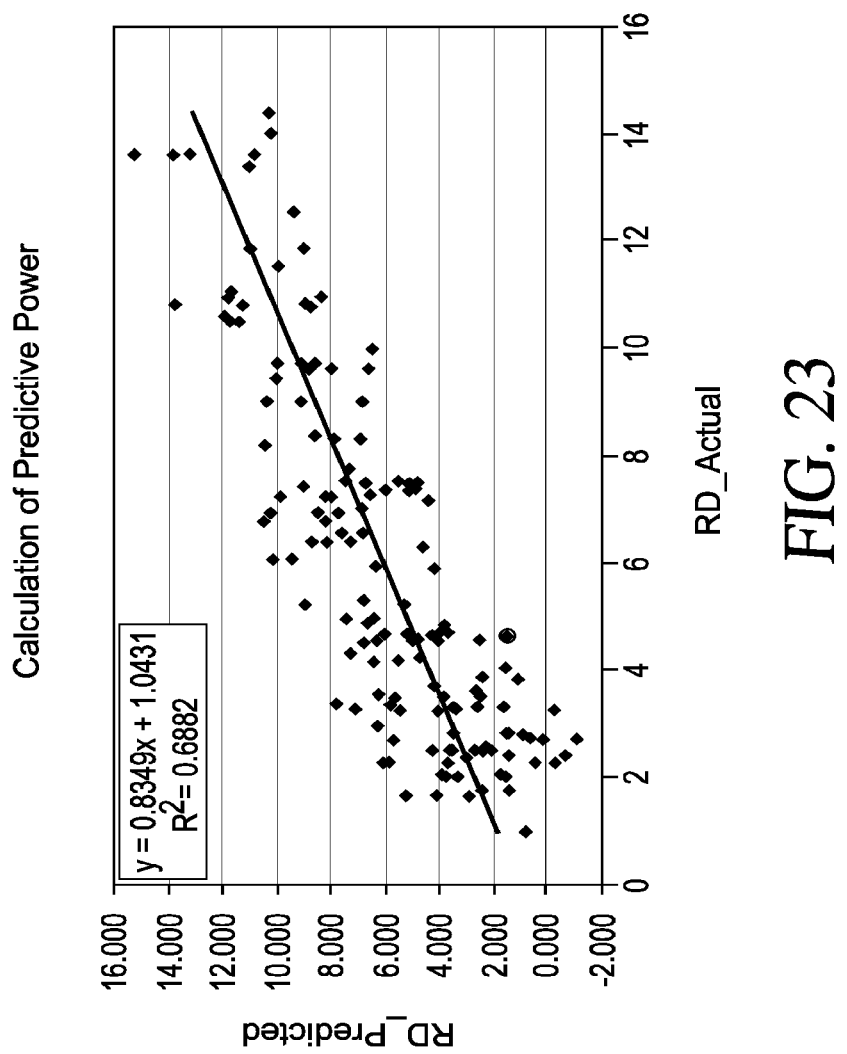
FIG. 23 provides an example of a regression analysis showing the predictive power of the ten models combined on the glucose disposal rate (Rd).

The model: BMI and the biomarker metabolites glucose, 3-methyl-2-oxobutyric acid, 1,5-anhydroglucitol and metabolite-6268; was used on a new cohort to predict insulin sensitivity (Rd). The model was developed to predict insulin sensitivity (i.e. Rd) using plasma samples collected from a cohort with varying levels of insulin sensitivity and BMI less than 27.9 and BMI greater than 27.9, as described above. The samples used to test the model for this analysis were obtained from 19 Caucasian males aged 18-39, average age of 25.6, that had been diagnosed with metabolic syndrome and 19 healthy, age-matched, Caucasian males. Plasma samples and serum samples were evaluated. The results of this analysis show that the model could correctly predict insulin sensitivity in this new cohort using either plasma (FIG. 21) or serum (FIG. 22) samples.

Example 4

Treatment Response Biomarkers

Biomarkers that are predictive of response to treatment were identified through comparisons of subjects that were 'non-responders' (i.e. those with little or no change (<15%) in Rd between baseline and 12 weeks post-treatment) and those subjects that were responsive to the treatment (i.e. 'responders'). Biomarkers that were predictive of subjects as treatment responders or non-responders were based on compound levels at baseline only. The responders were defined either as those subjects with either a Rd change of 35% or higher or as those with a Rd change of 15% or higher. Data was analyzed by comparing Non-responders with both classes of Responders. Both analyses (i.e. Non-responder with Rd change under 15% vs Responder with Rd change over 35%, Non-responder with Rd change under 15% vs Responder with Rd change over 15%) were then combined and those biomarkers with a p value of <0.1 in EITHER of the 2 analyses were identified. The biomarkers are listed in Table 27. The biomarker measurements before treatment were predictive of thiazolidinedione (TZD) response, and thus can be used to select patients for treatment with TZD drugs. Experiments are planned to evaluate the biomarkers as predictive to other treatments for insulin sensitivity, pre-diabetes and diabetes control such as other therapeutic agents (e.g. metformin, etc.), weight loss, nutrition and other lifestyle modifications. This group of predictive biomarkers provide an extremely valuable tool for personalized medicine.

TABLE 27

Biomarkers to Classify Responders or Non-Responders of Treatment

| COMPOUND | LIB_ID | COMP_ID | P value (Responder vs Non-Responder) |
|---|---|---|---|
| Metabolite - 11737 | 200 | 33082 | 0.0007 |
| Metabolite - 11849 | 201 | 33194 | 0.0013 |
| inositol | 50 | 19934 | 0.0041 |
| glycerophosphorylcholine (GPC) | 200 | 15990 | 0.0043 |
| phenylalanine | 200 | 64 | 0.0045 |
| acetylcarnitine | 200 | 32198 | 0.0049 |
| linoleate (18:2(n-6)) | 201 | 32673 | 0.0079 |
| Metabolite - 11845 | 201 | 33190 | 0.0098 |
| tryptophan | 200 | 54 | 0.0107 |
| Metabolite - 10407 | 50 | 25522 | 0.0113 |
| Metabolite - 11379 | 201 | 32696 | 0.0117 |
| Metabolite - 9727 | 50 | 24077 | 0.0136 |
| Metabolite - 11205 | 200 | 32519 | 0.0151 |
| Metabolite - 11883 | 200 | 33228 | 0.0168 |

TABLE 27-continued

Biomarkers to Classify Responders or Non-Responders of Treatment

| COMPOUND | LIB_ID | COMP_ID | P value (Responder vs Non-Responder) |
|---|---|---|---|
| Metabolite - 10954_200 | 200 | 32734 | 0.0178 |
| glycerol | 50 | 15122 | 0.0182 |
| gondoate-20-1-n-9- | 201 | 32402 | 0.0182 |
| Metabolite - 03832_201 | 201 | 32553 | 0.0209 |
| oleate (18:1(n-9)) | 201 | 32630 | 0.0225 |
| Metabolite - 11793 | 200 | 33138 | 0.0225 |
| gamma-glutamylphenylalanine- | 200 | 33362 | 0.0231 |
| Metabolite - 11560 | 201 | 32877 | 0.0242 |
| Metabolite - 11247 | 201 | 32564 | 0.0273 |
| Metabolite - 11887 | 201 | 33232 | 0.0317 |
| Metabolite - 11206 | 200 | 32520 | 0.0317 |
| tyrosine | 200 | 1299 | 0.0317 |
| Metabolite - 12064 | 201 | 33416 | 0.0317 |
| EDTA* | 201 | 32511 | 0.0317 |
| Metabolite - 11790 | 200 | 33135 | 0.0338 |
| 3-hydroxybutyrate (BHBA) | 50 | 542 | 0.0339 |
| palmitoleate (16:1(n-7)) | 201 | 32628 | 0.0412 |
| lysine | 50 | 1301 | 0.0468 |
| Metabolite - 11314 | 200 | 32631 | 0.0468 |
| Metabolite - 11204 | 200 | 32518 | 0.0468 |
| Metabolite - 11437 | 201 | 32754 | 0.0491 |
| alpha linolenate (18:3(n-3)) | 201 | 32416 | 0.0499 |
| peptide-DSGEGDFXAEGGGVR | 200 | 31548 | 0.0531 |
| Metabolite - 11874 | 201 | 33219 | 0.0531 |
| palmitate (16:0) | 201 | 1336 | 0.0547 |
| methionine | 201 | 1302 | 0.0566 |
| glycerol 3-phosphate (G3P) | 50 | 15365 | 0.0566 |
| Metabolite - 2800 | 50 | 16287 | 0.0593 |
| Metabolite - 11522 | 201 | 32839 | 0.0611 |
| Metabolite - 11421 | 200 | 32738 | 0.062 |
| Metabolite - 11881 | 201 | 33226 | 0.0637 |
| 4-methyl-2-oxopentanoate | 201 | 22116 | 0.0637 |
| quinate | 50 | 18335 | 0.0649 |
| pelargonate-9-0- | 201 | 12035 | 0.0676 |
| creatinine | 200 | 513 | 0.0676 |
| 3-methyl-2-oxobutyrate | 201 | 21047 | 0.0676 |
| Metabolite - 11235 | 201 | 32552 | 0.0692 |
| Metabolite - 6272 | 50 | 19377 | 0.071 |
| Metabolite - 10360 | 50 | 25402 | 0.0726 |
| saccharin | 201 | 21151 | 0.0734 |
| Metabolite - 11593 | 201 | 32910 | 0.0742 |
| ornithine | 50 | 1493 | 0.076 |
| cholate | 201 | 22842 | 0.0775 |
| 1,6-anhydroglucose | 50 | 21049 | 0.0787 |
| Metabolite - 11435 | 201 | 32752 | 0.0829 |
| Metabolite - 11832 | 201 | 33177 | 0.0891 |
| deoxycholate | 201 | 1114 | 0.0902 |
| Metabolite - 11880 | 201 | 33225 | 0.0902 |
| docosahexaenoate (DHA) | 50 | 19323 | 0.0927 |
| Metabolite - 12056 | 200 | 33408 | 0.0981 |
| Metabolite - 3075 | 50 | 12754 | 0.0987 |

Recursive pardoning analysis was carried out on the subjects. Baseline levels (i.e. prior to treatment) of the biomarker compounds were determined in the Responders (subjects with a post-treatment increase in Rd≥35%, N=28) and the Non-Responders (subjects with a post-treatment Rd increase of <15%, N=14). The results of this analysis showed that the subjects were classified with an AUC of 0.8214. The analysis further identified "Metabolite-11737" as a biomarker that is particularly important in the classification of responders and non-responders. Using the baseline level of only this biomarker, 22 of 28 Responders were correctly classified and 12 of 14 Non-Responders were correctly classified. This marker alone had a sensitivity of 78.6% and a specificity of 85.7%. The Positive Predictive Value (PPV) was 91.7% and the Negative Predictive Value (NPV) was 66.7%.

Biomarkers that are pharmacodynamic (PD) biomarkers of treatment effectiveness were identified through comparisons of non-responders (i.e. those with little or no change (<15%) in Rd between baseline and 12 weeks post-treatment) vs responders. The PD biomarkers were based on the difference between baseline and 12 weeks post-treatment. Biomarkers were identified that showed changes from baseline levels upon TZD treatment and tracked with the change in insulin sensitivity in those subjects. These biomarkers are listed in Table 28.

TABLE 28

Pharmacodynamic Biomarkers of Treatment Response

| COMPOUND | COMP_ID | LIB_ID | P-Value (Responder vs Non-Responder) |
|---|---|---|---|
| Metabolite - 11737 | 33082 | 200 | 0.0007 |
| Metabolite - 11849 | 33194 | 201 | 0.0013 |
| palmitoylglycerol (monopalmitin) | 21127 | 50 | 0.0041 |
| glutamate | 12751 | 50 | 0.0041 |
| glycerophosphorylcholine (GPC) | 15990 | 200 | 0.0043 |
| acetylcarnitine | 32198 | 200 | 0.0049 |
| gamma-glutamylphenylalanine | 33362 | 200 | 0.0052 |
| alpha-tocopherol | 1561 | 50 | 0.0053 |
| glucose | 20488 | 50 | 0.0062 |
| phenylalanine | 64 | 200 | 0.0071 |
| inositol | 19934 | 50 | 0.0075 |
| Metabolite - 9727 | 24077 | 50 | 0.0079 |
| Metabolite - 11385 | 32702 | 200 | 0.0083 |
| Metabolite - 11845 | 33190 | 201 | 0.0098 |
| tryptophan | 54 | 200 | 0.0107 |
| Metabolite - 10407 | 25522 | 50 | 0.0113 |
| erythritol | 20699 | 50 | 0.0136 |
| Metabolite - 11205 | 32519 | 200 | 0.0151 |
| Metabolite - 11883 | 33228 | 200 | 0.0168 |
| Metabolite - 10954 | 32734 | 200 | 0.0178 |
| methionine | 1302 | 201 | 0.0196 |
| Metabolite - 03832 | 32553 | 201 | 0.0209 |
| 5-oxoproline | 1494 | 200 | 0.0242 |
| Metabolite - 4611 | 17028 | 50 | 0.0242 |
| linoleate (18:2(n-6)) | 32673 | 201 | 0.0258 |
| galactonic acid | 27719 | 50 | 0.0259 |
| Metabolite - 11247 | 32564 | 201 | 0.0273 |
| dipalmitin | 27392 | 50 | 0.0297 |
| tyrosine | 1299 | 200 | 0.0317 |
| Metabolite - 11379 | 32696 | 201 | 0.035 |
| Metabolite - 11560 | 32877 | 201 | 0.0387 |
| Metabolite - 11437 | 32754 | 201 | 0.0491 |
| Metabolite - 11206 | 32520 | 200 | 0.0492 |
| Metabolite - 11475 | 32792 | 201 | 0.0564 |
| Metabolite - 11254 | 32571 | 200 | 0.0564 |
| Metabolite - 10610 | 27889 | 50 | 0.0564 |
| glycerol 3-phosphate (G3P) | 15365 | 50 | 0.0566 |
| gondoate-20-1-n-9 | 32402 | 201 | 0.0566 |
| Metabolite - 2800 | 16287 | 50 | 0.0593 |
| Metabolite - 11386 | 32703 | 200 | 0.06 |
| Metabolite - 4055 | 16120 | 50 | 0.06 |
| Metabolite - 11421 | 32738 | 200 | 0.062 |
| Metabolite - 11244 | 32561 | 201 | 0.0637 |
| Metabolite - 6486 | 19487 | 50 | 0.0637 |
| Metabolite - 7846 | 20950 | 50 | 0.0637 |
| quinate | 18335 | 50 | 0.0649 |

TABLE 28-continued

Pharmacodynamic Biomarkers of Treatment Response

| COMPOUND | COMP_ID | LIB_ID | P-Value (Responder vs Non-Responder) |
|---|---|---|---|
| Metabolite - 11881 | 33226 | 201 | 0.0649 |
| 3-methyl-2-oxovalerate | 15676 | 201 | 0.0676 |
| Metabolite - 9045 | 22602 | 50 | 0.0676 |
| Metabolite - 4360 | 16650 | 50 | 0.0676 |
| Metabolite - 11788 | 33133 | 200 | 0.0676 |
| Metabolite - 6272 | 19377 | 50 | 0.071 |
| 3-hydroxybutyrate (BHBA) | 542 | 50 | 0.071 |
| oleate (18:1(n-9)) | 32630 | 201 | 0.071 |
| Metabolite - 10360 | 25402 | 50 | 0.0726 |
| saccharin | 21151 | 201 | 0.0734 |
| Metabolite - 11593 | 32910 | 201 | 0.0742 |
| Metabolite - 11790 | 33135 | 200 | 0.0749 |
| kynurenine | 15140 | 200 | 0.076 |
| Metabolite - 4357 | 16634 | 50 | 0.076 |
| Metabolite - 3100 | 12782 | 50 | 0.076 |
| cholate | 22842 | 201 | 0.0775 |
| 1,6-anhydroglucose | 21049 | 50 | 0.0787 |
| Metabolite - 11887 | 33232 | 201 | 0.081 |
| glycerol | 15122 | 50 | 0.081 |
| Metabolite - 06126 | 32557 | 201 | 0.0829 |
| Metabolite - 4986 | 17627 | 50 | 0.0853 |
| Metabolite - 3099 | 12781 | 50 | 0.0902 |
| Metabolite - 11314 | 32631 | 200 | 0.0921 |
| docosahexaenoate (DHA) | 19323 | 50 | 0.0927 |
| Metabolite - 11522 | 32839 | 201 | 0.0954 |
| Metabolite - 01142 | 32747 | 201 | 0.0954 |
| Metabolite - 3075 | 12754 | 50 | 0.0987 |

Recursive pardoning analysis was carried out on the subjects. Baseline levels (i.e. prior to treatment) and post-treatment levels of the biomarker compounds were determined in the Responders (subjects with a post-treatment increase in Rd≥35%, N=28) and the Non-Responders (subjects with a post-treatment Rd increase of <15%, N=14). The results of this analysis showed that the subjects were classified with an AUC of 0.7679. Additional experiments are planned to evaluate the biomarkers as PD biomarkers for other insulin sensitivity, pre-diabetes and diabetes therapeutic agents (e.g. metformin, etc.) as well as treatments involving modification to diet (e.g. weight loss, nutrition) and lifestyle (e.g. exercise).

Example 5

Analytical Characterization of Unnamed Biomarkers Compounds

Table 29 below includes analytical characteristics of each of the unnamed metabolites listed in the Tables above. The table includes, for each listed Metabolite, the retention time (RT), retention index (RI), mass, quant mass, and polarity obtained using the analytical methods described above. "Mass" refers to the mass of the C12 isotope of the parent ion used in quantification of the compound. "Polarity" indicates the polarity of the quantitative ion as being either positive (+) or negative (−).

TABLE 29

Analytical characteristics of biomarker metabolites.

| COMP_ID | COMPOUND | LIBRARY | RT | RI | MASS | POLARITY |
|---|---|---|---|---|---|---|
| 25532 | Metabolite - 10413 | 50 | 12.53 | 2042.7 | 204.1 | +L |
| 25602 | Metabolite - 10432 | 50 | 12.29 | 2031.5 | 204 | +L |
| 27256 | Metabolite - 10500 | 50 | 5.3 | 1229.9 | 211 | +L |
| 27264 | Metabolite - 10503 | 50 | 7.28 | 1452.4 | 244 | +L |
| 27889 | Metabolite - 10610 | 50 | 11.93 | 1987 | 204 | +L |
| 30288 | Metabolite - 10750 | 50 | 5.51 | 1265 | 102.9 | +L |
| 30290 | Metabolite - 10752 | 50 | 6.07 | 1323.7 | 231 | +L |
| 30832 | Metabolite - 10814 | 50 | 12.84 | 2094 | 204.1 | +L |
| 31373 | Metabolite - 10878 | 50 | 8.22 | 1583 | 334.1 | +L |
| 31509 | Metabolite - 10931 | 50 | 12.02 | 1984 | 174.1 | +L |
| 31518 | Metabolite - 10933 | 50 | 11.99 | 1979 | 318.1 | +L |
| 12781 | Metabolite - 3099 | 50 | 11.77 | 2002.3 | 204 | +L |
| 12782 | Metabolite - 3100 | 50 | 11.85 | 2010.7 | 204 | +L |
| 12795 | Metabolite - 3113 | 50 | 12.73 | 2111.4 | 406.2 | +L |
| 16120 | Metabolite - 4055 | 50 | 12.04 | 2021.4 | 304.1 | +L |
| 16138 | Metabolite - 4080 - retired for 1-palmitoyl-sn-glycero-3 -phosphocholine | 50 | 14.02 | 2266.9 | 299 | +L |
| 16509 | Metabolite - 4273 | 50 | 10.34 | 1844.2 | 457.2 | +L |
| 16511 | Metabolite - 4274 | 50 | 10.37 | 1854.7 | 158.1 | +L |
| 16512 | Metabolite - 4275 - retired-part of X-3078 | 50 | 10.68 | 1884.6 | 345.2 | +L |
| 16518 | Metabolite - 4276 - retired for gamma-tocopherol* | 50 | 13.92 | 2261 | 223.1 | +L |
| 16634 | Metabolite - 4357 | 50 | 8 | 1540.5 | 216 | +L |
| 16650 | Metabolite - 4360 | 50 | 9.15 | 1678.4 | 347.2 | +L |
| 16665 | Metabolite - 4364 - retired for L -asparagine-3 | 50 | 10.66 | 1852.1 | 232 | +L |
| 16666 | Metabolite - 4365 | 50 | 11.05 | 1893.1 | 204 | +L |
| 16829 | Metabolite - 4503 | 50 | 8.39 | 1589.3 | 227.2 | +L |
| 17028 | Metabolite - 4611 - retired for erythronic acid* | 50 | 8.07 | 1546.9 | 292.1 | +L |
| 17330 | Metabolite - 4769 retired for glutamine -2 | 50 | 11.3 | 1916.6 | 156 | +L |
| 17389 | Metabolite - 4796 | 50 | 3.53 | 1043.2 | 117 | +L |
| 17690 | Metabolite - 5207 | 50 | 7.41 | 1493.6 | 151 | +L |
| 18120 | Metabolite - 5348 | 50 | 9.25 | 1681.5 | 217.9 | +L |
| 19462 | Metabolite - 6446 | 50 | 3.49 | 1021.1 | 204.1 | +L |
| 19478 | Metabolite - 6467 | 50 | 11.09 | 1893.4 | 320.1 | +L |
| 19487 | Metabolite - 6486 | 50 | 11.6 | 1949.8 | 217 | +L |
| 19576 | Metabolite - 6627 | 50 | 11.96 | 1990.7 | 304.2 | +L |
| 19983 | Metabolite - 6955 | 50 | 11.82 | 1979.1 | 306.1 | +L |
| 12162 | Metabolite - A-2339 | 50 | 3.86 | 1109.8 | 221.0 | +L |
| 12222 | Metabolite - A-2374 | 50 | 7.35 | 1510.9 | 188.0 | +L |
| 12803 | Metabolite - A-2441 | 50 | 13.94 | 2270.9 | 129.0 | +L |
| 16074 | Metabolite - A-2758 | 50 | 8.22 | 1597.1 | 211.0 | +L |
| 16285 | Metabolite - A-2798 | 50 | 3.44 | 1005.8 | 163.0 | +L |
| 16287 | Metabolite - A2800 | 50 | 3.53 | 1015.5 | 191.1 | +L |
| 24360 | Metabolite -10206 | 50 | 9.04 | 1639.0 | 243.0 | +L |
| 25402 | Metabolite -10360 | 50 | 10.23 | 1780.0 | 204.0 | +L |
| 25429 | Metabolite -10369 | 50 | 10.92 | 1859.0 | 333.0 | +L |
| 25459 | Metabolite -10395 | 50 | 9.94 | 1768.9 | 156.0 | +L |
| 25522 | Metabolite -10407 | 50 | 9.94 | 1748.0 | 217.1 | +L |
| 25548 | Metabolite -10419 | 50 | 16.29 | 2527.0 | 311.3 | +L |
| 25584 | Metabolite -10425 | 50 | 7.52 | 1488.8 | 123.9 | +L |
| 25597 | Metabolite -10427 | 50 | 11.21 | 1911.1 | 183.0 | +L |
| 25598 | Metabolite -10428 | 50 | 11.31 | 1922.0 | 156.0 | +L |
| 25599 | Metabolite -10429 | 50 | 11.60 | 1953.5 | 265.0 | +L |
| 25607 | Metabolite -10437 | 50 | 8.43 | 1596.0 | 331.1 | +L |
| 25609 | Metabolite -10439 | 50 | 8.84 | 1643.3 | 331.1 | +L |
| 25649 | Metabolite -10450 | 50 | 17.00 | 2643.0 | 371.3 | +L |
| 27137 | Metabolite -10498 | 50 | 12.06 | 1991.8 | 299.1 | +L |
| 27271 | Metabolite -10504 | 50 | 9.94 | 1763.0 | 348.2 | +L |
| 27272 | Metabolite -10505 | 50 | 10.82 | 1862.0 | 457.3 | +L |
| 27273 | Metabolite -10506 | 50 | 11.30 | 1914.0 | 218.1 | +L |
| 27275 | Metabolite -10507 | 50 | 11.97 | 1988.0 | 370.2 | +L |
| 27278 | Metabolite -10510 | 50 | 15.77 | 2470.0 | 297.2 | +L |
| 27279 | Metabolite -10511 | 50 | 17.12 | 2645.0 | 309.3 | +L |
| 27288 | Metabolite -10517 | 50 | 10.16 | 1775.0 | 419.2 | +L |
| 27326 | Metabolite -10527 | 50 | 11.71 | 1950.0 | 221.1 | +L |

TABLE 29-continued

Analytical characteristics of biomarker metabolites.

| COMP_ID | COMPOUND | LIBRARY | RT | RI | MASS | POLARITY |
|---|---|---|---|---|---|---|
| 27678 | Metabolite -10584 - retired for glucose-3 | 50 | 10.15 | 1779.0 | 217.0 | +L |
| 27841 | Metabolite -10595 | 50 | 4.14 | 1101.0 | 151.0 | +L |
| 27888 | Metabolite -10609 | 50 | 11.70 | 1961.0 | 348.2 | +L |
| 27890 | Metabolite -10611 | 50 | 12.03 | 1998.0 | 369.1 | +L |
| 28059 | Metabolite -10650 | 50 | 10.26 | 1800.6 | 345.1 | +L |
| 29817 | Metabolite -10683 | 50 | 5.12 | 1213.8 | 171.0 | +L |
| 30265 | Metabolite -10732 | 50 | 12.22 | 2024.0 | 204.0 | +L |
| 30273 | Metabolite -10736 | 50 | 10.03 | 1814.0 | 342.1 | +L |
| 30282 | Metabolite -10744 | 50 | 15.75 | 2503.0 | 311.2 | +L |
| 12533 | Metabolite -2915 | 50 | 3.77 | 1099.0 | 174.0 | +L |
| 12593 | Metabolite -2973 | 50 | 4.74 | 1213.4 | 281.0 | +L |
| 12604 | Metabolite -2981 | 50 | 5.21 | 1265.2 | 211.0 | +L |
| 12609 | Metabolite -2986 | 50 | 5.56 | 1304.3 | 201.0 | +L |
| 12625 | Metabolite -3002 | 50 | 6.74 | 1440.8 | 296.0 | +L |
| 12626 | Metabolite -3003 | 50 | 6.79 | 1446.6 | 218.0 | +L |
| 12638 | Metabolite -3011 | 50 | 7.08 | 1479.2 | 174.0 | +L |
| 12639 | Metabolite -3012 | 50 | 7.17 | 1489.8 | 232.0 | +L |
| 12644 | Metabolite -3016 | 50 | 7.58 | 1537.5 | 186.0 | +L |
| 12645 | Metabolite -3017 | 50 | 7.61 | 1541.4 | 246.0 | +L |
| 12647 | Metabolite -3019 | 50 | 7.74 | 1556.4 | 260.0 | +L |
| 12648 | Metabolite -3020 | 50 | 7.81 | 1564.1 | 292.0 | +L |
| 12650 | Metabolite -3022 | 50 | 7.98 | 1584.9 | 142.0 | +L |
| 12656 | Metabolite -3025 | 50 | 8.11 | 1600.3 | 274.0 | +L |
| 12658 | Metabolite -3026 | 50 | 8.17 | 1606.1 | 274.0 | +L |
| 12663 | Metabolite -3030 | 50 | 8.62 | 1659.7 | 320.0 | +L |
| 12666 | Metabolite -3033 | 50 | 8.88 | 1689.4 | 117.0 | +L |
| 12667 | Metabolite -3034 | 50 | 8.92 | 1694.9 | 299.0 | +L |
| 12673 | Metabolite -3040 | 50 | 9.27 | 1735.7 | 274.0 | +L |
| 12726 | Metabolite -3058 | 50 | 9.70 | 1786.9 | 335.0 | +L |
| 12742 | Metabolite -3067 | 50 | 10.02 | 1824.2 | 132.0 | +L |
| 12751 | Metabolite -3073 | 50 | 10.17 | 1838.8 | 362.0 | +L |
| 12753 | Metabolite -3074 | 50 | 10.22 | 1844.5 | 204.0 | +L |
| 12754 | Metabolite -3075 | 50 | 10.36 | 1857.9 | 204.0 | +L |
| 12756 | Metabolite -3077 | 50 | 10.44 | 1866.2 | 308.0 | +L |
| 12757 | Metabolite -3078 | 50 | 10.65 | 1887.0 | 203.0 | +L |
| 12767 | Metabolite -3087 | 50 | 11.19 | 1942.0 | 174.0 | +L |
| 12768 | Metabolite -3088 | 50 | 11.23 | 1946.1 | 372.0 | +L |
| 12770 | Metabolite -3090 | 50 | 11.31 | 1955.0 | 243.0 | +L |
| 12771 | Metabolite -3091 | 50 | 11.41 | 1966.2 | 232.0 | +L |
| 12773 | Metabolite -3093 | 50 | 11.50 | 1975.6 | 204.0 | +L |
| 12774 | Metabolite -3094 | 50 | 11.55 | 1980.6 | 299.0 | +L |
| 12777 | Metabolite -3097 | 50 | 11.64 | 1990.4 | 204.0 | +L |
| 12780 | Metabolite -3098 | 50 | 11.75 | 2003.0 | 308.0 | +L |
| 12783 | Metabolite -3101 | 50 | 11.93 | 2022.2 | 290.0 | +L |
| 12785 | Metabolite -3103 | 50 | 12.09 | 2039.8 | 290.0 | +L |
| 12789 | Metabolite -3107 | 50 | 12.21 | 2053.2 | 204.0 | +L |
| 12790 | Metabolite -3108 | 50 | 12.24 | 2056.5 | 246.0 | +L |
| 12791 | Metabolite -3109 | 50 | 12.56 | 2092.6 | 202.0 | +L |
| 12796 | Metabolite -3114 | 50 | 12.79 | 2120.6 | 204.0 | +L |
| 16028 | Metabolite -3998 | 50 | 5.22 | 1252.7 | 171.0 | +L |
| 16044 | Metabolite -4005 | 50 | 6.53 | 1401.3 | 86.0 | +L |
| 16060 | Metabolite -4014 | 50 | 7.17 | 1474.9 | 252.0 | +L |
| 16070 | Metabolite -4019 | 50 | 7.68 | 1534.5 | 174.0 | +L |
| 16071 | Metabolite -4020 | 50 | 7.91 | 1561.5 | 220.0 | +L |
| 16116 | Metabolite -4051 | 50 | 11.56 | 1970.2 | 357.0 | +L |
| 16290 | Metabolite -4133 | 50 | 4.35 | 1108.9 | 198.0 | +L |
| 16308 | Metabolite -4147 | 50 | 10.07 | 1767.1 | 290.0 | +L |
| 16496 | Metabolite -4251 | 50 | 4.09 | 1130.7 | 217.0 | +L |
| 16506 | Metabolite -4271 | 50 | 9.69 | 1777.4 | 419.0 | +L |
| 16653 | Metabolite -4361 | 50 | 9.40 | 1706.2 | 232.0 | +L |
| 16655 | Metabolite -4362 | 50 | 10.02 | 1779.9 | 319.0 | +L |
| 16819 | Metabolite -4496 | 50 | 6.76 | 1398.2 | 204.0 | +L |
| 16821 | Metabolite -4498 | 50 | 7.06 | 1434.9 | 103.0 | +L |
| 16831 | Metabolite -4504 | 50 | 8.46 | 1597.1 | 244.0 | +L |
| 16843 | Metabolite -4510 | 50 | 9.70 | 1740.1 | 254.0 | +L |
| 16848 | Metabolite -4511 | 50 | 10.09 | 1788.4 | 206.0 | +L |
| 16859 | Metabolite -4516 | 50 | 11.00 | 1886.5 | 217.0 | +L |
| 16860 | Metabolite -4517 | 50 | 11.06 | 1892.7 | 217.0 | +L |
| 16865 | Metabolite -4522 | 50 | 12.26 | 2025.4 | 217.0 | +L |
| 16983 | Metabolite -4598 | 50 | 6.69 | 1392.2 | 170.0 | +L |
| 16984 | Metabolite -4599 | 50 | 7.42 | 1471.1 | 113.0 | +L |
| 17064 | Metabolite -4624 | 50 | 10.01 | 1779.1 | 342.0 | +L |
| 17083 | Metabolite -4634 | 50 | 11.00 | 1884.3 | 333.0 | +L |
| 17327 | Metabolite -4767 | 50 | 8.77 | 1626.2 | 117.0 | +L |
| 17359 | Metabolite -4791 | 50 | 10.29 | 1796.4 | 366.5 | +L |

TABLE 29-continued

Analytical characteristics of biomarker metabolites.

| COMP_ID | COMPOUND | LIBRARY | RT | RI | MASS | POLARITY |
|---|---|---|---|---|---|---|
| 17390 | Metabolite -4806 | 50 | 4.20 | 1122.8 | 105.0 | +L |
| 17614 | Metabolite -4966 | 50 | 9.66 | 1749.4 | 218.0 | +L |
| 17627 | Metabolite -4986 | 50 | 11.56 | 1956.4 | 204.0 | +L |
| 17971 | Metabolite -5210 | 50 | 8.47 | 1616.4 | 254.0 | +L |
| 17975 | Metabolite -5211 | 50 | 8.77 | 1652.1 | 326.0 | +L |
| 17978 | Metabolite -5213 | 50 | 8.97 | 1675.3 | 111.0 | +L |
| 17987 | Metabolite -5228 | 50 | 6.97 | 1442.5 | 181.0 | +L |
| 18118 | Metabolite -5346 | 50 | 8.33 | 1573.0 | 202.0 | +L |
| 18122 | Metabolite -5349 | 50 | 10.10 | 1782.2 | 312.0 | +L |
| 18146 | Metabolite -5366 | 50 | 12.49 | 2044.7 | 204.0 | +L |
| 18147 | Metabolite -5367 | 50 | 12.77 | 2079.3 | 171.0 | +L |
| 18232 | Metabolite -5403 | 50 | 5.92 | 1300.2 | 319.0 | +L |
| 18273 | Metabolite -5420 | 50 | 9.09 | 1669.0 | 417.0 | +L |
| 18384 | Metabolite -5487 | 50 | 7.01 | 1426.3 | 204.0 | +L |
| 18388 | Metabolite -5491 | 50 | 8.30 | 1575.9 | 129.0 | +L |
| 18868 | Metabolite -5847 | 50 | 12.35 | 2040.0 | 288.2 | +L |
| 18929 | Metabolite -5907 | 50 | 8.69 | 1643.2 | 229.1 | +L |
| 19110 | Metabolite -5978 | 50 | 7.52 | 1468.9 | 232.1 | +L |
| 19362 | Metabolite -6226 | 50 | 4.38 | 1137.4 | 154.0 | +L |
| 19363 | Metabolite -6227 | 50 | 5.00 | 1210.5 | 196.1 | +L |
| 19364 | Metabolite -6246 | 50 | 6.94 | 1428.2 | 160.1 | +L |
| 19367 | Metabolite -6266 | 50 | 9.15 | 1683.5 | 240.2 | +L |
| 19368 | Metabolite -6267 | 50 | 9.32 | 1704.5 | 257.1 | +L |
| 19370 | Metabolite -6268 | 50 | 9.91 | 1773.8 | 271.1 | +L |
| 19372 | Metabolite -6269 - retired for inositol-3 | 50 | 10.88 | 1880.9 | 217.1 | +L |
| 19374 | Metabolite -6270 | 50 | 11.35 | 1929.6 | 320.2 | +L |
| 19377 | Metabolite -6272 | 50 | 12.60 | 2069.6 | 131.0 | +L |
| 19383 | Metabolite -6286 | 50 | 16.36 | 2553.7 | 311.3 | +L |
| 19397 | Metabolite -6326 | 50 | 7.66 | 1510.9 | 144.1 | +L |
| 19402 | Metabolite -6346 | 50 | 8.00 | 1550.8 | 263.2 | +L |
| 19405 | Metabolite -6347 | 50 | 8.16 | 1568.7 | 244.1 | +L |
| 19414 | Metabolite -6350 | 50 | 11.41 | 1937.2 | 169.0 | +L |
| 19490 | Metabolite -6488 | 50 | 12.25 | 2021.7 | 204.1 | +L |
| 19494 | Metabolite -6506 | 50 | 12.81 | 2084.7 | 204.1 | +L |
| 19596 | Metabolite -6647 | 50 | 9.13 | 1696.7 | 197.1 | +L |
| 19597 | Metabolite -6648 | 50 | 9.17 | 1702.1 | 313.2 | +L |
| 19599 | Metabolite -6649 | 50 | 11.47 | 1955.4 | 299.2 | +L |
| 19623 | Metabolite -6671 | 50 | 9.65 | 1738.4 | 229.0 | +L |
| 19955 | Metabolite -6907 | 50 | 9.22 | 1686.9 | 337.1 | +L |
| 19961 | Metabolite -6913 | 50 | 9.53 | 1726.0 | 171.0 | +L |
| 19968 | Metabolite -6930 | 50 | 10.32 | 1809.4 | 331.2 | +L |
| 19969 | Metabolite -6931 | 50 | 10.35 | 1819.6 | 267.1 | +L |
| 20299 | Metabolite -7266 | 50 | 7.82 | 1517.6 | 115.0 | +L |
| 20950 | Metabolite -7846 | 50 | 5.10 | 1208.1 | 145.1 | +L |
| 21011 | Metabolite -7888 | 50 | 15.96 | 2513.3 | 311.3 | +L |
| 21012 | Metabolite -7889 | 50 | 16.83 | 2629.4 | 311.3 | +L |
| 21013 | Metabolite -7890 | 50 | 17.76 | 2752.2 | 129.0 | +L |
| 21415 | Metabolite -8209 | 50 | 14.77 | 2338.0 | 456.5 | +L |
| 21421 | Metabolite -8214 | 50 | 17.13 | 2646.6 | 311.2 | +L |
| 21586 | Metabolite -8359 | 50 | 7.14 | 1457.8 | 253.0 | +L |
| 21630 | Metabolite -8402 | 50 | 15.27 | 2424.0 | 283.1 | +L |
| 21631 | Metabolite -8403 | 50 | 15.96 | 2516.6 | 309.2 | +L |
| 22020 | Metabolite -8749 - retired for fructose-4 | 50 | 9.74 | 1763.0 | 204.1 | +L |
| 22032 | Metabolite -8766 | 50 | 12.22 | 2034.0 | 315.1 | +L |
| 22054 | Metabolite -8792 | 50 | 17.61 | 2737.0 | 129.0 | +L |
| 22320 | Metabolite -8889 | 50 | 8.62 | 1635.0 | 521.2 | +L |
| 22480 | Metabolite -8987 | 50 | 7.02 | 1449.7 | 160.1 | +L |
| 22494 | Metabolite -8994 | 50 | 10.76 | 1879.0 | 447.2 | +L |
| 22507 | Metabolite -9010 - retired for adenosine - 1 | 50 | 12.98 | 2126.2 | 217.1 | +L |
| 22548 | Metabolite -9026 | 50 | 8.45 | 1600.0 | 156.0 | +L |
| 22555 | Metabolite -9027 | 50 | 8.50 | 1605.0 | 357.2 | +L |
| 22570 | Metabolite -9033 | 50 | 9.61 | 1736.4 | 217.1 | +L |
| 22572 | Metabolite -9034 | 50 | 9.63 | 1739.1 | 241.1 | +L |
| 22577 | Metabolite -9035 | 50 | 9.82 | 1760.7 | 285.1 | +L |
| 22600 | Metabolite -9043 | 50 | 11.75 | 1974.1 | 204.1 | +L |
| 22601 | Metabolite -9044 | 50 | 13.38 | 2169.0 | 204.1 | +L |
| 22602 | Metabolite -9045 | 50 | 13.91 | 2239.0 | 450.3 | +L |
| 22609 | Metabolite -9047 | 50 | 8.06 | 1574.0 | 243.2 | +L |
| 22649 | Metabolite -9108 | 50 | 11.20 | 1896.0 | 156.0 | +L |
| 22880 | Metabolite -9286 | 50 | 8.77 | 1617.5 | 221.0 | +L |
| 22895 | Metabolite -9299 | 50 | 10.54 | 1827.5 | 305.1 | +L |
| 22993 | Metabolite -9448 | 50 | 14.86 | 2352.5 | 343.2 | +L |

TABLE 29-continued

Analytical characteristics of biomarker metabolites.

| COMP_ID | COMPOUND | LIBRARY | RT | RI | MASS | POLARITY |
|---|---|---|---|---|---|---|
| 24074 | Metabolite -9706 | 50 | 4.39 | 1107.0 | 190.0 | +L |
| 24076 | Metabolite -9726 | 50 | 4.91 | 1167.0 | 245.0 | +L |
| 24077 | Metabolite -9727 | 50 | 5.24 | 1204.0 | 177.0 | +L |
| 10737 | Isobar 01 | 61 | 1.45 | 1481.0 | 225.0 | −i |
| 10743 | Isobar 04 | 61 | 1.52 | 1567.0 | 195.0 | −i |
| 10746 | Isobar 06 | 61 | 2.13 | 2160.0 | 118.0 | +i |
| 10750 | Isobar 08 | 61 | 10.04 | 10116.0 | 138.0 | +i |
| 12459 | Isobar 10 | 61 | 1.40 | 1527.0 | 147.0 | +i |
| 16233 | Isobar 13 | 61 | 1.40 | 1530.0 | 193.0 | −i |
| 16232 | Isobar 17 | 61 | 1.49 | 1620.0 | 175.0 | +i |
| 16235 | Isobar 19 | 61 | 1.55 | 1700 | 199 | −i |
| 16244 | Isobar 21 | 61 | 1.59 | 1620.0 | 241.0 | +i |
| 16228 | Isobar 22 | 61 | 1.55 | 1635.0 | 148.0 | +i |
| 16229 | Isobar 24 | 61 | 1.43 | 1545.0 | 153.0 | +i |
| 16226 | Isobar 28 | 61 | 1.46 | 1525.0 | 120.0 | +i |
| 18829 | Isobar 45 | 61 | 8.38 | 8475.0 | 166.2 | +i |
| 18882 | Isobar 47 | 61 | 15.51 | 15700.0 | 498.4 | −i |
| 21404 | Isobar 48 | 61 | 1.50 | 1550.0 | 106.1 | +i |
| 21410 | Isobar 52 | 61 | 1.55 | 1650.0 | 134.1 | +i |
| 21418 | Isobar 56 | 61 | 2.45 | 2850.0 | 130.1 | +i |
| 22258 | Isobar 58 | 61 | 1.38 | 1620.0 | 164.0 | +i |
| 22259 | Isobar 59 | 61 | 1.82 | 1700.0 | 189.1 | +i |
| 22261 | Isobar 60 | 61 | 4.26 | 4725.0 | 148.9 | −i |
| 22262 | Isobar 61 | 61 | 9.30 | 9675.0 | 174.8 | −i |
| 22803 | Isobar 66 | 61 | 15.06 | 15500.0 | 450.2 | +i |
| 27773 | Isobar 71 | 61 | 1.57 | 1700.0 | 206.9 | −i |
| 32718 | Metabolite - 01342_200 | 200 | 2.8 | 2848 | 265.1 | +i |
| 32735 | Metabolite - 01911_200 | 200 | 4.26 | 4275 | 464.1 | +i |
| 32596 | Metabolite - 02250_200 - retired for piperine | 200 | 5.14 | 5158 | 286.2 | +i |
| 32672 | Metabolite - 02546_200 | 200 | 0.75 | 764 | 129.2 | +i |
| 32829 | Metabolite - 03653_200 - retired for stachydrine | 200 | 0.82 | 826 | 144.2 | +i |
| 32595 | Metabolite - 08893_200 | 200 | 5.19 | 5200 | 431.9 | +i |
| 32734 | Metabolite - 10954_200-retired for (+/−) octanoyl carnitine | 200 | 4.14 | 4229 | 288.2 | +i |
| 32514 | Metabolite - 11200 - retired for 1-palmitoyl-sn-glycero-3-phosphocholine | 200 | 5.62 | 5637 | 496.4 | +i |
| 32516 | Metabolite - 11202 - retired for 1-stearoyl-sn-glycero-3-phosphocholine | 200 | 5.8 | 5823 | 524.4 | +i |
| 32517 | Metabolite - 11203 - retired for 1-Oleoyl-sn-glycero-3-phosphocholine | 200 | 5.65 | 5665 | 522.4 | +i |
| 32518 | Metabolite - 11204 | 200 | 5.26 | 5263 | 229.2 | +i |
| 32519 | Metabolite - 11205 - retired for 1-linoleoyl GPC | 200 | 5.55 | 5558 | 520.4 | +i |
| 32520 | Metabolite - 11206 | 200 | 0.59 | 575 | 138.8 | +i |
| 32578 | Metabolite - 11261 | 200 | 3.69 | 3600 | 286.2 | +i |
| 32631 | Metabolite - 11314 | 200 | 0.64 | 634 | 243 | +i |
| 32632 | Metabolite - 11315 | 200 | 1.19 | 1210 | 130.2 | +i |
| 32644 | Metabolite - 11327 | 200 | 5.16 | 5176 | 269.2 | +i |
| 32652 | Metabolite - 11335 | 200 | 0.97 | 991 | 229.2 | +i |
| 32654 | Metabolite - 11337 | 200 | 1 | 1020 | 160.2 | +i |
| 32671 | Metabolite - 11354 | 200 | 0.76 | 770 | 146.2 | +i |
| 32738 | Metabolite - 11421 | 200 | 4.54 | 4575 | 314.2 | +i |
| 32786 | Metabolite - 11469 | 200 | 3.82 | 3874 | 239.1 | +i |
| 32793 | Metabolite - 11476 | 200 | 4.52 | 4525 | 189.1 | +i |
| 32875 | Metabolite - 11558 | 200 | 5.64 | 5606 | 420.2 | +i |
| 32971 | Metabolite - 11654 - retired for isovaleryl-L-carnitine | 200 | 2.53 | 2500 | 246.2 | +i |

TABLE 29-continued

Analytical characteristics of biomarker metabolites.

| COMP_ID | COMPOUND | LIBRARY | RT | RI | MASS | POLARITY |
|---|---|---|---|---|---|---|
| 33080 | Metabolite - 11735 | 200 | 2.51 | 2584 | 207.2 | +i |
| 33081 | Metabolite - 11736 | 200 | 2.58 | 2639 | 379.4 | +i |
| 33082 | Metabolite - 11737 | 200 | 2.7 | 2747 | 235.2 | +i |
| 33132 | Metabolite - 11787 | 200 | 1.13 | 1126 | 148.1 | +i |
| 33135 | Metabolite - 11790 | 200 | 3.4 | 3472 | 823.3 | +i |
| 33138 | Metabolite - 11793 | 200 | 3.57 | 3634 | 601.1 | +i |
| 33228 | Metabolite - 11883 | 200 | 5.54 | 5524 | 544.3 | +i |
| 33323 | Metabolite - 11977 | 200 | 3.21 | 3287 | 270.1 | +i |
| 33403 | Metabolite - 12051 | 200 | 5.83 | 5739 | 456.4 | +i |
| 33408 | Metabolite - 12056 | 200 | 1.12 | 1129 | 156.2 | +i |
| 33531 | Metabolite - 12116 | 200 | 1.6 | 1640 | 286.1 | +i |
| 33587 | Isobar: cis-9, cis-11, trans-11 eicosenoate | 201 | 6.13 | 5955 | 309.4 | −i |
| 32747 | Metabolite - 01142_201-retired for 2-hydroxy-3-methylbutyric acid | 201 | 1.19 | 1176 | 117.2 | −i |
| 32588 | Metabolite - 01327_201 | 201 | 4.25 | 4242 | 583.2 | −i |
| 32609 | Metabolite - 01345_201 - retired for epiandrosterone sulfate | 201 | 4.9 | 4887 | 369.2 | −i |
| 32587 | Metabolite - 02249_201 | 201 | 4.03 | 4025 | 267.2 | −i |
| 32550 | Metabolite - 02272_201 | 201 | 1.97 | 1958 | 189 | −i |
| 32756 | Metabolite - 02276_201 | 201 | 3.35 | 3339 | 199.1 | −i |
| 32553 | Metabolite - 03832_201 | 201 | 2.2 | 2199 | 173.1 | −i |
| 32557 | Metabolite - 06126_201 | 201 | 2.69 | 2684 | 203.1 | −i |
| 32753 | Metabolite - 09789_201 | 201 | 2.62 | 2613 | 153.1 | −i |
| 32548 | Metabolite - 11231 | 201 | 1.47 | 1471 | 330 | −i |
| 32561 | Metabolite - 11244 | 201 | 3.78 | 3771 | 224.2 | −i |
| 32564 | Metabolite - 11247 | 201 | 3.94 | 3932 | 213.1 | −i |
| 32616 | Metabolite - 11299 | 201 | 4.9 | 4893 | 507.2 | −i |
| 32619 | Metabolite - 11302 | 201 | 5.01 | 4998 | 397.3 | −i |
| 32625 | Metabolite - 11308 | 201 | 5.15 | 5133 | 365.3 | −i |
| 32635 | Metabolite - 11318 | 201 | 5.81 | 5699 | 476.3 | −i |
| 32637 | Metabolite - 11320 - retired duplicate of X-12528 | 201 | 5.85 | 5740 | 593.9 | −i |
| 32648 | Metabolite - 11331 - retired EDTA ions | 201 | 0.69 | 686 | 164.2 | −i |
| 32656 | Metabolite - 11339 - retired-EDTA ions | 201 | 0.69 | 689 | 156.2 | −i |
| 32682 | Metabolite - 11365 - retired for arachidonic acid | 201 | 5.61 | 5527 | 303.3 | −i |
| 32696 | Metabolite - 11379 - retired for cis-10-heptadecenoic acid | 201 | 5.65 | 5566 | 267.3 | −i |
| 32732 | Metabolite - 11415 - retired-EDTA ions | 201 | 0.69 | 692 | 313.1 | −i |
| 32748 | Metabolite - 11431 | 201 | 1.58 | 1575 | 330 | −i |
| 32754 | Metabolite - 11437 | 201 | 2.89 | 2888 | 231 | −i |
| 32757 | Metabolite - 11440 | 201 | 3.58 | 3571 | 246.3 | −i |
| 32760 | Metabolite - 11443 | 201 | 3.92 | 3910 | 225.3 | −i |
| 32761 | Metabolite - 11444 | 201 | 3.99 | 3983 | 541.2 | −i |
| 32769 | Metabolite - 11452 | 201 | 4.12 | 4109 | 352.1 | −i |
| 32792 | Metabolite - 11475 | 201 | 4.25 | 4240 | 383.2 | −i |
| 32795 | Metabolite - 11478 | 201 | 4.3 | 4286 | 165.2 | −i |
| 32807 | Metabolite - 11490 | 201 | 4.77 | 4762 | 279.8 | −i |
| 32813 | Metabolite - 11496 | 201 | 5.58 | 5508 | 271.3 | −i |
| 32839 | Metabolite - 11522 | 201 | 4.76 | 4754 | 313.2 | −i |
| 32848 | Metabolite - 11531 | 201 | 4.86 | 4850 | 391.3 | −i |
| 32850 | Metabolite - 11533 | 201 | 4.91 | 4904 | 243.2 | −i |
| 32855 | Metabolite - 11538 | 201 | 4.93 | 4920 | 311.3 | −i |
| 32877 | Metabolite - 11560 | 201 | 5.29 | 5245 | 295.3 | −i |
| 32910 | Metabolite - 11593 | 201 | 0.79 | 790 | 189.2 | −i |
| 32970 | Metabolite - 11653 | 201 | 5.82 | 5686 | 331.3 | −i |
| 33172 | Metabolite - 11827 | 201 | 1.56 | 1575 | 312.1 | −i |
| 33177 | Metabolite - 11832 | 201 | 1.95 | 1962 | 216.1 | −i |

TABLE 29-continued

Analytical characteristics of biomarker metabolites.

| COMP_ID | COMPOUND | LIBRARY | RT | RI | MASS | POLARITY |
|---|---|---|---|---|---|---|
| 33185 | Metabolite - 11840 | 201 | 2.56 | 2574 | 135.2 | −i |
| 33190 | Metabolite - 11845 | 201 | 2.87 | 2891 | 615 | −i |
| 33194 | Metabolite - 11849 | 201 | 3.2 | 3229 | 266.2 | −i |
| 33198 | Metabolite - 11853 | 201 | 3.59 | 3602 | 187.1 | −i |
| 33210 | Metabolite - 11865 | 201 | 5.04 | 5037 | 456.2 | −i |
| 33219 | Metabolite - 11874 - retired for cis-5-Dodecenoic acid | 201 | 5.23 | 5199 | 197.3 | −i |
| 33225 | Metabolite - 11880 | 201 | 5.44 | 5378 | 537.4 | −i |
| 33226 | Metabolite - 11881 | 201 | 5.48 | 5414 | 380.3 | −i |
| 33227 | Metabolite - 11882 - retired for cis-5,8,11,14,17-eicosapentaenoic acid | 201 | 5.52 | 5445 | 301.3 | −i |
| 33232 | Metabolite - 11887 - retired for cis-11,14-eicosadienoic acid | 201 | 5.85 | 5736 | 307.4 | −i |
| 33237 | Metabolite - 11892 | 201 | 0.71 | 710 | 367.1 | −i |
| 33380 | Metabolite - 12029 | 201 | 0.68 | 683 | 329.1 | −i |
| 33388 | Metabolite - 12037 - retired for cis-10-nonadecenoic acid | 201 | 5.88 | 5795 | 295.4 | −i |
| 33389 | Metabolite - 12038 | 201 | 5.82 | 5736 | 245.3 | −i |
| 33415 | Metabolite - 12063 | 201 | 4.82 | 4822 | 427.2 | −i |
| 33416 | Metabolite - 12064 | 201 | 1 | 999 | 101.3 | −i |

While the invention has been described in detail and with reference to specific embodiments thereof, it will be apparent to one skilled in the art that various changes and modifications can be made without departing from the spirit and scope of the invention.

What is claimed is:

1. A method of classifying a subject according to glucose tolerance as having normal glucose tolerance (NGT), impaired glucose tolerance (IGT), or type-2 diabetes, the method comprising:
analyzing a biological sample from a subject to determine a level(s) of one or more biomarkers for glucose tolerance in the sample, wherein the one or more biomarkers are selected from the group consisting of 2-hydroxybutyrate, pantothenate, linoleoyl LPC, and 4-methyl-2-oxopentanoate; and
comparing the level(s) of the one or more biomarkers in the sample to glucose tolerance reference levels of the one or more biomarkers in order to classify the subject as having NGT, IGT, or type-2 diabetes.

2. The method of claim 1, further comprising
analyzing the biological sample from the subject to determine a level(s) of one or more additional biomarkers for glucose tolerance in the sample, wherein the one or more additional biomarkers are selected from the group consisting of trigonelline (N-methylnicotinate), hydrocinnamic acid, creatine, oleate, xanthine, mannose, 3-hydroxybutyrate, alpha-ketoglutarate, 3-methyl-2-oxobutyrate, 3-methyl-2-oxovalerate, glycine, isoleucine, leucine, phenylalanine, serine, tyrosine, oleoyl LPC, linolenate, linoleate, glycerophosphorylcholine (GPC), stearate, adrenate, and valine;
wherein the comparing step further comprises comparing the level(s) of the one or more additional biomarkers in the sample to glucose tolerance reference levels of the one or more additional biomarkers in order to classify the subject as having NGT, IGT, or type-2 diabetes.

3. The method of claim 2, wherein the method further comprises determining one or more of the subject's measurements of fasting plasma insulin, fasting plasma glucose, fasting plasma pro-insulin, fasting free fatty acids, HDL-cholesterol, LDL-cholesterol, C-peptide, adiponectin, peptide YY, hemoglobin A1C, waist circumference, body weight, and body mass index.

4. The method of claim 3, wherein the method further comprises using one or more of the determined level(s) of the one or more biomarkers, the determined level(s) of the one or more additional biomarkers, and the one or more determined measurements of the subject in a mathematical model to classify the subject as having NGT, IGT, or type-2 diabetes.

5. The method of claim 1, wherein the biological sample is blood, blood plasma, or blood serum.

6. The method of claim 1, wherein the analysis method for the sample is mass spectrometry.

7. The method of claim 1, wherein the biological sample is blood, blood plasma, or blood serum and the analysis method for the sample is mass spectrometry.

8. A method of classifying a subject according to glucose tolerance as having normal glucose tolerance (NGT), impaired glucose tolerance (IGT), or type-2 diabetes, the method comprising:
analyzing a biological sample from a subject to determine a level of 2-hydroxybutyrate; and
comparing the level of 2-hydroxybutyrate in the sample to a glucose tolerance reference level of 2-hydroxybutyrate in order to classify the subject as having NGT, IGT, or type-2 diabetes.

9. The method of claim 8, further comprising:
analyzing the biological sample from the subject to determine a level(s) of one or more additional biomarkers for glucose tolerance in the sample, wherein the one or more additional biomarkers are selected from the group consisting of trigonelline (N-methylnicotinate), hydrocinnamic acid, pantothenate, linoleoyl LPC, creatine, oleate, xanthine, mannose, 3-hydroxybutyrate, alpha-ketoglutarate, 3-methyl-2-oxobutyrate, 3-methyl-2-oxovalerate, 4-methyl-2-oxopentanoate, glycine, isoleucine, leucine, phenylalanine, serine, tyrosine, oleoyl LPC, linolenate, linoleate, glycerophosphorylcholine (GPC), stearate, adrenate, and valine;
  wherein the comparing step further comprises comparing the level(s) of the one or more additional biomarkers in the sample to glucose tolerance reference levels of the one or more additional biomarkers in order to classify the subject as having NGT, IGT, or type-2 diabetes.

10. The method of claim 9, wherein the method further comprises determining one or more of the subject's measurements of fasting plasma insulin, fasting plasma glucose, fasting plasma pro-insulin, fasting free fatty acids, HDL-cholesterol, LDL-cholesterol, C-peptide, adiponectin, peptide YY, hemoglobin A1C, waist circumference, body weight, and body mass index.

11. The method of claim 10, wherein the method further comprises using one or more of the determined level of 2-hydroxybutyrate, the determined level(s) of the one or more additional biomarkers, and the one or more determined measurements of the subject in a mathematical model to classify the subject as having NGT, IGT, or type-2 diabetes.

12. The method of claim 8, wherein the biological sample is blood, blood plasma, or blood serum.

13. The method of claim 8, wherein the analysis method for the sample is mass spectrometry.

14. The method of claim 8, wherein the biological sample is blood, blood plasma, or blood serum and the analysis method for the sample is mass spectrometry.

15. A method of classifying a subject according to glucose tolerance as having normal glucose tolerance (NGT), impaired glucose tolerance (IGT), or type-2 diabetes, the method comprising
  analyzing a biological sample from a subject to determine levels of biomarkers for glucose tolerance in the sample, wherein the biomarkers comprise all of 2-hydroxybutyrate, pantothenate, linoleoyl LPC, oleate, 3-hydroxybutyrate, 4-methyl-2-oxopentanoate, and serine; and
  comparing the levels of the biomarkers in the sample to glucose tolerance reference levels of the biomarkers in order to classify the subject as having NGT, IGT, or type-2 diabetes.

16. The method of claim 15, further comprising:
  analyzing the biological sample from the subject to determine a level(s) of one or more additional biomarkers for glucose tolerance in the sample, wherein the one or more additional biomarkers are selected from the group consisting of trigonelline (N-methylnicotinate), hydrocinnamic acid, creatine, xanthine, mannose, alpha-ketoglutarate, 3-methyl-2-oxobutyrate, 3-methyl-2-oxovalerate, glycine, isoleucine, leucine, phenylalanine, tyrosine, oleoyl LPC, linolenate, linoleate, glycerophosphorylcholine (GPC), stearate, adrenate, and valine;
  wherein the comparing step further comprises comparing the level(s) of the one or more additional biomarkers in the sample to glucose tolerance reference levels of the one or more additional biomarkers in order to classify the subject as having NGT, IGT, or type-2 diabetes.

17. The method of claim 16, wherein the method further comprises determining one or more of the subject's measurements of fasting plasma insulin, fasting plasma glucose, fasting plasma pro-insulin, fasting free fatty acids, HDL-cholesterol, LDL-cholesterol, C-peptide, adiponectin, peptide YY, hemoglobin A1C, waist circumference, body weight, and body mass index.

18. The method of claim 17, wherein the method further comprises using one or more of the determined levels of the biomarkers, the determined level(s) of the one or more additional biomarkers, and one or more of the determined measurements of the subject in a mathematical model to classify the subject as having NGT, IGT, or type-2 diabetes.

19. The method of claim 15, wherein the biological sample is blood, blood plasma, or blood serum.

20. The method of claim 15, wherein the analysis method for the sample is mass spectrometry.

* * * * *

UNITED STATES PATENT AND TRADEMARK OFFICE
CERTIFICATE OF CORRECTION

PATENT NO. : 8,809,008 B2  
APPLICATION NO. : 13/966475  
DATED : August 19, 2014  
INVENTOR(S) : Hu et al.

Page 1 of 1

It is certified that error appears in the above-identified patent and that said Letters Patent is hereby corrected as shown below:

In the Specification,

Column 16, line 44, after "may", please insert --be--;

Column 29, line 18, after "one or", please insert --more--;

Column 65, lines 17-18, please delete "an IR Score of 40 was obtained at a third time point,";

Column 134, lines 42-43, please delete "and the Importance plot is shown in Figure #";

Column 146, line 51, please replace "pardoning" with --partitioning--; and

Column 148, line 39, please replace "pardoning" with --partitioning--.

Signed and Sealed this  
Ninth Day of June, 2015

Michelle K. Lee  
*Director of the United States Patent and Trademark Office*